United States Patent
Warner et al.

(10) Patent No.: US 11,712,433 B2
(45) Date of Patent: Aug. 1, 2023

(54) COMPOSITIONS COMPRISING PKM2 MODULATORS AND METHODS OF TREATMENT USING THE SAME

(71) Applicant: Sumitomo Pharma Oncology, Inc., Marlborough, MA (US)

(72) Inventors: Steven L. Warner, Sandy, UT (US); David J. Bearss, Alpine, UT (US); Jason Marc Foulks, Sandy, UT (US)

(73) Assignee: Sumitomo Pharma Oncology, Inc., Marlborough, MA (US)

( * ) Notice: Subject to any disclaimer, the term of this patent is extended or adjusted under 35 U.S.C. 154(b) by 399 days.

(21) Appl. No.: 16/826,131

(22) Filed: Mar. 20, 2020

(65) Prior Publication Data

US 2020/0297698 A1    Sep. 24, 2020

Related U.S. Application Data

(60) Provisional application No. 62/822,751, filed on Mar. 22, 2019, provisional application No. 62/875,940, (Continued)

(51) Int. Cl.
*A61K 31/4155* (2006.01)
*A61K 35/04* (2006.01)
(Continued)

(52) U.S. Cl.
CPC .......... *A61K 31/4155* (2013.01); *A61K 35/04* (2013.01); *A61P 35/00* (2018.01);
(Continued)

(58) Field of Classification Search
CPC .... A61K 31/4155; A61K 35/04; A61K 45/06; C07K 16/2818; C07K 16/2827
See application file for complete search history.

(56) References Cited

U.S. PATENT DOCUMENTS 2,779,780 A    1/1957  Middleton
5,366,991 A   11/1994  Bettarini et al.
(Continued)

FOREIGN PATENT DOCUMENTS

EP    0 606 046 A1    7/1994
EP    0 780 386 A1    6/1997
(Continued)

OTHER PUBLICATIONS

Gunturi et al. (Expertopinion on Investigational drugs, 2015, 24(2):253-260). (Year: 2015).*

(Continued)

*Primary Examiner* — Savitha M Rao
(74) *Attorney, Agent, or Firm* — Hamilton, Brook, Smith & Reynolds, P.C.

(57) ABSTRACT

A compound of Structure (I):

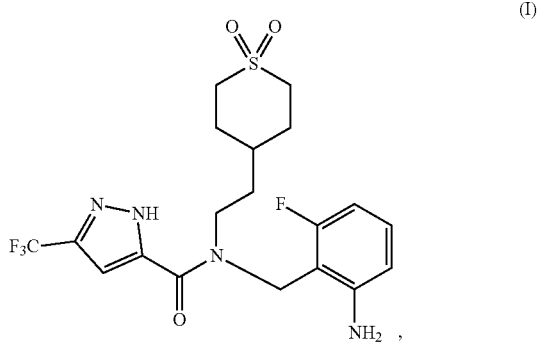

or a pharmaceutically acceptable salt thereof, alone or in combination with a second therapeutic agent, as well as
(Continued)

methods of treating a PKM2-mediated disease or disorder using the same are provided herein.

19 Claims, 35 Drawing Sheets

Related U.S. Application Data filed on Jul. 18, 2019, provisional application No. 62/926,417, filed on Oct. 25, 2019.

(51) Int. Cl.
*C07K 16/28* (2006.01)
*A61K 45/06* (2006.01)
*A61P 35/00* (2006.01)
*A61P 35/02* (2006.01)

(52) U.S. Cl.
CPC .......... *A61P 35/02* (2018.01); *C07K 16/2818* (2013.01); *C07K 16/2827* (2013.01); *A61K 45/06* (2013.01)

(56) References Cited

U.S. PATENT DOCUMENTS

| | | | |
|---|---|---|---|
| 5,587,458 A | 12/1996 | King et al. |
| 5,621,002 A | 4/1997 | Bosslet et al. |
| 5,747,498 A | 5/1998 | Schnur et al. |
| 5,792,783 A | 8/1998 | Tang et al. |
| 5,834,504 A | 11/1998 | Tang et al. |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 6,284,764 B1 | 9/2001 | Kath et al. |
| 7,030,242 B2 | 4/2006 | Noe et al. |
| 7,332,582 B2 | 2/2008 | Hardy et al. |
| 7,488,802 B2 | 2/2009 | Collins et al. |
| 7,695,715 B2 | 4/2010 | Hardy et al. |
| 7,943,743 B2 | 5/2011 | Korman et al. |
| 8,168,179 B2 | 5/2012 | Honjo et al. |
| 8,217,149 B2 | 7/2012 | Irving et al. |
| 8,349,832 B2 | 1/2013 | Foley et al. |
| 8,354,443 B2 | 1/2013 | Chen et al. |
| 8,460,927 B2 | 6/2013 | Chen |
| 8,501,953 B2 | 8/2013 | Salituro et al. |
| 8,524,720 B2 | 9/2013 | Bebbington et al. |
| 8,552,050 B2 | 10/2013 | Cantley et al. |
| 8,552,154 B2 | 10/2013 | Freeman et al. |
| 8,552,156 B2 | 10/2013 | Takayanagi et al. |
| 8,637,550 B2 | 1/2014 | Farrow et al. |
| 8,686,030 B2 | 4/2014 | Huang |
| 8,686,119 B2 | 4/2014 | Rotem-Yehudar et al. |
| 8,735,553 B1 | 5/2014 | Li et al. |
| 8,779,108 B2 | 7/2014 | Queva et al. |
| 8,841,305 B2 | 9/2014 | Thomas et al. |
| 8,841,418 B2 | 9/2014 | Karsunky et al. |
| 8,907,053 B2 | 12/2014 | Sasikumar et al. |
| 8,927,697 B2 | 1/2015 | Davis et al. |
| 8,993,731 B2 | 3/2015 | Tyson |
| 9,102,727 B2 | 8/2015 | Freeman et al. |
| 9,163,087 B2 | 10/2015 | Kuchroo et al. |
| 9,175,082 B2 | 11/2015 | Zhou et al. |
| 9,205,148 B2 | 12/2015 | Langermann et al. |
| 9,244,059 B2 | 1/2016 | Triebel et al. |
| 9,328,077 B2 | 5/2016 | Salituro et al. |
| 9,394,257 B2 | 7/2016 | Ho et al. |
| 9,447,054 B2 | 9/2016 | Song et al. |
| 9,458,132 B2 | 10/2016 | Cianchetta et al. |
| 9,505,839 B2 | 11/2016 | Longberg et al. |
| 9,605,070 B2 | 3/2017 | Sabato et al. |
| 9,683,048 B2 | 6/2017 | Freeman et al. |
| 9,988,452 B2 | 6/2018 | Freeman et al. |
| 10,207,996 B2 | 2/2019 | Ho et al. |
| 10,472,328 B2 | 11/2019 | Ho et al. |
| 10,766,865 B2 | 9/2020 | Ho et al. |
| 2005/0085524 A1 | 4/2005 | Okada et al. |
| 2007/0032529 A1 | 2/2007 | Takagi et al. |
| 2007/0060589 A1 | 3/2007 | Purandare et al. |
| 2012/0122849 A1 | 5/2012 | Salituro et al. |
| 2015/0259420 A1 | 9/2015 | Triebel et al. |
| 2015/0344436 A1* | 12/2015 | Ho ........................ A61P 11/00 544/371 |
| 2016/0280697 A1 | 9/2016 | Salituro et al. |
| 2018/0155297 A1 | 6/2018 | Mahajan et al. |
| 2018/0215738 A1 | 8/2018 | Mahajan et al. |
| 2020/0109120 A1 | 4/2020 | Ho et al. |
| 2020/0179384 A1 | 6/2020 | Lee et al. |
| 2020/0237766 A1 | 7/2020 | Siddiqui-Jain et al. |
| 2021/0002233 A1 | 1/2021 | Ho et al. |
| 2022/0162200 A1 | 5/2022 | Siddiqui-Jain et al. |

FOREIGN PATENT DOCUMENTS

| | | |
|---|---|---|
| EP | 0 818 442 A2 | 1/1998 |
| EP | 0 931 788 A2 | 7/1999 |
| EP | 1 004 578 A2 | 5/2000 |
| GB | 9912961.1 | 6/1999 |
| JP | 6-263738 A | 9/1994 |
| JP | 2861087 B2 | 2/1999 |
| JP | 2001-172261 A | 6/2001 |
| JP | 2002-363164 A | 12/2002 |
| JP | 2004-512277 A | 4/2004 |
| JP | 2008-534671 A | 8/2008 |
| JP | 2012-505247 A | 3/2012 |
| JP | 2012-522847 A | 9/2012 |
| JP | 2015-536325 A | 12/2015 |
| WO | 90/05719 A1 | 5/1990 |
| WO | 95/19970 A1 | 7/1995 |
| WO | 95/21613 A1 | 8/1995 |
| WO | 96/27583 A1 | 9/1996 |
| WO | 96/33172 A1 | 10/1996 |
| WO | 97/13760 A1 | 4/1997 |
| WO | 97/22596 A1 | 6/1997 |
| WO | 97/32856 A1 | 9/1997 |
| WO | 98/02434 A1 | 1/1998 |
| WO | 98/02437 A1 | 1/1998 |
| WO | 98/02438 A1 | 1/1998 |
| WO | 98/03516 A1 | 1/1998 |
| WO | 98/07697 A1 | 2/1998 |
| WO | 98/14451 A1 | 4/1998 |
| WO | 98/30566 A1 | 7/1998 |
| WO | 98/33768 A1 | 8/1998 |
| WO | 98/34915 A1 | 8/1998 |
| WO | 98/34918 A1 | 8/1998 |
| WO | 98/50356 A1 | 11/1998 |
| WO | 98/54093 A1 | 12/1998 |
| WO | 99/07675 A1 | 2/1999 |
| WO | 99/10349 A1 | 3/1999 |
| WO | 99/16755 A1 | 4/1999 |
| WO | 99/24440 A1 | 5/1999 |
| WO | 99/29667 A1 | 6/1999 |
| WO | 99/35132 A1 | 7/1999 |
| WO | 99/35146 A1 | 7/1999 |
| WO | 99/52889 A1 | 10/1999 |
| WO | 99/52910 A1 | 10/1999 |
| WO | 99/61422 A1 | 12/1999 |
| WO | 99/62890 A1 | 12/1999 |
| WO | 00/35436 A2 | 6/2000 |
| WO | 00/74681 A1 | 12/2000 |
| WO | 01/60814 A2 | 8/2001 |
| WO | 02/06213 A2 | 1/2002 |
| WO | 02/066470 A1 | 8/2002 |
| WO | WO 03/064383 A2 | 8/2003 |
| WO | 03/076424 A1 | 9/2003 |
| WO | 03/077914 A1 | 9/2003 |
| WO | 2004/078163 A2 | 9/2004 |
| WO | 2006/106425 A2 | 10/2006 |
| WO | 2007/014011 A2 | 2/2007 |
| WO | 2007/084786 A1 | 7/2007 |
| WO | WO 2008/132601 A1 | 11/2008 |
| WO | 2009/028280 A1 | 3/2009 |

(56) References Cited

FOREIGN PATENT DOCUMENTS

| | | |
|---|---|---|
| WO | 2009/036082 A2 | 3/2009 |
| WO | 2009/055730 A1 | 4/2009 |
| WO | WO 2009/044273 A2 | 4/2009 |
| WO | WO 2009/114335 A2 | 9/2009 |
| WO | WO 2010/019570 A1 | 2/2010 |
| WO | WO 2010027827 A2 | 3/2010 |
| WO | WO 2011066342 A2 | 6/2011 |
| WO | 2012/056319 A1 | 5/2012 |
| WO | 2012/083246 A1 | 6/2012 |
| WO | 2012/092442 A1 | 7/2012 |
| WO | 2012/123076 A1 | 9/2012 |
| WO | WO 2012145493 A1 | 10/2012 |
| WO | 2012/160447 A1 | 11/2012 |
| WO | 2013/005157 A1 | 1/2013 |
| WO | WO 2013079174 A1 | 6/2013 |
| WO | WO 2014022758 A1 | 2/2014 |
| WO | 2014/062838 A1 | 4/2014 |
| WO | WO 2014055897 A2 | 4/2014 |
| WO | 2014/074848 A1 | 5/2014 |
| WO | WO 2014100079 A1 | 6/2014 |
| WO | WO 2014140180 A1 | 9/2014 |
| WO | WO 2014179664 A2 | 11/2014 |
| WO | WO 2014194302 A2 | 12/2014 |
| WO | WO 2014209804 A1 | 12/2014 |
| WO | WO 2015061668 A1 | 4/2015 |
| WO | WO 2015081158 A1 | 6/2015 |
| WO | WO 2015085847 A1 | 6/2015 |
| WO | WO 2015109124 A2 | 7/2015 |
| WO | WO 2015112800 A1 | 7/2015 |
| WO | WO 2015112805 A1 | 7/2015 |
| WO | WO 2015116539 A1 | 8/2015 |
| WO | WO 2015181342 A1 | 12/2015 |
| WO | WO 2015195163 A1 | 12/2015 |
| WO | WO 2015200119 A1 | 12/2015 |
| WO | WO 2016000619 A1 | 1/2016 |
| WO | WO 2016028672 A1 | 2/2016 |
| WO | WO 2016071448 A1 | 5/2016 |
| WO | WO 2016092419 A1 | 6/2016 |
| WO | WO 2016111947 A2 | 7/2016 |
| WO | WO 2016144803 A2 | 9/2016 |
| WO | WO 2016187316 A1 | 11/2016 |
| WO | 2019/075367 A1 | 4/2019 |
| WO | WO 2020/198067 A1 | 10/2020 |
| WO | WO 2020/198077 A1 | 10/2020 |
| WO | WO 2021/003417 A1 | 1/2021 |

OTHER PUBLICATIONS

Jenkins et al. (British Journal of Cancer, 2018, 118, 9-16) (Year: 2018).*

U.S. Appl. No. 16/755,868, filed Apr. 13, 2020, N/A.

Anastasiou et al., "Inhibition of pyruvate kinase M2 by reactive oxygen species contributes to cellular antioxidant responses," *Science* 334(6060):1278-1283, 2011. (Author Manuscript, 12 pages).

Anastasiou et al., "Pyruvate kinase M2 activators promote tetramer formation and suppress tumorigenesis," *Nat. Chem. Biol.* 8(10):839-847, 2012.

Ashizawa et al., "In Vivo Regulation of Monomer-Tetramer Conversion of Pyruvate Kinase Subtype M2 by Glucose Is Mediated via Fructose 1,6-Bisphosphate," *The Journal of Biological Chemistry* 266(25):16842-16846, 1991.

Behar et al., "Abstract 4065: Modulation of cancer metabolism with novel PKM2 activators exerts anti-tumor activity," *Proceedings of the 102nd Annual Meeting of the American Association for Cancer Research*, Apr. 2-6, 2011, Orlando, Florida (4 pages).

Boxer et al., "Evaluation of Substituted N,N'-Diarylsulfonamides as Activators of the Tumor Cell Specific M2 Isoform of Pyruvate Kinase," *J. Med. Chem.* 53(3):1048-1055, 2010 (NIH Public Access Author Manuscript, available in PMC Feb. 11, 2011)(25 pages).

Chen et al., "The oxygen sensor PHD3 limits glycolysis under hypoxia via direct binding to pyruvate kinase," *Cell Research* 21(6):983-986, 2011.

Gao et al., "Pyruvate Kinase M2 Regulates Gene Transcription by Acting as a Protein Kinase," *Mol Cell.* 45(5):598-609, 2012.

Goldberg et al., "Pyruvate kinase M2-specific siRNA induces apoptosis and tumor regression," *J. Exp. Med.* 209(2):217-224, 2012.

Hitosugi et al., "Tyrosine Phosphorylation Inhibits PKM2 to Promote the Warburg Effect and Tumor Growth," *Sci. Signal.* 2(97):1-16, 2009 (NIH Public Access Author Manuscript, available in PMC Jan. 28, 2010)(16 pages).

Jiang et al., "Evaluation of Thieno[3,2-b]pyrrole[3,2-d]pyridazinones as Activators of the Tumor Cell Specific M2 Isoform of Pyruvate Kinase," *Bioorg. Med. Chem. Lett.* 20(11):3387-3393, 2010 (NIH Public Access Author Manuscript, available in PMC Jun. 1, 2011)(20 pages).

Kosugi et al., "MUC1-C Oncoprotein Regulates Glycolysis and Pyruvate Kinase m2 Activity in Cancer Cells," *PLoS One* 6(11):e28234:1-14, 2011.

Locasale et al., "Genetic selection for enhanced serine metabolism in cancer development," *Cell Cycle* 10(22):3812-3813, 2011.

Lv et al., "Acetylation Targets the M2 Isoform of Pyruvate Kinase for Degradation through Chaperone-Mediated Autophagy and Promotes Tumor Growth," *Molecular Cell* 42:719-730, 2011.

Mazurek et al., "Effect of Extracellular AMP on Cell Proliferation and Metabolism of Breast Cancer Cell Lines with High and Low Glycolytic Rates," *The Journal of Biological Chemistry* 272(8):4941-4952, 1997.

Parnell et al., "Pharmacologic Activation of PKM2 Slows Lung Tumor Xenograft Growth," *Molecular Cancer Therapeutics* 72(8):1453-1460, 2013.

Peterson et al., "Abstract B024: PKM2 activation suppresses cellular ROS scavenging capacity and potentiates doxorubicin antitumor activity," *Proceedings of the AACR-NCI-EORTC International Conference*, Oct. 26-30, 2017, Philadelphia, Pennsylvania. (5 pages).

Presek et al., "Pyruvate kinase type M2 is phosphorylated at tyrosine residues in cells transformed by Rous sarcoma virus," *FEBS Letters* 242(1):194-198, 1988.

Presek et al., "Similarities between a Phosphoprotein (pp60src)-associated Protein Kinase of Rous Sarcoma Virus and a Cyclic Adenosine 3':5'-Monophosphate-independent Protein Kinase That Phosphorylates Pyruvate Kinase Type M2," *Cancer Research* 40:1733-1741, 1980.

Shiga et al., "Insecticidal Activity of N-Acyl-N-(4-aryloxybenzyl)pyrazole-5-carboxamides," *J. Pestic. Sci.* 28:313-314, 2003.

STN Registry No. 1305273-34-0, "1H-Pyrazole-3-carboxamide, 5-amino-N-(1,3-benzodioxol-5-ylmethyl)-N-[(4-methylphenyl) methyl]-," Jun. 3, 2011, 1 page.

STN Registry No. 1287423-79-3, "1H-Pyrazole-3-carboxamide, N-[(2,3-dihydro-2-methyl-5-benzofuranyl)methyl]-N-(3-methoxypropyl)-5-(trifluoromethyl)-," Apr. 29, 2011, 1 page.

STN Registry No. 1268814-75-0, "1H-Pyrazole-5-carboxamide, N-(1,3-benzodioxol-5-ylmethyl)-3-cyclopropyl-N-ethyl-," Mar. 18, 2011, 1 page.

Tamada et al., "Modulation of Glucose Metabolism by CD44 Contributes to Antioxidant Status and Drug Resistance in Cancer Cells," *Cancer Res.* 72(6):1438-1448, 2012.

Tamada et al., "Pyruvate Kinase M2: Multiple Faces for Conferring Benefits on Cancer Cells," *Clin. Cancer Res.* 18(20):5554-5561, 2012.

Vander Heiden et al., "Understanding the Warburg Effect: The Metabolic Requirements of Cell Proliferation," *Science* 324(5930):1029-1033, 2009 (NIH Public Access Author Manuscript, available in PMC Apr. 5, 2010)(12 pages).

Walsh et al., "2-oxo-N-aryl-1,2,3,4-tetrahydroquinoline-6-sulfonamides as activators of the tumor cell specific M2 isoform of pyruvate kinase," *Bioorg. Med. Chem. Lett.* 21(21):6322-6327, 2011 (NIH Public Access Author Manuscript, available in PMC Dec. 1, 2011)(21 pages).

Xu et al., "Discovery of 3-(trifluoromethyl)-1??-pyrazole-5-carboxamide activators of the M2 isoform of pyruvate kinase (PKM2)," *Bioorganic & Medicinal Chemistry Letters* 24:515-519, 2014.

(56) References Cited

OTHER PUBLICATIONS

Ye et al., "Pyruvate kinase M2 promotes de novo serine synthesis to sustain mTORC1 activity and cell proliferation," *PNAS* 109(18):6904-6909, 2012.
Zhang et al., "New pyridin-3-ylmethyl carbamodithioic esters activate pyruvate kinase M2 and potential anticancer lead compounds," *Bioorganic & Medicinal Chemistry* 23:4815-4823, 2015.
Zwerschke et al., "Modulation of type M2 pyruvate kinase activity by the human papillomavirus type 16 E7 oncoprotein," *Proc. Natl. Acad. Sci. USA* 96:1291-1296, 1999.
Altenberg et al., "Genes of glycolysis are ubiquitously overexpressed in 24 cancer classes," Genomics 84(6):1014-1020, 2004.
Azoitei et al., "PKM2 promotes tumor angiogenesis by regulating HTF-1α through NF-κB activation," Molecular Cancer 15(3):1-15, 2016.
Barros-Núñez et al., "Chapter 2: The Classification, Mechanisms of Activation and Roles in Cancer Development of Oncogenes," Oncogenes:41-84, 2013.
Bhandari et al., "Molecular Landmarks of Tumor Hypoxia across Cancer Types," Nature Genetics 51(Feb.):308-321, 2019.
Broutin et al., "Insights into Significance of Combined Inhibition of MEK and m-TOR Signalling Output in KRAS-Mutant Non-Small-Cell Lung Cancer," British Journal of Cancer 115:549-552, 2016.
Cairns et al., "Pharmacologically Increased Tumor Hypoxia Can Be Measured by 18F-Fluoroazomycin Arabinoside Positron Emission Tomography and Enhances Tumor Response to Hypoxic Cytotoxin PR-10 4," Clin Cancer Res 15(23):7170-7174, 2009.
CAS Registry No. 1029712-80-8, "Benzamide, 2-fluoro-N-methyl-4-[7-(6-quinolinylmethyl)imidazo[1,2-b][1,2,4]triazin-2-yl]-" Entered STN Jun. 22, 2008, 1 page.
CAS Registry No. 1035555-63-5, "Pyrido[2,3-d]pyrimidine-4,7(3H,8H)-dione, 3-[(2R)-2,3-dihydroxypropyl]-6-fluoro-5-[(2-fluoro-4-iodophenyl)amino]-8-methyl-" Entered STN Jul. 23, 2008, 1 page.
CAS Registry No. 1211441-98-3, "7H-Pyrrolo[2,3-d]pyrimidine-6-carboxamide, 7-cyclopentyl-N,N-dimethyl-2-[[5-(1-piperazinyl)-2-pyridinyl]amino]-" Entered STN Mar. 18, 2010, 1 page.
CAS Registry No. 1236699-92-5 (Deleted CAS Registry No. 1204531-26-9, "4-Pyridinecarboxamide, N-[(2S)-2,3-dihydroxypropyl]-3-[(2-fluoro-4-iodophenyl)amino]-" Entered STN Aug. 19, 2010, 1 page.
CAS Registry No. 1246560-33-7, "2-Pyrimidinamine, 5-[8-methyl-9-(1-methylethyl)-2-(4-morpholinyl)-9H-purin-6-yl]-" Entered STN Oct. 19, 2010, 1 page.
CAS Registry No. 212141-51-0, " 1-Phthalazinamine, N-(4-chlorophenyl)-4-(4-pyridinylmethyl)-, hydrochloride (1:2)" Entered STN Oct. 4, 1998, 1 page.
CAS Registry No. 2457-80-9, "Adenosine, 5'-S-methyl-5'-thio-" Entered STN Nov. 16, 1984, 1 page.
CAS Registry No. 475108-18-0, "Urea, N-[2-chloro-4-[(6,7-dimethoxy-4-quinolinyl)oxy]phenyl]-N'-(5-methyl-3-isoxazolyl)-" Entered STN Dec. 4, 2002, 1 page.
CAS Registry No. 6023 06-29-6, "2-Pyrimidinamine, 4-[2-methyl-1-(1-methylethyl)-1H-imidazol-5-yl]-N-[4-(methylsulfonyl)phenyl]-" Entered STN Oct. 10, 2003, 1 page.
CAS Registry No. 653592-04-2, "3-Pyrrolidinol, 1-[(4-amino-5H-pyrrolo[3,2-d]pyrimidin-7-yl)methyl]-4-[(methylthio)methyl]-, (3R,4S)-" Entered STN Feb. 24, 2004, 1 page.
CAS Registry No. 656247-17-5 (Deleted STN Registry No. 928326-83-4, "1H-Indole-6-carboxylic acid, 2,3-dihydro-3-[[[4-[methyl[2-(4-methyl-1-piperazinyl)acetyl]amino]phenyl]amino]phenylmethylene]-2-oxo-, methyl ester, (3Z)-" Entered STN Mar. 1, 2004, 1 page.
CAS Registry No. 755037-03-7, "2-Pyridinecarboxamide, 4-[4-[[[[4-chloro-3-(trifluoromethyl)phenyl]amino]carbonyl]amino]-3-fluorophenoxy]-N-methyl-" Entered STN Oct. 1, 2004, 1 page.
CAS Registry No. 837364-57-5, "3-Pyridinemethanamine, 5-[3-(5,7-difluoro-1H-benzimidazol-2-yl)-1H-indazol-5-yl]-N-ethyl-4-methyl-" Entered STN Feb. 25, 2005, 1 page.
CAS Registry No. 844442-3 8-2, "1H-Pyrazole-3-carboxamide, 4-[(2,6-dichlorobenzoyl)amino]-N-4-piperidinyl-" Entered STN Mar. 8, 2005, 1 page.
CAS Registry No. 857876-30-3, "3-Pyridinecarboxamide, N-(2,3-dihydro-3,3-dimethyl-1H-indol-6-yl)-2-[(4-pyridinylmethyl)amino]-, phosphate (1:2)" Entered STN Aug. 1, 2005, 1 page.
CAS Registry No. 869363-13-3, "Benzoic acid, 4-[[9-chloro-7-(2,6-difluorophenyl)-5H-pyrimido[5,4-d][2]benzazepin-2-yl]amino]-" Entered STN Dec. 6, 2005, 1 page.
CAS Registry No. 877399-52-5, "2-Pyridinamine, 3-[(1R)-1-(2,6-dichloro-3-fluorophenyl)ethoxy]-5-[1-(4-piperidinyl)-1H-pyrazol-4-yl]-" Entered STN Mar. 21, 2006, 1 page.
CAS Registry No. 905281-76-7, "1H-Inden-1-one, 2,3-dihydro-5-[1-(2-hydroxyethyl)-3-(4-pyridinyl)1IH-pyrazol-4-yl]-, oxime" Entered STN Aug. 29, 2006, 1 page.
CAS Registry No. 918504-65-1, " 1-Propanesulfonamide, N-[3-[[5-(4-chlorophenyl)-1H-pyrrolo[2,3-b]pyridin-3-yl]carbonyl]-2,4-difluorophenyl]-" Entered STN Jan. 26, 2007, 1 page.
CAS Registry No. 920113-03-7, "4H-1-Benzopyran-4-one, 2-(2-chlorophenyl)-5,7-dihydroxy-8-[(2R,3S)-2-(hydroxymethyl)-1-methyl-3-pyrrolidinyl]-, hydrochloride (1:1)" Entered STN Feb. 8, 2007, 1 page.
CAS Registry No. 927880-90-8, "1H-Benzimidazol-2-amine, 1-methyl-5-[[2-[5-(trifluoromethyl)-1H-imidazol-2-yl]-4-pyridinyl]oxy]-N-[4-(trifluoromethyl)phenyl]-" Entered STN Mar. 22, 2007, 1 page.
CAS Registry No. 934660-93-2 (Deleted CAS Registry No. 1029872-29-4), "Methanone, [3,4-difluoro-2-[(2-fluoro-4-iodophenyl)amino]phenyl][3-hydroxy-3-(2S)-2-piperidinyl-1-azetidinyl]-" Entered STN May 13, 2007, 1 page.
R: 950769-58-1, "Urea, N-[5-(1,1-dimethylethyl)-3-isoxazolyl]-N'-[4-[7-[2-(4-morpholinyl)ethoxy]imidazo[2,1-b]benzothiazol-2-yl]phenyl]-" Entered STN Oct. 16, 2007, 1 page.
CAS Registry Number: 951209-71-5, "IRX 2" Entered STN Oct. 23, 2007, 1 page.
CAS Registry Number: 958852-01-2, "2,4-Thiazolidinedione, 5-[[4-(4-pyridinyl)-6-quinolinyl]methylene]-, (5Z)-" Entered STN Dec. 19, 2007, 1 page.
Christofk et al., "The M2 splice isoform of pyruvate kinase is important for cancer metabolism and tumour growth," Nature 452(7184):230-233, 2008.
Chu et al., "Risk of hand-foot skin reaction with sorafenib: A systematic review and meta-analysis," *Acta Oncol.* 47:176-186, 2008.
Compound Summary for CID 3025986 (CAS Registry No. 345627-80-7), Pub Chem, Created Aug. 8, 2005, 25 pages.
Compound Summary for CID 50992434 (Deprecated CAS Registry No. 1204531-25-8), Pub Chem, Created Apr. 4, 2011, 24 pages.
DeBerardinis et al., "The Biology of Cancer: Metabolic Reprogramming Fuels Cell Growth and Proliferation," *Cell Metabolism* 7:11-20, 2008.
Eigenbrodt et al., "Structural and kinetic differences between the $M_2$ type pyruvate kinases from lung and various tumors," *Biomed. Biochem. Acta.* 42(11-12):S278-282, 1983.
Hamid et al., "Safety and Tumor Responses with Lambrolizumab (Anti-PD-1) in Melanoma," the England Journal of Medicine 369(2):134-144, 2013.
Hasan et al., "PKM2 and HTF-1-a Regulation in Prostate Cancer Cell Lines," Plos One 13(9):1-14, 2018).
Hoskin et al., "Hypoxia in Prostate Cancer: Correlation of BOLD-MRI With Pimonidazole Immunohistochemistry—Initial Observations," Int. J. Radiation Oncology Biol. Phys., 68(4):1065-1071, 2007.
Jaing et al., "Role of the tumor microenvironment in PDL1/PD-1-mediated tumor immune escape," *Molecular Cancer* 18(10):1-17, 2019.
Jing et al., "Role of Hypoxia in Cancer Therapy by Regulating the Tumor Microenvironment," *Molecular Cancer* 18(157):1-15, 2019.
Knutson et al., "Synergistic Anti-Tumor Activity of EZH2 Inhibitors and Glucocorticoid Receptor Adonists in Models of Germinal Center Non-Hodgkin Lymphomas," PLoS One 9(12):e111840, 2014.
Luo et al., "Pyruvate Kinase M2 is a PHD3-Stimulated Coactivator for Hypoxia-Inducible Factor 1," Cell 145:732-744, 2011.

(56) References Cited

OTHER PUBLICATIONS

Mazurek et al., "Pyruvate kinase type M2 and its role in tumor growth and spreading," Semin. Cancer Biol. 15(4):300-308, 2005.
Mazurek et al., "Pyruvate kinase type M2: A key regulator of the metabolic budget system in tumor cells," Int. Biochem. Cell. Biol. 43(7):969-980, 2011.
Minotti et al., "Anthracyclines: Molecular Advances and Pharmacologic Developments in Antitumor Activity and Cardiotoxicity," Pharmacol. Rev. 56(2):185-229, 2004.
Mortensen et al., "PAZA PET/CT Hypoxia Imaging in Patients with Squamous Cell Carcinoma of the Head and Neck Treated with Radiotherapy: Results from the DAHANCA 24 Trial," Radiotherapy and Oncology 705:14-20, 2012.
O'Connor et al., "Oxygen-Enhanced MR1 Accurately Identifies, Quantifies, and Maps Tumor Hypoxia in Preclinical Cancer Models," Cancer Research 76(4):787-795, 2015.
Richardson et al., "Management of treatment-emergent peripheral neuropathy in multiple myeloma," Leukemia 26(4):595-608, 2012.
Rosenblatt et al., "PD-1 blockade by CT-011, anti PD-1 antibody, enhances ex-vivo T cell responses to autologous dendritic/myeloma fusion vaccine," J. Immunother. 34(5):409-418, 2011.
Sommakia, S., et al., "606-PKM2 Activation Modulates the Tumor-Immune Microenvironment and Enhances Response to Checkpoint Inhibitors in Preclinical Solid Tumor Models", AACR Annual Meeting 2021—Virtual-Poster to be presented durin Session PO.CL06.)(-Modifiers of the Tumor Microenvironment on Apr. 10, 2021, downloaded from AACR website, URL: https://www.abstractsonline.com/pp8/#!/9325/presentation/1500 on Mar. 30, 2021, 2 pages.
Tachibana et al., "Tumor Hypoxia Detected by 18F-fluoromisonidazole Positron Emission Tomography (Fmiso Pet) as a Prognostic Indicator of Radiotherapy (RT)," Anticancer Research 38(3):1775-1781, 2018.
Valable et al., "Imaging of brain Oxygenation with Magnetic Resonance Imaging: A Validation with Positron Emission Tomography in the Healthy and Tumoural Brain," Journal of Cerebral Blood Flow & Metabolism 37(7):2584-2597, 2017.
Yang et al., "Pyruvate kinase M2 at a glance," Journal of Cell Science 128:1655-1660, 2015.
Yasumizu et al., "PKM2 under hypoxic environment causes resistance to mTOR inhibitor in human castration resistant prostate cancer," Oncotarget 9(45):27698-27707, 2018.
Zhu et al., "RNAi Screen of the Druggable Genome Identifies Modulators of Proeasome Inhibitor Sensitivity in Myeloma Including CDK5," Blood 117(14):3847-3857, 2011.
Chan, T. et al., "Abstract 2307: Elucidation of a unique regulatory mechanism for TNK1 provides potential therapeutic targeting opportunities in cancer," Cancer Research, vol. 81; Suppl 13; 2307; 4 pages (2021).
Forostyan, T.V. et al., "Abstract 1478: TP-5809, A Novel TNK1 Inhibitor, Suppresses TNK1 Dependent Signaling and Tumor Growth in a Preclinical Model of Hodgkin's Lymphoma," Cancer Research, vol. 81; Suppl 13; 1478; 4 Pages (2021).
Lüpertz, R., et al., "Dose-and Time-Dependent Effects of Doxorubicin on Cytotoxicity, Cell Cycle and Apoptotic Cell Death in Human Colon Cancer Cells", Toxicology, 271:115-121 (2010).
Pathi, S. et al., "Abstract B080: PKM2 activation modulates metabolism and enhances immune response in solid tumor models," Mol. Cancer Ther., vol. 18; Suppl 12; B080; 5 pages (2019).
Pathi, S. et al., "PKM2 Activation Modulates Metabolism and Enhances Immune Response in Solid Tumor Models," Abstract No. B080, Poster (2019).
Sommakia, S., et al., "PKM2 activation modulates the tumor-immune microenvironment and enhances response to checkpoint inhibitors in preclinical solid tumor models," AACR Annual Meeting; Poster (2021).
Tai, W. et al., "SH2 domain-containing phosphatase 1 regulates pyruvate kinase M2 in hepatocellular carcinoma," Oncotarget, vol. 7; No. 16; 22193-22205 (2016).

\* cited by examiner

COMPOSITIONS COMPRISING PKM2 MODULATORS AND METHODS OF TREATMENT USING THE SAME

FIELD

The present disclosure relates to combination therapies, compositions comprising such combination therapies, and their use for the treatment of PKM2-mediated diseases or disorders.

BACKGROUND

PKM2 is upregulated in cancer cells (Altenberg B., Greulich K. O., *Genomics* 84(6):1014-20 (2004)) and has been shown to increase tumorigenicity compared to the alternatively spliced and constitutively active PKM1 isoform (Christofk H. R., Vander Heiden M. G., Harris M. H., et al., *Nature* 452(7184):230-33 (2008); Goldberg M. S., Sharp P. A., *J. Exp. Med.* 209(2):217-24 (2012)). The shift from PKM1 to PKM2 metabolically reprograms cells to create an environment where the tumorigenic cells are able to balance their energetic needs with their requirements for biomolecular building blocks to support cell growth. Cancer cells shift their dependence from PKM1 to PKM2 through multiple mechanisms, including oncoprotein binding (Kosugi M., Ahmad R., Alam M., Uchida Y., Kufe D., *PLoS One* 6(11):e28234 (2011); Zwerschke W., Mazurek S., Massimi P., Banks L., Eigenbrodt E., Jansen-Durr P., *Proc. Nat'l Acad. Sci. U.S.A.* 96(4):1291-96 (1999)), tyrosine phosphorylation (Hitosugi T., Kang S., Vander Heiden M. G., et al., *Sci. Signal* 2(97):ra73 (2009); Presek P., Glossmann H., Eigenbrodt E., et al., *Cancer Res.* 40(5):1733-41 (1980); Presek P., Reinacher M., Eigenbrodt E., *FEBS Lett.* 242(1): 194-98 (1988)), lysine acetylation (Lv L., Li D., Zhao D., et al., *Mol. Cell* 42(6):719-30 (2011)), cysteine oxidation (Anastasiou D., Poulogiannis G., Asara J. M., et al., *Science* 334(6060):1278-83 (2011)), and prolyl hydroxylation (Chen N., Rinner O., Czernik D., et al., *Cell Res.* 21(6):983-86 (2011)). In each case, PKM2 activity correlates with increased tumorigenicity. As a partially active enzyme, PKM2 creates an opportunity where both small molecule PKM2 activators (Boxer M. B., Jiang J. K., Vander Heiden M. G., et al., *J. Med. Chem.* 53(3):1048-55 (2010); Jiang J. K., Boxer M. B., Vander Heiden M. G., et al., *Bioorg. Med. Chem. Lett.* 20(11):3387-93 (2010); Walsh M. J., Brimacombe K. R., Veith H., et al., *Bioorg. Med. Chem. Lett.* 21(21):6322-27 (2011)) and inhibitors could potentially disrupt the metabolic balance that cancer cells require. Therefore, both PKM2 activators and inhibitors have been proposed to be useful anti-cancer therapies.

PKM2, particularly in dimer form, has been associated with tumor metabolism in a hypoxic environment: *Pyruvate Kinase M2 at a Glance*, Yang, W. and Lu, Z., *Journal of Cell Science* 128: pp 1655-1660 (2015) and associated therewith, a host of mechanisms promoting tumor mutagenesis and immune escape have been identified, for example, as described in: *Role of the Tumor Microenvironment in PD-L1/PD-1-mediated Tumor Immune Escape*, Jiang, X. et al., *Molecular Cancer* 18(10): pp 1-17 (2019) DOI/10.1186/s12943-018-0928-4; *PKM2 Promotes Tumor Angiogenesis by Regulating HIF-1-α through NF-κB Activation*, Azoitei, N. et al., *Molecular Cancer* 15(03): pp 1-15 (2016) DOI/10.1186/s12943-015-0490-2; *PKM2 Under Hypoxic Environment Causes Resistance to mTOR inhibitor in Human Castration Resistant Prostate Cancer*, Yasumizu, Y. et al., *Oncotarget*, 9:(45), pp 27698-27707 (2018); *Pyruvate Kinase M2 is a PHD3-Stimulated Coactivator for Hypoxia-Inducible Factor* 1, Luo, W. et al., Cell, 145: pp 732-744 (2011); The Biology of Cancer: Metabolic Reprogramming Fuels Cell Growth and Proliferation, DeBerardinis, R. J. et al., Cell Metabolism, 7: pp 11-20 (2008), DOI10.1016/j.cmet:2007.10.002.

More recently, *Molecular Landmarks of Tumor Hypoxia Across Cancer Types*, Bhandari, V. et al., *Nature Genetics*, 51 (February): pp 308-321 (2019), the microenvironments within a tumor have been examined. Not-withstanding that there is a range of hypoxia in tumors generally (e.g., squamous cell tumors of the head and neck, cervix, and lung being the most hypoxic and adenocarcinomas of the thyroid and prostate being the least hypoxic of the 19 tumor types surveyed in the study), the investigators identified a range of hypoxic environments within a given tumor type suggesting that the identification of hypoxic tumor variants within a given tumor type may afford a means of addressing sensitivity or resistance to PKM2- or Immune Checkpoint-targeted IO therapy for such tumor types.

There remains a need for new treatments and therapies for PKM2-mediated disorders or diseases.

SUMMARY

The present disclosure provides combination therapies, and pharmaceutical compositions thereof, which comprise a PKM2-modulating compound (e.g., an activator of PKM2). The present disclosure further provides methods of treating PKM2-mediated disorders or diseases, comprising administering to a subject in need thereof an effective amount of a combination therapy comprising a PKM2-modulating compound (e.g., the compound of Structure (I)).

One aspect of the present disclosure provides a method of treating a cancer, the method comprising administering to a subject in need thereof an effective amount of a compound of Structure (I):

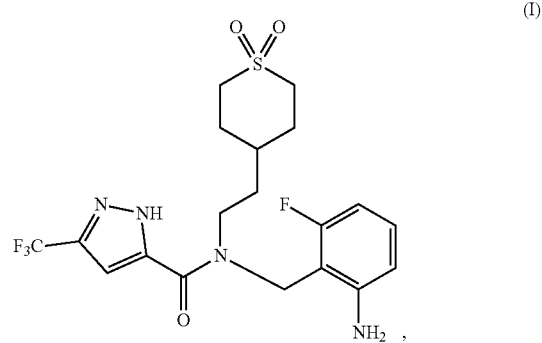 [SMILES: Nc1cccc(F)c1CN(CCC1CCS(=O)(=O)CC1)C(=O)c1cc(C(F)(F)F)n[nH]1]

or a pharmaceutically acceptable salt thereof and an immunological checkpoint inhibitor.

In yet another aspect of the present disclosure, a method is provided for treating cancer, the method comprising administering to a subject in need thereof an effective amount of a compound of Structure (I), or a pharmaceutically acceptable salt thereof. In some embodiments the cancer is an advanced solid tumor.

In yet another aspect of the present disclosure, a method is provided for treating a cancer, the method comprising administering to a subject in need thereof an effective amount of a compound of Structure (I), or a pharmaceutically acceptable salt thereof and a kinase inhibitor. In embodiments, the kinase inhibitor does not include sorafenib.

In yet another aspect of the present disclosure, a method is provided for treating an EGFR-mutant non-small cell lung cancer (NSCLC), the method comprising administering to a subject in need thereof an effective amount of a compound of Structure (I), or a pharmaceutically acceptable salt thereof.

In yet another aspect of the present disclosure, a method is provided for treating a cancer, the method comprising administering to a subject in need thereof an effective amount of a compound of Structure (I), or a pharmaceutically acceptable salt thereof; and a ferroptosis inducer. In embodiments, the ferroptosis inducer does not include erastin, sorafenib, or cisplatin.

In yet another aspect of the present disclosure, a method is provided for treating NPM-ALK anaplastic large cell lymphoma, the method comprising administering to a subject in need thereof an effective amount of a compound of Structure (I), or a pharmaceutically acceptable salt thereof.

In various embodiments, the method does not include administering a reactive oxygen species-producing anti-cancer drug to the subject.

In yet another aspect of the present disclosure a method is provided for treating a cancer, the method comprising administering to a patient population identified as having a cancerous tumor containing a glycolic metabolic environment an effective amount of a compound of Structure (I):

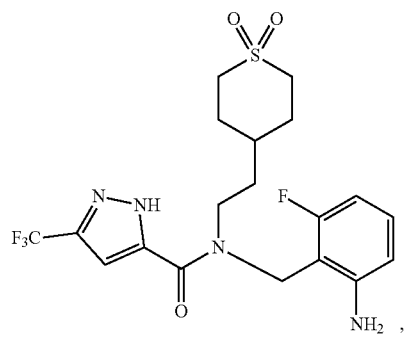

or a pharmaceutically acceptable salt thereof. In some embodiments, treatment with the compound of Structure I is accompanied by increased levels of glucose in said cancerous tumor microenvironment. In some embodiments the method comprises administering the compound of Formula I in conjunction with one or more additional therapeutic agents. In some embodiments the method comprises administering additionally one or more checkpoint inhibitors.

In yet another aspect of the present disclosure a method is provided for treating a cancer, the method comprising altering a tumor microenvironment by administering to a subject in need thereof an amount of a compound of Structure (I) or a pharmaceutically acceptable salt thereof, that is sufficient to decrease or eliminate T-regulatory cells and/or increase lymphocyte infiltration within the tumor microenvironment, thereby making the tumor susceptible to treatment with an immunotherapy agent:

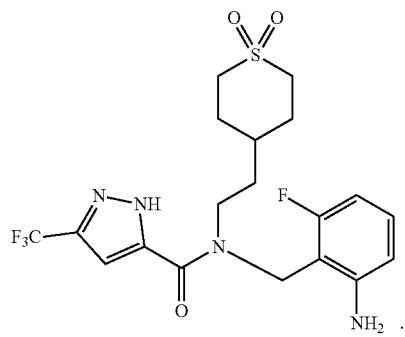

In some embodiments the method comprises additionally that administration of a compound of Structure (I) is preceded by, followed by, or concomitant with administration of one or more additional therapeutic agents. In some embodiments the additional therapeutic agent is an immunotherapy agent. In some embodiments where treatment includes administration of an immunotherapy agent, the agent is one or more of a PD-1, PD-L1, or CTLA-4 inhibitor. In some embodiments said treatment activates PKM2 within said tumor microenvironment. In some embodiments treatment with the compound of Structure I decreases one or more of glucose 6-phosphate, phosphoglycerate, phosphoenolpyruvate and/or lactate within the tumor microenvironment.

In some embodiments treatment is provided for a hematopoietic cancer. In some embodiments treatment is provided for a solid tumor cancer. In some embodiments treatment is provided for a cancer which is a Myelodysplastic syndrome (MDS). In some embodiments treatment is provided for a cancer which has a VHL mutation. In some embodiments treatment is provided for a cancer which is lung cancer, non-small cell lung cancer (NSCLC), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, hematological malignancies, MDS, acute myeloid leukemia (AML), multiple myeloma, follicular lymphoma, acute lymphoblastic leukemia (ALL), chronic lymphocytic leukemia (CLL) and non-Hodgkin's lymphoma, bladder cancer and prostate cancer.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

FIG. 18A shows the results for Groups 1-8, and FIG. 18B shows the results for Groups 9-16.

FIG. 19A shows the results for Groups 1-8, and FIG. 19B shows the results for Groups 9-16.

FIG. 20A shows the results for Groups 1-8, and FIG. 20B shows the results for Groups 9-16.

FIG. 21A shows the results for Groups 1-8, and FIG. 21B shows the results for Groups 9-16.

FIG. 22A shows the results for Groups 1-4, FIG. 22B shows the results for Groups 5-8, FIG. 22C shows the results for Groups 9-12, and FIG. 22C shows the results for Groups 13-16.

FIG. 23A shows the results for Groups 1-8, and FIG. 23B shows the results for Groups 9-16.

DETAILED DESCRIPTION

Figure 1:
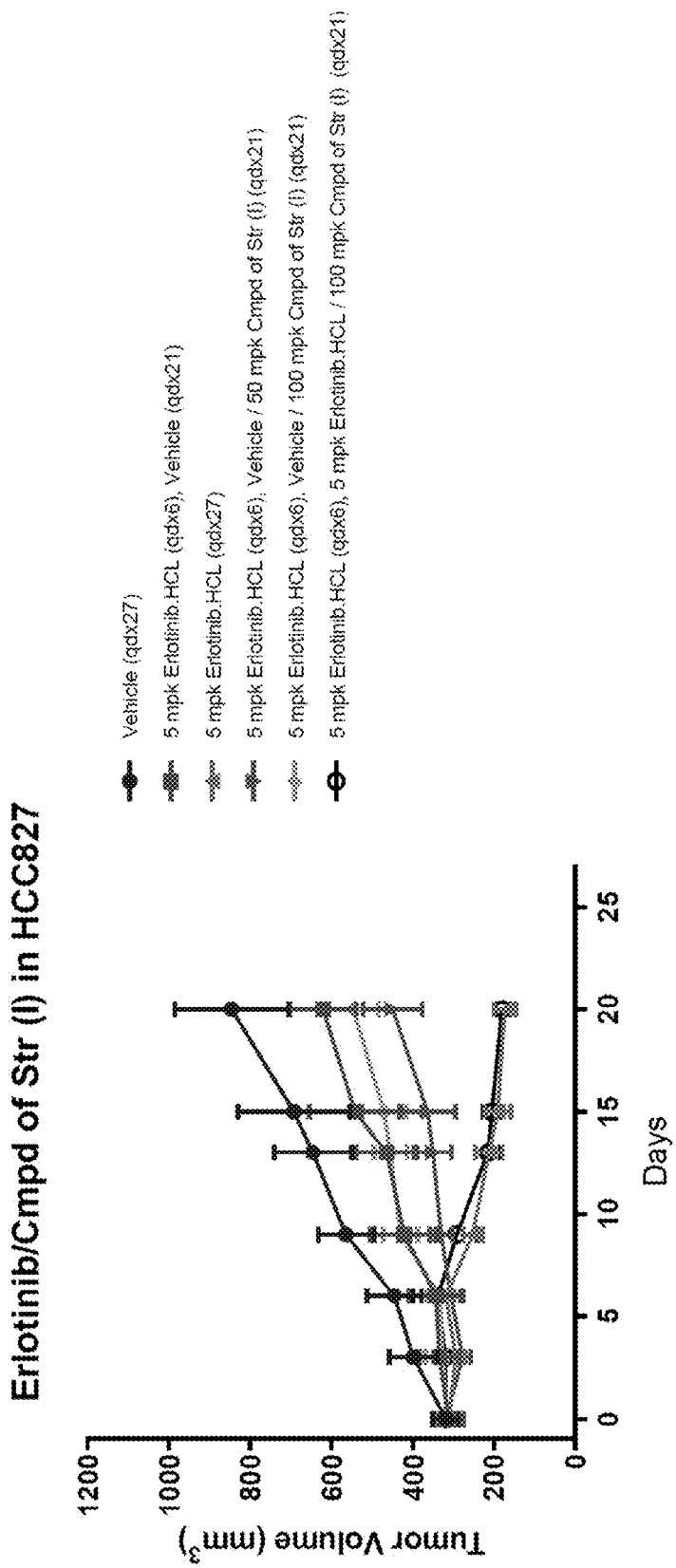
FIG. 1 shows tumor volumes in an EGFR HCC827 xenograft model plotted as a function of time (in days).

Various (enumerated) embodiments of the disclosure are described herein. It will be recognized that features specified in each embodiment may be combined with other specified features to provide further embodiments of the present disclosure.

Embodiment 1

A method of treating a cancer, the method comprising administering to a subject in need thereof an effective amount of a compound of Structure (I):

or a pharmaceutically acceptable salt thereof; and
an immunological checkpoint inhibitor.

Embodiment 2

A method of treating an advanced solid tumor, the method comprising administering to a subject in need thereof an effective amount of a compound of Structure (I), or a pharmaceutically acceptable salt thereof.

Embodiment 3

The method of embodiment 2, wherein the advanced solid tumor has progressed on an immuno-oncology agent.

Embodiment 4

The method of embodiment 2 or 3, further comprising administering to the subject an effective amount of an immunological checkpoint inhibitor.

Embodiment 5

The method of embodiment 1 or 4, wherein the immunological checkpoint inhibitor is a CTLA-4 inhibitor, a PD-1 inhibitor, a PD-L1 inhibitor, an OX40 inhibitor, or a combination thereof.

Embodiment 6

The method of any one of embodiments 1, 4, and 5, wherein the immunological checkpoint inhibitor is a PD-1 inhibitor, a PD-L1 inhibitor, an OX40 inhibitor, or a combination thereof.

Embodiment 7

The method of embodiment 1, 4, or 5, wherein the immunological checkpoint inhibitor comprises a CTLA-4 inhibitor and a PD-1 inhibitor.

Embodiment 8

The method of any one of embodiments 5 and 7, wherein the CTLA-4 inhibitor comprises Ipilimumab, Tremelimumab, or a combination thereof.

Embodiment 9

The method of any one of embodiments 5-8, wherein the PD-1 inhibitor comprises Nivolumab, Pembrolizumab, Pidilizumab, Cemiplimab, or a combination thereof.

Embodiment 10

The method of any one of embodiments 5-9, wherein the PD-1 inhibitor comprises Nivolumab, Pembrolizumab, or a combination thereof.

Embodiment 11

The method of embodiment 5 or 6, wherein the PD-L1 inhibitor comprises Avelumab, Atezolizumab, Durvalumab, or a combination thereof.

Embodiment 12

The method of embodiment 5 or 6, wherein the PD-L1 inhibitor comprises Avelumab, Atezolizumab, or a combination thereof.

Embodiment 13

The method of embodiment 5 or 6, wherein the OX40 inhibitor comprises BMS 986178.

Embodiment 14

A method of treating a cancer, the method comprising administering to a subject in need thereof an effective amount of a compound of Structure (I), or a pharmaceutically acceptable salt thereof; and a kinase inhibitor.

Embodiment 15

The method of embodiment 14, wherein the kinase inhibitor is a tyrosine kinase inhibitor.

Embodiment 16

The method of embodiment 15, wherein the tyrosine kinase inhibitor is a receptor tyrosine kinase (RTK) inhibitor.

Embodiment 17

A method of treating an EGFR-mutant non-small cell lung cancer (NSCLC), the method comprising administering to a subject in need thereof an effective amount of a compound of Structure (I), or a pharmaceutically acceptable salt thereof.

Embodiment 18

The method of embodiment 17, wherein the EGFR-mutant NSCLC has progressed on a tyrosine kinase inhibitor.

Embodiment 19

The method of embodiment 17 or 18, further comprising administering to the subject an effective amount of a receptor tyrosine kinase (RTK) inhibitor.

Embodiment 20

The method of embodiment 16 or 19, wherein the RTK inhibitor is an epidermal growth factor receptor (EGFR) inhibitor, a vascular endothelial growth factor (VEGF) inhibitor, an ErbB2 inhibitor, a platelet-derived growth factor (PDGF) receptor inhibitor, or a combination thereof.

Embodiment 21

The method of embodiment 20, wherein the EFGR inhibitor comprises cetuximab, osimertinib, gefitinib, erlotinib, afatinib, or a combination thereof.

Embodiment 22

The method of embodiment 20, wherein the VEGF inhibitor comprises bevacizumab.

Embodiment 23

The method of embodiment 20, wherein the ErbB2 inhibitor comprises trastuzumab.

Embodiment 24

The method of embodiment 14, wherein the kinase inhibitor is a serine/threonine (S/T) kinase inhibitor.

Embodiment 25

The method of embodiment 24, wherein the S/T kinase inhibitor is a B-RAF inhibitor, a cyclin dependent kinase (CDK) inhibitor, a phosphoinositide 3-kinase (PI3K) inhibitor, a mitogen-activated protein kinase, or a combination thereof.

Embodiment 26

The method of any one of embodiments 14-16 and 19-25, with the proviso that the kinase inhibitor or RTK inhibitor does not include sorafenib.

Embodiment 27

A method of treating a cancer, the method comprising administering to a subject in need thereof an effective amount of a compound of Structure (I), or a pharmaceutically acceptable salt thereof; and a ferroptosis inducer.

Embodiment 28

The method of embodiment 27, wherein the ferroptosis inducer comprises sulfasalazine.

Embodiment 29

The method of embodiment 27 or 28, with the proviso that the ferroptosis inducer does not include erastin, sorafenib, or cisplatin.

Embodiment 30

The method of any one of embodiments 1, 5-16, and 20-29, wherein the cancer is a hematologic cancer.

Embodiment 31

The method of embodiment 30, wherein the hematologic cancer is selected from the group consisting of acute myelogenous leukemia (AML), multiple myeloma, follicular lymphoma, acute lymphoblastic leukemia (ALL), chronic lymphocytic leukemia (CLL) and non-Hodgkin's lymphoma.

Embodiment 32

The method of embodiment 30, wherein the hematologic cancer is NPM-ALK anaplastic large cell lymphoma.

Embodiment 33

The method of any one of embodiments 1, 5-16, and 20-29, wherein the cancer is a solid tumor cancer.

Embodiment 34

The method of embodiment 33, wherein the solid tumor cancer is lung cancer, pancreatic cancer, skin cancer, uterine cancer, ovarian cancer, colo-rectal cancer, breast cancer, hepatocellular cancer, kidney cancer, or a combination thereof.

Embodiment 35

The method of embodiment 33 or 34, wherein the solid tumor cancer is a carcinoma.

Embodiment 36

The method of embodiment 34 or 35, wherein the solid tumor cancer is lung cancer.

Embodiment 37

The method of embodiment 36, wherein the solid tumor cancer is a NSCLC.

Embodiment 38

The method of any one of embodiments 33-37, wherein the solid tumor cancer is an EFGR-mutant cancer, a BRAF-mutant cancer, a ROS1-mutant cancer, an ALK-mutant cancer, or a combination thereof.

Embodiment 39

The method of embodiment 37 or 38, wherein the solid tumor cancer is an EGFR-mutant NSCLC.

Embodiment 40

The method of embodiment 39, wherein the EGFR-mutant NSCLC has progressed on a tyrosine kinase inhibitor.

Embodiment 41

The method of any one of embodiments 33-35, wherein the solid tumor cancer is colon cancer.

Embodiment 42

The method of any one of embodiments 33-41, wherein the solid tumor cancer is an advanced solid tumor cancer.

Embodiment 43

The method of embodiment 42, wherein advanced solid tumor cancer has progressed on an immuno-oncology agent.

Embodiment 44

A method of treating NPM-ALK anaplastic large cell lymphoma, the method comprising administering to a subject in need thereof an effective amount of a compound of Structure (I), or a pharmaceutically acceptable salt thereof.

Embodiment 45

The method of any one of embodiments 1-44, with the proviso that the method does not include administering a reactive oxygen species-producing anti-cancer drug to the subject.

Embodiment 46

A pharmaceutical combination for use in a method for treating a cancer in a subject in need thereof, the pharmaceutical combination comprising an effective amount of a compound of Structure (I), or a pharmaceutically acceptable salt thereof; and a kinase inhibitor.

Embodiment 47

The pharmaceutical combination of embodiment 46, wherein the kinase inhibitor is a tyrosine kinase inhibitor.

Embodiment 48

The pharmaceutical combination of embodiment 47, wherein the tyrosine kinase inhibitor is a receptor tyrosine kinase (RTK) inhibitor.

Embodiment 49

A pharmaceutical composition for use in a method of treating an EGFR-mutant NSCLC, the pharmaceutical composition comprising an effective amount of a compound of Structure (I), or a pharmaceutically acceptable salt thereof.

Embodiment 50

The pharmaceutical composition of embodiment 49, wherein the EGFR-mutant NSCLC has progressed on a tyrosine kinase inhibitor.

Embodiment 51

The pharmaceutical composition of embodiment 49 or 50, wherein the method further comprises administering to the subject an effective amount of a receptor tyrosine kinase (RTK) inhibitor.

Embodiment 52

The pharmaceutical combination or composition of embodiment 48 or 51, wherein the RTK inhibitor is an epidermal growth factor receptor (EGFR) inhibitor, a vascular endothelial growth factor (VEGF) inhibitor, an ErbB2 inhibitor, a platelet-derived growth factor (PDGF) receptor inhibitor, or a combination thereof.

Embodiment 53

The pharmaceutical combination or composition of embodiment 52, wherein the EFGR inhibitor comprises cetuximab, osimertinib, gefitinib, erlotinib, afatinib, or a combination thereof.

Embodiment 54

The pharmaceutical combination or composition of embodiment 52, wherein the VEGF inhibitor comprises bevacizumab.

Embodiment 55

The pharmaceutical combination or composition of embodiment 52, wherein the ErbB2 inhibitor comprises trastuzumab.

Embodiment 56

The pharmaceutical combination of embodiment 46, wherein the kinase inhibitor is a serine/threonine (S/T) kinase inhibitor.

Embodiment 57

The pharmaceutical combination of embodiment 56, wherein the S/T kinase inhibitor is a B-RAF inhibitor, a cyclin dependent kinase (CDK) inhibitor, a phosphoinositide 3-kinase (PI3K) inhibitor, a mitogen-activated protein kinase, or a combination thereof.

Embodiment 58

The pharmaceutical combination or composition of any one of embodiments 46-48 and 51-57, with the proviso that the kinase inhibitor or RTK inhibitor does not include sorafenib.

Embodiment 59

The pharmaceutical combination of any one of embodiments 46-48 and 51-58, wherein the compound of Structure (I), and the kinase inhibitor or RTK inhibitor only come into contact with each other in a human body.

Embodiment 60

A pharmaceutical combination for use in a method for treating a cancer in a subject in need thereof, the pharmaceutical combination comprising an effective amount of a compound having Structure (I), or a pharmaceutically acceptable salt thereof; and an immunological checkpoint inhibitor.

Embodiment 61

A pharmaceutical composition for use in a method of treating an advanced solid tumor in a subject in need thereof, the pharmaceutical composition comprising an effective amount of a compound of Structure (I), or a pharmaceutically acceptable salt thereof.

Embodiment 62

The pharmaceutical composition of embodiment 61, wherein the advanced solid tumor has progressed on an immuno-oncology agent.

Embodiment 63

The pharmaceutical composition of embodiment 61 or 62, wherein the method further comprises administering to the subject an effective amount of an immunological checkpoint inhibitor.

Embodiment 64

The pharmaceutical combination or composition of embodiment 60 or 63, wherein the immunological checkpoint inhibitor is a CTLA-4 inhibitor, a PD-1 inhibitor, a PD-L1 inhibitor, an OX40 inhibitor, or a combination thereof.

Embodiment 65

The pharmaceutical combination or composition of any one of embodiments 60, 63, and 64, wherein the immunological checkpoint inhibitor is a PD-1 inhibitor, a PD-L1 inhibitor, an OX40 inhibitor, or a combination thereof.

Embodiment 66

The pharmaceutical combination or composition of any one of embodiments, 60, 63, and 64 wherein the immunological checkpoint inhibitor comprises a CTLA-4 inhibitor and a PD-1 inhibitor.

Embodiment 67

The pharmaceutical combination or composition of embodiment 64 or 66, wherein the CTLA-4 inhibitor comprises Ipilimumab, Tremelimumab, or a combination thereof.

Embodiment 68

The pharmaceutical combination or composition of any one of embodiments 64-67, wherein the PD-1 inhibitor comprises Nivolumab, Pembrolizumab, Pidilizumab, Cemiplimab, or a combination thereof.

Embodiment 69

The pharmaceutical combination or composition of any one of embodiments 64-68, wherein the PD-1 inhibitor comprises Nivolumab, Pembrolizumab, or a combination thereof.

Embodiment 70

The pharmaceutical combination or composition of any one of embodiments 64, 65, and 67-69, wherein the PD-L1 inhibitor comprises Avelumab, Atezolizumab, Durvalumab, or a combination thereof.

Embodiment 71

The pharmaceutical combination or composition of any one of embodiments 64, 65, and 67-70, wherein the PD-L1 inhibitor comprises Avelumab, Atezolizumab, or a combination thereof.

Embodiment 72

The pharmaceutical combination or composition of any one of embodiments 64, 65, and 67-71, wherein the OX40 inhibitor comprises BMS 986178.

Embodiment 73

The pharmaceutical combination of any one of embodiments 60 and 63-72, wherein the compound of Structure (I), and the immunological checkpoint inhibitor only come into contact with each other in a human body.

Embodiment 74

A pharmaceutical combination for use in a method for treating a cancer in a subject in need thereof, the pharmaceutical combination comprising an effective amount of a compound having Structure (I), or a pharmaceutically acceptable salt thereof; and a ferroptosis inducer.

Embodiment 75

The pharmaceutical combination of embodiment 74, wherein the ferroptosis inducer comprises sulfasalazine.

Embodiment 76

The pharmaceutical combination of embodiment 74 or 75, with the proviso that the ferroptosis inducer does not include erastin, sorafenib, or cisplatin.

Embodiment 77

The pharmaceutical combination of any one of embodiments 46-76, with the proviso that the pharmaceutical combination does not include a reactive oxygen species-producing anti-cancer drug.

Embodiment 78

The pharmaceutical combination of any one of embodiments 46-48, 51-60, and 64-77, wherein the cancer is a hematologic cancer.

Embodiment 79

The pharmaceutical combination of embodiment 78, wherein the hematologic cancer is selected from acute myelogenous leukemia (AML), multiple myeloma, follicular lymphoma, acute lymphoblastic leukemia (ALL), chronic lymphocytic leukemia (CLL) and non-Hodgkin's lymphoma.

Embodiment 80

The pharmaceutical combination of claim 79, wherein the hematologic cancer is NPM-ALK anaplastic large cell lymphoma.

Embodiment 81

The pharmaceutical combination of any one of embodiments 46, 47, 52-60, and 64-76, wherein the cancer is a solid tumor cancer.

Embodiment 82

The pharmaceutical combination of embodiment 46, 47, 52-77, or 81, wherein the solid tumor cancer is lung cancer, pancreatic cancer, skin cancer, uterine cancer, ovarian cancer, colo-rectal cancer, breast cancer, hepatocellular cancer, kidney cancer, or a combination thereof.

Embodiment 83

The pharmaceutical combination of embodiment 81 or 82, wherein the solid tumor cancer is a carcinoma.

Embodiment 84

The pharmaceutical combination of embodiment 82 or 83, wherein the solid tumor cancer is lung cancer.

Embodiment 85

The pharmaceutical combination of embodiment 84, wherein the solid tumor cancer is a NSCLC.

Embodiment 86

The pharmaceutical combination of any one of embodiments 81-85, wherein the solid tumor cancer is an EFGR-mutant cancer, a BRAF-mutant cancer, a ROS1-mutant cancer, an ALK-mutant cancer, or a combination thereof.

Embodiment 87

The pharmaceutical combination of embodiment 85 or 86, wherein the NSCLC is an EFGR-mutant NSCLC.

Embodiment 88

The pharmaceutical combination of any one of embodiment 85-87, wherein the NSCLC is an EGFR-mutant NSCLC that has progressed on a tyrosine kinase inhibitor.

Embodiment 89

The pharmaceutical combination of any one of embodiments 81-83, wherein the solid tumor cancer is colon cancer.

Embodiment 90

The pharmaceutical combination of any one of embodiments 81-89, wherein the solid tumor cancer is an advanced solid tumor cancer.

Embodiment 91

The pharmaceutical combination of embodiment 90, wherein the advanced solid tumor cancer has progressed on an immuno-oncology agent.

Embodiment 92

The pharmaceutical combination of any one of embodiments 74-91, wherein the compound of Structure (I), and the ferroptosis inhibitor only come into contact with each other in a human body.

Embodiment 93

A pharmaceutical composition for treating NPM-ALK anaplastic large cell lymphoma in a subject in need thereof, pharmaceutical composition comprising an effective amount of a compound of Structure (I), or a pharmaceutically acceptable salt thereof.

Embodiment 94

A method of treatment of cancer comprising identifying a patient population having a cancerous tumor containing a hypoxic environment and administering thereto a compound of Structure I:

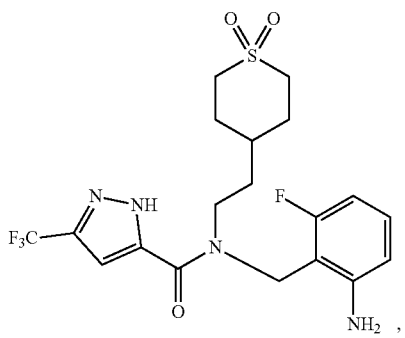

(I)

or a pharmaceutically acceptable salt thereof.

Embodiment 95

A method of treatment comprising altering a tumor microenvironment by administering to a subject in need thereof an amount of a compound of Structure I:

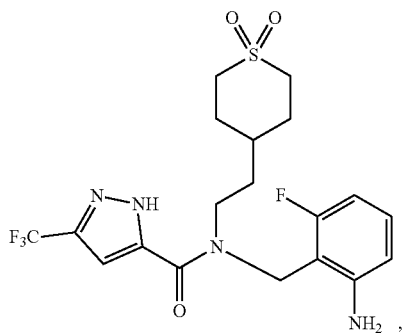

(I)

or a pharmaceutically acceptable salt thereof, that is sufficient to decrease or eliminate T-regulatory cells and/or increase lymphocyte infiltration, thereby rendering the tumor susceptible to treatment with an immunotherapy agent.

Embodiment 96

The method of treatment of either Embodiment 94 or 95 which includes administering additionally one or more therapeutic agents.

Embodiment 97

The method of Embodiment 96 where the additional therapeutic agents administered are immunotherapeutic agents.

Embodiment 98

The method of any of Embodiments 96 or 97 wherein the additional therapeutic agents are checkpoint inhibitors.

Embodiment 99

The method of Embodiment 96 to 98 wherein the additional therapeutic agents are one or more of a PD-1 inhibitor, a PD-L1 inhibitor, and a CTLA-4 inhibitor.

Embodiment 100

The method of embodiment 96 to 99, wherein the additional therapeutic agents are selected from nivolumab and ipilmumab

Embodiment 101

The method of any of Embodiments 96 though 100 wherein the additional therapeutic agents are administered preceding, following, or contemporaneously with the administration of the compound of Formula I.

Other features of the present disclosure will be apparent in view of the above descriptions of exemplary embodiments that are given for illustration of the disclosure and are not intended to be limiting thereof.

Definitions

For purposes of interpreting this specification, the following definitions will apply, and whenever appropriate, terms used in the singular will also include the plural. Terms used in the specification have the following meanings unless the context clearly indicates otherwise.

All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the present disclosure otherwise claimed.

The terms "a," "an," "the" and similar terms used in the context of the present disclosure (especially in the context of the claims) are to be construed to cover both the singular and plural unless otherwise indicated herein or clearly contradicted by the context.

The phrase "pharmaceutically acceptable" indicates that the substance or composition must be compatible chemically and/or toxicologically, with the other ingredients comprising a formulation, and/or the mammal being treated therewith.

Unless specified otherwise, the term "compound of Structure (I)" refers to the compound, as well as isomers, including, for example, structural isomers, and conformational isomers (including rotamers and atropisomers), tautomers, isotopically labeled compounds (including deuterium substitutions), and inherently formed moieties (e.g., tautomers, polymorphs, solvates and/or hydrates). Salts are included as well, in particular pharmaceutically acceptable salts.

Conformational isomers (or conformers) are isomers that can differ by rotations about one or more bonds. Rotamers are conformers that differ by rotation about only a single bond. These terms include atropisomers.

The term "atropisomer" refers to a rotational isomer which is fixed in a particular conformation of axial or planar chirality arising from steric hinderance creating a sufficiently high barrier to the rotation necessary to achieve other conformations due to, for example, steric interference, that the particular isomer is capable of being isolated.

A "tautomer" refers to a proton shift from one atom of a molecule to another atom of the same molecule. Embodiments include tautomers of the compound of Structure (I).

All processes used to prepare the compound of Structure (I) and intermediates made therein are considered to be part of the present disclosure. The compound of Structure (I) may be purified by conventional methods, for example, by chromatography or fractional crystallization.

Depending on the process conditions the end products of the present disclosure are obtained either in free (neutral) or salt form. Both the free form and the salts of these end products are within the scope of the present disclosure. If so desired, one form of a compound may be converted into another form. A free base or acid may be converted into a salt; a salt may be converted into the free compound or another salt; or a mixture of isomeric compounds may be separated into the individual isomers.

Pharmaceutically acceptable salts are preferred. However, other salts may be useful, e.g., in isolation or purification steps which may be employed during preparation and, thus, are within the scope of the present disclosure.

As used herein, "pharmaceutically acceptable salts" refer to derivatives of the disclosed compounds wherein the parent compound is modified by making acid or base salts thereof. For example, pharmaceutically acceptable salts include acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate/hydroxymalonate, mandelate, mesylate, methylsulphate, mucate, naphthoate, napsylate, nicotinate, nitrate, octadecanoate, oleate, oxalate, palmitate, pamoate, phenylacetate, phosphate/hydrogen phosphate/dihydrogen phosphate, polygalacturonate, propionate, salicylates, stearate, succinate, sulfamate, sulfosalicylate, tartrate, tosylate, trifluoroacetate and xinofoate salt forms.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

The compound of Structure (I) may be capable of forming co-crystals with suitable co-crystal formers. These co-crystals may be prepared from the compound of Structure (I) by known co-crystal forming procedures. Such procedures include grinding, heating, co-subliming, co-melting, or contacting in solution the compound of Structure (I) with the co-crystal former under crystallization conditions and isolating co-crystals thereby formed. Suitable co-crystal formers include those described in WO 2004/078163. Hence the present disclosure further provides co-crystals comprising the compound of Structure (I). In some embodiments, the co-crystal comprises the compound of Structure (I) and a co-crystal former.

Any formula given herein is also intended to represent unlabeled forms as well as isotopically labeled forms of the compound of Structure (I). Isotopically labeled compounds have structures depicted by the formulas given herein except that one or more atoms in the labelled version of the compound contains one or more isotopes present in a statistically significant greater proportion than would be present due to natural abundance of an atom having a selected atomic mass or mass number. Examples of isotopes that can be incorporated into the compound of Structure (I) in this respect include isotopes of hydrogen, carbon, nitrogen, fluorine, oxygen, phosphorous, sulfur, chlorine and iodine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I, respectively. The present disclosure includes various isotopically labeled compounds as defined herein, for example those into which radioactive isotopes, such as $^3$H and $^{14}$C, or those into which non-radioactive isotopes, such as $^2$H and $^{13}$C have been incorporated. Such isotopically labelled compounds are useful, for example, in metabolic studies (with $^{14}$C), reaction kinetic studies (with, for example, $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies.

Further, substitution with heavier isotopes, particularly deuterium (i.e., $^2$H or D) may afford certain therapeutic advantages resulting from greater metabolic stability, for example, increased in vivo half-life or reduced dosage requirements or an improvement in therapeutic index. It is understood that deuterium in this context is regarded as a substituent of the compound of Structure (I). The concentration of such a heavier isotope, specifically deuterium, may be defined by the isotopic enrichment factor. The term "isotopic enrichment factor," as used herein, means the ratio between the isotopic abundance and the natural abundance of a specified isotope. If a substituent in a compound of the present disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

An isotopically labeled compound of Structure (I) can generally be prepared by conventional techniques known to those skilled in the art or by processes disclosed in the schemes or in the examples and preparations described herein (or analogous to those described herein), by substituting an appropriate or readily available isotopically-labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

The term "solvate" means a physical association of the compound of Structure (I) with one or more solvent molecules, whether organic or inorganic. This physical association includes hydrogen bonding. In certain instances, the solvate will be capable of isolation, for example, when one or more solvent molecules are incorporated in the crystal lattice of a crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include hydrates, ethanolates, methanolates, and isopropanolates. Methods of solvation are generally known in the art.

As used herein, "polymorph(s)" refers to crystalline form(s) having the same chemical structure/composition but different spatial arrangements of the molecules and/or ions forming the crystals. The compound of Structure (I) can be provided as amorphous solids or crystalline solids. Lyophilization can be employed to provide the compound of Structure (I) as a solid.

The term "PKM2-mediated disorder or disease" refers to any disorder or disease which is directly or indirectly regulated by PKM2.

The term "PKM2" refers to the gene or protein pyruvate kinase muscle isozyme M2.

The term "malignancy," also called cancer, refers to diseases in which abnormal cells divide without control and can invade nearby tissues. Malignant cells can also spread to other parts of the body through the blood and lymph systems. There are several main types of malignancy. Carcinoma is a malignancy that begins in the skin or in tissues that line or cover internal organs. Sarcoma is a malignancy that begins in bone, cartilage, fat, muscle, blood vessels, or other connective or supportive tissue. Leukemia is a malignancy that starts in blood-forming tissue, such as the bone marrow, and causes large numbers of abnormal blood cells to be produced and enter the blood. Lymphoma and multiple myeloma are malignancies that begin in the cells of the immune system. Central nervous system cancers are malignancies that begin in the tissues of the brain and spinal cord.

The term "solid tumor" refers to malignancies/cancers formed of abnormal masses of tissue that usually do not contain cysts or liquid areas. Solid tumors are named/classified according to the tissue/cells of origin. Examples include sarcomas and carcinomas.

The term "leukemia" refers to hematologic or blood cell malignancies/cancers that begin in blood-forming tissue, such as the bone marrow. Examples include acute myeloid leukemia (AML), chronic myeloid leukemia (CML), acute lymphocytic leukemia (ALL) and chronic lymphocytic leukemia (CLL).

The term "lymphoma" refers to lymphatic cell malignancies/cancers that begin in the cells of the immune system. Examples include non-Hodgkin lymphoma and multiple myeloma.

As used herein, the term "subject" refers to an animal. Typically, the animal is a mammal. A subject also refers to, for example, primates (e.g., humans), cows, sheep, goats, horses, dogs, cats, rabbits, rats, mice, fish, birds, and the like. In certain embodiments, the subject is a primate. In yet other embodiments, the subject is a human. Exemplary subjects include human beings of any age with risk factors for cancer disease.

As used herein, a subject is "in need of" a treatment if such subject (preferably, a human) would benefit biologically, medically or in quality of life from such treatment.

As used herein, the term "inhibit", "inhibition," or "inhibiting" refers to the reduction or suppression of a given condition, symptom, or disorder, or disease, or a significant decrease in the baseline activity of a biological activity or process.

As used herein, the term "treat," "treating," or "treatment" of any disease/disorder refers to the treatment of the disease/disorder in a subject, such as a mammal, particularly a human, and includes: (a) ameliorating the disease/disorder (e.g., slowing or arresting or reducing the development of the disease/disorder, or at least one of the clinical symptoms thereof); (b) relieving or modulating the disease/disorder (e.g., halting progression (stabilization) causing regression, or causing remission of the disease/disorder), either physically (e.g., stabilization of a discernible symptom), physiologically (e.g., stabilization of a physical parameter), or both); (c) alleviating or ameliorating at least one physical parameter including those which may not be discernible by the subject; and/or (d) preventing or delaying the onset or development or progression of the disease or disorder from occurring in a subject (e.g., mammal), in particular, when such subject (e.g., mammal) is predisposed to the disease or disorder but has not yet been diagnosed as having it.

The term "an effective amount" of the compound of Structure (I) refers to an amount of the compound of Structure (I) that will elicit the biological or medical response of a subject, for example, reduction or inhibition of an enzyme or a protein activity, or ameliorate symptoms, alleviate conditions, reverse, halt, slow, or delay disease progression, or prevent a disease, etc. In one embodiment, the term "an effective amount" refers to the amount of the compound of Structure (I) that, when administered to a subject, is effective to (1) at least partially alleviate, inhibit, prevent and/or ameliorate a condition, or a disorder or a disease mediated by PKM2; or (2) modulate the activity of PKM2, in particular, modulate it to a tetramer form in the cellular environment. In some embodiments an "effective amount" of the compound of Structure I is that amount which is sufficient to affect a desired change in a tumor microenvironment.

In another embodiment, the term "an effective amount" refers to the amount of the compound of Structure (I) that, when administered to a cell, or a tissue, or a non-cellular biological material, or a medium, is effective to at least partially activate or increase the activity of PKM2; or at least partially activate or increase the expression of PKM2.

The effective amount can vary depending on such factors as the size and weight of the subject, or the type of illness. One of ordinary skill in the art would be able to study the factors contained herein and make the determination regarding the effective amount of the compound of Structure (I) without undue experimentation.

The regimen of administration and the schedule of administering additional therapeutic compounds in conjunction with the compound of Structure I can affect what constitutes an effective amount. The compound of Structure (I) can be administered to the subject either prior to or after the onset of a PKM2-mediated condition. Further, several divided dosages, as well as staggered dosages, can be administered daily or sequentially, or the dose can be continuously infused, or can be a bolus injection. Further, the dosages of the compound of Structure (I) can be proportionally increased or decreased as indicated by the exigencies of the therapeutic or prophylactic situation.

Therapeutic Combinations and Pharmaceutical Compositions

The present disclosure includes combination therapies that comprise the compound of Structure (I) and one or more additional therapeutic agent(s) (e.g., but not limited to, a kinase inhibitor, for example an RTK, BTK, Pl3K, CDK, MEK, or PIM inhibitor, an immunotherapy agent (10 agent), for example, but not limited to, monoclonal antibodies, cytokines, CAR T-therapy, one or more immunological checkpoint inhibitors (also referred to as a "checkpoint inhibitor"), a ferroptosis inducer, etc.). The term "combination therapy" refers to the administration of two or more therapeutic agents to treat a therapeutic disease, disorder or condition described in the present disclosure. Such administration encompasses co-administration of these therapeutic agents in a substantially simultaneous manner, as well as a dosing schedule which includes: (i) contemporaneous administration of the various agents, or administering agents in a scheduled manner preceding, following, or contemporaneously with administration of a compound of Structure I. In some embodiments a compound of Structure I may be administered along with other therapeutic agents such as in a single capsule having a fixed ratio of active ingredients. Alternatively, such administration encompasses co-administration in multiple, or in separate containers (e.g., capsules, powders, and liquids) for each active ingredient. The compound of Structure (I) and the second therapeutic agent can be administered via the same administration route or via different administration routes. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the diseases, conditions or disorders described herein. In particular embodiments, the combination therapy comprises the compound of Structure (I) and a second therapeutic agent, with the proviso that the combination therapy does not include an anti-cancer drug having a mechanism of action that increases production of ROS in cancer cells (referred to as a "ROS-producing anti-cancer drug").

Combination therapies of the present disclosure include a combination therapy comprising the compound of Structure (I) and a kinase inhibitor. Kinase inhibitors disrupt signal transduction between cells. Kinase inhibitors include, but are not limited to, tyrosine kinase inhibitors (e.g., osimertinib, gefitinib, erlotinib, afatinib, sorafenib, etc.) and serine/threonine kinase inhibitors (e.g., GSK690693 (GSK), XL418 (Exelisis Inc.), sorafenib, VQD-002 (VioQuest Pharmaceuticals), etc.). In various embodiments, a combination therapy of the present disclosure comprises the compound of Structure (I) and a kinase inhibitor. In some such embodiments, the activity of the kinase that is inhibited by the kinase inhibitor is associated with a cancer.

In embodiments, a combination therapy of the present disclosure comprises the compound of Structure (I) and a tyrosine kinase inhibitor. In some embodiments, a combination therapy of the present disclosure comprises the compound of Structure (I) and a tyrosine kinase inhibitor, with the proviso that the combination therapy does not include a ROS-producing anti-cancer drug. In some embodiments, a combination therapy of the present disclosure comprises the compound of Structure (I) and a tyrosine kinase inhibitor, with the proviso that the combination therapy does not include sorafenib.

Kinase inhibitors include inhibitors of members of the receptor tyrosine kinase (RTK) family. The RTK family includes epidermal growth factor receptor (EGFR), which may be inhibited, e.g., by osimertinib, gefitinib, erlotinib, and afatinib; VEGF, which may be inhibited, e.g., by bevacizumab; and erbB2, which may be inhibited, e.g., by trastuzumab. Therapies that inhibit members of the RTK family, including therapeutic agents that inhibit EGFR, VEGF, or erbB2, may be combined with a PKM2-modulating compound to treat disease. In some embodiments, a combination therapy of the present disclosure comprises the compound of Structure (I) and a kinase inhibitor, with the proviso that the combination therapy does not include a ROS-producing anti-cancer drug.

In embodiments, a combination therapy of the present disclosure comprises the compound of Structure (I) and an EFGR inhibitor. In embodiments, a combination therapy of the present disclosure comprises the compound of Structure (I) and an EFGR inhibitor, with the proviso that the combination therapy does not include a ROS-producing anti-cancer drug. In some embodiments, the EGFR inhibitor is cetuximab (Erbitux®), osimertinib, gefitinib (e.g., Iressa®), erlotinib (e.g., erlotinib hydrochloride (Tarceva®)), afatinib, C225 (ImClone Systems, Inc., New York, N.Y.), anti-EGFR 22Mab (ImClone Systems, Inc., New York, N.Y.), ZD-1839 (AstraZeneca), BMX-1382 (Boehringer Ingelheim), MDX-447 (Medarex Inc., Annandale, N.J.), OLX-103 (Merck & Co., Whitehouse Station, N.J.), EGF fusion toxin (Seragen Inc., Hopkinton, Mass.), panitumumab, dacomitinib, or a combination thereof. In some embodiments, the EGFR inhibitor is one or more of the EGFR inhibitors described in WO 95/19970 (published Jul. 27, 1995), WO 98/14451 (published Apr. 9, 1998), WO 98/02434 (published Jan. 22, 1998), or U.S. Pat. No. 5,747,498 (issued May 5, 1998), which are incorporated by reference herein for their teachings regarding the same.

In various embodiments, a combination therapy of the present disclosure comprises the compound of Structure (I) and an EGFR inhibitor selected from cetuximab (Erbitux®), osimertinib, gefitinib (e.g., Iressa®), erlotinib (e.g., erlotinib hydrochloride (Tarceva®)), afatinib, or a combination thereof. In further embodiments, a combination therapy of the present disclosure comprises the compound of Structure (I) and an EGFR inhibitor selected from panitumumab, dacomitinib, or both.

In embodiments, a combination therapy of the present disclosure comprises the compound of Structure (I) and a vascular endothelial growth factor (VEGF) inhibitor. In embodiments, a combination therapy of the present disclosure comprises the compound of Structure (I) and a VEGF inhibitor, with the proviso that the combination therapy does not include a ROS-producing anti-cancer drug. In some such embodiments, the VEGF inhibitor is bevacizumab, SU-5416 (Sugen Inc., South San Francisco, Calif.), SU-6668 (Sugen Inc., South San Francisco, Calif.), IM862 (Cytran Inc., Kirkland, Wash.), anti-VEGF monoclonal antibody (Genentech, Inc.), angiozyme, sunitinib, vandetanib, a synthetic ribozyme (Ribozyme (Boulder, Colo.) and Chiron (Emeryville, Calif.)), or a combination thereof. In some embodiments, the VEGF inhibitor is one or more VEGF inhibitors described in WO 01/60814 A3 (published Aug. 23, 2001), WO 99/24440 (published May 20, 1999), WO/1999/062890 (published Sep. 12, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), or WO 98/02437 (published Jan. 22, 1998), all of which are incorporated herein by reference for their teachings regarding the same.

In various embodiments, a combination therapy of the present disclosure comprises the compound of Structure (I) and bevacizumab. In some embodiments, a combination therapy of the present disclosure comprises the compound of Structure (I) and sunitinib, vandetanib, or both.

In embodiments, a combination therapy of the present disclosure comprises the compound of Structure (I) and an ErbB2 inhibitor. In embodiments, a combination therapy of the present disclosure comprises the compound of Structure (I) and an ErbB2 inhibitor, with the proviso that the combination therapy does not include a ROS-producing anti-cancer drug. In some such embodiments, the ErbB2 inhibitor is trastuzumab, GW-282974 (Glaxo Wellcome plc), AR-209 (Aronex Pharmaceuticals Inc., The Woodlands, Tex.), 2B-1 (Chiron), or a combination thereof. In some embodiments, the ErbB2 inhibitor is one or more ErbB2 inhibitors described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), U.S. Pat. No. 6,284,764 (issued Sep. 4, 2001), and U.S. Pat. No. 5,877,305 (issued Mar. 2, 1999), which are all incorporated herein by reference for their teachings regarding the same.

In various embodiments, a combination therapy of the present disclosure comprises the compound of Structure (I) and lapatinib.

In embodiments, a combination therapy of the present disclosure comprises the compound of Structure (I) and a platelet-derived growth factor (PDGF) receptor inhibitor. In embodiments, a combination therapy of the present disclosure comprises the compound of Structure (I) and a PDGF receptor inhibitor, with the proviso that the combination therapy does not include a ROS-producing anti-cancer drug. In some such embodiments, the PDGF receptor inhibitor is imatinib (Gleevec®); linifanib (N-[4-(3-amino-1H-indazol-4-yl)phenyl]-N'-(2-fluoro-5-methylphenyl)urea, also known as ABT 869, available from Genentech); sunitinib malate (Sutent®); quizartinib (AC220, CAS 950769-58-1); pazopanib (Votrient®); axitinib (Inlyta®); sorafenib (Nexavar®); vargatef (BIBF1120, CAS 928326-83-4); telatinib (BAY57-9352, CAS 332012-40-5); vatalanib dihydrochloride (PTK787, CAS 212141-51-0); and motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470), or a combination thereof. In some embodiments, the combination therapy includes a PDGF receptor inhibitor, with the proviso that the PDGF receptor inhibitor is not sorafenib.

In embodiments, a combination therapy of the present disclosure comprises the compound of Structure (I) and an ALK inhibitor. In embodiments, a combination therapy of the present disclosure comprises the compound of Structure (I) and an ALK inhibitor, with the proviso that the combination therapy does not include a ROS-producing anti-cancer drug. In some such embodiments, the ALK inhibitor is crizotinib (Xalkori®).

In embodiments, a combination therapy of the present disclosure comprises a compound of Structure (I) and a MET inhibitor. In embodiments, a combination therapy of the present disclosure comprises the compound of Structure (I) and a MET inhibitor, with the proviso that the combination therapy does not include a ROS-producing anti-cancer drug. In some such embodiments, the MET inhibitor is capmatinib (INC280, CAS 1029712-80-8).

In embodiments, a combination therapy of the present disclosure comprises the compound of Structure (I) and a serine/threonine kinase inhibitor. In some embodiments, a combination therapy of the present disclosure comprises the compound of Structure (I) and a serine/threonine kinase inhibitor, with the proviso that the combination therapy does not include a ROS-producing anti-cancer drug. In some embodiments, a combination therapy of the present disclosure comprises the compound of Structure (I) and a serine/threonine kinase inhibitor, with the proviso that the combination therapy does not include sorafenib.

In some embodiments, the serine/threonine kinase inhibitor is a cyclin-dependent kinase (CDK) inhibitor. In embodiments, a combination therapy of the present disclosure comprises the compound of Structure (I) and a CDK inhibitor, with the proviso that the combination therapy does not include a ROS-producing anti-cancer drug. In some embodiments, the CDK inhibitor is ribociclib (LEE011, CAS 1211441-98-3); aloisine A; alvocidib (also known as flavopiridol or HMR-1275, 2-(2-chlorophenyl)-5,7-dihydroxy-8-[(3 S,4R)-3-hydroxy-1-methyl-4-piperidinyl]-4-chromenone, and described in U.S. Pat. No. 5,621,002); crizotinib (PF-02341066, CAS 877399-52-5); 2-(2-chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); indisulam (E7070); roscovitine (CYC202); 6-acetyl-8-cyclopentyl-5-methyl-2-(5-piperazin-1-yl-pyridin-2-ylamino)-8H-pyrido[2,3-d]pyrimidin-7-one, hydrochloride (PD0332991); dinaciclib (SCH727965); N-[5-[[(5-tert-butyloxazol-2-yl)methyl]thio]thiazol-2-yl]piperidine-4-carboxamide (BMS 387032, CAS 345627-80-7); 4-[[9-chloro-7-(2,6-difluorophenyl)-5H-pyrimido[5,4-d][2]benzazepin-2-yl]amino]-benzoic acid (MLN8054, CAS 869363-13-3); 5-[3-(4,6-difluoro-1H-benzimidazol-2-yl)-1H-indazol-5-yl]-N-ethyl-4-methyl-3-pyridinemethanamine (AG-024322, CAS 837364-57-5); 4-(2,6-dichlorobenzoylamino)-1H-pyrazole-3-carboxylic acid N-(piperidin-4-yl)amide (AT7519, CAS 844442-38-2); 4-[2-methyl-1-(1-methylethyl)-1H-imidazol-5-yl]-N-[4-(methylsulfonyl)phenyl]-2-pyrimidinamine (AZD5438, CAS 602306-29-6); palbociclib (PD-0332991); (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394); or a combination thereof.

In certain embodiments, the additional therapeutic agent is a CDK inhibitor. For example, in some embodiments, the CDK inhibitor is an inhibitor of CDK1, CDK2, CDK4, CDK5, CDK6, CDK7, CDK9, or a combination thereof. In particular embodiments, the CDK inhibitor is a CDK9 inhibitor. In some embodiments, the CDK inhibitor is alvocidib, or a pharmaceutically acceptable salt thereof. In some embodiments, the CDK inhibitor is a prodrug of alvocidib having the following structure:

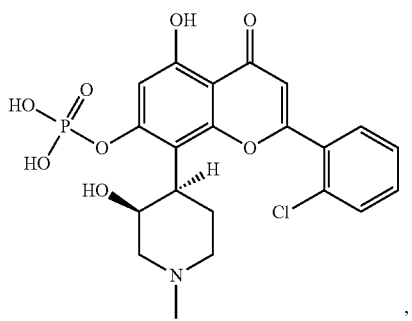 [SMILES: CN1CC[C@H](c2c(OP(=O)(O)O)cc(O)c3c(=O)cc(-c4ccccc4Cl)oc23)[C@H](O)C1]

or a pharmaceutically acceptable salt thereof.

In further embodiments, the serine/threonine kinase inhibitor is a phosphoinositide 3-kinase (PI3K) inhibitor. In embodiments, a combination therapy of the present disclosure comprises a compound of Structure (I) and a PI3K inhibitor, with the proviso that the combination therapy does not include a ROS-producing anti-cancer drug. In some embodiments, the PI3K inhibitor is 4-[2-(1H-indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO2007/084786); alpelisib (BYL719): (5Z)-5-[[4-(4-pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7), everolimus (AFINITOR®) or a combination thereof.

In embodiments, the kinase inhibitor is a mitogen-activated protein kinase (MEK) inhibitor. In some embodiments, a combination therapy of the present disclosure comprises a compound of Structure (I) and a MEK inhibitor, with the proviso that the combination therapy does not include a ROS-producing anti-cancer drug. In some embodiments, the MEK inhibitor is XL-518 (also known as GDC-0973, Cas No. 1029872-29-4, available from ACC Corp.); selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); 2-[(2-chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-dihydroxypropoxy]-3,4-difluoro-2-[(2-fluoro-4-iodophenyl)amino]-benzamide (also known as PD0325901 and described in PCT Publication No. WO2002006213); 2,3-bis[amino[(2-aminophenyl)thio]methylene]-butanedinitrile (also known as U0126 and described in U.S. Pat. No. 2,779,780); N-[3,4-difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3 S,4R,5Z,8S,9S,11E)-14-(ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-amino-3'-methoxyflavone (also known as PD98059 available from Biaffin GmbH & Co., KG, Germany); (R)-3-(2,3-dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); trametinib dimethyl sulfoxide (GSK-1120212, CAS 1204531-25-80); 2-(fluoro-4-iodophenylamino)-N-(2-hydroxyethoxy)-1,5-dimethyl-6-oxo-1,6-dihydropyridine-3-carboxamide (AZD 8330); 3,4-difluoro-2-[(2-fluoro-4-iodophenyl)amino]-N-(2-hydroxyethoxy)-5-[(3-oxo-[1,2]oxazinan-2-yl)methyl] benzamide (CH 4987655 or Ro 4987655); 5-[(4-bromo-2-fluorophenyl)amino]-4-fluoro-N-(2-hydroxyethoxy)-1-methyl-1H-benzimidazole-6-carboxamide (MEK162), or a combination thereof.

In embodiments, the kinase inhibitor is a B-RAF inhibitor. In some embodiments, a combination therapy of the present disclosure comprises a compound of Structure (I) and a B-RAF inhibitor, with the proviso that the combination therapy does not include a ROS-producing anti-cancer drug. In some embodiments, the B-RAF inhibitor is regorafenib (BAY73-4506, CAS 755037-03-7); tuvizanib (AV951, CAS 475108-18-0); vemurafenib (Zelboraf®, PLX-4032, CAS 918504-65-1); encorafenib (also known as LGX818); 1-methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-hydroxyethyl)-3-(pyridin-4-yl)-1H-pyrazol-4-yl]-2,3-dihydroinden-1-one oxime (GDC-0879, CAS 905281-76-7); 5-[2-[4-[2-(dimethylamino)ethoxy]phenyl]-5-(4-pyridinyl)-1H-imidazol-4-yl]-2,3-dihydro-1H-Inden-1-one oxime (GSK2118436 or SB590885); (+/−)-methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662), dabrafenib (Tafinlar®), N-(3-(5-chloro-1H-pyrrolo[2,3-b]pyridine-3-carbonyl)-2,4-difluorophenyl)propane-1-sulfonamide (also known as PLX4720), or a combination thereof.

Further combination therapies of the present disclosure include a combination therapy comprising a compound of Structure (I) and a checkpoint inhibitor. Immunological checkpoints prevent the immune system from attacking cells in an indiscriminate manner, and can hinder T cells from killing diseased cells that have avoided immune attack. Inhibiting checkpoint proteins may be used to initiate or boost the immune response against such cells. Checkpoint inhibitors include inhibitors of CTLA-4, B7-1, B7-2, PD-1 and PD-L1 (e.g., CTLA-4, PD-1 and PD-L1), such as ipilimumab, nivolumab, pembrolizumab, avelumab, and atezolizumab. Therapies that inhibit checkpoint proteins, including therapeutic agents that inhibit CTLA-4, PD-1 or PD-L1, may be combined with a PKM2-modulating compound to treat disease. In some embodiments, a combination therapy of the present disclosure comprises a compound of Structure (I) and a checkpoint inhibitor, with the proviso that the combination therapy does not include a ROS-producing anti-cancer drug.

In embodiments, a combination therapy of the present disclosure comprises a compound of Structure (I) and a CTLA-4 inhibitor, with the proviso that the combination therapy does not include a ROS-producing anti-cancer drug. Examples of CTLA-4 inhibitors include, but are not limited to, Tremelimumab (AstraZeneca/Medimmune); ALPN-202 (Alpine Immune Sciences); RP2 (Replimune); BMS-986249, BMS-986218 (Bristol-Myers Squibb); Zalifrelimab (Agenus); BMS-986249 (CytomX Therapeutics); BCD-217 (BIOCAD); Onc-392 (OncoImmune); IBI310 (Innovent Biologics); KN046 (Alphamab); MK-1308 (Merck & CO); Onc-392 (Pfizer); REGN4659 (Regeneron Pharmaceuticals); XmAb20717, XmAb22841 (Xencor); Anti-CTLA-4 NF (Bristol-Myers Squibb); MEDI5752 (AstraZeneca); AGEN1181 (Agenus); MGD019 (MacroGenics); ATOR-1015 (Alligator Bioscience); BCD-145 (BIOCAD); PSB205 (Sound Biologics); CS1002 (CStone Pharmaceuticals); ADU-1604 (Aduro Biotech); PF-06753512 (Pfizer); AGEN2041 (Agenus); Ipilimumab (Hualan Biological Engineering); ATOR-1144 (Alligator Bioscience); Zalifrelimab (UroGen Pharma, Recepta Biopharma); HLX13 (Shanghai Henlius Biotech); ISA203 (ISA Pharmaceuticals); PRS-300 Series A (Pieris Pharmaceuticals); JHL1152 (ipilimumab, JHL Biotech); BA3071 (BioAtla); AGEN2041 (Recepta Biopharma); RP3 (Replimune); CG0161 (Cold Genesys); APL-509 (Apollomics); AGEN2041 (Ludwig Institute for Cancer Research); APC 101 (Advanced Proteome Therapeutics); BA3071 (BeiGene); BPI-002 (BeyondSpring Pharmaceuticals); CTLA-4 Antibody (Tikcro Technologies); APL-509 (JSR); PBP1701 (ipilimumab, Prestige BioPharma); DB002, 08003 (DotBio); OR-2299 (OncoResponse); or Yervoy (ipilimumab, Bristol-Meyers Squib).

In some such embodiments, the CTLA-4 inhibitor comprises ipilimumab (YERVOY®), tremelimumab, or a combination thereof.

In various embodiments, a combination therapy of the present disclosure comprises a compound of Structure (I) and a CTLA-4 inhibitor selected from ipilimumab and tremelimumab, or a combination thereof. In particular embodiments, the CTLA-4 inhibitor is ipilimumab.

In embodiments, a combination therapy of the present disclosure comprises a compound of Structure (I) and a PD-1 inhibitor. In some embodiments, the PD-1 inhibitor comprises nivolumab, pembrolizumab, pidilizumab, cemiplimab, or a combination thereof.

Immune checkpoint inhibitors of interest for use in combination with compounds of the present disclosure include: PD-1 inhibitors, such as pembrolizumab (KEYTRUDA®), nivolumab (OPDIVO®), cemiplimab (LIBTAY®), spartalizumab (PDR001), Pidilizumab (CureTech), MEDI0680 (Medimmune), cemiplimab (REGN2810), dostarlimab (TSR-042), PF-06801591 (Pfizer), tislelizumab (BGB-A317), camrelizumab (INCSHR1210, SHR-1210), and AMP-224 (Amplimmune).

In further embodiments, the PD-1 inhibitor comprises nivolumab, pembrolizumab, or a combination thereof. In particular embodiments, the PD-1 inhibitor is Pembrolizumab (also known as Lambrolizumab, MK-3475, MK03475, SCH-900475, and KEYTRUDA®). Pembrolizumab and other anti-PD-1 antibodies are disclosed in Hamid, O. et al. (2013) New England Journal of Medicine 369 (2): 134-44, U.S. Pat. No. 8,354,509, and WO 2009/114335, incorporated by reference in their entirety. In particular embodiments, the PD-1 inhibitor is Nivolumab (also known as MDX-1106, MDX-1106-04, ONO-4538, BMS-936558, or OPDIVO®). Nivolumab (clone 5C4) and other anti-PD-1 antibodies are disclosed in U.S. Pat. No. 8,008,449 and WO 2006/121168, incorporated by reference in their entirety. In some other embodiments, the PD-1 inhibitor is AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (BioThera Solutions), GLS-010 (Gloria Pharmaceuticals; WuXi Biologics), AK103, AK104, AK105 (Akesio Biopharma; Hangzhou Hansi Biologics; Hanzhong Biologics), LZMO09 (Livzon), HLX-10 (Henlius Biotech), MEDI0680 (Medimmune), PDF001 (Novartis), PF-06801591 (Pfizer), Pidilizumab (CureTech), REGN2810 (Regeneron), TSR-042 (Tesaro) also known as ANB011, or CS1003 (CStone Pharmaceuticals) MEDI0680 (Medimmune), is also known as AMP-514. MEDI0680 and other anti-PD-1 antibodies are disclosed in U.S. Pat. No. 9,205,148 and WO 2012/145493, incorporated by reference in their entirety. Pidilizumab is also known as CT-011. Pidilizumab and other anti-PD-1 antibodies are disclosed in Rosenblatt, J. et al. (2011) J Immunotherapy 34(5): 409-18, U.S. Pat. Nos. 7,695,715, 7,332,582, and 8,686,119, incorporated by reference in their entirety.

In one embodiment, the anti-PD-1 antibody molecule is Cemiplimab (LIBTAYO®). In one embodiment, the anti-PD-1 antibody molecule is Sintilimab. In one embodiment, the anti-PD-1 antibody molecule is Toripalimab. In one embodiment, the anti-PD-1 antibody molecule is Camrelizumab.

Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

In embodiments, a combination therapy of the present disclosure comprises a compound of Structure (I) and a PD-L1 inhibitor. Examples of PD-L1 inhibitors include, but are not limited to: Bavencio (avelumab, EMD Serono); Tecentriq (atezolizumab, Genentech); durvalumab (Imfinzi, Astra Zeneca); SHR-1316 (Jiangsu Hengrui Medicine); CS1001 (Ligand Pharmaceuticals); Tecentriq (atezolizumab, Halozyme Therapeutics); Envafolimab (TRACON Pharmaceuticals); KN035 (envafolimab, 3D Medicines, Alphamab); CS1001 (CStone Pharmaceuticals); Imfinzi (durvalumab, Bristol-Myers Squibb); CX-072 (CytomX Therapeutics); STI-1014 (Sorrento Therapeutics, Lonza, NantWorks, Lee's Pharmaceutical Holdings); LYN00102 (Lynkcell); A167 (Harbour BioMed, Kelun Group), BGB-A333 (BeiGene); LY3300054 (lodapolimab, Eli Lilly); GS-4224 (Gilead Sciences); STI-A1015 (Yuhan); STI-A1015 (Sorrento Therapeutics); BCD 135 (BIOCAD); CK-301 (Cosibelimab, Checkpoint Therapeutics, TG Therapeutics); APL-502 (Apollomics); AK106 (Akeso Biopharma); MSB2311 (Transcenta Holding); TG-1501 (TG Therapeutics); FAZ053 (Novartis); MT-6035 (Molecular Templates); Icaritin & ZKAB001 (Lonza, Lee's Pharmaceutical Holdings, Sorrento Therapeutics, Shenogen Pharma Group); TRIDENT Antibody (MacroGenics, Zai Lab); YBL-007 (Ahn-Gook Pharmaceutical, Y-Biologics); HTI-1316 (Hengrui Therapeutics); JS003 (Shanghai Junshi Biosciences); ND021 (Numab Therapeutics); Toca 521 (Tocgen); KN035 (envafolimab, Ascletis Pharma); STT01 (STCube); ND021 (CStone Pharmaceuticals); DB002, DB004 (DotBio); MT5050 (Molecular Templates); or KD036 (Kadmon Holdings, Inc.), avelumab (BAVENCIO®), durvalumab (IMFINZI®), FAZ053 (Novartis), and BMS-936559 (Bristol-Myers Squibb); and drugs that target CTLA-4, such as ipilimumab (YERVOY®).

In some embodiments, the PD-L1 inhibitor comprises avelumab, atezolizumab, durvalumab, or a combination thereof. In further embodiments, the PD-L1 inhibitor comprises avelumab, atezolizumab, or a combination thereof, atezolizumab (TECENTRIQ®), avelumab (BAVENCIO®), durvalumab (IMFINZI®), FAZ053 (Novartis), and BMS-936559 (Bristol-Myers Squibb), or a combination thereof. In particular embodiments, the PD-L1 inhibitor is Atezolizumab also known as MPDL3280A, RG7446, RO5541267, YW243.55.S70, or TECENTRIQ™. Atezolizumab and other anti-PD-L1 antibodies are disclosed in U.S. Pat. No. 8,217,149, incorporated by reference in its entirety. In particular embodiments, the PD-L1 inhibitor is Avelumab also known as MSB0010718C. Avelumab and other anti-PD-L1 antibodies are disclosed in WO 2013/079174, incorporated by reference in its entirety. In particular embodiments, the PD-L1 inhibitor is Durvalumab also known as MEDI4736. Durvalumab and other anti-PD-L1 antibodies are disclosed in U.S. Pat. No. 8,779,108, incorporated by reference in its entirety. In certain embodiments, the PD-L1 inhibitor is KN035 (Alphamab; 3DMed), BMS 936559 (Bristol-Myers Squibb), CS1001 (CStone Pharmaceuticals), FAZ053 (Novartis), SHR-1316 (Hengrui Medicine), TQB2450 (Chiatai Tianqing), STI-A1014 (Zhaoke Pharm; Lee's Pharm), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entirety. In some embodiments, the PD-L1 inhibitor is a monoclonal antibody (e.g., as made by Hisun Pharm and applying for clinical trials as of this filing).

In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety. In one embodiment, the anti-PD-L1 antibody molecule comprises the CDRs, variable regions, heavy chains and/or light chains of BAP058-Clone O or BAP058-Clone N disclosed in US 2016/0108123.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entirety.

In embodiments, a combination therapy of the present disclosure comprises a compound of Structure (I) and an OX40 inhibitor. In some embodiments, the OX40 inhibitor comprises BMS 986178.

In various embodiments, a combination therapy of the present disclosure comprises two or more of a CLTA-4 inhibitor, a PD-1 inhibitor, a PD-L1 inhibitor, and an OX40 inhibitor. In some embodiments, a combination therapy of the present disclosure comprises a PD-1 inhibitor and a CTLA-4 inhibitor.

Further combination therapies of the present disclosure include a combination therapy comprising a compound of Structure (I) and a ferroptosis inducer. Ferroptosis is an iron-dependent type of programmed cell death that involves disruption of the oxidative degradation of lipids due, in part, to reduced activity of glutathione-dependent antioxidation enzymes. Ferroptotic cells accumulate lipid peroxides and may exhibit higher cellular concentrations of reactive oxygen species (ROS) than normal cells. Inducing ferroptosis in cells can occur by multiple pathways, including by reducing the levels of cellular glutathione, leading to inhibition of tumor growth and enhanced sensitivity to additional therapies, such as doxorubicin. Inducers of ferroptosis include erastin, sorafenib, sulfasalazine, and cisplatin. Therapies that induce ferroptosis, including therapeutic agents that reduce cellular glutathione levels, may be combined with a PKM2-modulating compound to treat disease.

In embodiments, a combination therapy of the present disclosure comprises a compound of Structure (I) and a ferroptosis inducer, with the proviso that the combination therapy does not include a ROS-producing anti-cancer drug. In further embodiments, a combination therapy of the present disclosure comprises a compound of Structure (I) and a ferroptosis inducer, with the proviso that the ferroptosis inducer is not erastin, sorafenib, or cisplatin. In some embodiments, the ferroptosis inducer comprises sulfasalazine.

In various embodiments, a combination therapy of the present disclosure comprises a compound of Structure (I) and sulfasalazine.

In some embodiments, the immune checkpoint inhibitor is a LAG-3 inhibitor. In some embodiments, the LAG-3 inhibitor is chosen from LAG525 (Novartis), BMS-986016 (Bristol-Myers Squibb), or TSR-033 (Tesaro).

In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420.

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entirety. In one embodiment, the anti-LAG-3 antibody molecule is IMP761 (Prima BioMed).

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety.

In one embodiment, the anti-LAG-3 inhibitor is a soluble LAG-3 protein, e.g., IMP321 (Prima BioMed), e.g., as disclosed in WO 2009/044273, incorporated by reference in its entirety.

In some embodiments, the immune checkpoint inhibitor is a TIM-3 inhibitor. In some embodiments, the TIM-3 inhibitor is MGB453 (Novartis) or TSR-022 (Tesaro).

In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274.

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

In embodiments, an AXL kinase inhibitor, such as a compound of structure (I) or a pharmaceutically acceptable salt of a compound of structure (I) (e.g., a tartrate salt), is administered to a subject in need thereof in combination with a bromodomain inhibitor, a histone deacetylase (HDAC), or both.

A bromodomain inhibitor inhibits at least one bromodomain protein, such as Brd2, Brd3, Brd4 and/or BrdT, for example Brd4. In some of these embodiments, the bromodomain inhibitor is JQ-1 (Nature 2010 Dec. 23; 468(7327): 1067-73), B12536 (ACS Chem. Biol. 2014 May 16; 9(5): 1160-71; Boehringer Ingelheim), TG101209 (ACS Chem. Biol. 2014 May 16; 9(5):1160-71), OTX015 (Mol. Cancer Ther. November 201312; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22):9831-7; Cancer Res. 2013 Jun. 1; 73(11):3336-46; Structural Genomics Consortium) of CPI-0610 (Constellation Pharmaceuticals). In some embodiments, the bromodomain inhibitor is TG101209, B12536, OTX015, C244, IBET762, IBET151, or PFI-1.

A HDAC inhibitor inhibits at least one HDAC protein. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. In some of these embodiments, the HDAC inhibitor is trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3): 106771) or valproic acid (EMBO J. 2001 Dec. 17; 20(24): 6969-78). For example, in some embodiments the HDAC inhibitor is panobinostat, vorinostat, MS275, belinostat, or LBH589. In some embodiments, the HDAC inhibitor is panobinostat or SAHA.

Chimeric Antigen Receptor T-Cell (CAR-T) therapies my be employed along with a compound of Structure I or a pharmaceutically acceptable salt thereof. CAR-T therapies of particular interest for use in combination with compounds of the present disclosure include: Tisagenlecleucel (Novartis), Axicabtagene ciloleucel (Kite), and Tocilizumab and Atlizumab (Roche).

In some embodiments, methods of the present disclosure further comprise administering radiation therapy to the subject.

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In some of the foregoing embodiments, the method is for treating liver cancer, refractory cancers (e.g., non-small cell lung cancer), lung cancer, esophageal cancer, Hodgkin's lymphoma, NK/T-cell lymphoma, or melanoma. In some specific embodiments, the method is for treating esophageal squamous cell carcinoma, gastric cancer, lung cancer, nasopharyngeal carcinoma, bladder cancer, soft tissue sarcoma, diffuse large B-cell lymphoma, head and neck squamous cell carcinomas, kidney cancer, urothelial carcinoma, ovarian cancer, uterine cancer, or pancreatic cancer.

Other embodiments provide methods for combination therapies in which an agent known to modulate other pathways, or other components of the same pathway, or even overlapping sets of target enzymes are used in combination with a compound of comprising administering an effective amount of Structure I, or a pharmaceutically acceptable salt thereof with chemotherapeutic agents, therapeutic antibodies, and radiation treatment, to provide a synergistic or additive therapeutic effect.

Many chemotherapeutics are presently known in the art and can be used in combination with a compound of Structure I, or a pharmaceutically acceptable salt thereof. In some embodiments, the chemotherapeutic is selected from the group consisting of mitotic inhibitors, alkylating agents, hypomethylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Other embodiments provide methods for combination therapies in which an agent known to modulate other pathways, or other components of the same pathway, or even overlapping sets of target enzymes are used in combination with a compound of comprising administering an effective amount of Structure I, or a pharmaceutically acceptable salt thereof with chemotherapeutic agents, therapeutic antibodies, and radiation treatment, to provide a synergistic or additive therapeutic effect.

Non-limiting examples of therapeutic agents that can be used in combinations with a compound of Structure I, or a pharmaceutically acceptable salt thereof are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above.

MET inhibitors: capmatinib (INC280, CAS 1029712-80-8).

Platelet-derived growth factor (PDGF) receptor inhibitors: imatinib (Gleevec®); linifanib (N-[4-(3-amino-1H-indazol-4-yl)phenyl]-N'-(2-fluoro-5-methylphenyl)urea, also known as ABT 869, available from Genentech); sunitinib malate (Sutent®); quizartinib (AC220, CAS 950769-58-1); pazopanib (Votrient®); axitinib (Inlyta®); sorafenib (Nexavar®); vargatef (BIBF1120, CAS 928326-83-4); telatinib (BAY57-9352, CAS 332012-40-5); vatalanib dihydrochloride (PTK787, CAS 212141-51-0); and motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470).

Phosphoinositide 3-kinase (PI3K) inhibitors: 4-[2-(1H-Indazol-4-yl)-6-[[4-(methyl sulfonyl)piperazin-1-yl]methyl]thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO 2007/084786); alpelisib (BYL719): (5Z)-5-[[4-(4-Pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7) and everolimus (AFINITOR®).

Cyclin-dependent kinase (CDK) inhibitors: ribociclib (LEE011, CAS 1211441-98-3); aloisine A; alvocidib (also known as flavopiridol or HMR-1275, 2-(2-chlorophenyl)-5,7-dihydroxy-8-[(3 S,4R)-3-hydroxy-1-methyl-4-piperidinyl]-4-chromenone, and described in U.S. Pat. No. 5,621,002); crizotinib (PF-02341066, CAS 877399-52-5); 2-(2-chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); indisulam (E7070); roscovitine (CYC202); 6-acetyl-8-cyclopentyl-5-methyl-2-(5-piperazin-1-yl-pyridin-2-ylamino)-8H-pyrido[2,3-d]pyrimidin-7-one, hydrochloride (PD0332991); dinaciclib (SCH727965); N-[5-[[(5-tert-butyloxazol-2-yl)methyl]thio]thiazol-2-yl]piperidine-4-carboxamide (BMS 387032, CAS 345627-80-7); 4-[[9-chloro-7-(2,6-difluorophenyl)-5H-pyrimido[5,4-d][2]benzazepin-2-yl]amino]-benzoic acid (MLN8054, CAS 869363-13-3); 5-[3-(4,6-difluoro-1H-benzimidazol-2-yl)-1H-indazol-5-yl]-N-ethyl-4-methyl-3-pyridinemethanamine (AG-024322, CAS 837364-57-5); 4-(2,6-dichlorobenzoylamino)-1H-pyrazole-3-carboxylic acid N-(piperidin-4-yl)amide (AT7519, CAS 844442-38-2); 4-[2-methyl-1-(1-methylethyl)-1H-imidazol-5-yl]-N-[4-(methylsulfonyl)phenyl]-2-pyrimidinamine (AZD5438, CAS 602306-29-6); palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl]oxy]-2-butanol (BAY 10000394).

Mitogen-activated protein kinase (MEK) inhibitors: XL-518 (also known as GDC-0973, CAS No. 1029872-29-4, available from ACC Corp.); selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO 2003/077914); 2-[(2-chloro-4-iodophenyl)amino]-N-(cyclopropylmethoxy)-3,4-difluoro-benzamide (also known as CI-1040 or PD184352 and described in PCT Publication No. WO 2000/035436); N-[(2R)-2,3-dihydroxypropoxy]-3,4-difluoro-2-[(2-fluoro-4-iodophenyl)amino]-benzamide (also known as PD0325901 and described in PCT Publication No. WO 2002/006213); 2,3-bis[amino[(2-aminophenyl)thio]methylene]-butanedinitrile (also known as U0126 and described in U.S. Pat. No. 2,779,780); N-[3,4-difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO 2007/014011); (3S,4R,5Z,8S,9S,11E)-14-(ethylamino)-8,9,16-trihydroxy-3,4-dimethyl-3,4,9; 19-tetrahydro-1H-2-benzoxacyclotetradecine-1,7(8H)-dione] (also known as E6201 and described in PCT Publication No. WO 2003/076424); 2'-amino-3'-methoxyflavone (also known as PD98059 available from Biaffin GmbH & Co., KG, Germany); (R)-3-(2,3-dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); trametinib dimethyl sulfoxide (GSK-1120212, CAS 1204531-25-80); 2-(2-fluoro-4-iodophenylamino)-N-(2-hydroxyethoxy)-1,5-dimethyl-6-oxo-1,6-dihydropyridine-3-carboxamide (AZD 8330); 3,4-difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655); and 5-[(4-bromo-2-fluorophenyl)amino]-4-fluoro-N-(2-hydroxyethoxy)-1-methyl-1H-benzimidazole-6-carboxamide (MEK162).

m-TOR inhibitors, for example, AZD2014, as described by Broutin et al. in Insights into Significance of Combined Inhibition of MEK and m-TOR Signalling Output in KRAS-mutant Non-Small-Cell Lung Cancer, British J. of Cancer (2016) 115, pp 549-552, which publication, along with its references, is incorporated herein by reference.

Hypomethylating agents (HMA), for example, decitabine and azacytidine.

B-RAF inhibitors: regorafenib (BAY73-4506, CAS 755037-03-7); tuvizanib (AV951, CAS 475108-18-0); vemurafenib (ZELBORAF®, PLX-4032, CAS 918504-65-1); encorafenib (also known as LGX818); 1-methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-hydroxyethyl)-3-(pyridin-4-yl)-1H-pyrazol-4-yl]-2,3-dihydroinden-1-one oxime (GDC-0879, CAS 905281-76-7); 5-[2-[4-[2-(dimethylamino)ethoxy]phenyl]-5-(4-pyridinyl)-1H-imidazol-4-yl]-2,3-dihydro-1H-inden-1-one oxime (GSK2118436 or SB590885); (+/−)-methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662), dabrafenib (TAFINLAR®), and N-(3-(5-chloro-1H-pyrrolo[2,3-b]pyridine-3-carbonyl)-2,4-difluorophenyl)propane-1-sulfonamide (also known as PLX4720).

Proteasome inhibitors: bortezomib (VELCADE®), N-5-benzyloxycarbonyl-Ile-Glu(O-tert-butyl)-Ala-leucinal (PSI), carfilzomib and ixazomib (e.g., bortezomib), marizomib (NPI-0052), delanzomib (CEP-18770), O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912). A RNAi screen identified TNK1 as a potential modulator of proteasome inhibitor sensitivity in myeloma. Zhu et al., Blood (2011) 117 (14): 3847-3857. In some embodiments, a compound of Structure I, or a pharmaceutically acceptable salt thereof, is administered in combination with a proteasome inhibitor described herein, e.g., for the treatment of multiple myeloma.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO).

Non-limiting examples of therapeutic agents that can be used in combinations with a compound of Structure I, or a pharmaceutically acceptable salt thereof, are mTOR inhibitors. Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23 S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.04,9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3);

emsirolimus, (5-{2,4-Bis[(3 S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-inner salt (SEQ ID NO: 1482) (SF1126, CAS 936487-67-1), and XL765.

Where desired, a compound of Structure I or a pharmaceutically acceptable salt thereof can be used in combination with commonly prescribed anti-cancer drugs (for example, but not limited to: anti-metabolites; DNA-fragmenting agents; DNA-crosslinking agents; intercalating agents; protein synthesis inhibitors; topoisomerase I and II poisons (for example camptothecin, topotecan); microtubule-directed agents; kinase inhibitors; hormones; and hormone antagonists. Examples of some of these additional agents include, but are not limited to, Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

In some embodiments, a compound of Structure I or a pharmaceutically acceptable salt thereof, is administered to a subject in need thereof in combination with a CDK9 inhibitor, such as Alvocidib. In a related embodiment, a pharmaceutically acceptable salt of a compound of Structure (I) is administered to a subject in need thereof in combination with a CDK9 inhibitor, such as Alvocidib. The administration may be before, concurrently or after administration of the CDK9 inhibitor. In some embodiments, a compound of Structure I, or a pharmaceutically acceptable salt thereof, is administered to a subject in need thereof in combination with a CDK9 inhibitor, such as Alvocidib for treatment of pancreatic cancer.

In some embodiments, the CDK inhibitor is a CDK2, CDK4, CDK6, CDK7, CDK8, CDK9, CDK10, and/or CDK11 inhibitor. In some embodiments, the CDK inhibitor is a CDK7, CDK9 inhibitor, or both. In some embodiments, the CDK inhibitor is dinaciclib (ACS Med. Chem. Lett. 2010 May 17; 1(5):204-8; Mol. Cancer Ther. 2010 August; 9(8):2344-53; Merck, Sharp and Dohme), AT7519 (J. Med. Chem. 2008 Aug. 28; 51(16):4986-99; Astex Pharmaceutical) or palbociclib (J. Med. Chem. 2005 Apr. 7; 48(7):2388-406; Pfizer). In certain embodiments, the CDK inhibitor is a CDK9 inhibitor, such as alvocidib. The alvocidib may be administered as the free bases, as a pharmaceutically acceptable salt or as a prodrug. In certain embodiments, the CDK9 inhibitor is alvocidib. in other embodiments, the CDK9 inhibitor is a pharmaceutically acceptable salt of alvocidib. In other embodiments, the CDK9 inhibitor is a prodrug of alvocidib. Prodrugs of alvocidib include those disclosed in WO 2016/187316, the full disclosure of which is hereby incorporated by reference in its entirety.

Embodiments further relate to a method of administering a compound of Structure I, or a pharmaceutically acceptable salt thereof, to a subject in need thereof in combination with a BTK inhibitor (e.g., Ibrutinib) or a CDK9 inhibitor (e.g., Alvocidib) provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of a compound of Structure I, or a pharmaceutically acceptable salt thereof, in this combination therapy can be determined as described herein.

In one embodiment a compound of Structure I, or a pharmaceutically acceptable salt thereof, is administered to a subject in need thereof in combination with an ATR inhibitor, such as AZD6738 or VX-970. The administration may be before, concurrently or after administration of the ATR inhibitor. In one specific embodiment, the combination of a compound of Structure I, or a pharmaceutically acceptable salt thereof, and an ATR inhibitor, such as AZD6738 or VX-970 is administered in treatment of non-small cell lung cancer. In some of the foregoing embodiments, the ATR inhibitor is a combination of AZD6738 and VX-970. In some embodiments the compound of Structure I, or a pharmaceutically acceptable salt thereof, is administered prior to the administration of an ATR inhibitor to sensitize the tumor to the ATR inhibitor.

In some of the foregoing embodiments, the non-small cell lung cancer comprises TCGA lung adenocarcinoma, one or more LUAD tumors, TCGA lung squamous cell carcinoma, one or more LUSC tumors, one or more MDACC PROSPECT tumors, one or more MDACC BATTLE1 tumors, one or more BATTLE2 tumors, or combinations thereof. In some embodiments, the non-small cell lung cancer comprises TCGA LUAD tumors, for example, tumors enriched in ALK translocations. In some embodiments, the non-small cell lung cancer comprises TCGA LUAD tumors, for example, tumors comprising one or more EGFR mutations.

In some embodiments, radiation therapy can be administered in combination with administration of a compound of Structure I, or a pharmaceutically acceptable salt thereof. Exemplary radiation therapies include external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At211, I131, I125, Y90, Re186, Re188, Sm153, Bi212, P32, and radioactive isotopes of Lu). Suitable radiation sources for use as a cell conditioner of the present invention include both solids and liquids. By way of non-limiting example, the radiation source can be a radionuclide, such as I125, I131, Yb169, Ir192 as a solid source, I125 as a solid source, or other radionuclides that emit photons, beta particles, gamma radiation, or other therapeutic rays. The radioactive material can also be a fluid made from any solution of radionuclide(s), e.g., a solution of I125 or I131, or a radioactive fluid can be produced using a slurry of a suitable fluid containing small particles of solid radionuclides, such as Au198, Y90. Moreover, the radionuclide(s) can be embodied in a gel or radioactive micro spheres.

Without being limited by any theory, a compound of Structure I, or a pharmaceutically acceptable salt thereof, may render abnormal cells more sensitive to treatment with radiation for purposes of killing and/or inhibiting the growth of such cells. Accordingly, some embodiments include a method for sensitizing abnormal cells in a mammal to treatment with radiation which comprises administering to the mammal a compound of Structure I, or a pharmaceutically acceptable salt thereof, in an amount is effective in sensitizing abnormal cells to treatment with radiation, which amount can be determined according to the means for ascertaining effective amounts of such compounds and salts described herein.

A compound of Structure I, or a pharmaceutically acceptable salt thereof, can also be used in combination with an amount of one or more substances selected from anti-angiogenesis agents, signal transduction inhibitors, antiproliferative agents, glycolysis inhibitors, or autophagy inhibitors.

Anti-angiogenesis agents include, for example, MMP-2 (matrix-metalloproteinase 2) inhibitors, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Embodiments of MMP-2 and MMP-9 inhibitors include those that have little or no activity inhibiting MMP-1. Other embodiments include those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in some embodiments are AG-3340, RO 323555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In other embodiments, agents useful in methods for combination therapy with a compound of Structure I, or a pharmaceutically acceptable salt thereof, include, but are not limited to: Erlotinib, Afatinib, Iressa, GDC0941, MLN1117, BYL719 (Alpelisib), BKM120 (Buparlisib), CYT387, GLPG0634, Baricitinib, Lestaurtinib, momelotinib, Pacritinib, Ruxolitinib, TG101348, Crizotinib, tivantinib, AMG337, cabozantinib, foretinib, onartuzumab, NVP-AEW541, Dasatinib, Ponatinib, saracatinib, bosutinib, trametinib, selumetinib, cobimetinib, PD0325901, RO5126766, Axitinib, Bevacizumab, Bostutinib, Cetuximab, Crizotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, Vemurafenib, Irinotecan, Taxol, Docetaxel, Rapamycin or MLN0128.

In some embodiments, a compound of Structure I, or a pharmaceutically acceptable salt thereof, is administered in combination with an epidermal growth factor receptor tyrosine kinase (EGFR) inhibitor, including EGFR inhibitors which are whole antibodies, for example cetuximab (Erbitux®). Examples of EGFR inhibitors include erlotinib, osimertinib, cetuximab, gefitinib, necitumumab, lapatinib, neratinib, panitumumab, vandetanib, and necitumumab. A compound of Structure I, or a pharmaceutically acceptable salt thereof, in combination with an EGFR inhibitor may be useful, for example, in the treatment of cancers that are related to EGFR dysregulation, such as non-small-cell lung cancer (NSCLC), pancreatic cancer, breast cancer, and colon cancer. EGFR may be dysregulated, for example, due to activating mutations in exons 18, 19, 20, or 21. In particular embodiments, the EGFR inhibitor is erlotinib or osimertinib. In particular embodiments, a compound of Structure I, or a pharmaceutically acceptable salt thereof, in combination with an EGFR inhibitor is used to treat EGFR-mutated NSCLC. In particular embodiments, a compound of Structure I, or a pharmaceutically acceptable salt thereof, in combination with an EGFR inhibitor is used to treat an EGFR inhibitor-resistant cancer.

In certain embodiments, a compound of Structure I, or a pharmaceutically acceptable salt thereof, is administered in combination with Erlotinib. In some embodiments, such a combination is used to treat pancreatic cancer. In other embodiments, such a combination is used to treat lung cancer. In further embodiments, the lung cancer is non-small cell lung cancer.

In certain embodiments, a compound of Structure I, or a pharmaceutically acceptable salt thereof, is administered in combination with osmertinib. In some embodiments, such a combination is used to treat lung cancer. In further embodiments, the lung cancer has an EGFR mutation.

A compound of Structure (I), or a pharmaceutically acceptable salt thereof, and/or a second therapeutic agent (e.g., a kinase inhibitor, a checkpoint inhibitor, a ferroptosis inducer, etc.) are typically used as a pharmaceutical composition (e.g., a compound of Structure (I), or a pharmaceutically acceptable salt thereof, and/or a second therapeutic agent, and at least one pharmaceutically acceptable carrier). A "pharmaceutically acceptable carrier (diluent or excipient)" refers to media generally accepted in the art for the delivery of biologically active agents to subject, such as animals, in particular, mammals, including, generally recognized as safe (GRAS) solvents, dispersion media, coatings, surfactants, antioxidants, preservatives (e.g., antibacterial agents, antifungal agents), isotonic agents, absorption delaying agents, salts, preservatives, drug stabilizers, binders, buffering agents (e.g., maleic acid, tartaric acid, lactic acid, citric acid, acetic acid, sodium bicarbonate, sodium phosphate, and the like), disintegration agents, lubricants, sweetening agents, flavoring agents, dyes, and the like and combinations thereof, as would be known to those skilled in the art (see, for example, Allen, L. V., Jr. et al., *Remington: The Science and Practice of Pharmacy* (2 Volumes), 22nd Edition, Pharmaceutical Press (2012)).

The present disclosure provides a pharmaceutical composition comprising a compound of Structure (I), or a pharmaceutically acceptable salt thereof, and a second therapeutic agent and a pharmaceutically acceptable carrier. In a further embodiment, the composition comprises at least two pharmaceutically acceptable carriers, such as those described herein. For purposes of the present disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present disclosure can be made up in a solid form (including capsules, tablets, pills, granules, powders or suppositories), or in a liquid form (including solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol, for tablets also;

c) binders, e.g., magnesium aluminum silicate, starch paste, gelatin, tragacanth, methylcellulose, sodium carboxymethylcellulose and/or polyvinylpyrrolidone, if desired;

d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of the compound of Structure (I), or a pharmaceutically acceptable salt thereof, and/or a second therapeutic agent in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of Structure (I), or a pharmaceutically acceptable salt thereof, and/or a second therapeutic agent with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will, in particular, be appropriate for dermal application, e.g., for the treatment of skin cancer, e.g., for prophylactic use in sun creams, lotions, sprays and the like. They are, thus, particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example, a dry blend with lactose, or a mixed component particle, for example, with phospholipids) from a dry powder inhaler or an aerosol spray presentation from a pressurized container, pump, spray, atomizer or nebulizer, with or without the use of a suitable propellant.

The present disclosure further provides anhydrous pharmaceutical compositions and dosage forms comprising a compound of Structure (I), or a pharmaceutically acceptable salt thereof, and/or a second therapeutic agent as active ingredients, since water may facilitate the degradation of certain compounds.

Anhydrous pharmaceutical compositions and dosage forms of the disclosure can be prepared using anhydrous or low-moisture containing ingredients and low-moisture or low-humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include hermetically sealed foils, plastics, unit dose containers (e.g., vials), blister packs, and strip packs.

The present disclosure further provides pharmaceutical compositions and dosage forms that comprise one or more agents that reduce the rate by which the compound described herein as an active ingredient will decompose. Such agents, which are referred to herein as "stabilizers," include antioxidants such as ascorbic acid, pH buffers, or salt buffers, etc.

A compound of Structure (I), or a pharmaceutically acceptable salt thereof, and/or a second therapeutic agent is typically formulated into pharmaceutical dosage forms to provide an easily controllable dosage of the drug and to give the patient an elegant and easily handleable product. The dosage regimen for a compound of Structure (I), or a pharmaceutically acceptable salt thereof, and/or a second therapeutic agent will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration; the renal and hepatic function of the patient; and the effect desired. A compound of Structure (I), or a pharmaceutically acceptable salt thereof, and/or a second therapeutic agent may be administered in a single daily dose, or the total daily dosage may be administered in divided doses of two, three, or four times daily.

In certain instances, it may be advantageous to administer a compound of Structure (I), or a pharmaceutically acceptable salt thereof, and/or a second therapeutic agent in combination with one or more additional therapeutically active agents independently selected from anti-cancer agents, anti-allergic agents, anti-emetics, pain relievers, immunomodulators and cytoprotective agents. In some embodiments, the compound of Structure (I), or a pharmaceutically acceptable salt thereof, and/or a second therapeutic agent is administered in combination with one or more additional therapeutically active agents, with the proviso that the combination does not include a ROS-producing anti-cancer drug.

General anti-cancer agents considered for use in combination therapies include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), Gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin®). In embodiments, the combination therapy includes a general anti-cancer agent, with the proviso that the anti-cancer agent is not a ROS-producing anti-cancer drug. In some embodiments, the combination therapy includes a general anti-cancer agent, with the proviso that the anti-cancer agent is not carboplatin (Paraplatin®), cisplatin (Platinol®), doxorubicin hydrochloride (Adriamycin®, Rubex®), or L-asparaginase (ELSPAR®).

Anti-cancer agents of particular interest for combinations with a compound of Structure (I) include:

Purine antimetabolites and/or inhibitors of de novo purine synthesis: pemetrexed (Alimta®), gemcitabine (Gemzar®), 5-fluorouracil (Adrucil®, Carac® and Efudex®), methotrexate (Trexall®), capecitabine (Xeloda®), floxuridine (FUDR®), decitabine (Dacogen®), azacitidine (Vidaza® and Azadine®), 6-mercaptopurine (Purinethol®), cladribine (Leustatin®, Litak® and Movectro®), fludarabine (Fludara®), pentostatin (Nipent®), nelarabine (Arranon®), clofarabine (Clolar® and Evoltra®), and cytarabine (Cytosar®).

MTAP inhibitors: (3R,4S)-1-((4-amino-5H-pyrrolo[3,2-d]pyrimidin-7-yl)methyl)-4-((methylthio)methyl)pyrrolidin-3-ol (MT-DADMe-Immucillin-A, CAS 653592-04-2).

Methylthioadenosine: (2R,3R,4S,5S)-2-(6-amino-9H-purin-9-yl)-5-((methylthio)methyl)tetrahydrofuran-3,4-diol (CAS 2457-80-9).

p53-MDM2 inhibitors: (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one; (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one; [(4S,5R)-2-(4-tert-butyl-2-ethoxyphenyl)-4,5-bis(4-chlorophenyl)-4,5-dimethylimidazol-1-yl]-[4-(3-methylsulfonylpropyl) piperazin-1-yl]methanone (RG7112); 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl] amino]-3-methoxybenzoic acid (RG7388); SAR299155; 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (AMG232); {(3R,5R,6S)-5-(3-Chlorophenyl)-6-(4-chlorophenyl)-1-[(2S,3S)-2-hydroxy-3-pentanyl]-3-methyl-2-oxo-3-piperidinyl}acetic acid (AM-8553); (±)-4-[4,5-Bis(4-chlorophenyl)-2-(2-isopropoxy-4-methoxy-phenyl)-4,5-dihydro-imidazole-1-carbonyl]-piperazin-2-one (Nutlin-3), 2-Methyl-7-[Phenyl (phenylamino)methyl]-8-quinolinol (NSC 66811); 1-N-[2-(1H-indol-3-yl)ethyl]-4-N-pyridin-4-ylbenzene-1,4-diamine (JNJ-26854165); 4-[4,5-bis(3,4-chlorophenyl)-2-(2-isopropoxy-4-methoxy-phenyl)-4,5-dihydro-imidazole-1-carboxyl]-piperazin-2-one (Caylin-1); 4-[4,5-bis(4-trifluoromethyl-phenyl)-2-(2-isopropoxy-4-methoxy-phenyl)-4,5-dihydro-imidazole-1-carboxyl]-piperazin-2-one (Caylin-2); 5-[[3-Dimethylamino)propyl]amino]-3,10-dimethylpyrimido[4,5-b]quinoline-2,4(3H,10H)-dione dihydrochloride (HLI373); and trans-4-Iodo-4'-boranyl-chalcone (SC204072).

PIM kinase inhibitors:

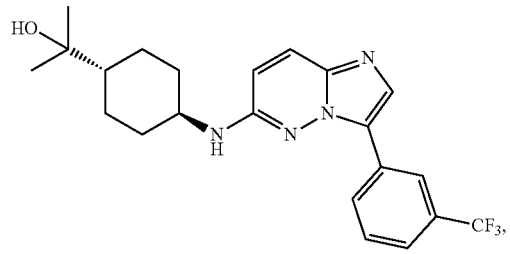 [SMILES: CC(C)(O)[C@H]1CC[C@H](Nc2ccc3ncc(-c4cccc(C(F)(F)F)c4)n3n2)CC1]

or a pharmaceutically acceptable salt thereof.

Some patients may experience allergic reactions to a compound of Structure (I) and/or other anti-cancer agent(s) during or after administration; therefore, anti-allergic agents are often administered to minimize the risk of an allergic reaction. Suitable anti-allergic agents include corticosteroids (Knutson, S., et al., *PLoS One, DOI:*10.1371/journal-.pone.0111840 (2014)), such as dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

Some patients may experience nausea during and after administration of a compound of Structure (I) and/or other anti-cancer agent(s); therefore, anti-emetics are used in preventing nausea (upper stomach) and vomiting. Suitable anti-emetics include aprepitant (Emend®), ondansetron (Zofran®), granisetron HCl (Kytril®), lorazepam (Ativan®. dexamethasone (Decadron®), prochlorperazine (Compazine®), casopitant (Rezonic® and Zunrisa®), and combinations thereof.

Medication to alleviate the pain experienced during the treatment period is often prescribed to make the patient more comfortable. Common over-the-counter analgesics, such Tylenol®, are often used. However, opioid analgesic drugs such as hydrocodone/paracetamol or hydrocodone/acetaminophen (e.g., Vicodin®), morphine (e.g., Astramorph® or Avinza®), oxycodone (e.g., OxyContin® or Percocet®), oxymorphone hydrochloride (Opana®), and fentanyl (e.g., Duragesic®) are also useful for moderate or severe pain.

Immunomodulators of particular interest for combinations with a compound of Structure (I) include: afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy. Suitable cytoprotective agents include amifostine (Ethyol®), glutamine, dimesna (Tavocept®), mesna (Mesnex®), dexrazoxane (Zinecard® or Totect®), xaliproden (Xaprila®), and leucovorin (also known as calcium leucovorin, citrovorum factor and folinic acid).

The structure of the active compounds identified by code numbers, generic or trade names may be taken from the actual edition of the standard compendium "The Merck Index" or from databases, e.g., Patents International (e.g., IMS World Publications).

In one embodiment, the present disclosure provides pharmaceutical compositions comprising compound of Structure (I), or a pharmaceutically acceptable salt thereof, a second therapeutic agent, and/or other anti-cancer agent(s), together with a pharmaceutically acceptable carrier suitable for administration to a human or animal subject.

In particular, compositions will either be formulated together as a combination therapeutic, or formulated and administered separately.

In another embodiment, the present disclosure provides methods of treating human or animal subjects suffering from a cellular proliferative disease, such as malignancy. The present disclosure provides methods of treating a human or animal subject in need of such treatment, comprising administering to the subject an effective amount of a compound of Structure (I), or a pharmaceutically acceptable salt thereof, a second therapeutic agent, and/or other anti-cancer agent(s).

In combination therapy for treatment of a malignancy, a compound of Structure (I), or a pharmaceutically acceptable salt thereof, a second therapeutic agent, and/or other anti-cancer agent(s) may be administered simultaneously, concurrently, or sequentially with no specific time limits, wherein such administration provides therapeutically effective levels of the at least two compounds in the body of the subject.

In an embodiment, a compound of Structure (I), or a pharmaceutically acceptable salt thereof, a second therapeutic agent, and/or other anti-cancer agent(s) is generally administered sequentially in any order by infusion or orally. The dosing regimen may vary depending upon, for example, the stage of the disease, physical fitness of the patient, safety profiles of the individual drugs, and tolerance of the individual drugs, as well as other criteria well-known to the attending physician and medical practitioner(s) administering the combination. A compound of Structure (I), or a pharmaceutically acceptable salt thereof, a second therapeutic agent, and/or other anti-cancer agent(s) may be administered within minutes of each other, or hours, days, or weeks apart depending upon the particular cycle being used for treatment. In addition, the cycle could include administration of one drug more often than the other during the treatment cycle and at different doses per administration of the drug.

In another aspect of the present disclosure, a kit comprising two or more separate pharmaceutical compositions, at least one of which contains a compound of Structure (I), or a pharmaceutically acceptable salt thereof, is provided. In one embodiment, the kit comprises means for separately retaining said compositions, such as a container, divided bottle, or divided foil packet. An example of such a kit is a blister pack, as typically used for the packaging of tablets, capsules and the like.

The kit of the present disclosure may be used for administering different dosage forms, for example, oral and parenteral, for administering the separate compositions at different dosage intervals, or for titrating the separate compositions against one another. To assist compliance, the kit of the present disclosure typically comprises directions for administration.

A compound of Structure (I), or a pharmaceutically acceptable salt thereof, and/or a second therapeutic agent may also be used to advantage in combination with known therapeutic processes, for example, the administration of hormones or especially radiation. A compound of Structure (I) may in particular be used as a radiosensitizer, especially for the treatment of tumors which exhibit poor sensitivity to radiotherapy.

In the combination therapies of the present disclosure, a compound of Structure (I), or a pharmaceutically acceptable salt thereof, and/or a second therapeutic agent may be manufactured and/or formulated by the same or different manufacturers. Moreover, a compound of Structure (I), or a pharmaceutically acceptable salt thereof, and/or a second therapeutic agent may be brought together into a combination therapy: (i) prior to release of the combination product to physicians (e.g., in the case of a kit comprising a compound of Structure (I) and the second therapeutic agent); (ii) by the physician (or under the guidance of the physician) shortly before administration; or (iii) in the patient themselves, e.g., during sequential administration of a compound of Structure (I) and the second therapeutic agent.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition or combination of the present disclosure can be in unit dosage of about 1 mg to about 1000 mg of active ingredient(s) for a subject of about 50 kg to about 70 kg, or about 1 mg to about 500 mg or about 1 mg to about 250 mg or about 1 mg to about 150 mg or about 0.5 mg to about 100 mg, or about 1 mg to about 50 mg of active ingredient(s). The therapeutically effective dosage of a compound, the pharmaceutical composition, or the combinations thereof, is dependent, for example, on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties may be demonstrable in vitro and in vivo tests using advantageously mammals, e.g., mice, rats, dogs, monkeys or isolated organs, tissues and preparations thereof. A compound of Structure (I), or a pharmaceutically acceptable salt thereof, and/or a second therapeutic agent can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. An effective amount in vivo may range depending on the route of administration, between about 0.1 mg/kg to about 500 mg/kg, or between about 1 mg/kg to about 100 mg/kg.

Pharmacology and Utility

The compound of Structure (I), or a pharmaceutically acceptable salt thereof, compositions thereof, and combination therapies thereof are effective for treating various malignancies, including cancers.

Accordingly, one embodiment provides a method comprising administering a therapeutically effective amount of a compound of Structure (I), or a pharmaceutically acceptable salt thereof, composition, and combination therapy as described in any of the foregoing embodiments to a subject in need thereof. One embodiment provides a method of modulating PKM2, comprising administering a therapeutically effective amount of a compound of Structure (I), or a pharmaceutically acceptable salt thereof, composition, and/or combination therapy as described in any of the foregoing embodiments to a subject in need thereof. In more specific embodiments, the modulating comprises activating PKM2. For example, the activating of PKM2 may be for treatment of cancer.

PKM2 plays a critical role in the regulation of the innate immune response and, thus, PKM2 activation may reverse the immune-suppressive microenvironment often observed in cancers in part by decreasing tumor lactate levels and favoring glucose utilization by immune cells over cancer cells. Accordingly, one embodiment provides a method of decreasing tumor lactate levels and/or increasing glucose utilization by immune cells over cancer cells, comprising administering a therapeutically effective amount of a compound of Structure (I), or a pharmaceutically acceptable salt thereof, composition, and/or combination therapy as described in any of the foregoing embodiments to a subject in need thereof. One embodiment provides a method of modulating a tumor microenvironment, comprising administering a therapeutically effective amount of a compound of Structure (I), or a pharmaceutically acceptable salt thereof, alone, as a modulator of a tumor microenvironment, or as part of a combination therapy as described in any of the foregoing embodiments to a subject in need thereof, wherein it is believed that decreasing tumor lactate levels, increasing glucose utilization and/or modulating tumor microenvironment may leave tumors otherwise resistant to additional therapeutic agents, susceptible to treatment by them. In some embodiments, and without being bound by theory, this is believed to be associated with modulating the dimeric form of PKM2 to a tetrameric form of PKM2 within the cellular environment.

In various other embodiments, the disclosure is directed to a method for treating cancer comprising administering a compound of Structure (I), or a pharmaceutically acceptable salt thereof, or a composition or combination therapy described above to a subject (e.g., a mammal) in need thereof.

In other embodiments, the compounds of the present disclosure inhibit cancer cell proliferation.

The compounds and compositions of the disclosure will also find utility in a broad range of diseases, disorders, and conditions mediated by PKM2. Such diseases may include, by way of example and not limitation, cancers such as lung cancer, non-small cell lung cancer (NSCLC), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy. Some embodiments include methods for treating cancers such as hematological malignancies. For example, in some embodiments the cancer is acute myeloid leukemia (AML). Still other cancers include multiple myeloma, follicular lymphoma, acute lymphoblastic leukemia (ALL), chronic lymphocytic leukemia (CLL) and non-Hodgkin's lymphoma. Other cancers include bladder cancer and prostate cancer.

In some embodiments, the compound of Structure I, or a pharmaceutically acceptable salt thereof, will be used to treat Renal Cell Carcinoma which has been classified as Intermediate-Risk or Poor-Risk stage IV. In some embodiments, the compound of Structure I, or a pharmaceutically acceptable salt thereof, will be used to treat first line Stage III or Stage IV unresectable advanced melanoma. In some embodiments, the compound of Structure I, or a pharmaceutically acceptable salt thereof, will be used to treat colorectal cancer that is characterized with microsatellite instability-High (MSI-H) or mismatch repair deficient (dMMR) that has progressed following treatment with a fluoropyrimidine, oxaliplatin, and irinotecan. In some embodiments, the compound of Structure I, or a pharmaceutically acceptable salt thereof, will be used to treat patients suffering from advanced Renal Cell Carcinoma who have failed prior anti-angiogenic therapy.

In some embodiments, the compound of Structure I will be of use in the provision of treatment for a hematopoietic cancer, for example, but not limited to, Myelodysplastic syndromes (MDS) and the various forms of leukemia mentioned herein. In some embodiments, the compound of Structure I will be of use in the provision of treatment for a solid tumor cancer, for example, but not limited to, renal cell carcinoma or any of the other solid tumor cancers mentioned herein. In some embodiments the compound of Structure I will be of use in the provision of treatment for a patient having a cancer which exhibits a VHL mutation.

Therefore, in one embodiment, the compound of Structure (I), or a pharmaceutically acceptable salt thereof, or a composition or combination therapy described herein may be useful to treat any one of the above-listed malignancy types.

Provided herein are methods for treating cancer comprising administering an effective amount of a compound of Structure (I), or a pharmaceutically acceptable salt thereof, to a subject in need thereof, and a RTK inhibitor.

Another embodiment provides a method for treating a subject having or at risk of developing cancer, the method comprising administering to the subject a composition comprising an effective amount of a compound of Structure (I), or a pharmaceutically acceptable salt thereof, and a RTK inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and a RTK inhibitor to a subject identified as being at risk of developing cancer. In some embodiments, the methods further include administering an effective amount of a compound of Structure (I), or a pharmaceutically acceptable salt thereof, and a RTK inhibitor to a subject suspected to have cancer.

In some embodiments, provided are methods for prophylactically treating cancer comprising administering an effective amount of a compound of Structure (I), or a pharmaceutically acceptable salt thereof, and a RTK inhibitor to a subject in need thereof.

In some embodiments, provided are methods for preventing cancer comprising administering an effective amount of a compound of Structure (I), or a pharmaceutically acceptable salt thereof, and a RTK inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and a RTK inhibitor.

Provided herein are methods for treating cancer comprising administering an effective amount of a compound of Structure (I), or a pharmaceutically acceptable salt thereof, and an EGFR inhibitor to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; and an EGFR inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and an EGFR (e.g., erlotinib) to a subject identified as being at risk of developing cancer. In some embodiments, the methods further include administering an effective amount of a compound of Structure (I), or a pharmaceutically acceptable salt thereof, and an EGFR inhibitor (e.g., erlotinib) to a subject suspected to have cancer.

In some embodiments, provided are methods for prophylactically treating cancer comprising administering an effective amount of a compound of Structure (I), or a pharmaceutically acceptable salt thereof, and an EGFR inhibitor (e.g., erlotinib) to a subject in need thereof.

In some embodiments, provided are methods for preventing cancer comprising administering an effective amount of a compound of Structure (I), or a pharmaceutically acceptable salt thereof, and an EGFR inhibitor (e.g., erlotinib) to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and an EGFR inhibitor (e.g., erlotinib).

Provided herein are methods for treating cancer comprising administering an effective amount of a compound of Structure (I), or a pharmaceutically acceptable salt thereof, to a subject in need thereof, and a VEGF inhibitor (e.g., bevacizumab).

Another embodiment provides a method for treating a subject having or at risk of developing cancer, the method comprising administering to the subject a composition comprising an effective amount of a compound of Structure (I), or a pharmaceutically acceptable salt thereof; and a VEGF inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and a VEGF inhibitor (e.g., bevacizumab) to a subject identified as being at risk of developing cancer. In some embodiments, the methods further include administering an effective amount of a compound of Structure (I), or a pharmaceutically acceptable salt thereof, and a VEGF inhibitor (e.g., bevacizumab) to a subject suspected to have cancer.

In some embodiments, provided are methods for prophylactically treating cancer comprising administering an effective amount of a compound of Structure (I), or a pharmaceutically acceptable salt thereof, and a VEGF inhibitor (e.g., bevacizumab) to a subject in need thereof.

In some embodiments, provided are methods for preventing cancer comprising administering an effective amount of a compound of Structure (I), or a pharmaceutically acceptable salt thereof, and a VEGF inhibitor (e.g., bevacizumab) to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and a VEGF inhibitor (e.g., bevacizumab).

Provided herein are methods for treating cancer comprising administering an effective amount of a compound of Structure (I), or a pharmaceutically acceptable salt thereof, to a subject in need thereof, and an ErbB2 inhibitor.

Another embodiment provides a method for treating a subject having or at risk of developing cancer, the method comprising administering to the subject a composition comprising an effective amount of a compound of Structure (I), or a pharmaceutically acceptable salt thereof; and an ErbB2 inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and an ErbB2 inhibitor to a subject identified as being at risk of developing cancer. In some embodiments, the methods further include administering an effective amount of a compound of Structure (I), or a pharmaceutically acceptable salt thereof, and an ErbB2 inhibitor to a subject suspected to have cancer.

In some embodiments, provided are methods for prophylactically treating cancer comprising administering an effective amount of a compound of Structure (I), or a pharmaceutically acceptable salt thereof, and an ErbB2 inhibitor to a subject in need thereof.

In some embodiments, provided are methods for preventing cancer comprising administering an effective amount of a compound of Structure (I), or a pharmaceutically acceptable salt thereof, and an ErbB2 inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and an ErbB2 inhibitor.

Provided herein are methods for treating cancer comprising administering an effective amount of a compound of Structure (I), or a pharmaceutically acceptable salt thereof, and an immunological checkpoint inhibitor to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; and an immunological checkpoint inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and an immunological checkpoint inhibitor to a subject identified as being at risk of developing cancer. In some embodiments, the methods further include administering an effective amount of a compound of Structure (I), or a pharmaceutically acceptable salt thereof, and an immunological checkpoint inhibitor to a subject suspected to have cancer.

In some embodiments, provided are methods for prophylactically treating cancer comprising administering an effective amount of a compound of Structure (I), or a pharmaceutically acceptable salt thereof, and an immunological checkpoint inhibitor to a subject in need thereof.

In some embodiments, provided are methods for preventing cancer comprising administering an effective amount of a compound of Structure (I), or a pharmaceutically acceptable salt thereof, and an immunological checkpoint inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and an immunological checkpoint inhibitor.

Provided herein are methods for treating cancer comprising administering an effective amount of a compound of Structure (I), or a pharmaceutically acceptable salt thereof, and a CTLA-4 inhibitor to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; and a CTLA-4 inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and a CTLA-4 inhibitor to a subject identified as being at risk of developing cancer. In some embodiments, the methods further include administering an effective amount of a compound of Structure (I), or a pharmaceutically acceptable salt thereof, and a CTLA-4 inhibitor to a subject suspected to have cancer.

In some embodiments, provided are methods for prophylactically treating cancer comprising administering an effective amount of a compound of Structure (I), or a pharmaceutically acceptable salt thereof, and a CTLA-4 inhibitor to a subject in need thereof.

In some embodiments, provided are methods for preventing cancer comprising administering an effective amount of a compound of Structure (I), or a pharmaceutically acceptable salt thereof, and a CTLA-4 inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and a CTLA-4 inhibitor.

Provided herein are methods for treating cancer comprising administering an effective amount of a compound of Structure (I), or a pharmaceutically acceptable salt thereof, and a PD-1 inhibitor to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; and a PD-1 inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and a PD-1 inhibitor to a subject identified as being at risk of developing cancer. In some embodiments, the methods further include administering an effective amount of a compound of Structure (I), or a pharmaceutically acceptable salt thereof, and a PD-1 inhibitor to a subject suspected to have cancer.

In some embodiments, provided are methods for prophylactically treating cancer comprising administering an effective amount of a compound of Structure (I), or a pharmaceutically acceptable salt thereof, and a PD-1 inhibitor to a subject in need thereof.

In some embodiments, provided are methods for preventing cancer comprising administering an effective amount of a compound of Structure (I), or a pharmaceutically acceptable salt thereof, and a PD-1 inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and a PD-1 inhibitor.

Provided herein are methods for treating cancer comprising administering an effective amount of a compound of Structure (I), or a pharmaceutically acceptable salt thereof, and a PD-L1 inhibitor to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; and a PD-L1 inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and a PD-L1 inhibitor to a subject identified as being at risk of developing cancer. In some embodiments, the methods further include administering an effective amount of a compound of Structure (I), or a pharmaceutically acceptable salt thereof, and a PD-L1 inhibitor to a subject suspected to have cancer.

In some embodiments, provided are methods for prophylactically treating cancer comprising administering an effective amount of a compound of Structure (I), or a pharmaceutically acceptable salt thereof, and a PD-L1 inhibitor to a subject in need thereof.

In some embodiments, provided are methods for preventing cancer comprising administering an effective amount of a compound of Structure (I), or a pharmaceutically acceptable salt thereof, and a PD-L1 inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and a PD-L1 inhibitor.

Provided herein are methods for treating cancer comprising administering an effective amount of a compound of Structure (I), or a pharmaceutically acceptable salt thereof, to a subject in need thereof, and an OX40 inhibitor.

Another embodiment provides a method for treating a subject having or at risk of developing cancer, the method comprising administering to the subject a composition comprising an effective amount of a compound of Structure (I), or a pharmaceutically acceptable salt thereof; and an OX40 inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, and an OX40 inhibitor to a subject identified as being at risk of developing cancer. In some embodiments, the methods further include administering an effective amount of a compound of Structure (I), or a pharmaceutically acceptable salt thereof, and an OX40 inhibitor to a subject suspected to have cancer.

In some embodiments, provided are methods for prophylactically treating cancer comprising administering an effective amount of a compound of Structure (I), or a pharmaceutically acceptable salt thereof, and an OX40 inhibitor to a subject in need thereof.

In some embodiments, provided are methods for preventing cancer comprising administering an effective amount of a compound of Structure (I), or a pharmaceutically acceptable salt thereof, and an OX40 inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and an OX40 inhibitor.

Provided herein are methods for treating cancer comprising administering an effective amount of a compound of Structure (I), or a pharmaceutically acceptable salt thereof, a PD-1 inhibitor, and a CTLA-4 inhibitor to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; a PD-1 inhibitor; and a CTLA-4 inhibitor.

In some embodiments, the methods described herein involve identifying a subject being at risk of developing cancer. In some embodiments, the methods described herein further include administering an effective amount of a compound of Structure (I), or a pharmaceutically acceptable salt thereof, a PD-1 inhibitor, and a CTLA-4 inhibitor to a subject identified as being at risk of developing cancer. In some embodiments, the methods further include administering an effective amount of a compound of Structure (I), or a pharmaceutically acceptable salt thereof, a PD-1 inhibitor, and a CTLA-4 inhibitor to a subject suspected to have cancer.

In some embodiments, provided are methods for prophylactically treating cancer comprising administering an effective amount of a compound of Structure (I), or a pharmaceutically acceptable salt thereof, a PD-1 inhibitor, and a CTLA-4 inhibitor to a subject in need thereof.

In some embodiments, provided are methods for preventing cancer comprising administering an effective amount of a compound of Structure (I), or a pharmaceutically acceptable salt thereof, a PD-1 inhibitor, and a CTLA-4 inhibitor to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, a PD-1 inhibitor, and a CTLA-4 inhibitor.

It is known that tumor cells utilize a glycolic metabolic pathway that provides certain advantages to proliferation and that cancer cells persist in anoxic, hypoxic, or severely hypoxic environment (herein, glycolic metabolic environment): *The Biology of Cancer: Metabolic Reprogramming Fuels Cell Growth and Proliferation,* DeBerardinis, R. J. et al., Cell Metabolism, 7: pp 11-20 (2008), DOI10.1016/j.cmet:2007.10.002; *Role of Hypoxia in Cancer Therapy by Regulating the Tumor Microenvironment*; Jing, X. et al., Molecular Cancer, 18(157): pp 1-15 (2019) DOI10.1186/s12943-019-1089-9; *Molecular Landmarks of Tumor Hypoxia Across Cancer Types*; Bhandari, V. et al., Nature Genetics 51(February); pp 308-318 (2019), DOI/10.1038/s41588-018-0318-2.

Hypoxic environments within a tumor may be detected using one or more of the following techniques: (i) identifying mRNA-based (or protein) hypoxia signatures from any of the following gene signatures Buffa, Winter, Ragnum, West, Sorensen, Elvidge, Hu and Seigneuric, for example, as described in Molecular Landmarks of Tumor Hypoxia Across Cancer Types, Bhandari, V. et al., Nature Genetics, 51 (February): pp 308-321 (2019); (ii) direct measurement of hypoxia in tumors using an imaging technique, for example, MRI or PET, for example, as are described in: Pharmacologically Increased Tumor Hypoxia Can Be Measured by $^{18}$F-Fluoroazomycin Arabinoside Positron Emission Tomography and Enhances Tumor Response to Hypoxic Cytotoxin PR-104, Cairns, R. A. et al., Clin Cancer Res., 15(23): pp 7170-7174 (2009), DOI:10.1158/1078-0432, CCR-09-1676; Hypoxia in Prostate Cancer: Correlation of BOLD-MRI With Pimonidazole Immunohistochemistry—Initial Observations, Hoskin, P. J. et al., Int. J. Radiation Oncology Biol. Phys., 68(4): pp 1065-1071 (2007), DOI:10.1016/j.ijrobp.2007.01.018. In some instances these observations have been made using MM techniques that include StOs-MRI (tissue saturation studied by magnetic resonance imaging, for example, as described in, for example, Imaging of brain Oxygenation with Magnetic Resonance Imaging: A Validation With Positron Emission Tomography in the Healthy and Tumoural Brain, Valable, S et al., Journ. Of Cerebral Blood Flow & Metabolism, 37(7), pp 2584-25-97 (2017), DOI: 10.1177/0271678X16671965, and OE-MRI (oxygen-enhanced MRI) as described in, for example, Oxygen-Enhanced MM Accurately Identifies, Quantifies, and Maps Tumor Hypoxia in Preclinical Cancer Models, O'Connor, J. P. B. et al., Cancer Research, 76(4): pp 787-795 (2015), COI: 10.1158/0008-5472.CAN-15-2062. In some instances observations of hypoxic tissue in tumors have been identified by PET (positron emissions tomography) utilizing radio-labeled tracers such as FMISO (fluoromisonidazole, which contains 18F), for example, as described in Tumor Hypoxia Detected by 18F-fluoromisonidazole Positron Emission Tomography (FMISO PET) as a Prognostic Indicator of Radiotherapy (RT), Tachibana, I. et al., Anticancer Res, 38 (3): pp 1775-1781 (March 2018) and FAZA (18F-labeled nitroimidazole nucleoside analogue 1-(5-fluoro-5-deoxy-α-D-arabinofuranosyl)-2-nitroimidazole), as described in PAZA PET/CT Hypoxia Imaging in Patients With Squamous Cell Carcinoma of the Head and Neck Treated with Radiotherapy: Results From the DAHANCA 24 Trial, Mortensen, L. S. et al., 105: pp 14-20 (2012) DOI/10.1016/j.radonc.2012.09.015; (iii) identification of VHL loss of function mutations which, it will be appreciated, may be detected by next-gen sequencing, in particular identification of one of several different types of known mutations including missense mutations, nonsense mutations and splicing mutations, as is known, the loss of VHL function results in the stabilization and overexpression of HIF1alpha protein and constitutive angiogenic signaling even when oxygen is present, as is known also, VHL mutations are diverse and often result from the inheritance of a mutation in one copy of VHL that is accompanied over time with sporadic mutation in the second copy of the VHL protein leading to cancer; and (iv) in some rare instances where it may be present, mutations which are directly in HIF1-alpha, which may be identified using sequencing techniques familiar to one of ordinary skill in the art.

Hypoxia in tumor tissue has been associated with tumor proliferation, metastasis, and resistance to immunotherapeutics. Studies of several tumor types have implicated PKM2 in the hypoxic glycolytic pathway, and associated therewith its role in reprogramming the metabolic pathway in tumor tissues. PKM2 is also associated with impeding mechanisms which ordinarily would suppress tumor activity, or stabilization of processes which otherwise would lead to cell death, and is associated with mechanisms within the tumor which promote resistance to various antitumor agents, for example, checkpoint and mTOR inhibitors: *PKM2 Promotes Tumor Angiogenesis by Regulating HIF-1-α through NF-κB Activation*, Azoitei, N. et al., Molecular Cancer 15(03): pp 1-15 (2016) DOI/10.1186/s12943-015-0490-2; *PKM2 Under Hypoxic Environment Causes Resistance to mTOR inhibitor in Human Castration Resistant Prostate Cancer*, Yasumizu, Y. et al., Oncotarget, 9:(45), pp 27698-27707 (2018); *Pyruvate Kinase M2 is a PHD3-Stimulated Coactivator for Hypoxia-Inducible Factor 1*, Luo, W. et al., Cell, 145: pp 732-744 (2011); *PKM2 and HIF-1-α Regulation in Prostate Cancer Cell Lines*, Hasan, D. et al., PLOS ONE, 13(9), pp 1-14 (2018) DOI/10.1371/journal.pone.0203745. In accordance with the foregoing, tumors operating in a hypoxic regime depend upon the action of pyruvate kinase M2 for the production of energy and the cellular building blocks for proliferation, as well as having a role in promoting various processes associated with tumor proliferation and IO escape. Therefore, introduction of a PKM2 activator into this environment will alter the microenvironment in a manner that will decrease cell metabolism, reduce the tumor's ability to proliferate, leave the tumor vulnerable to immuno-oncology agents and cell death. In particular, treatment of tumors operating in a hypoxic environment, for example, Kidney Renal Clear Cell Carcinoma, Lung Adenocarcinoma, Skin Cutaneous Melanoma, Glioblastoma Multiforme, Ovarian Serous Cystadenocarcinoma, Bladder and Urothelial Carcinoma, Uterine Corpus Endometrioid Carcinoma, Colon/Rectum adenocarcinoma, Cervical Squamous Cell Carcinoma, Endocervical Adenocarcinoma, Lung Squamous Cell Carcinoma, and Head and Neck Squamous Cell Carcinoma with the compound of Formula 1, alone or in combination with one or more immune checkpoint inhibitors, for example, a PD-1, PD-L1, and CTLA-4 checkpoint inhibitor will inhibit or reverse tumor progression or lead to tumor apoptosis.

Provided herein are methods for treating cancer comprising administering an effective amount of a compound of Structure (I), or a pharmaceutically acceptable salt thereof, and a ferroptosis inducer to a subject in need thereof.

Another embodiment provides a method for treating a subject having or at risk of developing cancer, the method comprising administering to the subject a composition comprising an effective amount of a compound of Structure (I), or a pharmaceutically acceptable salt thereof; and a ferroptosis inducer.

In some embodiments, the methods described herein involve identifying a subject being at risk of developing cancer. In some embodiments, the methods described herein further include administering an effective amount of a compound of Structure (I), or a pharmaceutically acceptable salt thereof, and a ferroptosis inducer to a subject identified as being at risk of developing cancer. In some embodiments, the methods further include administering an effective amount of a compound of Structure (I), or a pharmaceutically acceptable salt thereof, and a ferroptosis inducer to a subject suspected to have cancer.

In some embodiments, provided are methods for prophylactically treating cancer comprising administering an effective amount of a compound of Structure (I), or a pharmaceutically acceptable salt thereof, and a ferroptosis inducer to a subject in need thereof.

In some embodiments, provided are methods for preventing cancer comprising administering an effective amount of a compound of Structure (I), or a pharmaceutically acceptable salt thereof, and a ferroptosis inducer to a subject in need thereof.

In another aspect, a method is provided for treating a subject having or at risk of developing cancer, the method comprising administering to the subject in need thereof an effective amount of a compound of Structure (I), or a pharmaceutically acceptable salt thereof, and a ferroptosis inducer.

In any of the above embodiments, the ferroptosis inducer does not include erastin, sorafenib, or cisplatin. In any of the above embodiments, the method does not include administering a reactive oxygen species-producing anti-cancer drug to the subject.

In embodiments, the cancer is an EFGR-mutant cancer, a BRAF-mutant cancer, a ROS1-mutant cancer, an ALK-mutant cancer, or a combination thereof. In particular embodiments, the cancer is an EFGR-mutant cancer. In other embodiments, a BRAF-mutant cancer. In further embodiments, the cancer is a ROS1-mutant cancer. In still further embodiments, the cancer is an ALK-mutant cancer.

In some specific embodiments, the cancer is lung cancer (e.g., non-small cell lung cancer). For example, in certain embodiments the cancer is an EGFR-mutant non-small cell lung cancer. In particular embodiments, the EGFR-mutant non-small cell lung cancer is resistant to treatment with tyrosine kinase inhibitors (TKI). In specific embodiments, the EGFR-mutant non-small cell lung cancer is progressing on treatment with a TKI.

Provided herein are methods for treating cancer comprising administering an effective amount of a compound of Structure (I), or a pharmaceutically acceptable salt thereof, to a subject in need thereof, wherein the cancer is an EGFR-mutant NSCLC. Some embodiments provide a method for treating an EGFR-mutant NSCLC comprising administering an effective amount of a compound of Structure (I) or a pharmaceutically acceptable salt to a subject in need thereof.

Another embodiment provides a method for treating a subject having or at risk of developing an EGFR-mutant NSCLC, the method comprising administering to the subject a composition comprising an effective amount of a compound of Structure (I), or a pharmaceutically acceptable salt thereof.

In some embodiments, the methods described herein involve identifying a subject being at risk of developing an EGFR-mutant NSCLC. In some embodiments, the methods described herein further include administering an effective amount of a compound of Structure (I), or a pharmaceutically acceptable salt thereof, to a subject identified as being at risk of developing an EGFR-mutant NSCLC. In some embodiments, the methods further include administering an effective amount of a compound of Structure (I), or a pharmaceutically acceptable salt thereof, to a subject suspected to have an EGFR-mutant NSCLC.

In some embodiments, provided are methods for prophylactically treating a cancer comprising administering an effective amount of a compound of Structure (I), or a pharmaceutically acceptable salt thereof, to a subject in need thereof, wherein the cancer is an EGFR-mutant NSCLC. In some embodiments, provided are methods for prophylactically treating an EGFR-mutant NSCLC comprising administering an effective amount of a compound of Structure (I), or a pharmaceutically acceptable salt thereof to a subject in need thereof.

In some embodiments, provided are methods for preventing cancer comprising administering an effective amount of a compound of Structure (I), or a pharmaceutically acceptable salt thereof, to a subject in need thereof, wherein the cancer is an EGFR-mutant NSCLC. In some embodiments, provided are methods for preventing an EGFR-mutant NSCLC comprising administering an effective amount of a compound of Structure (I), or a pharmaceutically acceptable salt thereof, to a subject in need thereof.

In another aspect, a method is provided for treating a subject having or at risk of developing an EGFR-mutant NSCLC, the method comprising administering to the subject in need thereof an effective amount of a compound of Structure (I), or a pharmaceutically acceptable salt thereof.

Provided herein are methods for treating cancer comprising administering an effective amount of a compound of Structure (I), or a pharmaceutically acceptable salt thereof, to a subject in need thereof, wherein the cancer is an EGFR-mutant NSCLC progressing on a TKI. Some embodiments provide a method for treating an EGFR-mutant NSCLC progressing on a TKI comprising administering an effective amount of a compound of Structure (I) or a pharmaceutically acceptable salt to a subject in need thereof.

Another embodiment provides a method for treating a subject having or at risk of developing an EGFR-mutant NSCLC progressing on a TKI, the method comprising administering to the subject a composition comprising an effective amount of a compound of Structure (I), or a pharmaceutically acceptable salt thereof.

In some embodiments, the methods described herein involve identifying a subject being at risk of developing an EGFR-mutant NSCLC progressing on a TKI. In some embodiments, the methods described herein further include administering an effective amount of a compound of Structure (I), or a pharmaceutically acceptable salt thereof, to a subject identified as being at risk of developing an EGFR-mutant NSCLC progressing on a TKI. In some embodiments, the methods further include administering an effective amount of a compound of Structure (I), or a pharmaceutically acceptable salt thereof, to a subject suspected to have an EGFR-mutant NSCLC progressing on a TKI.

In some embodiments, provided are methods for prophylactically treating a cancer comprising administering an effective amount of a compound of Structure (I), or a pharmaceutically acceptable salt thereof, to a subject in need thereof, wherein the cancer includes an EGFR-mutant NSCLC progressing on a TKI. In some embodiments, provided are methods for prophylactically treating an EGFR-mutant NSCLC progressing on a TKI comprising administering an effective amount of a compound of Structure (I), or a pharmaceutically acceptable salt thereof, to a subject in need thereof.

In some embodiments, provided are methods for preventing cancer comprising administering an effective amount of a compound of Structure (I), or a pharmaceutically acceptable salt thereof, to a subject in need thereof, wherein the cancer is an EGFR-mutant NSCLC progressing on a TKI. In some embodiments, provided are methods for preventing an EGFR-mutant NSCLC progressing on a TKI comprising administering an effective amount of a compound of Structure (I), or a pharmaceutically acceptable salt thereof, to a subject in need thereof.

In another aspect, a method is provided for treating a subject having or at risk of developing an EGFR-mutant NSCLC progressing on a TKI, the method comprising administering to the subject in need thereof an effective amount of a compound of Structure (I), or a pharmaceutically acceptable salt thereof.

Provided herein are methods for treating cancer comprising administering an effective amount of a compound of Structure (I), or a pharmaceutically acceptable salt thereof, to a subject in need thereof, and a RTK inhibitor (e.g., erlotinib) wherein the cancer is an EGFR-mutant NSCLC progressing on a TKI. Some embodiments provide a method for treating an EGFR-mutant NSCLC progressing on a TKI comprising administering an effective amount of a compound of Structure (I) or a pharmaceutically acceptable salt and a RTK inhibitor (e.g., erlotinib) to a subject in need thereof.

Another embodiment provides a method for treating a subject having or at risk of developing an EGFR-mutant NSCLC progressing on a TKI, the method comprising administering to the subject a composition comprising an effective amount of a compound of Structure (I), or a pharmaceutically acceptable salt thereof, and a RTK inhibitor (e.g., erlotinib).

In some embodiments, the methods described herein involve identifying a subject being at risk of developing an EGFR-mutant NSCLC progressing on a TKI. In some embodiments, the methods described herein further include administering an effective amount of a compound of Structure (I), or a pharmaceutically acceptable salt thereof, and a RTK inhibitor (e.g., erlotinib) to a subject identified as being at risk of developing an EGFR-mutant NSCLC progressing on a TKI. In some embodiments, the methods further include administering an effective amount of a compound of Structure (I), or a pharmaceutically acceptable salt thereof, and a RTK inhibitor (e.g., erlotinib) to a subject suspected to have an EGFR-mutant NSCLC progressing on a TKI.

In some embodiments, provided are methods for prophylactically treating a cancer comprising administering an effective amount of a compound of Structure (I), or a pharmaceutically acceptable salt thereof, and a RTK inhibitor (e.g., erlotinib) to a subject in need thereof, wherein the cancer includes an EGFR-mutant NSCLC progressing on a TKI. In some embodiments, provided are methods for prophylactically treating an EGFR-mutant NSCLC progressing on a TKI, comprising administering an effective amount of a compound of Structure (I), or a pharmaceutically acceptable salt thereof, and a RTK inhibitor (e.g., erlotinib) to a subject in need thereof.

In some embodiments, provided are methods for preventing cancer, comprising administering an effective amount of a compound of Structure (I), or a pharmaceutically acceptable salt thereof, and a RTK inhibitor (e.g., erlotinib) to a subject in need thereof, wherein the cancer is EGFR-mutant NSCLC. In some embodiments, provided are methods for preventing an EGFR-mutant NSCLC progressing on a TKI comprising administering an effective amount of a compound of Structure (I), or a pharmaceutically acceptable salt thereof, and a RTK inhibitor (e.g., erlotinib) to a subject in need thereof.

In another aspect, a method is provided for treating a subject having or at risk of developing an EGFR-mutant NSCLC progressing on a TKI, the method comprising administering to the subject in need thereof an effective amount of a compound of Structure (I), or a pharmaceutically acceptable salt thereof, and a RTK inhibitor (e.g., erlotinib).

In some embodiments, the cancer is a solid tumor, for example an advanced solid tumor. In particular embodiments, the advanced solid tumor is resistant to treatment with an immuno-oncology (IO) agent (e.g., a checkpoint inhibitor). In specific embodiments, the advanced solid tumor is resistant to treatment with an IO agent.

As used herein, "immuno-oncology agent" refers to any agent that, upon administration to a subject in an effective amount, modulates (e.g., stimulates, inhibits) an immune response to a cancer in the subject. Immuno-oncology agents include immunological checkpoint inhibitors, such as those described herein.

Provided herein are methods for treating cancer comprising administering an effective amount of a compound of Structure (I), or a pharmaceutically acceptable salt thereof, to a subject in need thereof, wherein the cancer is an advanced solid tumor. Some embodiments provide a method for treating an advanced solid tumor comprising administering an effective amount of a compound of Structure (I), or a pharmaceutically acceptable salt thereof, to a subject in need thereof.

Another embodiment provides a method for treating a subject having or at risk of developing an advanced solid tumor, the method comprising administering to the subject a composition comprising an effective amount of a compound of Structure (I), or a pharmaceutically acceptable salt thereof.

In some embodiments, the methods described herein involve identifying a subject being at risk of developing an advanced solid tumor. In some embodiments, the methods described herein further include administering an effective amount of a compound of Structure (I), or a pharmaceutically acceptable salt thereof, to a subject identified as being at risk of developing an advanced solid tumor. In some embodiments, the methods further include administering an effective amount of a compound of Structure (I), or a pharmaceutically acceptable salt thereof, to a subject suspected to have an advanced solid tumor.

In some embodiments, provided are methods for prophylactically treating a cancer comprising administering an effective amount of a compound of Structure (I), or a pharmaceutically acceptable salt thereof, to a subject in need thereof, wherein the cancer includes an advanced solid tumor. In some embodiments, provided are methods for prophylactically treating an advanced solid tumor comprising administering an effective amount of a compound of Structure (I), or a pharmaceutically acceptable salt thereof, to a subject in need thereof.

In some embodiments, provided are methods for preventing cancer comprising administering an effective amount of a compound of Structure (I), or a pharmaceutically acceptable salt thereof, to a subject in need thereof, wherein the cancer is an advanced solid tumor. In some embodiments, provided are methods for preventing an advanced solid tumor comprising administering an effective amount of a compound of Structure (I), or a pharmaceutically acceptable salt thereof, to a subject in need thereof.

In another aspect, a method is provided for treating a subject having or at risk of developing an advanced solid tumor, the method comprising administering to the subject in need thereof an effective amount of a compound of Structure (I), or a pharmaceutically acceptable salt thereof.

Provided herein are methods for treating cancer comprising administering an effective amount of a compound of Structure (I), or a pharmaceutically acceptable salt thereof, to a subject in need thereof, wherein the cancer is an advanced solid tumor advancing on an immuno-oncology agent. Some embodiments provide a method for treating an advanced solid tumor advancing on an immuno-oncology agent comprising administering an effective amount of a compound of Structure (I), or a pharmaceutically acceptable salt thereof, to a subject in need thereof.

Another embodiment provides a method for treating a subject having or at risk of developing an advanced solid tumor advancing on an immuno-oncology agent, the method comprising administering to the subject a composition comprising an effective amount of a compound of Structure (I), or a pharmaceutically acceptable salt thereof.

In some embodiments, the methods described herein involve identifying a subject being at risk of developing an advanced solid tumor advancing on an immuno-oncology agent. In some embodiments, the methods described herein further include administering an effective amount of a compound of Structure (I), or a pharmaceutically acceptable salt thereof, to a subject identified as being at risk of developing an advanced solid tumor advancing on an immuno-oncology agent. In some embodiments, the methods further include administering an effective amount of a compound of Structure (I), or a pharmaceutically acceptable salt thereof, to a subject suspected to have an advanced solid tumor advancing on an immuno-oncology agent.

In some embodiments, provided are methods for prophylactically treating a cancer comprising administering an effective amount of a compound of Structure (I), or a pharmaceutically acceptable salt thereof, to a subject in need thereof, wherein the cancer includes an advanced solid tumor advancing on an immuno-oncology agent. In some embodiments, provided are methods for prophylactically treating an advanced solid tumor advancing on an immuno-oncology agent comprising administering an effective amount of a compound of Structure (I), or a pharmaceutically acceptable salt thereof, to a subject in need thereof.

In some embodiments, provided are methods for preventing cancer comprising administering an effective amount of a compound of Structure (I), or a pharmaceutically acceptable salt thereof, to a subject in need thereof, wherein the cancer is an advanced solid tumor advancing on an immuno-oncology agent. In some embodiments, provided are methods for preventing an advanced solid tumor advancing on an immuno-oncology agent comprising administering an effective amount of a compound of Structure (I), or a pharmaceutically acceptable salt thereof, to a subject in need thereof.

In another aspect, a method is provided for treating a subject having or at risk of developing an advanced solid tumor advancing on an immuno-oncology agent, the method comprising administering to the subject in need thereof an effective amount of a compound of Structure (I), or a pharmaceutically acceptable salt thereof.

Provided herein are methods for treating cancer comprising administering an effective amount of a compound of Structure (I), or a pharmaceutically acceptable salt thereof, and an immunological checkpoint inhibitor to a subject in need thereof, wherein the cancer is an advanced solid tumor advancing on an immuno-oncology agent. Some embodiments provide a method for treating an advanced solid tumor advancing on an immuno-oncology agent comprising administering an effective amount of a compound of Structure (I) or a pharmaceutically acceptable salt thereof, and an immunological checkpoint inhibitor, to a subject in need thereof.

Another embodiment provides a method for treating a subject having or at risk of developing an advanced solid tumor advancing on an immuno-oncology agent, the method comprising administering to the subject a composition comprising an effective amount of a compound of Structure (I), or a pharmaceutically acceptable salt thereof, and an immunological checkpoint inhibitor.

In some embodiments, the methods described herein involve identifying a subject being at risk of developing an advanced solid tumor advancing on an immuno-oncology agent. In some embodiments, the methods described herein further include administering an effective amount of a compound of Structure (I), or a pharmaceutically acceptable salt thereof, and an immunological checkpoint inhibitor, to a subject identified as being at risk of developing an advanced solid tumor advancing on an immuno-oncology agent. In some embodiments, the methods further include administering an effective amount of a compound of Structure (I), or a pharmaceutically acceptable salt thereof, and an immunological checkpoint inhibitor, to a subject suspected to have an advanced solid tumor advancing on an immuno-oncology agent.

In some embodiments, provided are methods for prophylactically treating a cancer comprising administering an effective amount of a compound of Structure (I), or a pharmaceutically acceptable salt thereof, and an immunological checkpoint inhibitor, to a subject in need thereof, wherein the cancer includes an advanced solid tumor advancing on an immuno-oncology agent. In some embodiments, provided are methods for prophylactically treating an advanced solid tumor advancing on an immuno-oncology agent comprising administering an effective amount of a compound of Structure (I), or a pharmaceutically acceptable salt thereof, and an immunological checkpoint inhibitor, to a subject in need thereof.

In some embodiments, provided are methods for preventing cancer comprising administering an effective amount of a compound of Structure (I), or a pharmaceutically acceptable salt thereof, and an immunological checkpoint inhibitor, to a subject in need thereof, wherein the cancer is an advanced solid tumor advancing on an immuno-oncology agent. In some embodiments, provided are methods for preventing an advanced solid tumor advancing on an immuno-oncology agent comprising administering an effective amount of a compound of Structure (I), or a pharmaceutically acceptable salt thereof, and an immunological checkpoint inhibitor, to a subject in need thereof.

In another aspect, a method is provided for treating a subject having or at risk of developing an advanced solid tumor advancing on an immuno-oncology agent, the method comprising administering to the subject in need thereof an effective amount of a compound of Structure (I), or a pharmaceutically acceptable salt thereof, and an immunological checkpoint inhibitor.

In some other embodiments, the cancer is lymphoma. In specific embodiments, the lymphoma is large cell lymphoma. In particular embodiments, the lymphoma is large cell lymphoma such as nucleophosmin-anaplastic lymphoma kinase (NPM-ALK) anaplastic large cell lymphoma.

Provided herein are methods for treating cancer comprising administering an effective amount of a compound of Structure (I), or a pharmaceutically acceptable salt thereof, to a subject in need thereof, wherein the cancer is NPM-ALK anaplastic large cell lymphoma. Some embodiments provide a method for treating NPM-ALK anaplastic large cell lymphoma comprising administering an effective amount of a compound of Structure (I), or a pharmaceutically acceptable salt thereof, to a subject in need thereof.

Another embodiment provides a method for treating a subject having or at risk of developing NPM-ALK anaplastic large cell lymphoma, the method comprising administering to the subject a composition comprising an effective amount of a compound of Structure (I), or a pharmaceutically acceptable salt thereof.

In some embodiments, the methods described herein involve identifying a subject being at risk of developing NPM-ALK anaplastic large cell lymphoma. In some embodiments, the methods described herein further include administering an effective amount of a compound of Structure (I), or a pharmaceutically acceptable salt thereof, to a subject identified as being at risk of developing NPM-ALK anaplastic large cell lymphoma. In some embodiments, the methods further include administering an effective amount of a compound of Structure (I), or a pharmaceutically acceptable salt thereof, to a subject suspected to have NPM-ALK anaplastic large cell lymphoma.

In some embodiments, provided are methods for preventing cancer comprising administering an effective amount of a compound of Structure (I), or a pharmaceutically acceptable salt thereof, to a subject in need thereof, wherein the cancer is NPM-ALK anaplastic large cell lymphoma. In some embodiments, provided are methods for preventing NPM-ALK anaplastic large cell lymphoma comprising administering an effective amount of a compound of Structure (I), or a pharmaceutically acceptable salt thereof, to a subject in need thereof.

In another aspect, a method is provided for treating a subject having or at risk of developing NPM-ALK anaplastic large cell lymphoma, the method comprising administering to the subject in need thereof an effective amount of a compound of Structure (I), or a pharmaceutically acceptable salt thereof.

In any of the above embodiments, the method does not include administering a reactive oxygen species-producing anti-cancer drug to the subject.

Certain embodiments of the disclosed methods further include administering a chemotherapeutic agent concurrently, prior to or after administering the compound of Structure (I). The following examples are provided for purposes of illustration, not limitation.

EXAMPLES

Example 1

Treatment in Xenograft Model

A compound of Structure (I) was used in combination with erlotinib to dose mutant EGFR HCC827 cells in a xenograft model for non-small cell lung cancer. Samples were dosed as vehicle alone, with 5 mg/kg of erlotinib HCl alone and with 5 mg/kg of erlotinib HCl with either 50 or 100 mg/kg of a compound of Structure (I) over the course of 27 days. The tumor volumes are plotted as a function of time (in days) as shown in FIG. 1. The percent tumor growth inhibition (% TGI) for a dose of 50 mg/kg is 74%, and the % TGI for a dose of 100 mg/kg is 55.8%.

Example 2

Efficacy of the Compound of Structure (I) Alone and/or in Combination with Anti-PD-1 (RPM1-14) Against Established Syngeneic MC38 Colon Carcinoma in C57BL/6 Mice Summary On Day 1, female mice bearing MC38 tumors were sorted into six groups (n=8) with group mean tumor volumes of 102-104 mm$^3$. Vehicle (Tween80, Ethanol, and PEG400, in water) and the compound of Structure (I) were administered orally (p.o.) once a day for twenty-one days (qdx21). Anti-PD-1 was administered intraperitoneally (i.p.) at 5 mg/kg twice a week for two weeks (biwkx2). Treatment groups were as follows: Group 1 (control) received vehicle 1; Groups 2 and 3 received 50 and 100 mg/kg compound of Structure (I), respectively; Group 4 received anti-PD-1; Group 5 received 50 mg/kg compound of Structure (I) and anti-PD-1; Group 6 received 100 mg/kg compound of Structure (I) and anti-PD-1. Tumor volumes were measured twice a week using calipers. When the mean tumor volume of the control group approached 1000 mm$^3$ on Day 21, all groups were analyzed for tumor growth inhibition (TGI). Animals were euthanized as they reached the endpoint tumor volume of 1000 mm$^3$ or the last day of the study (Day 46), whichever came first. At endpoint, serum, spleens and tumors were collected from animals in all groups.

Efficacy was determined based primarily on percent tumor growth delay (TGD) and secondarily on percent tumor growth inhibition (TGI). TGD is defined as the percent increase in median time-to-endpoint (TTE) in treated versus control mice and was evaluated using the log rank (Mantel-Cox) test. TGI is defined as the percent difference between the Day 21 median tumor volumes (MTVs) of treated and control mice, and differences between MTVs were deemed significant at P≤0.05 using the Mann-Whitney U test. Treatment tolerability was assessed based on body weight changes and observations of treatment-related (TR) side effects.

The median time to endpoint (TTE) of vehicle control Group 1 was 19.1 days, establishing a maximum possible tumor growth delay (TGD) of 141% (equivalent to 26.9 days) in this 46-day study. The control TTE values ranged from 18.3 to 27.6, providing a sensitive assay for TGD analysis. Groups 2 and 3 (compound of Structure (I) at 50 and 100 mg/kg, respectively) produced TGDs of 19% and 70%, respectively. Group 2 TTEs did not differ statistically from control, while Group 3 results were significant compared to control (P≤0.001 v. Group 1). Anti-PD-1 monotherapy (Group 4) demonstrated a statistically significant tumor growth delay (TGD) of 121% (P≤0.01 v. Group 1). Groups 5 and 6 were dosed with anti-PD-1 in combination with compound of Structure (I) at 50 and 100 mg/kg, respectively. Both combination therapies achieved the maximum tumor growth delay possible of 141%. The results were significant compared to Group 1 (P≤0.001 v. Group 1) but not to anti-PD-1 monotherapy.

Significant Day 21 tumor growth inhibition (TGI) was not observed in Group 2 (compound of Structure (I) at 50 mg/kg), however, was observed in all other groups: Group 3 (65%), Group 4 (69%) and Group 6 (91%) (P≤0.01 v. Group 1), and Group 5 (93%) (P≤0.001 v. Group 1).

Negligible group mean body weight losses (≤0.8%) were observed in anti-PD-1 and compound of Structure (I)/anti-PD-1 combination therapies Groups 4, 5 and 6. Clinical observations were limited to occasional signs of tumor progression (tumor ulcerations, ruffled fur, hunched posture, lethargy, and/or low body temperature) that occurred across treatment groups.

In summary, compound of Structure (I) monotherapy showed activity in a dose responsive manner, with 100 mg/kg resulting in a significant 70% TGD in the syngeneic MC38 colon carcinoma model. Anti-PD-1 alone was significantly active in this model. When anti-PD-1 was dosed in combination with compound of Structure (I) at 50 or 100 mg/kg, there was significant survival benefit independent of compound of Structure (I) dose administration. Analysis on Day 21 of the study was in line with the results of the long-term outcome. Compound of Structure (I) at the 100 mg/kg dose reached potential therapeutic activity with 65% TGI. Anti-PD-1 therapy also led to a significant 69% TGI. In combination, anti-PD-1 and compound of Structure (I) produced above 90% TGI, also indicative of potential therapeutic activity. All treatments were well-tolerated.

Methods and Materials

Mice

Female C57BL/6 mice (C57BL/6NCrl, Charles River) were eleven weeks old with a body weight (BW) range of 18.2 to 24.8 g on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-o'Cobs™ Laboratory Animal Bedding in static microisolators on a 12-hour light cycle at 20-22° C. (68-72° F.) and 40-60% humidity. CR Discovery Services specifically complies with the recommendations of the *Guide for Care and Use of Laboratory Animals* with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

Tumor Cell Culture

The MC38 murine colon carcinoma cell line for this study was obtained from the American Type Culture Collection (ATCC) and maintained at CR Discovery Services in Dulbecco's Modified Eagle Medium (DMEM) containing 10% fetal bovine serum, 2 mM glutamine, 100 units/mL penicillin G sodium, 100 μg/mL streptomycin sulfate, and 25 μg/mL gentamicin. The cells were cultured in tissue culture flasks in a humidified incubator at 37° C., in an atmosphere of 5% $CO^2$ and 95% air.

In Vivo Implantation and Tumor Growth

On the day of implant, cultured MC38 cells were harvested during log phase growth and re-suspended in RPMI media at a concentration of $5 \times 10^6$ cells/mL. Tumors were initiated by subcutaneously implanting $5 \times 10^5$ MC38 cells (0.1 mL suspension) into the right flank of each test animal. Tumors were monitored as their volumes approached the target range of 80-120 mm$^3$. Eighteen days after tumor cell implantation, on Day 1 of the study, animals were sorted into six groups (n=8/group) with individual tumor volumes of 75 to 144 mm$^3$, and group mean tumor volumes of 102-104 mm$^3$. Tumors were measured with a caliper twice weekly for the duration of the study. Tumors were measured in two dimensions using calipers, and volume was calculated using the formula:

$$\text{Tumor Volume(mm}^3) = \frac{w^2 \times l}{2}$$

where w=width and l=length, in mm, of the tumor. Tumor weight may be estimated with the assumption that 1 mg is equivalent to 1 mm$^3$ of tumor volume.

Therapeutic Agents

The compound of Structure (I) was stored at −20° C. Anti-PD-1 clone RMP1-14 (rat IgG; BioXcell Lot No. 695318A1B) was stored at 4° C. and protected from the light. The vehicle was 2% Tween80:10% Ethanol:30% PEG400:58% deionized water (DI $H_2O$).

Dosing solutions of the compound of Structure (I) were prepared weekly by suspending the compound in ethanol with vortexing, then adding Tween80 and PEG400 with gentle vortexing followed by deionized water (DI $H_2O$) to yield 5 and 10 mg/mL opaque suspensions. Dosing solution was stored at 4° C. Remaining unformulated compound was returned to the client after study end.

On the day of dosing, antibody stock solution (6.78 mg/mL) was diluted with PBS to a final concentration of 0.5 mg/mL.

Treatment

On Day 1 of the study, female C57BL/6 mice with established subcutaneous MC38 tumors were sorted into six groups (n=8), and dosing was initiated according to the treatment plan summarized in Table 1 and are described below. The dosing volume for all therapies was 0.200 mL per 20 grams of body weight (10 mL/kg), and was scaled to the body weight of each individual animal.

Group 1 received vehicle 1 (Tween80, Ethanol, and PEG400, in water (in the following ratio: 2:10:30:58)) orally (p.o.) once a day for twenty-one days (qd×21) and served as the control and benchmark group for tumor engraftment and progression.

Group 2 received compound of Structure (I) at 50 mg/kg, p.o., qd×21.

Group 3 received compound of Structure (I) at 100 mg/kg, p.o., qd×21.

Group 4 received anti-PD-1 at 5 mg/kg, i.p., biwk×2.

Group 5 received compound of Structure (I) at 50 mg/kg, p.o., qd×21 in combination with anti-PD-1 at 5 mg/kg, i.p., biwk×2.

Group 6 received compound of Structure (I) at 100 mg/kg, p.o., qd×21 in combination with anti-PD-1 at 5 mg/kg, i.p., biwk×2.

Sampling

After TGI was reached, individual endpoints were reached at the end of the study (Day 46) or when individual tumor volumes approached 1000 mm³. Endpoint serum, tumor and spleen samples were collected from animals in all groups at endpoint.

Full blood volume was collected by terminal cardiac puncture under isoflurane anesthesia and processed to serum (no anti-coagulant), and frozen. Tumors and spleens were harvested immediately after blood collection. The spleens were fixed in formalin for twenty-four hours, then transferred to 70% ethanol. They were stored at room temperature until shipment to the client at study end. The tumors were divided into two parts. Part one was formalin fixed as described for the spleens and part two was snap frozen and stored at −80° C. until shipment. At completion of the study the serum and frozen tumors (part two) were shipped on dry ice (−80° C.) while the formalin fixed tissues were sent at ambient temperature to Tolero Pharmaceuticals, Inc.

Tumor Growth Inhibition (TGI) Analysis

Individual tumors were measured twice per week. Tumor growth inhibition (TGI) was determined on Day 21 using MTV (n), the median tumor volume for the number of animals, n. Percent tumor growth inhibition (% TGI) was defined as the difference between the MTV of the designated control group (Group 1) and the MTV of the treatment group, expressed as a percentage of the MTV of the control group:

% TGI=[1−(MTV$_{drug\ treated}$/MTV$_{control}$)]×100

CR Discovery Services considers any agent that leads to at least 60% TGI by this criterion to be potentially therapeutically active.

Endpoint and Tumor Growth Delay (TGD) Analysis

After TGI was reached, the study was converted for TGD analysis. Each individual animal was euthanized when its tumor reached the endpoint volume of 1000 mm³ or at the end of the study (Day 46), whichever came first. Animals that exited the study for tumor volume endpoint were documented as euthanized for tumor progression (TP), with the date of euthanasia. The time to endpoint (TTE) for analysis was calculated for each mouse by the following equation:

$$TTE = \frac{\log_{10}(\text{endpoint volume}) - b}{m}$$

where TTE is expressed in days, endpoint volume is expressed in mm³, b is the intercept, and m is the slope of the line obtained by linear regression of a log-transformed tumor growth data set. The data set consisted of the first observation that exceeded the endpoint volume used in analysis and the three consecutive observations that immediately preceded the attainment of this endpoint volume. The calculated TTE is usually less than the TP date, the day on which the animal was euthanized for tumor size. Animals with tumors that did not reach the endpoint volume were assigned a TTE value equal to the last day of the study (Day 46). In instances in which the log-transformed calculated TTE preceded the day prior to reaching endpoint or exceeded the day of reaching tumor volume endpoint, a linear interpolation was performed to approximate the TTE. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death.

Treatment outcome was evaluated from tumor growth delay (TGD), which is defined as the increase in the median time to endpoint (TTE) in a treatment group compared to the control group:

TGD=$T-C$, expressed in days, or as a percentage of the median TTE of the control group:

$$\% \ TGD = \frac{T - C}{C} \times 100$$

where:
T=median TTE for a treatment group, and
C=median TTE for the designated control group.

MTV and Criteria for Regression Responses

Treatment efficacy may also be determined from the tumor volumes of animals remaining in the study on the last day and from the number and magnitude of regression responses. The MTV(n) is defined as the median tumor volume on Day 46 in the number of evaluable animals remaining, n, whose tumors have not attained the volume endpoint.

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm³ for one or more of these three measurements. In a CR response, the tumor volume is less than 13.5 mm³ for three consecutive measurements during the study. Animals were scored only once during the study for a PR or CR event and only as a CR if both PR and CR criteria were satisfied. Any animal with a CR response at the end of the study was additionally classified as a tumor-free survivor (TFS).

Toxicity

Animals were weighed daily on Days 1-5, then twice per week until the completion of the study. The mice were observed frequently for overt signs of any adverse, TR side effects, and clinical signs were recorded when observed. Individual body weight was monitored as per protocol, and any animal with weight loss exceeding 30% for one measurement or exceeding 25% for three consecutive measurements was euthanized as a TR death (for treated groups). Group mean body weight loss was also monitored according to CR Discovery Services protocol. Acceptable toxicity was defined as a group mean body weight (BW) loss of less than 20% during the study and no more than 10% TR deaths. Any dosing regimen resulting in greater toxicity was considered above the maximum tolerated dose (MTD). Dosing was suspended in any group where mean weight loss exceeded acceptable limits. If group mean body weight recovered to acceptable levels, then dosing was modified to lower levels and/or reduced frequency, then resumed. Deaths were classified as TR if it was attributable to treatment side effects as evidenced by clinical signs and/or necropsy. A TR classification was also assigned to deaths by unknown causes during the dosing period or within 14 days of the last dose. A death was classified as NTR if there was no evidence that death was related to treatment side effects. NTR deaths may be further characterized based on cause of death. A death may be classified as NTRa if it resulted from an accident or human error. A death may be classified as NTRm if necropsy indicated that it might have resulted from tumor dissemination by invasion and/or metastasis. A death may be classified as NTRu if the cause of death was unknown and there was no available evidence of death related to treatment side effects, metastasis, accident or human error, although death due to treatment side effects cannot be excluded.

Statistical and Graphical Analyses

Prism (GraphPad) for Windows 8.0 was used for graphical presentations and statistical analyses. Study groups experiencing toxicity beyond acceptable limits (>20% group mean body weight loss or greater than 10% treatment related deaths) or having fewer than five evaluable observations, were not included in statistical analyses, being classified as non-evaluable (ne). Statistical analyses of the differences between Day 21 median tumor volumes (MTVs) of two groups were accomplished using the Mann-Whitney U test.

Survival was analyzed by the Kaplan-Meier method. The log rank test, which evaluates overall survival experience, was used to analyze the significance of the differences between the TTE values of two groups. Log rank analysis includes the data for all animals in a group except those assessed as NTR deaths. Two-tailed statistical analyses were conducted at significance level P=0.05. Statistical tests were not adjusted for multiple comparisons.

Prism summarizes test results as not significant (ns) at P>0.05, significant (symbolized by "*") at $0.01 < P \leq 0.05$, very significant ("") at $0.001 < P \leq 0.01$, and extremely significant ("*") at $P \leq 0.001$. Because tests of statistical significance do not provide an estimate of the magnitude of the difference between groups, all levels of significance were described as either significant or not significant within the text of this report. For all analyses, a two-sided P<0.05 was considered statistically significant.

A scatter plot was constructed to show TTE values for individual mice, by group. A box and whisker plot was constructed showing the Day 21 tumor volume data by group, with the "box" representing the 25th and 75th percentile of observations, the "line" representing the median of observations, and the "whiskers" representing the extreme observations. Individual, group median, and mean tumor volumes were plotted as a function of time. When an animal exited the study due to tumor size, the final tumor volume recorded for the animal was included with the data used to calculate the mean volume at subsequent time points. Error bars (when present) indicate one standard error of the mean (SEM). Kaplan-Meier plots show the percentage of animals in each group remaining in the study versus time. The Kaplan-Meier plot and log rank test share the same TTE data sets. Group body weight changes over the course of the study were plotted as percent mean change from Day 1. Tumor growth and body weight plots excluded the data for animals assessed as NTR deaths, and were truncated when fewer than 50% of the animals in a group remained in the study.

Results

Figure 2:
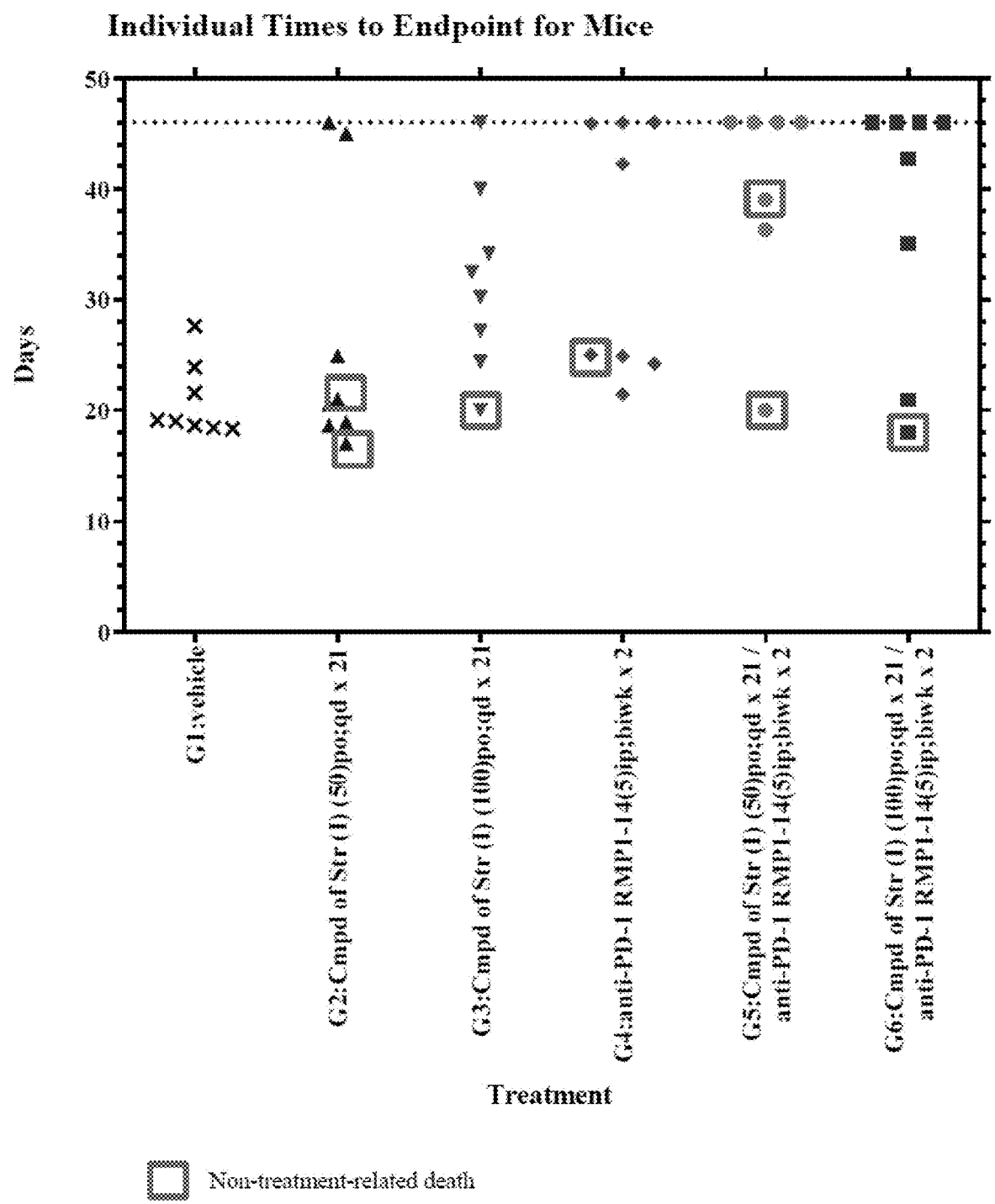
FIG. 2 provides a scatter plot showing the individual TTEs by group, as described in Example 2.
Figure 3:
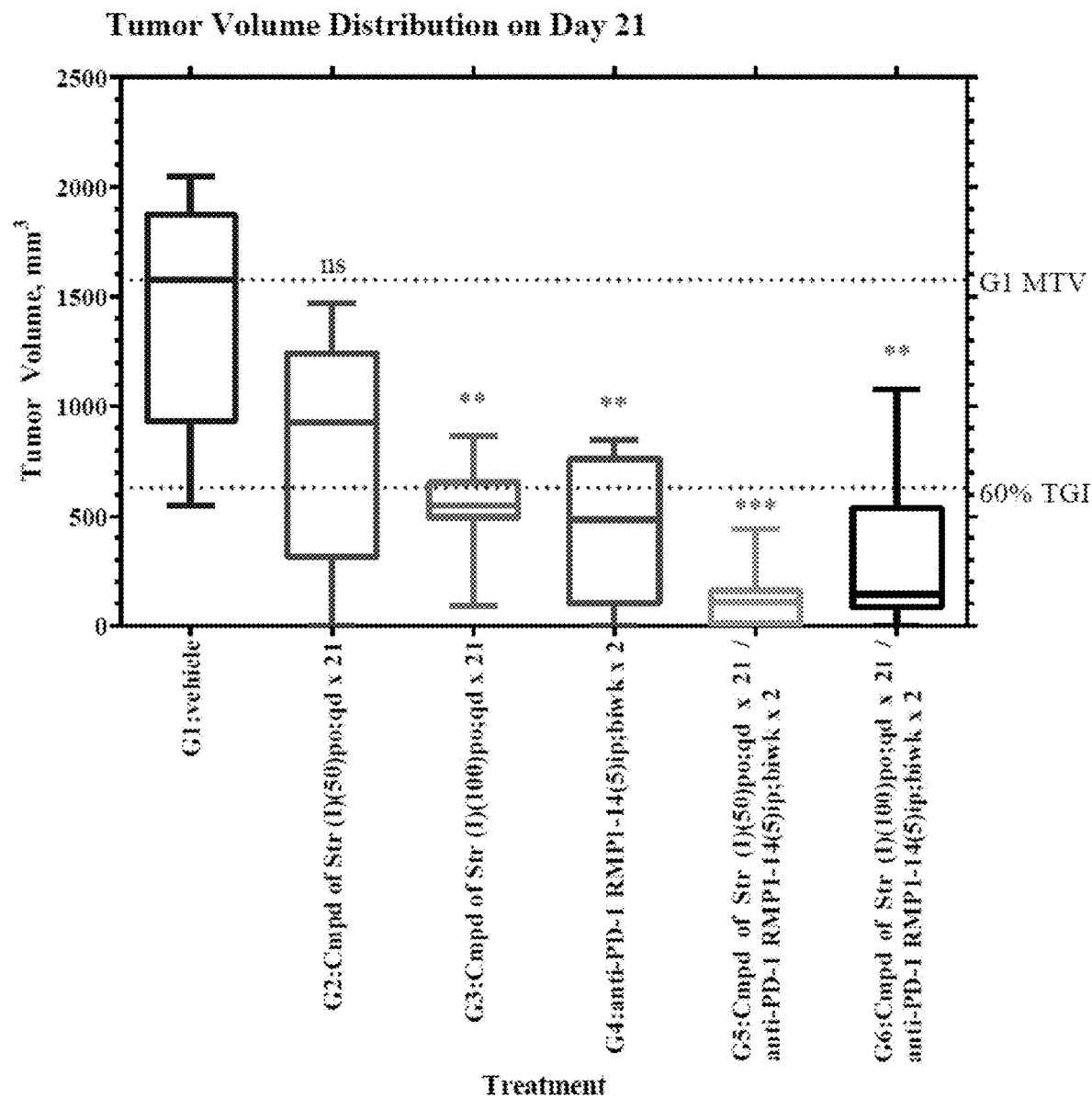
FIG. 3 illustrates tumor volume distribution by group on Day 21 using a box and whisker plot, as described in Example 2.
Figure 4:
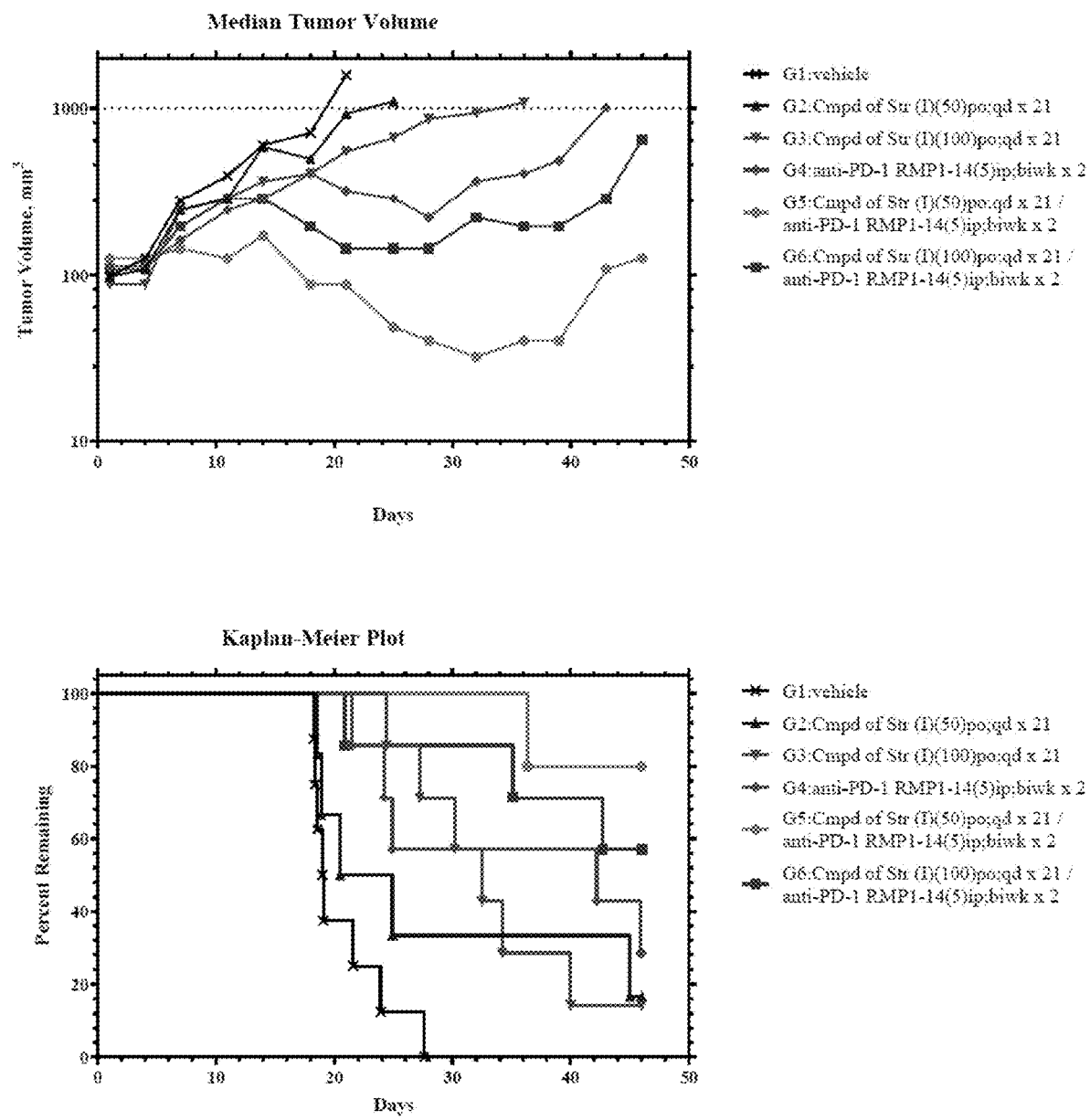
FIG. 4 includes plots of group median tumor growth (upper panel) and Kaplan-Meier survival (lower panel) for the study described in Example 2.
Figure 5:
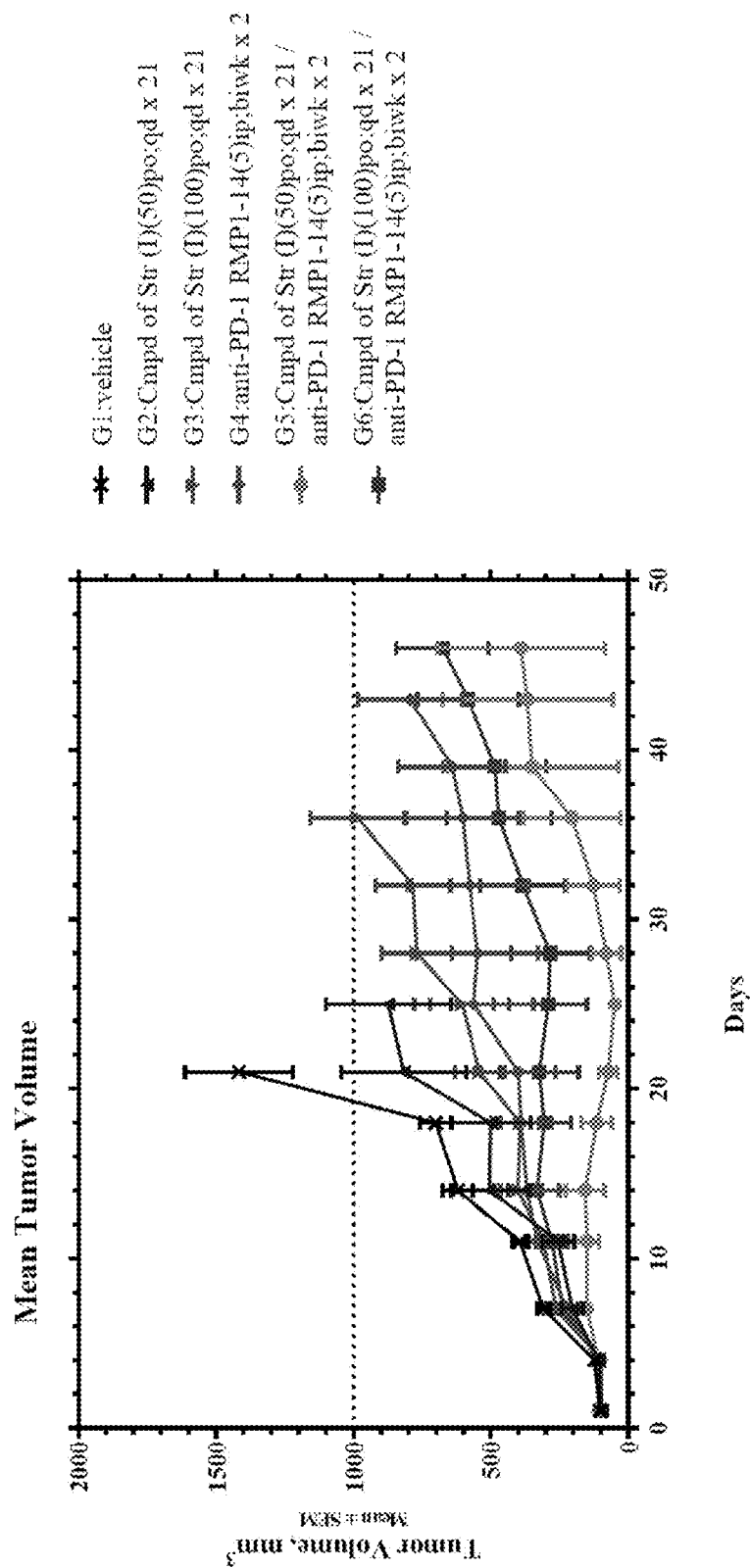
FIG. 5 plots group mean tumor growth±SEM for the study described in Example 2.
Figure 6A:
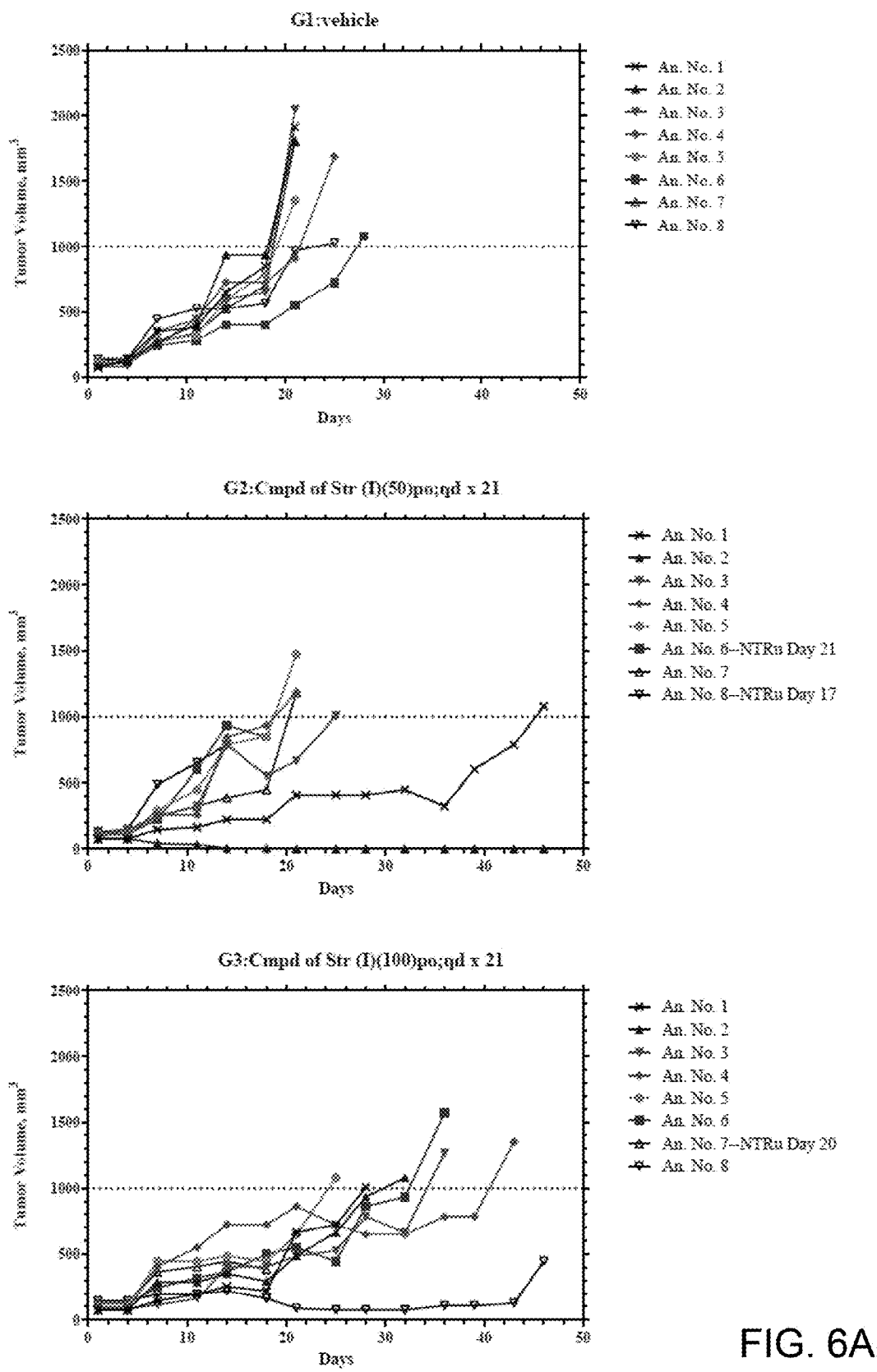
FIGS. 6A and 6B provide individual tumor growth curves for the study described in Example 2.
Figure 6B:
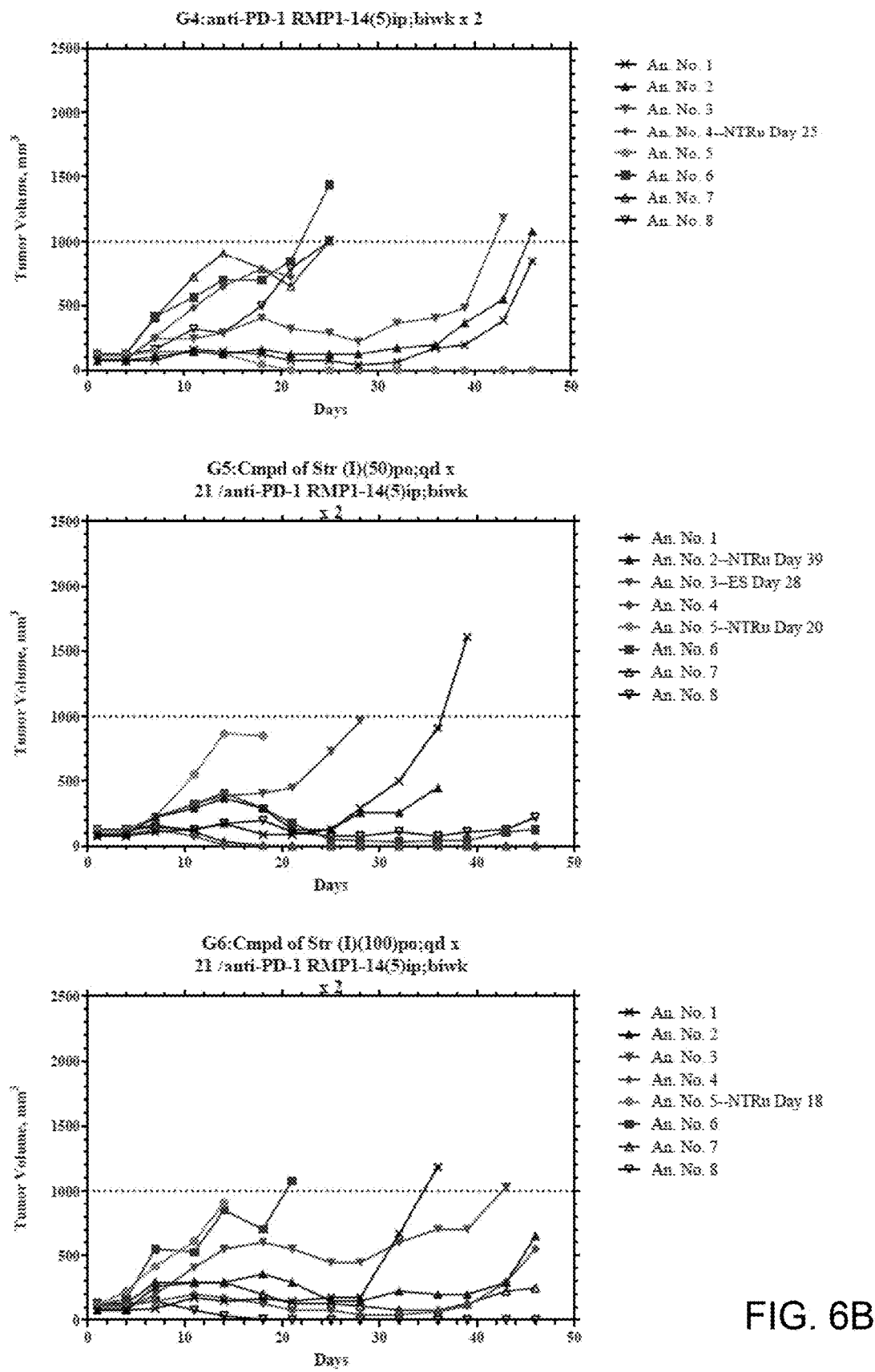
Figure 7:
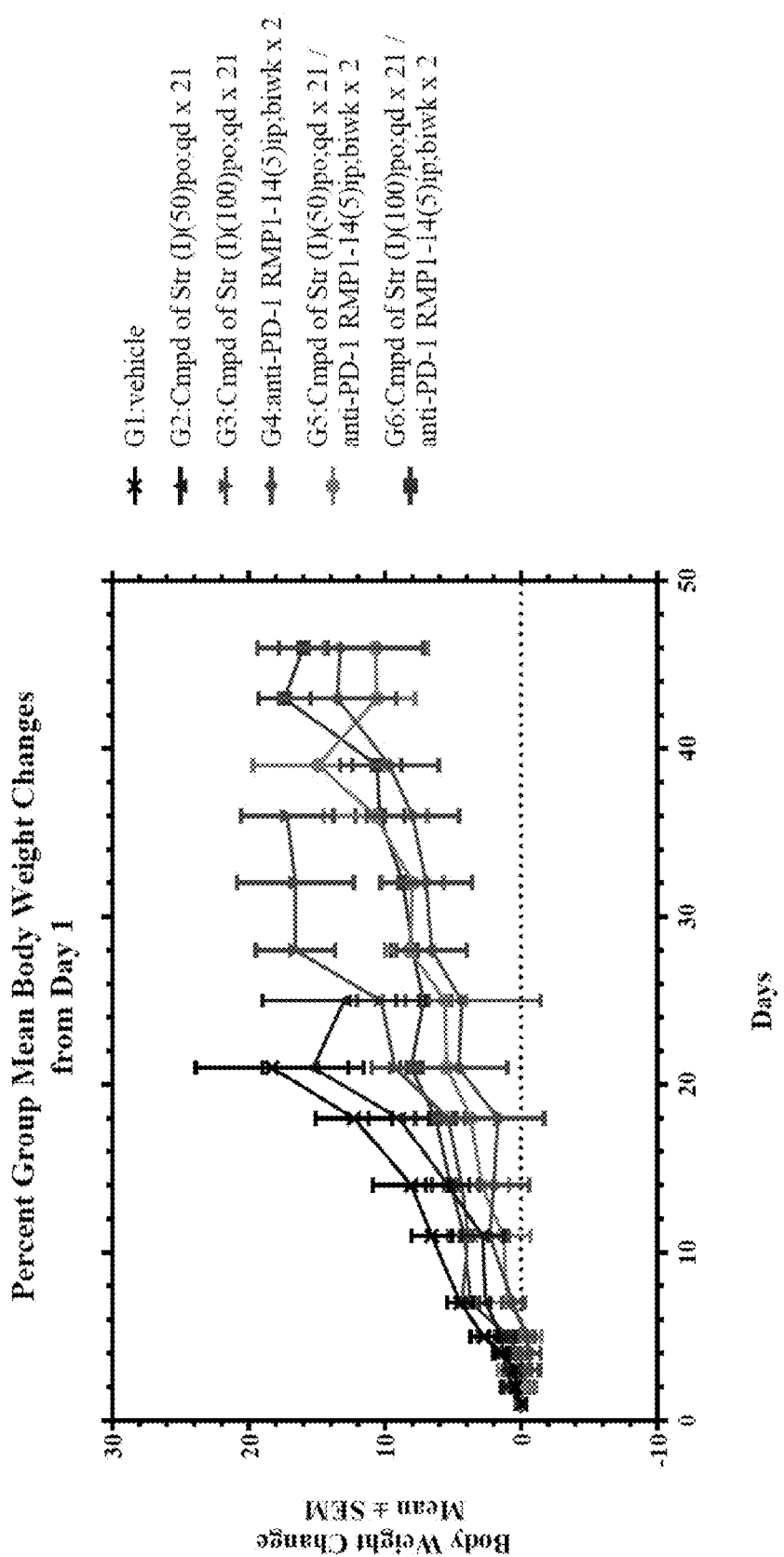
FIG. 7 illustrates percent mean body weight changes from Day 1 for each group, as described in Example 2.

Groups in the study were treated in accordance with the protocol summarized in Table 1. Table 2 presents the treatment responses for each group and Table 3 summarizes Day 21 tumor growth inhibition results. FIG. 2 provides a scatter plot showing the individual TTEs by group. FIG. 3 illustrates tumor volume distribution by group on Day 21 using a box and whisker plot. FIG. 4 includes plots of group median tumor growth (upper panel) and Kaplan-Meier survival (lower panel) for the study. FIG. 5 plots group mean tumor growth±SEM and FIGS. 6A-6B provide individual tumor growth curves. FIG. 7 illustrates percent mean body weight changes from Day 1 for each group.

Efficacy

Growth of MC38 Tumors in Vehicle-Treated Control Mice (Group 1)

Group 1 mice received vehicle (2% Tween80:10% Ethanol:30% PEG400: 58% DI $H_2O$) p.o., qd×21 and provided the standard of comparison for all treatment groups. The control TTE values ranged from 18.3 to 27.6, providing a sensitive assay for TGD analysis. The median tumor volume (MTV) (8) reached 1576 mm$^3$ on Day 21 (Table 3). The median time to endpoint (TTE) for Group 1 was 19.1 days, establishing a maximum possible tumor growth delay TGD of 26.9 days (141%) for the 46-day study (Table 2). All control tumors attained the 1000 mm$^3$ endpoint (Table 2). Tumor growth was progressive (FIG. 4 (upper panel), FIG. 5, and FIG. 6A.)

Response to Treatment with Compound of Structure (I) (Groups 2 and 3)

Group 2 received compound of Structure (I) at 50 mg/kg p.o. qd×21. The Group 2 MTV (6) at Day 21 was 925 mm$^3$, corresponding to a non-significant 41% TGI compared to Group 1 (P>0.05, Table 3). The median TTE for Group 2 was 22.7 days, corresponding to a non-significant TGD of 19% compared to control Group 1 (Table 2). Two NTRu deaths occurred in Group 2 (one each on Day 17 and 21). One animal reached the last day of the study (Day 46) with a tumor volume of 0 mm$^3$, which displayed as a tumor free survivor (TFS) that maintained complete regression (CR) (Table 2).

Group 3 received the compound of Structure (I) at 100 mg/kg p.o. qd×21. The Group 3 MTV (7) at Day 21 was 550 mm$^3$, corresponding to a significant 65% inhibition of tumor growth (TGI) compared to Group 1 (P≤0.01, Table 3). The median TTE for Group 3 was 32.5 days, corresponding to a significant 70% TGD (P≤0.001, Table 2). One NTRu death occurred on Day 20. One animal reached the last day of the study (Day 46) with a tumor volume of 446 mm$^3$, (Table 2).

Response to Treatment with Anti-PD-1 (Group 4)

Group 4 received anti-PD-1 at 5 mg/kg i.p. biwk×2. The Group 4 MTV (8) at Day 21 was 485 mm$^3$, corresponding to a significant 69% TGI compared to Group 1 (P≤0.01, Table 3). The median TTE for Group 4 was 42.2 days, corresponding to a significant TGD of 121% compared to Group 1 (P≤0.001, Table 2). Two animals reached the last day of the study (Day 46) with a final tumor volume of 847 and 0 mm$^3$, with one also noted as a tumor free survivor (TFS) that maintained complete regression (CR) (Table 2) (FIGS. 4 and 5).

Response to Compound of Structure (I) and Anti-PD-1 Combination Therapy (Groups 5 and 6)

Group 5 received anti-PD-1 and compound of Structure (I) as described in Table 2. The Group 5 MTV (7) at Day 21 was 108 mm$^3$, corresponding to a significant 93% TGI compared to Group 1 (P≤0.001) and compound of Structure (I) monotherapy (P≤0.05 v. Group 2) but not anti-PD-1 monotherapy (Table 3). The median TTE for Group 5 was assigned the maximum TTE attainable in the study of 46.0 days, corresponding to a significant 141% TGD compared to control (P≤0.001 v. Group 1) and compound of Structure (I) monotherapy (P≤0.05 v. Group 2) but not anti-PD-1 monotherapy (Table 2). Four animals reached the last day of the study (Day 46) with a MTV (4) of 63 mm3, one as a partial regression (PR) and two CR further classified as TFS.

Median and mean tumor growth was delayed compared to all groups except anti-PD-1 monotherapy Group 5 (FIGS. 4 and 5).

Group 6 received anti-PD-1 and compound of Structure (I) as described in Table 2. The Group 6 MTV (7) at Day 21 was 144 mm3, corresponding to a significant 91% TGI compared to Group 1 (P≤0.01) but not compound of Structure (I) (Group 2) monotherapy or anti-PD-1 monotherapy (Table 3). Group 6 was assigned the maximum TTE attainable in the study of 46.0 days, corresponding to a significant 141% TGD compared to control (P≤0.001 v. Group 1) but not anti-PD-1 or compound of Structure (I) (Group 3) monotherapy (Table 2). Four animals reached the last day of the study (Day 46) with a MTV (4) of 398 mm3, one as a CR further classified as TFS. Median and mean tumor growth was delayed compared to all groups except anti-PD-1 monotherapy Group 6 (FIGS. 4 and 5).

Adverse Events

Table 2 provides a summary of maximum mean body weight (BW) losses, treatment related (TR) and non-treatment related (NTR) deaths. FIG. 7 plots percent mean BW changes from Day 1 for each group. Clinical signs were recorded when observed. Negligible group mean BW losses on Day 3 were observed in anti-PD-1 Group 4 (0.6%), and both combination therapies Group 5 (0.8% Day 5) and 6 (0.4% Day 3). Deaths due to unknown causes (NTRu) occurred in Group 2 (one each on Days 17 and 21), Group 3 on Day 20, Group 4 on Day 25, Group 5 (one each on Days 20 and 39), and Group 6 on Day 18. Signs of tumor progression (low body temperature, weight loss, hunching, ruffled fur and/or tumor ulceration) were also recorded in one or two animals from each group.

Example 3

Figure 8:
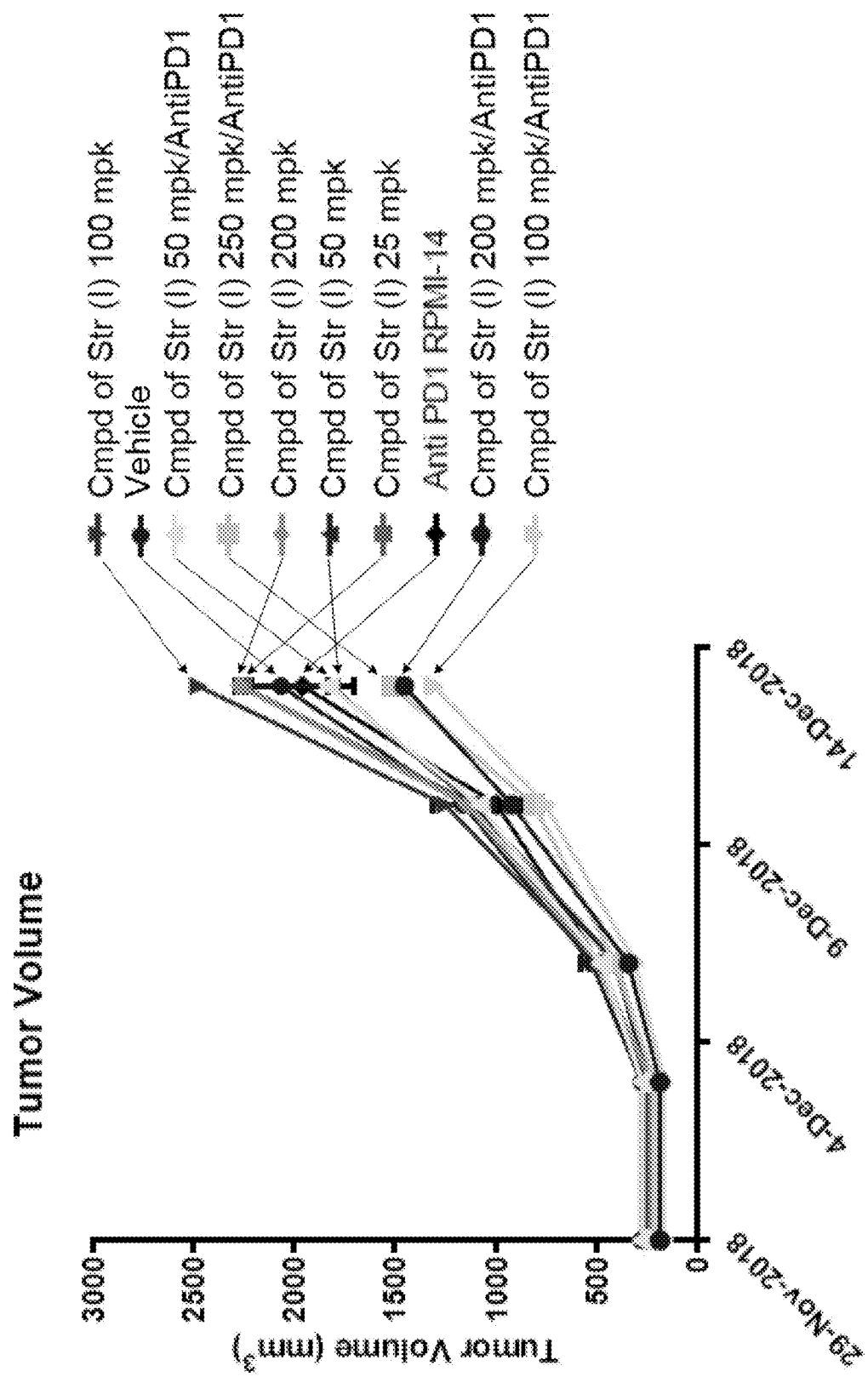
FIG. 8 shows a plot of tumor volume over time for mice treated with a compound of Structure (I) alone and in combination with an anti-PD-1 antibody.

In Vivo Synergy Between PKM2 Activator and Immunotherapy Agent 6-8-week-old C57BL/6 mice were injected on the hind flank with $5\times10^5$ MC38 colon cancer cells, mixed 1:1 in matrigel. When tumors reached approximately 100 mm$^3$, mice were stratified into treatment cohorts. Mice were dosed once daily with the compound of Structure (I), by oral gavage, and anti-PD-1 antibody (catalog #BE0146, clone RMP1-14, BioXCell), by intraperitoneal injection (FIG. 8). The compound of Structure (I) was formulated in Tween80: Ethanol:PEG400:Water (2:10:30:58) and the anti-PD-1 antibody was formulated in PBS. Tumor volumes were measured twice weekly for 21 days.

Tumors in mice treated with the compound of Structure (I) were inhibited by as much as 11.9% (% TGI, dosed at 50 milligrams per kilogram or mpk). In contrast, tumors in mice given the compound of Structure (I) and anti-PD-1 antibody were inhibited by 36.4% over the course of the treatment period (dosed at 100 mpk, see FIG. 8).

Example 4

Study of PKM2 Activator in a Serine- and Glycine-Depleted Diet

A xenograft study was performed using A549 lung cancer cells to interrogate the in vivo effect of treatment of a compound of Structure (I) with mice fed a traditional and a serine- and glycine-depleted diet. The traditional diet control was the Baker Amino Acid diet (catalog #5CC7, Test Diet) and the depleted diet was a modified Baker Amino Acid diet which compensated for serine and glycine depletion with increases in all remaining amino acids (catalog #5BJX, Test Diet). Mice (6-8 week-old female athymic nude) were housed under standard conditions, and allowed food and water ad libitum and injected with $1\times10^7$ A549 cells per mouse. Upon reaching a tumor volume of approximately 100-200 mm$^3$, mice were treated with a control (vehicle alone) or the compound of Structure (I). The compound of Structure (I) was administered by oral gavage at a concentration of 100 mpk, qd×21.

Figure 9:
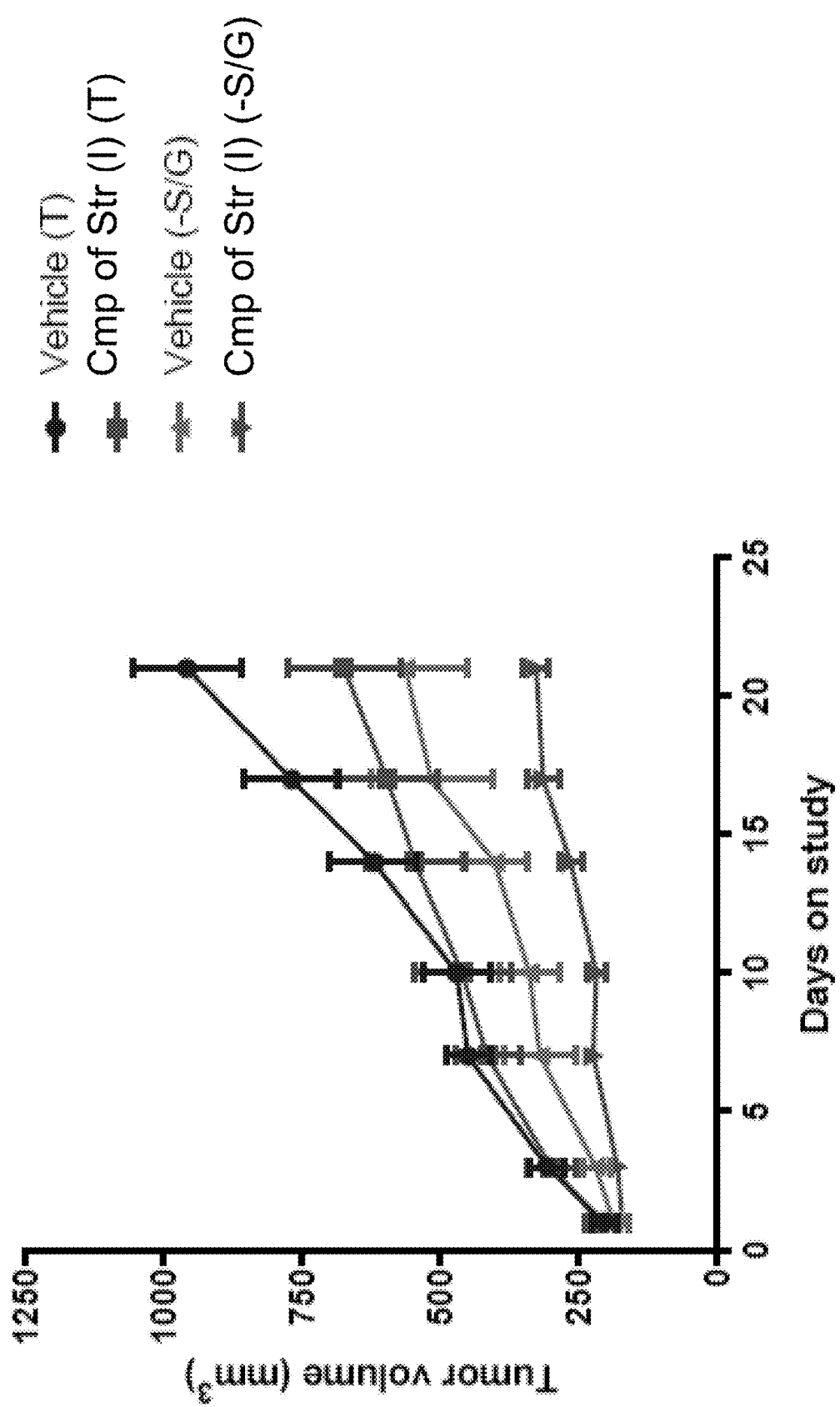
FIG. 9 shows tumor volume over time for mice fed with a traditional versus serine- and glycine-depleted diet.

Tumor volume and body weights were measured and recorded twice weekly (FIG. 9). Upon completion of the study, mice were euthanized and tumor tissues were harvested. As the data of FIG. 9 shows, treatment with the compound of Structure (I) in a serine- and glycine-depleted diet showed the best reduction of tumor volume. In addition, the mice treated in the study shown in FIG. 9 showed no significant body weight reduction or fluctuation while the compound of Structure (I) was being administered.

Example 5

Synergy Between Anthracycline Compounds and PKM2 Activator

A549 and Panc1 cells were plated using 384-well plates at a density of 1,200 cells per well. Cells were plated in RPMI media and allowed to adhere for 24 hours at 37° C. Cells were then treated with concentration gradients of doxorubicin (FIGS. 10A and 10B) in the presence and absence of the compound of Structure (I) at a concentration of 3 μM in replicates of 7 per condition. Cell viability was determined using the Cell-titer-Glo assay according to the manufacturer's protocol (Promega Biosciences, LLC). Doxorubicin was purchased from Apexbio (catalog #A1832) and prepared in DMSO.

Figures 10A, 10B:
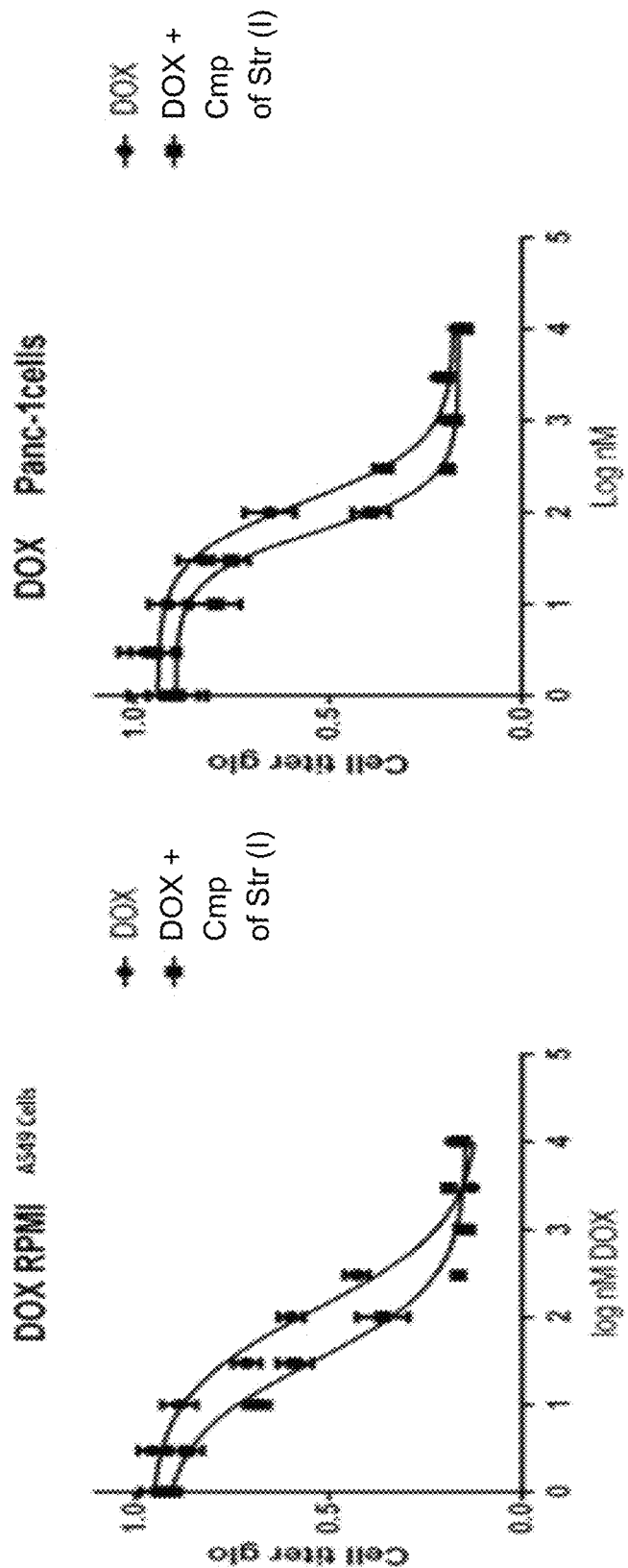
FIGS. 10A and 10B illustrate synergistic effect between the anthracycline and the compound of Structure (I).

The data clearly show increased anti-proliferative activity when the compound of Structure (I) was used in combination with the anthracycline-based anti-cancer compound. A549 and Panc1 cells were both tested for cell viability, each showing increased sensitivity to the combination relative to single agent treatment (FIGS. 10A and 10B). It should be noted that the compound of Structure (I) had no effect as a single agent on cell viability at the 3 μM dose level.

Example 6

Synergy Between EGFR Inhibitors and PKM2 Activator

A xenograft study was performed using HCC-827 lung cancer cells to interrogate the in vivo effect of treatment with a compound of Structure (I) and an exemplary EGFR inhibitor, erlotinib. Erlotinib was purchased from LC Labs (catalog #E-4007) and prepared in 0.2% (w/v) methylcellulose+0.1% (v/v) Tween80 in water. 6-8-week-old female athymic nude mice were housed under standard conditions and allowed food and water ad libitum. Mice were injected with $1\times10^7$ HCC-827 cells per mouse. Upon reaching a tumor volume of approximately 100-200 mm$^3$, mice were treated with vehicle (Tween80, ethanol, PEG400, and water, at the following ratio: 2:10:30:58) or the compound of Structure (I). Erlotinib was first administered daily for six days, followed by treatment with the compound of Structure (I). The compound of Structure (I) was then administered by oral gavage at concentrations up to 100 mpk.

Figure 11:
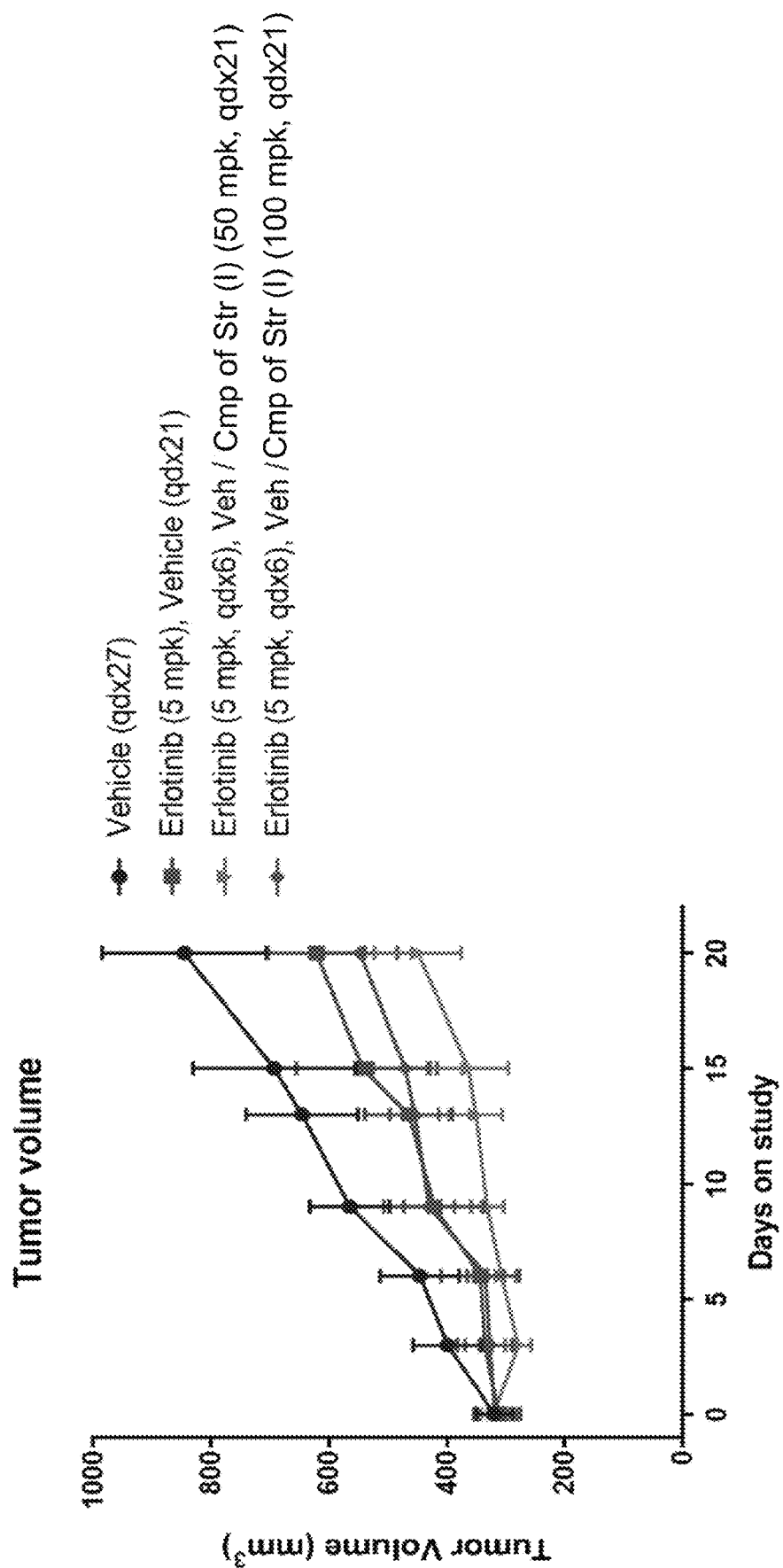
FIG. 11 depicts the tumor volume over time for mice treated with erlotinib in combination with the compound of Structure (I).

Tumor volume and body weights were measured and recorded twice weekly (FIG. 11). Upon completion of the study, mice were euthanized and tumor tissues were harvested. As the data of FIG. 11 shows, treatment with the compound of Structure (I) and erlotinib showed a reduction of tumor volume. In addition, the mice treated in the study shown in FIG. 11 showed no significant body weight reduction or fluctuation while the compound of Structure (I) was being administered.

Example 7

Biochemical PKM2 Activity

Figure 12:
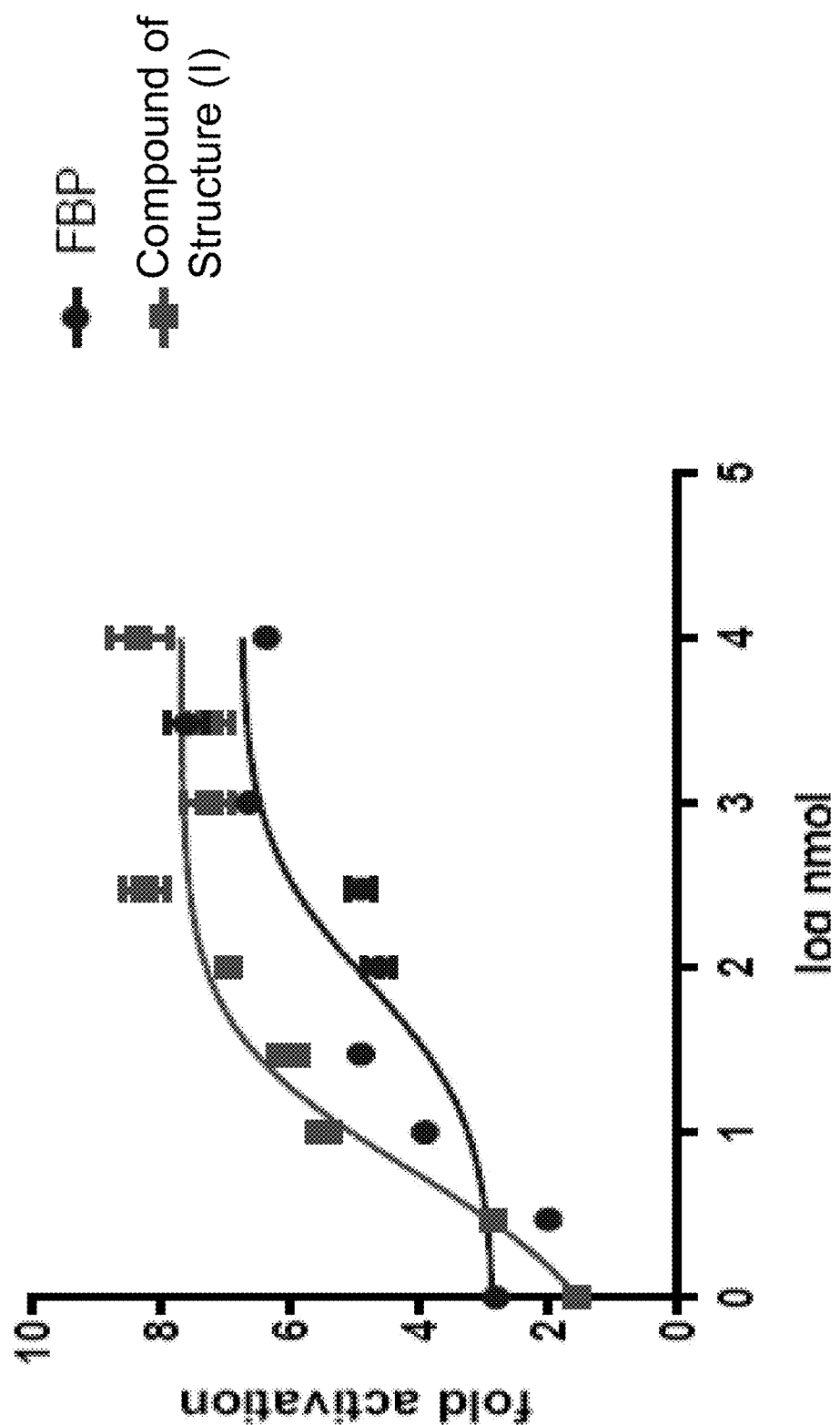
FIG. 12 compares fold activation of A549 cells treated with folate binding protein (FBP) or the compound of Structure (I).
Figure 13:
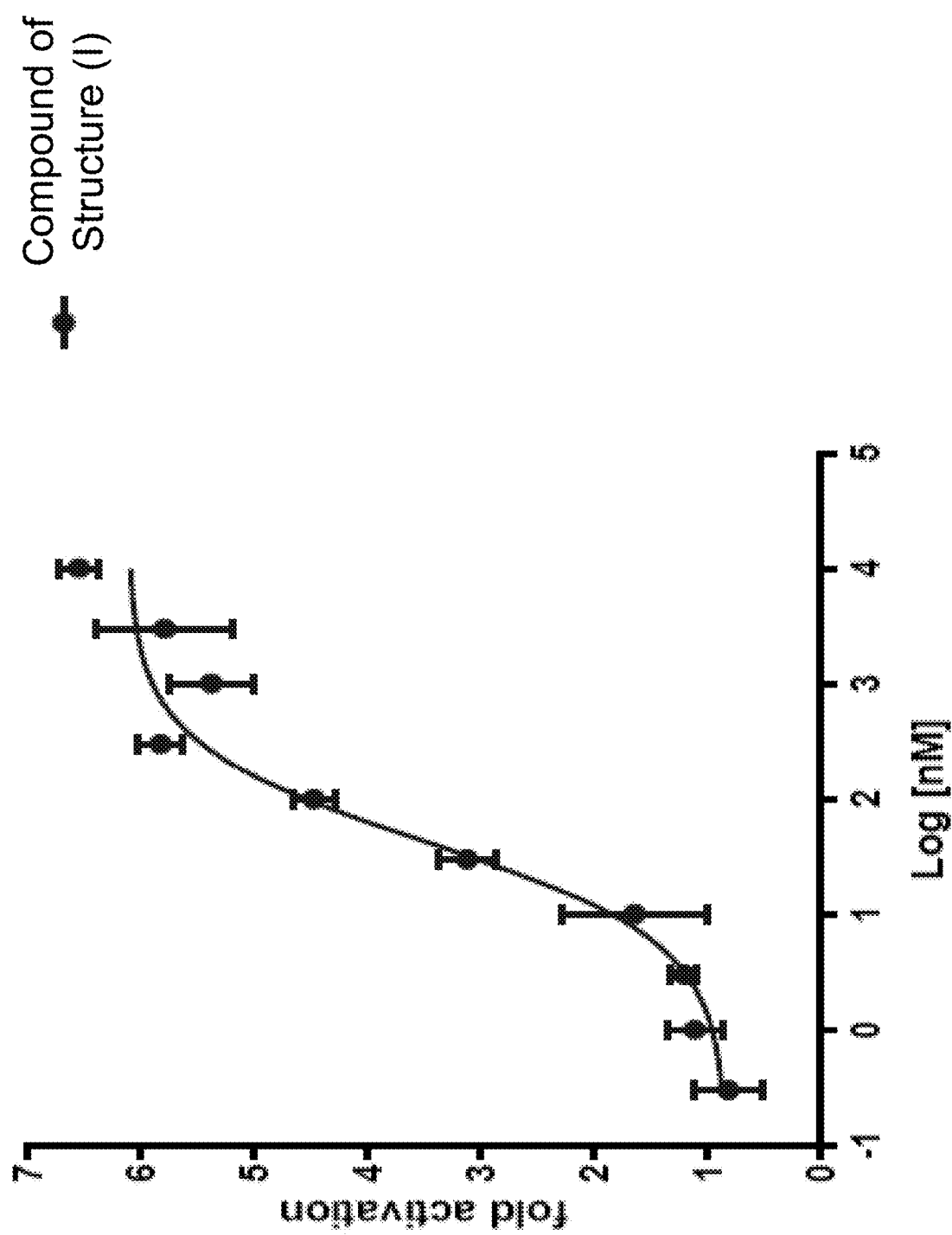
FIG. 13 shows the PKM2 activity for A549 cells treated with a compound of Structure (I).

A549 lung cancer cells were plated at 20,000 cells per well (96-well plate) in MEM media plus 10% FBS, with no additional glutamine or pyruvate. Following overnight incubation, cells were washed with PBS followed by 4 hour incubation in MEM media. The compound of Structure (I) was added to the cells in 1% final concentration DMSO. Folate binding protein (FBP) was used as a control compound and was purchased from Sigma Aldrich and prepared in PBS. After 30 minutes, cells were lysed, and pyruvate kinase activity in lysates was determined by Pyruvate Kinase Activity Assay (BioVision, Milpitas, Calif.). Maximum velocity values were calculated from the kinetic data, and $AC_{50}$ values were determined using Prism GraphPad Software (La Jolla, Calif.). Results are presented graphically in FIG. 12. The data for FIG. 13 was acquired according to this description as well.

Example 8

Cell Viability Assay

Figure 14:
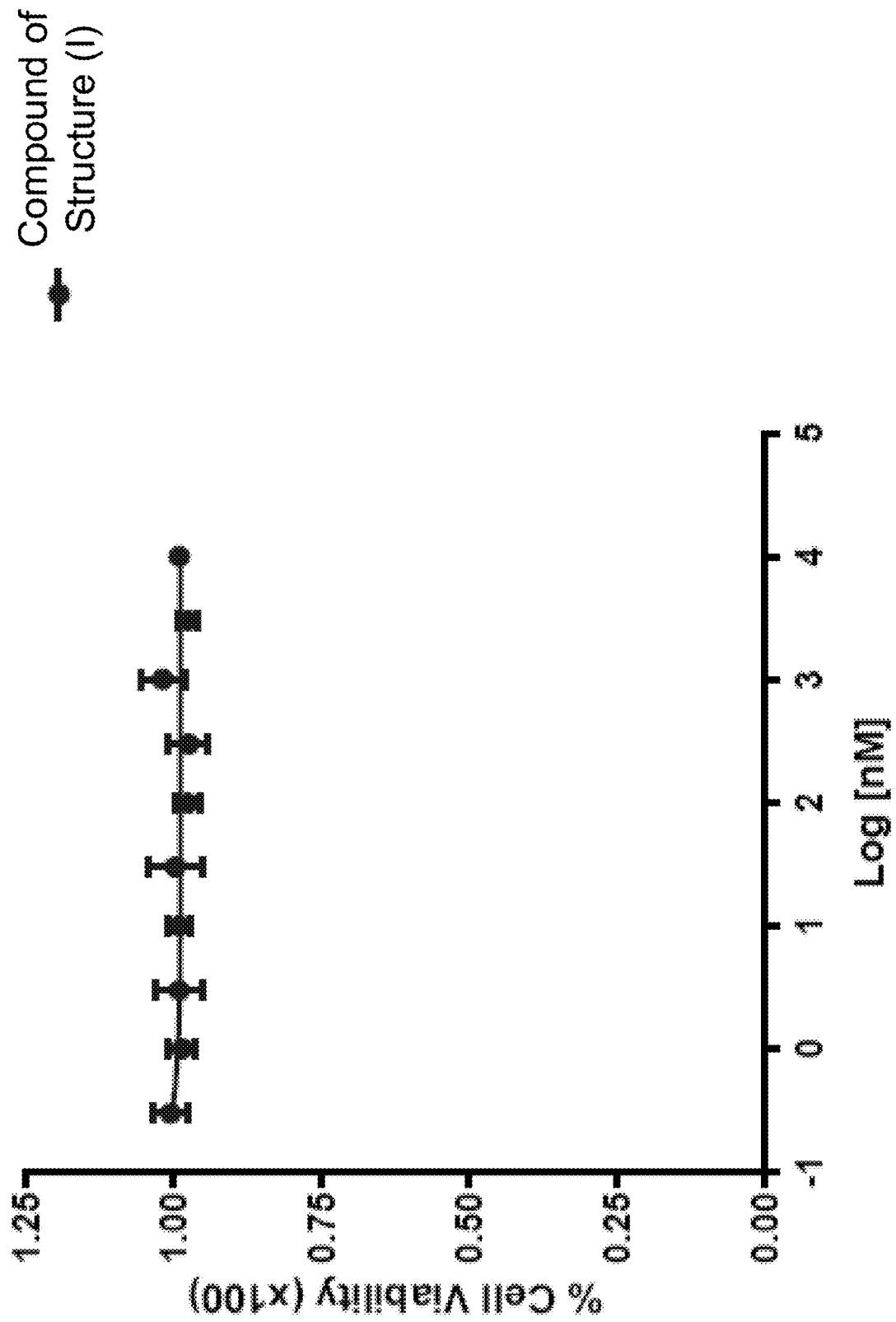
FIG. 14 shows cell viability for cells treated with the compound of Structure (I).

Cells were seeded at 5000 cells per well (in 96-well plate) in RPMI media+5% dialyzed serum. After 18 hours, DMSO or a compound of Structure (I) in 0.1% final concentration DMSO was added. After 72 hours, cell viability was determined according to the Cell-titer-Glo assay kit and protocol from Promega Biosciences, LLC (Madison, Wis.), and $EC_{50}$ values were determined using Prism GraphPad Software (La Jolla, Calif.) (FIG. 14).

Example 9

Cell Viability Assay

Figure 15:
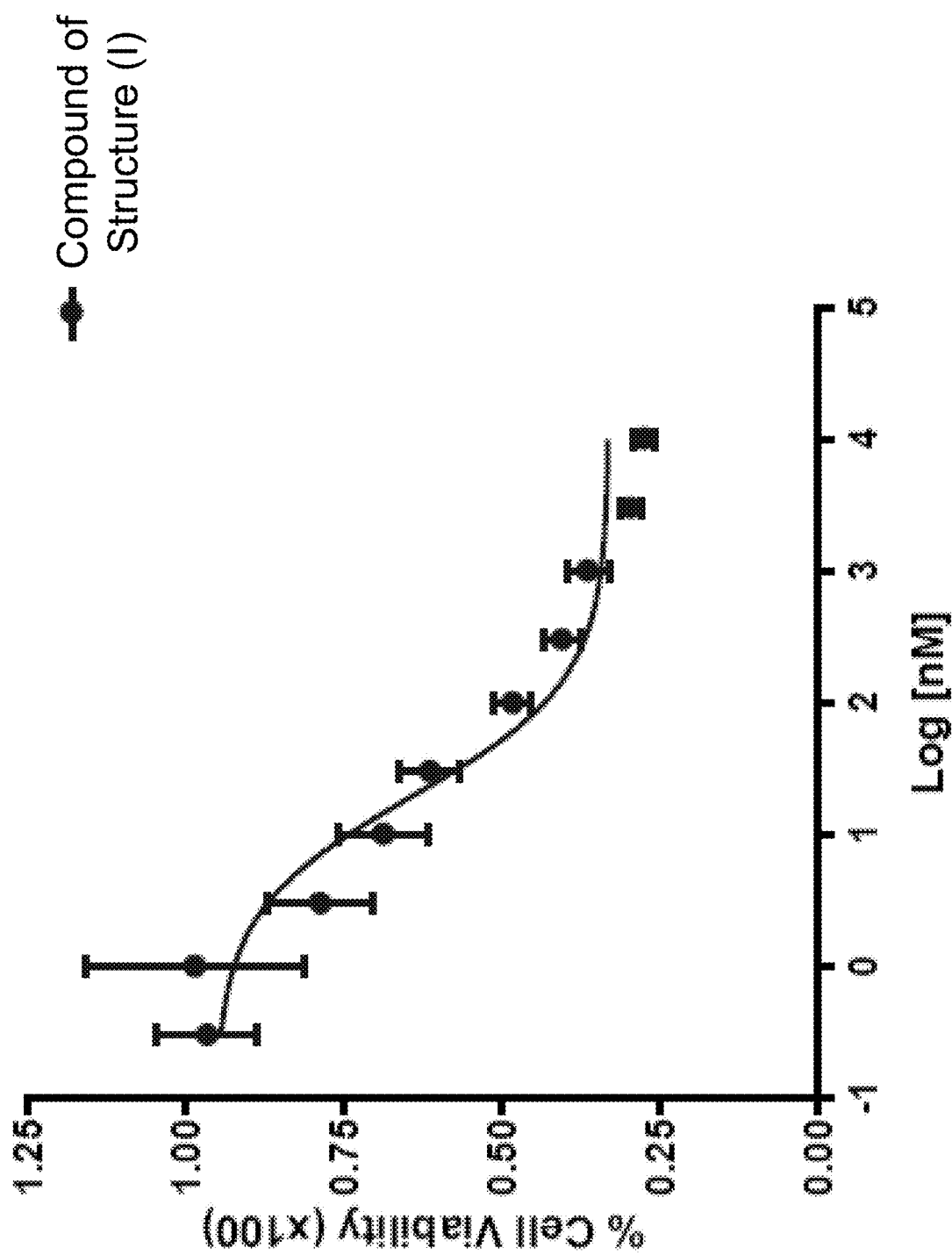
FIG. 15 shows cell viability for cells treated with the compound of Structure (I) when media was lacking serine.

Cells were seeded at 5000 cells per well (in 96-well plate) in MEM media lacking serine+5% dialyzed serum. After 18 hours, DMSO or a compound of Structure (I) in 0.1% final concentration DMSO was added. After 72 hours, cell viability was determined according to the Cell-titer-Glo assay kit and protocol from Promega Biosciences, LLC (Madison, Wis.), and $EC_{50}$ values were determined using Prism GraphPad Software (La Jolla, Calif.) (FIG. 15).

Figure 16:
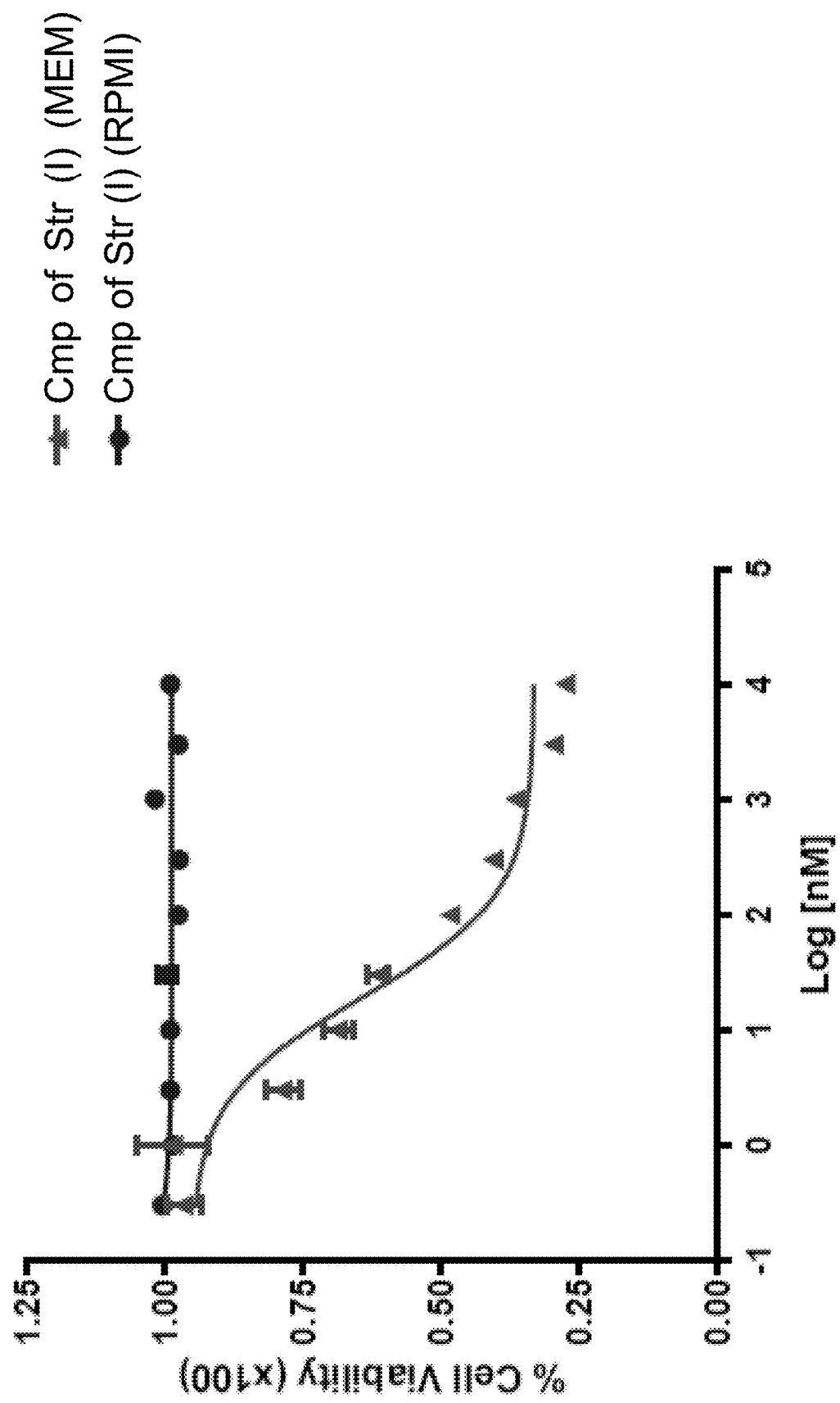
FIG. 16 compares the data shown in FIG. 14 and FIG. 15.

FIG. 16 shows that the compound of Structure (I) affects cells significantly less when serine is present in the media when tested according to the methods described in Examples 8 and 9.

Example 10

Study of PKM2 Activator and Glutathione Reduction

Figure 17:
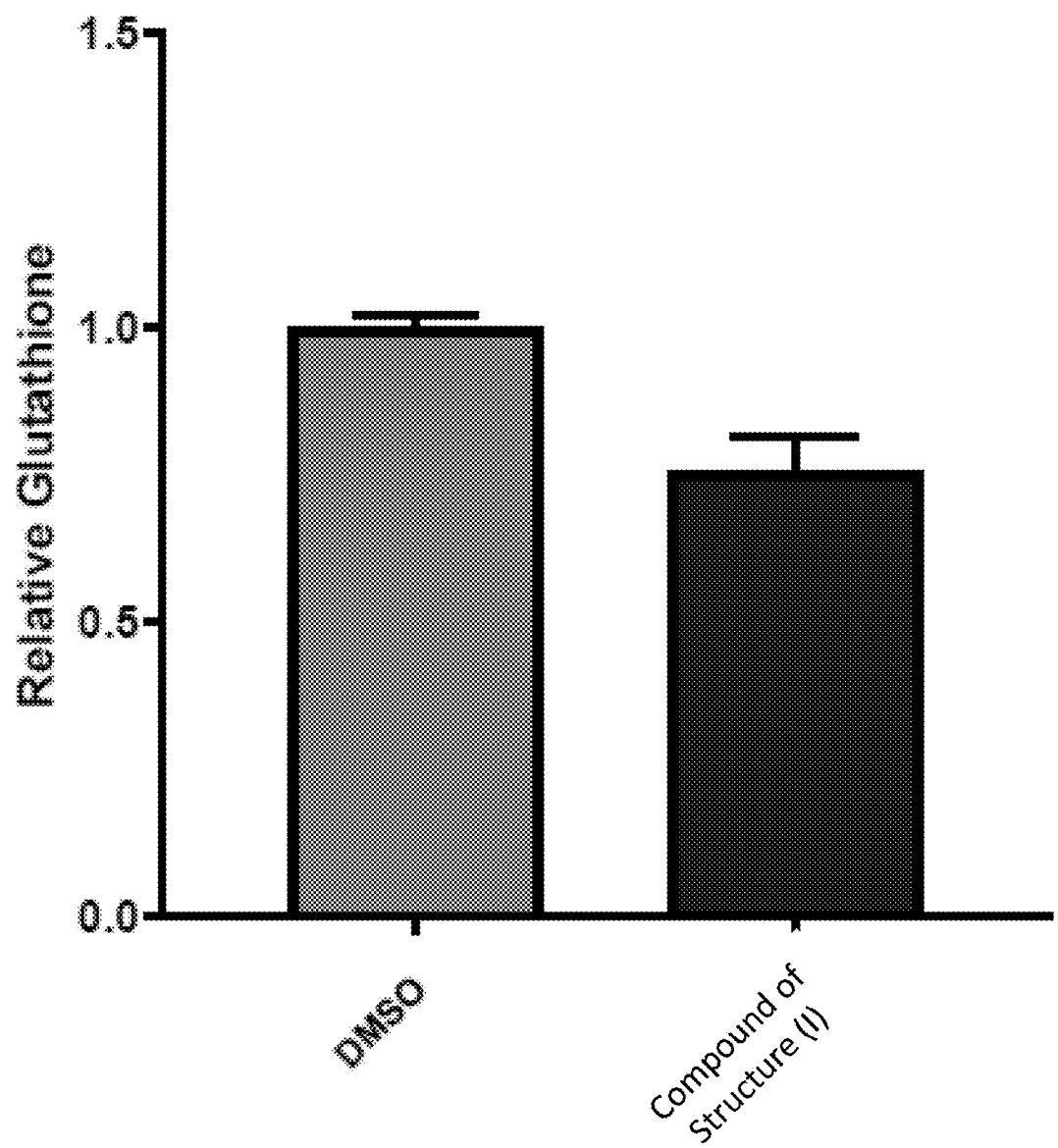
FIG. 17 depicts glutathione reduction in A549 cells when treated with the compound of Structure (I) compared to a control sample.

A549 cells were prepared according to Example 3 above. Those cells were treated with a compound of Structure (I) at a concentration of 10 and in replicates of 10 for each condition, relative to a blank control (DMSO). Cells were treated for 24 hours, and then glutathione levels were determined using a GSH-Glo assay kit and procedure from Promega (catalog #V6912). FIG. 17 shows decreased levels of glutathione for cells exposed to a compound of Structure (I).

Example 11

In Vivo Synergy Between a PKM2 Activator and Immunotherapy Agents in A Syngeneic MC38 Colon Carcinoma Mouse Model The efficacy of the compound of Structure (I) alone or in combination with anti-PD-1 and/or anti-CTLA-4 antibodies in a syngeneic MC38 colon carcinoma mouse model was investigated.

Summary

On Day 1 female C57BL/6 mice bearing MC38 tumors were sorted into 16 groups (n=10) with group mean tumor volumes between 90 and 92 150 mm³. Mice received oral (p.o.) doses of control vehicle or the compound of Structure (I) and/or intraperitoneal (i.p.) doses of anti-PD-1 and/or anti-CTLA-4 antibodies. Vehicle (Tween 80, ethanol, PEG400 in DI water (ratio 2:10:30:58)) and the compound of Structure (I) (25, 50, 100 or 200 mg/kg) were administered orally (p.o.) once a day for twenty-one days (qd×21). An anti-PD-1 antibody was administered intraperitoneally (i.p.) at 5 mg/kg twice a week for two weeks (biwk×2), and an anti-CTLA-4 antibody was administered i.p. at 5 mg/kg on Day 1 and 2.5 mg/kg on Days 4 and 7. The anti-PD-1 antibody is directed against the programmed cell death protein 1 (PD-1) surface receptor expressed on T cells, B cells and macrophages. Treatment groups were as follows: Group 1 (control) received vehicle; Groups 2 through 5 received 25, 50, 100 or 200 mg/kg the compound of Structure (I), respectively; Group 6 received 5 mg/kg anti-PD-1; Groups 7 through 10 received anti-PD-1 and 25, 50, 100 or 200 mg/kg of the compound of Structure (I), respectively; Group 11 received anti-CTLA-4 at 5 and 2.5 mg/kg; Groups 12 and 13 received anti-CTLA-4 and 50 or 100 mg/kg of the compound of Structure (I), respectively; Group 14 received anti-PD-1 and anti-CTLA-4; and Groups 15 and 16 received anti-PD-1, anti-CTLA-4 and 50 or 100 mg/kg of the compound of Structure (I), respectively. Tumor volumes were measured twice per week using calipers. When the mean tumor volume of the control group approached 1000 mm³ on Day 19, all groups were analyzed for tumor growth inhibition (TGI) and the study endpoint was converted to tumor growth delay (TGD). Animals were then individually euthanized as they reached the endpoint tumor volume of 1000 mm³ or the last day of the study (Day 44), whichever came first. At endpoint, serum, spleens and tumors were collected from all available animals in all groups and full blood volume (serum), spleens and tumors were sampled, and the time to endpoint (TTE) for each mouse was calculated.

Efficacy was determined based both on percent TGI and on percent TGD. TGI is defined as the percent difference between the Day 19 median tumor volumes (MTVs) of treated and control mice, and differences between MTVs were deemed significant at $P \leq 0.05$ using the Mann-Whitney U test. TGD is defined as the percent increase in median time-to-endpoint (TTE) in treated versus control mice and was evaluated using the log rank (Mantel-Cox) test. Log rank significance of differences in survival among groups, regression responses, and mean tumor growth were also calculated. Treatment tolerability was assessed based on body weight changes and observations of treatment-related (TR) side effects.

Control Group 1 displayed a median tumor volume (MTV) of 1216 mm$^3$ on Day 19. By comparison, the compound of Structure (I) monotherapy Groups 2 through 5 did not achieve statistically significant Day 19 tumor growth inhibition (TGI) with MTVs of 864 mm$^3$ (29% TGI), 1008 mm$^3$ (17% TGI), 666 mm$^3$ (45% TGI) and 726 mm$^3$ (40% TGI), respectively. Immune checkpoint inhibitors anti-PD-1 and anti-CTLA-4 alone or combined significantly inhibited tumor growth (TGI) by 68% (Group 6 anti-PD-1), 92% (Group 11 anti-CTLA-4) and 98% (Group 14 anti-PD-1 and anti-CTLA-4). The addition of the compound of Structure (I) to immune checkpoint inhibitor treatments did not significantly increase the Day 19 TGIs obtained by immune checkpoint inhibitors. Compared to anti-PD-1 monotherapy (TGI=68%), TGIs of 76, 70, 64 and 57% were achieved in treatment Groups 7 through 10, which combined anti-PD-1 with 25, 50, 100 and 200 mg/kg of the compound of Structure (I), respectively. Similarly, compared to anti-CTLA-4 monotherapy (TGI=92%), TGIs of 96 and 90% were achieved in treatment Groups 12 and 13, which combined anti-CTLA-4 with 50 and 100 mg/kg of the compound of Structure (I), respectively; and compared to the anti-PD-1/anti-CTLA-4 combination therapy (TGI=98%), TGIs of 98 and 99% were achieved in triple combination therapy Groups 15 and 16 (anti-PD-1/anti-CTLA-4 and 50 or 100 mg/kg of the compound of Structure (I), respectively).

The median time to endpoint (TTE) of vehicle control Group 1 was 16.9 days, establishing a maximum possible tumor growth delay (TGD) of 160% (equivalent to 27.1 days) in this 44-day study, and individual TTEs in the control group ranged from 13.9 to 44 days. By comparison, the compound of Structure (I) monotherapy Groups 2 through 5 did not achieve statistically significant tumor growth delay (TGD) with TTEs of 21.1 (25% TGD), 18.9 (12% TGD), 22.5 (33% TGD), and 20.8 days (23% TGD), respectively. Immune checkpoint inhibitors anti-PD-1 and anti-CTLA-4 alone or combined significantly delayed tumor growth (TGD) by 100% (Group 6 anti-PD-1) and by the maximum possible 160% in Group 11 anti-CTLA-4 and Group 14 anti-PD-1/anti-CTLA-4. The addition of the compound of Structure (I) to immune checkpoint inhibitor treatments did not significantly increase the level of tumor growth delay (TGD) obtained by immune checkpoint inhibitors. When compared to Group 6 anti-PD-1 monotherapy (TGD=100%), TGDs of 85% (Group 7) and 79% (Groups 8 through 10) were achieved in treatment groups that combined anti-PD-1 with 25, 50, 100 and 200 mg/kg of the compound of Structure (I), respectively. Similarly, compared to anti-CTLA-4 monotherapy (TGD=160%), TGDs of 160 and 153% were achieved in treatment Groups 12 and 13, which combined anti-CTLA-4 with 50 or 100 mg/kg of the compound of Structure (I), respectively; and compared to anti-PD-1/anti-CTLA-4 combination therapy (TGD=160%), TGDs of 160% were also achieved in triple combination therapy Groups 15 and 16 that received anti-PD-1/anti-CTLA-4 and 50 or 100 mg/kg of the compound of Structure (I), respectively.

Animals reached the end of the study on Day 44 in several treatment groups, including one animal in control Group 1 with a tumor volume of 787 mm$^3$; one animal in 100 mg/kg of the compound of Structure (I) monotherapy Group 4, which displayed partial regression (PR) and a final tumor volume of 162 mm$^3$; four animals in anti-PD-1 monotherapy Group 6 with a mean tumor volume of 410 mm$^3$, one of which displayed complete regression (CR); two animals in anti-PD-1/25 mg/kg of the compound of Structure (I) Group 7 with a mean tumor volume of 554 mm$^3$; and four or more animals with group mean tumor volumes of 1 mm$^3$ in all treatment groups receiving anti-CTLA-4 (Groups 11 through 16). Groups 11-16 tumor free survivors (TFS) ranged from three (Groups 11 and 13) to five (Group 12) to seven (Groups 14 and 15) to ten (Group 16).

Group mean body weight losses were negligible, ranging from 0 (Group 7) to 2.6% on Day 2 in control Group 1. One death due to unknown causes (NTRu) occurred in control Group 1 on Day 22. Two deaths designated as treatment-related (TR) occurred, one each in compound of Structure (I) monotherapy Groups 3 (50 mg/kg, TR death on Day 19) and 5 (200 mg/kg, TR death on Day 15). Additional deaths (designated NTRu) during the study occurred in Group 4 (one), Group 5 (one), Group 7 (two), Group 8 (one), Group 9 (two), Group 10 (one), Group 11 (one), Group 12 (two), Group 13 (one), and Group 15 (one); and dates of NTRu deaths ranged from Day 18 to Day 33. Clinical observations were limited to occasional signs of tumor progression (tumor ulcerations, ruffled fur, hunched posture, lethargy, and/or low body temperature) that occurred across multiple treatment groups.

In summary, under the conditions of this study, the compound of Structure (I) monotherapy at doses of 25, 50, 100 or 200 mg/kg did not significantly slow the progression of established syngeneic MC38 colon carcinoma tumors based on measurements of Day 19 median tumor volumes (MTVs) used to determine tumor growth inhibition (TGI) or median times to the Day 44 study endpoint (TTEs) used to determine tumor growth delay (TGD). The addition of the compound of Structure (I) at doses of 25, 50, 100 and/or 200 mg/kg did not significantly improve the efficacy of immune checkpoint inhibitor anti-PD-1 monotherapy, anti-CTLA-4 monotherapy or anti-PD-1/anti-CTLA-4 combination therapy, with the exception of 100 mg/kg of the compound of Structure (I)/anti-PD-1/anti-CTLA-4 triple therapy, which produced 10/10 tumor free survivors (TFS) compared to 7/10 in the anti-PD-1/anti-CTLA-4 combination group.

Methods and Materials

Mice

Female C57BL/6 mice (C57BL/6NCrl, Charles River) were ten weeks old with a body weight (BW) range of 18.3 to 24.9 g on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fiber. The mice were housed on irradiated Enrich-o'Cobs™ Laboratory Animal Bedding in static microisolators on a 12-hour light cycle at 20-22° C. (68-72° F.) and 40-60% humidity. The recommendations of the *Guide for Care and Use of Laboratory Animals* with respect to restraint, husbandry, surgical procedures, feed and fluid regulation, and veterinary care were observed.

Tumor Cell Culture

The MC38 murine colon carcinoma cell line for this study was obtained from the American Type Culture Collection (ATCC) and maintained in Dulbecco's Modified Eagle Medium (DMEM) containing 10% fetal bovine serum, 2 mM glutamine, 100 units/mL penicillin G sodium, 100 μg/mL streptomycin sulfate, and 25 μg/mL gentamicin. The cells were cultured in tissue culture flasks in a humidified incubator at 37° C., in an atmosphere of 5% $CO_2$ and 95% air.

In Vivo Implantation and Tumor Growth

On the day of implant, cultured MC38 cells were harvested during log phase growth and re-suspended in RPMI media at a concentration of 5×10$^6$ cells/mL. Tumors were initiated by subcutaneously implanting 5×10$^5$ MC38 cells (in a 0.1 mL suspension) into the right flank of each test animal. Tumors were monitored as their volumes approached the target range of 80 to 120 mm$^3$. Seventeen days after tumor cell implantation, on Day 1 of the study, animals were sorted into sixteen groups (n=10 per group) with individual tumor volumes of 63 to 144 mm$^3$, and group mean tumor volumes from 90 to 92 mm$^3$. Tumors were measured twice a week for the duration of the study in two dimensions using calipers, and volume was calculated using the formula:

$$\text{Tumor Volume}(\text{mm}^3) = \frac{w^2 \times l}{2}$$

where w=width and l=length, in mm, of the tumor. Tumor weight was estimated with the assumption that 1 mg is equivalent to 1 mm$^3$ of tumor volume.

Therapeutic Agents

The compound of Structure (I) (Lot No. SY18001241-11) was stored at −20° C. protected from the light prior to formulation. Anti-PD-1 clone RMP1-14 (rat IgG) (BioXcell Lot No. 717918O1) was stored at 4° C. and protected from the light. Anti-CTLA-4 clone 9H10 (BioXcell Lot No. 648318M1) was stored appropriately. The vehicle used was Tween 80, ethanol, PEG400 in DI water (ratio 2:10:30:58).

Dosing solutions of the compound of Structure (I) were prepared weekly by suspending the compound sequentially in ethanol, Tween 80, PEG400 and DI water, with gentle heat (≤40° C.) and/or sonication to yield colorless opaque dosing suspensions of 2.5, 5, 10 and 20 mg/mL in vehicle (Tween 80, ethanol, PEG400 in DI water (ratio 2:10:30:58)). Dosing solutions were stored at 4° C. protected from the light and delivered 25, 50, 100 and 200 mg/kg when administered in a volume of 10 mL/kg (0.2 mL/20 g mouse), adjusted to the body weight of each animal.

On each day of dosing, anti-PD-1 antibody stock solution (7.24 mg/mL) was diluted with PBS to obtain a dosing solution with a final concentration of 0.5 mg/mL, which delivered 5 mg/kg when administered in a volume of 10 mL/kg.

On each day of dosing, anti-CTLA-4 antibody stock solution (7.57 mg/mL) was diluted with PBS to obtain dosing solutions with a final concentration of 0.5 mg/mL (on Day 1) or 0.25 mg/mL (on Days 4 and 7), which delivered 5 and 2.5 mg/kg, respectively, when administered in a volume of 10 mL/kg.

Treatment

On Day 1 of the study, female C57BL/6 mice with established subcutaneous MC38 tumors were sorted into sixteen groups (n=10), and dosing was initiated according to the treatment plan summarized in Tables 4 and 5. All therapies were dosed at 10 mL/kg (0.200 mL per 20 gram mouse), scaled to the body weight of each animal.

Group 1 received vehicle (Tween 80, ethanol, and PEG400 in DI water (ratio 2:10:30:58)) orally (p.o.) once a day for twenty-one days (qd×21) and served as the control and benchmark group for tumor engraftment and progression.

Groups 2 through 5 received the compound of Structure (I) at 25, 50, 100 or 200 mg/kg, respectively, p.o., qd×21.

Group 6 received anti-PD-1 at 5 mg/kg, intraperitoneally (i.p.), twice a week for two weeks (biwk×2).

Groups 7 through 10 received anti-PD-1 at 5 mg/kg, i.p., biwk×2 in combination with the compound of Structure (I) at 25, 50, 100 or 200 mg/kg, respectively, p.o., qd×21.

Group 11 received anti-CTLA-4 i.p. at 5 mg/kg on Day 1 and at 2.5 mg/kg on Days 4 and 7.

Groups 12 and 13 received anti-CTLA-4 i.p. at 5 mg/kg on Day 1 and at 2.5 mg/kg on Days 4 and 7 in combination with the compound of Structure (I) at 50 or 100 mg/kg, respectively, p.o., qd×21.

Group 14 received anti-PD-1 at 5 mg/kg, i.p., biwk×2 and anti-CTLA-4 i.p. at 5 mg/kg on Day 1 and at 2.5 mg/kg on Days 4 and 7.

Groups 15 and 16 received anti-PD-1 at 5 mg/kg, i.p., biwk×2 and anti-CTLA-4 i.p. at 5 mg/kg on Day 1 and at 2.5 mg/kg on Days 4 and 7 in combination with the compound of Structure (I) at 50 or 100 mg/kg, p.o., qd×21.

Sampling

Serum, tumor and spleen samples were collected from all available animals at endpoint, defined as the last day of the study (Day 44) or when individual tumor volumes approached 1000 mm$^3$. Full blood volume was collected by terminal cardiac puncture under isoflurane anesthesia, processed for serum (without anti-coagulant), and stored at −80° C. Tumors and spleens were harvested immediately after blood collection, and tumors were divided into two portions. One tumor portion and the spleen from each available animal were fixed in formalin for forty-eight hours, transferred to 70% ethanol and stored at room temperature until shipment at ambient temperature at the end of the study. (Tumors ≤100 mm$^3$ were not divided and were only fixed in formalin.) The second tumor portion from each available animal was snap frozen and stored at −80° C. until shipment on dry ice at the end of the study.

Tumor Growth Inhibition (TGI) Analysis

Individual tumors were measured twice per week. Tumor growth inhibition (TGI) was determined on Day 19 using MTV (n), the median tumor volume for the number of animals, n. Percent tumor growth inhibition (% TGI) was defined as the difference between the MTV of the designated control group (Group 1) and the MTV of the treatment group, expressed as a percentage of the MTV of the control group:

% TGI=[1−(MTV treated/MTVcontrol)]×100

Any agent that leads to at least 60% TGI by this criterion is considered to be potentially therapeutically active.

Endpoint and Tumor Growth Delay (TGD) Analysis

After the day of TGI analysis, the study was continued in order to evaluate tumor growth delay (TGD). Individual animals were euthanized when tumors reached the endpoint volume of 1000 mm$^3$ or at the end of the study (Day 44), whichever came first. Animals that exited the study for tumor volume endpoint were documented as euthanized for tumor progression (TP), with the date of euthanasia. The time to endpoint (TTE) for analysis was calculated for each mouse by the following equation:

$$TTE = \frac{\log_{10}(endpointvolume) - b}{m}$$

where TTE is expressed in days, endpoint volume is expressed in mm$^3$, b is the intercept, and m is the slope of the line obtained by linear regression of a log-transformed tumor growth data set. The data set consisted of the first observation that exceeded the endpoint volume used in analysis and the three consecutive observations that immediately preceded the attainment of this endpoint volume. The calculated TTE is usually less than the TP date, the day on which the animal was euthanized for tumor size. Animals with tumors that did not reach the endpoint volume were assigned a TTE value equal to the last day of the study (Day 44). In instances in which the log-transformed calculated TTE preceded the day prior to reaching endpoint or exceeded the day of reaching tumor volume endpoint, a linear interpolation was performed to approximate the TTE. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death.

Treatment outcome was evaluated from tumor growth delay (TGD), which is defined as the increase in the median time to endpoint (TTE) in a treatment group compared to the control group:

$$TGD = T - C,$$

expressed in days, or as a percentage of the median TTE of the control group:

$$\% \; TGD = \frac{T-C}{C} \times 100$$

where:
T=median TTE for a treatment group, and
C=median TTE for the designated control group.

MTV and Criteria for Regression Responses

Treatment efficacy may also be determined from the tumor volumes of animals remaining in the study on the last day and from the number and magnitude of regression responses. The MTV(n) is defined as the median tumor volume on Day 44 in the number of evaluable animals remaining, n, whose tumors have not attained the volume endpoint.

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm$^3$ for one or more of these three measurements. In a CR response, the tumor volume is less than 13.5 mm$^3$ for three consecutive measurements during the study. Animals were scored only once during the study for a PR or CR event and only as a CR if both PR and CR criteria were satisfied. Any animal with a CR response at the end of the study was additionally classified as a tumor-free survivor (TFS).

Toxicity

Animals were weighed daily on Days 1-5, then twice a week until the completion of the study. The mice were observed frequently for overt signs of any adverse treatment related (TR) side effects, and clinical signs were recorded when observed. Individual body weight was monitored as per protocol, and any animal with weight loss exceeding 30% for one measurement or exceeding 25% for three consecutive measurements was euthanized as a TR death (for treated groups). Group mean body weight loss was also monitored. Acceptable toxicity was defined as a group mean body weight (BW) loss of less than 20% during the study and no more than 10% TR deaths among the remaining animals in each group at the time of death. Any dosing regimen resulting in greater toxicity was considered above the maximum tolerated dose (MTD). Dosing was suspended in any group where mean weight loss exceeded acceptable limits. If group mean body weight recovered to acceptable levels, then dosing was modified to lower levels and/or reduced frequency then resumed. Deaths were classified as TR if they were attributable to treatment side effects as evidenced by clinical signs and/or necropsy. A TR classification was also assigned to deaths by unknown causes during the dosing period or within 14 days of the last dose. A death was classified as NTR if there was no evidence that death was related to treatment side effects. NTR deaths may be further characterized based on cause of death. A death was classified as NTRa if it resulted from an accident or human error. A death was classified as NTRm if necropsy indicated that it might have resulted from tumor dissemination by invasion and/or metastasis. A death was classified as NTRu if the cause of death was unknown and there was no available evidence of death related to treatment side effects, metastasis, accident or human error, although death due to treatment side effects cannot be excluded.

Statistical and Graphical Analyses

Prism 8.0 (GraphPad) for Windows was used for graphical presentations and statistical analyses. Study groups experiencing toxicity beyond acceptable limits (>20% group mean body weight loss or greater than 10% treatment related deaths) or having fewer than five evaluable observations, were not included in statistical analyses, being classified as non-evaluable (ne). Statistical analyses of the differences between Day 19 median tumor volumes (MTVs) of two groups were accomplished using the Mann-Whitney U test. Survival was analyzed by the Kaplan-Meier method. The log rank test, which evaluates overall survival experience, was used to analyze the significance of the differences between the TTE values of two groups. Log rank analysis includes the data for all animals in a group except those assessed as NTR deaths. Two-tailed statistical analyses were conducted at significance level P=0.05. Statistical tests were not adjusted for multiple comparisons. Prism summarizes test results as not significant (ns) at P>0.05, significant (symbolized by "*") at $0.01 < P \leq 0.05$, very significant ("") at $0.001 < P \leq 0.01$, and extremely significant ("*") at $P \leq 0.001$. Because tests of statistical significance do not provide an estimate of the magnitude of the difference between groups, all levels of significance were described as either significant or not significant within the text of this report.

Figure 18A:
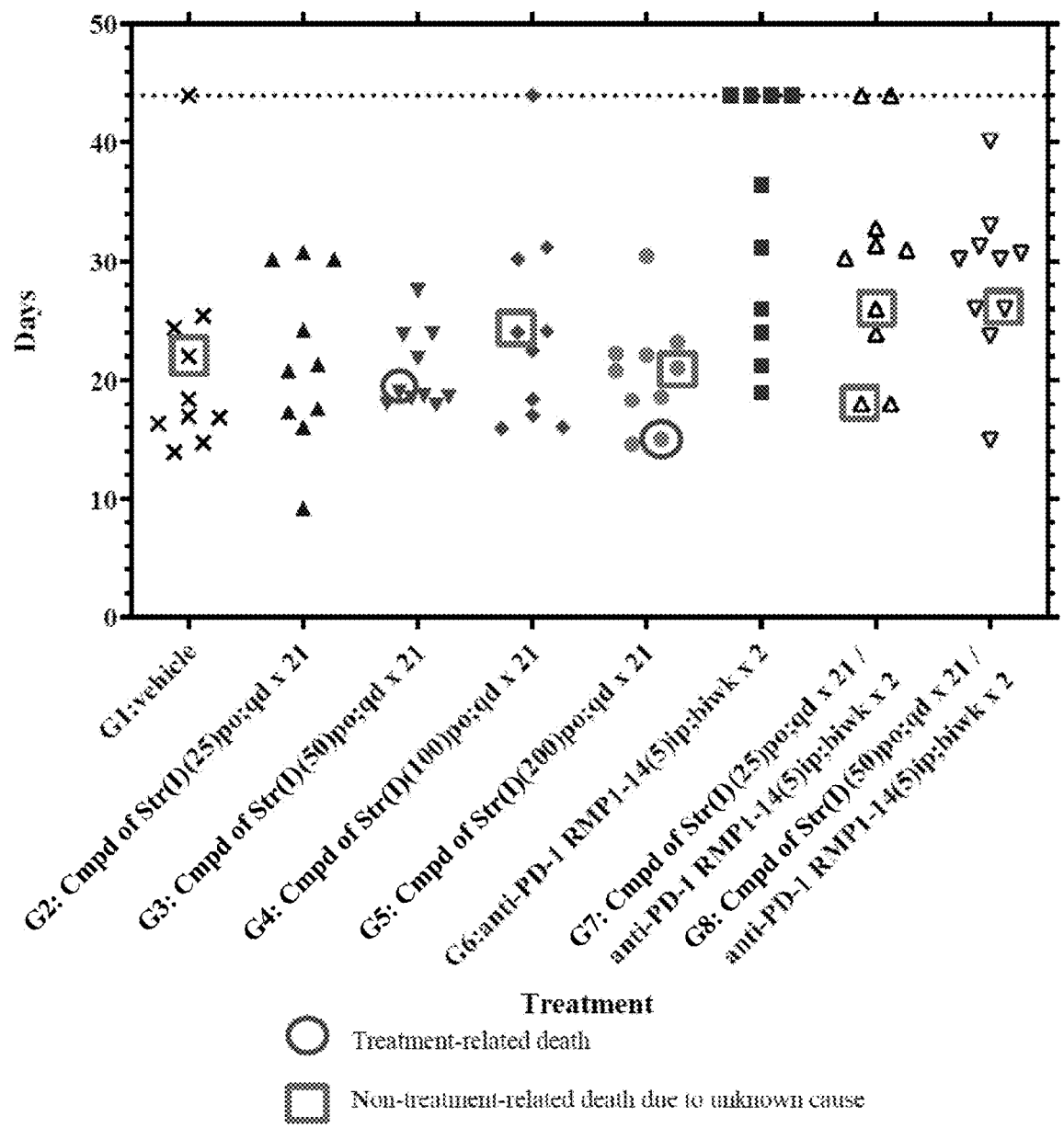
FIGS. 18A and 18B show plots of individual times to endpoint for mice in the MC38-e423 study described in Example 11.
Figure 18B:
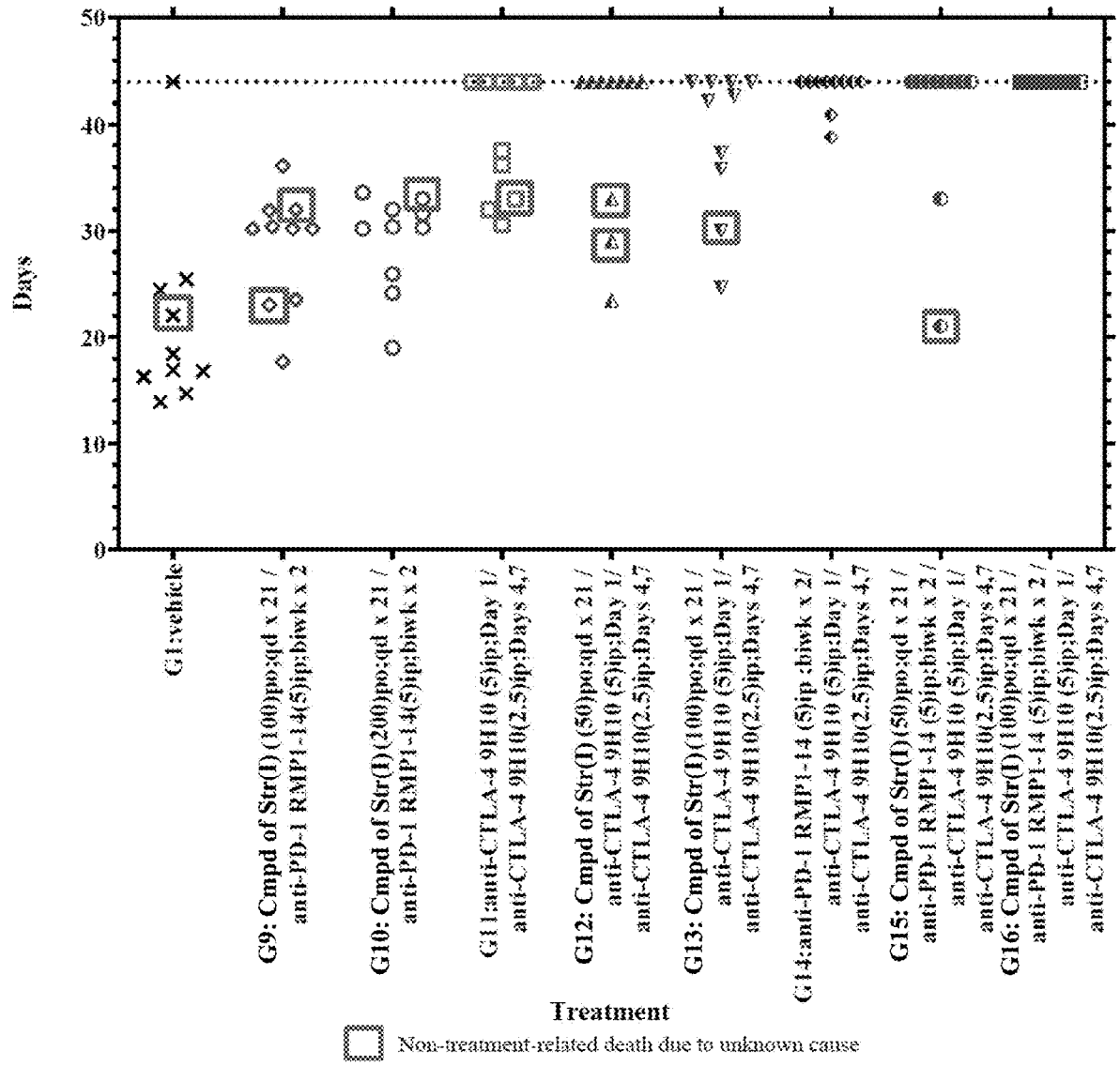
Figure 19A:
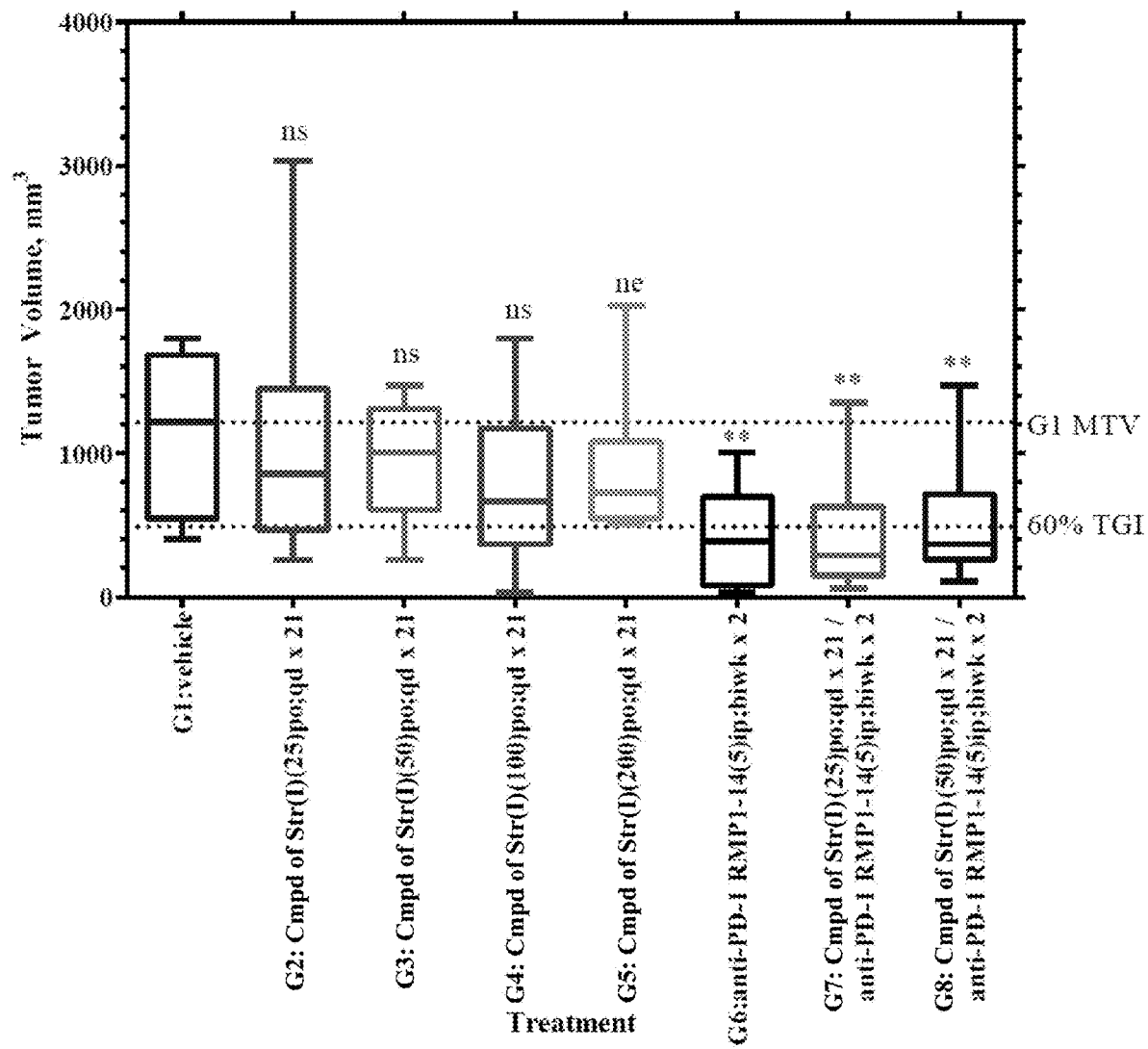
FIGS. 19A and 19B show plots of tumor volume distribution on day 19 in mice for the MC38-e423 study described in Example 11.
Figure 19B:
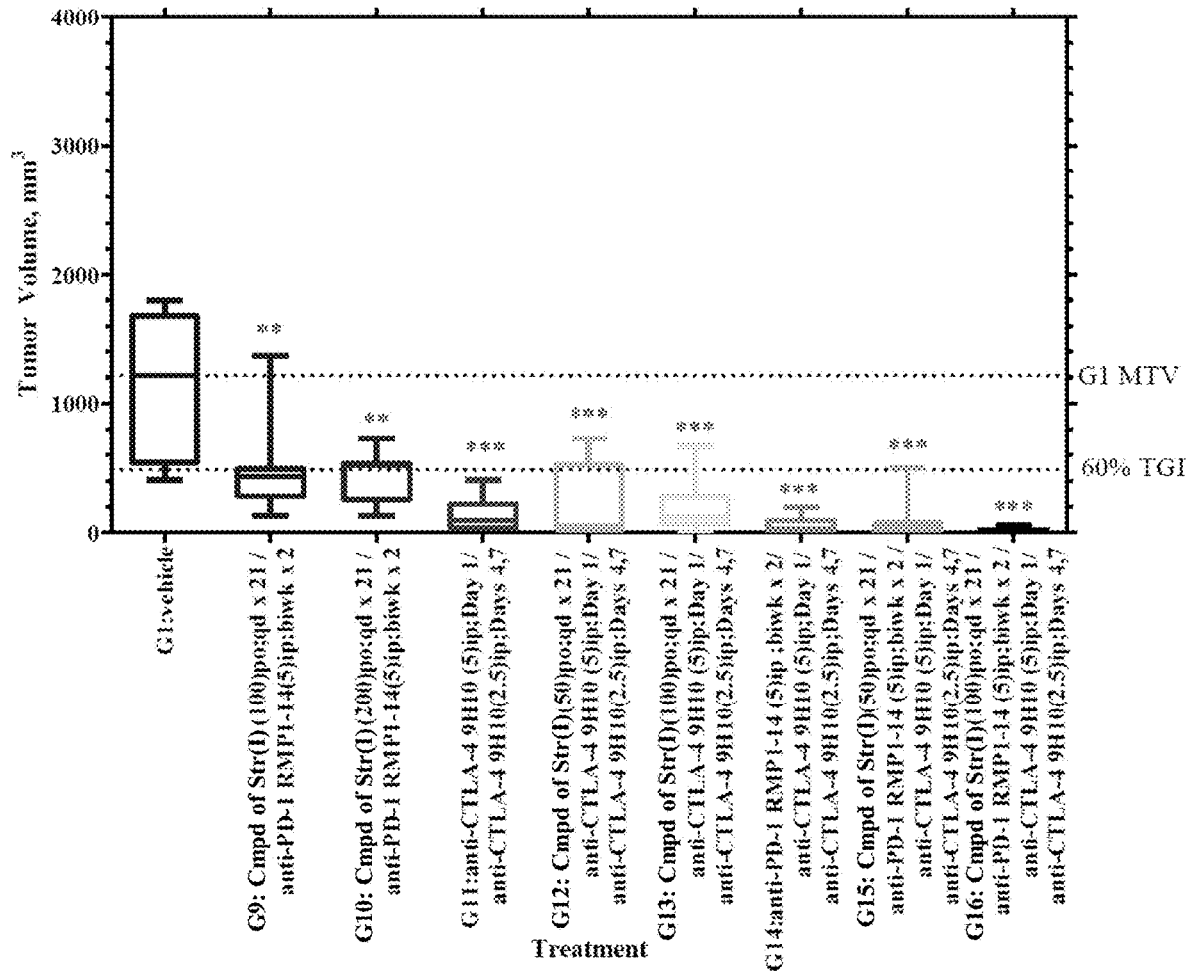

Scatter plots were constructed to show TTE values for individual mice, by group (FIGS. 18A and 18B). Box and whisker plots were constructed showing the distribution of Day 19 tumor volume data by group, with the "box" representing the 25th and 75th percentile of observations, the horizontal line representing the median of observations, and the "whiskers" representing the extreme observations (FIGS. 19A and 19B). Individual (FIGS. 22A through 22B), group median (FIGS. 20A and 20B, upper panels), and mean (FIGS. 21A and 21B) tumor volumes were plotted as a function of time. When an animal exited the study due to tumor size, the final tumor volume recorded for the animal was included with the data used to calculate the mean volume at subsequent time points. Error bars (when present) indicate one standard error of the mean (SEM). Kaplan-Meier plots show the percentage of animals in each group remaining in the study versus time; note that the Kaplan-Meier plot and log rank test share the same TTE data sets.

Figure 23A:
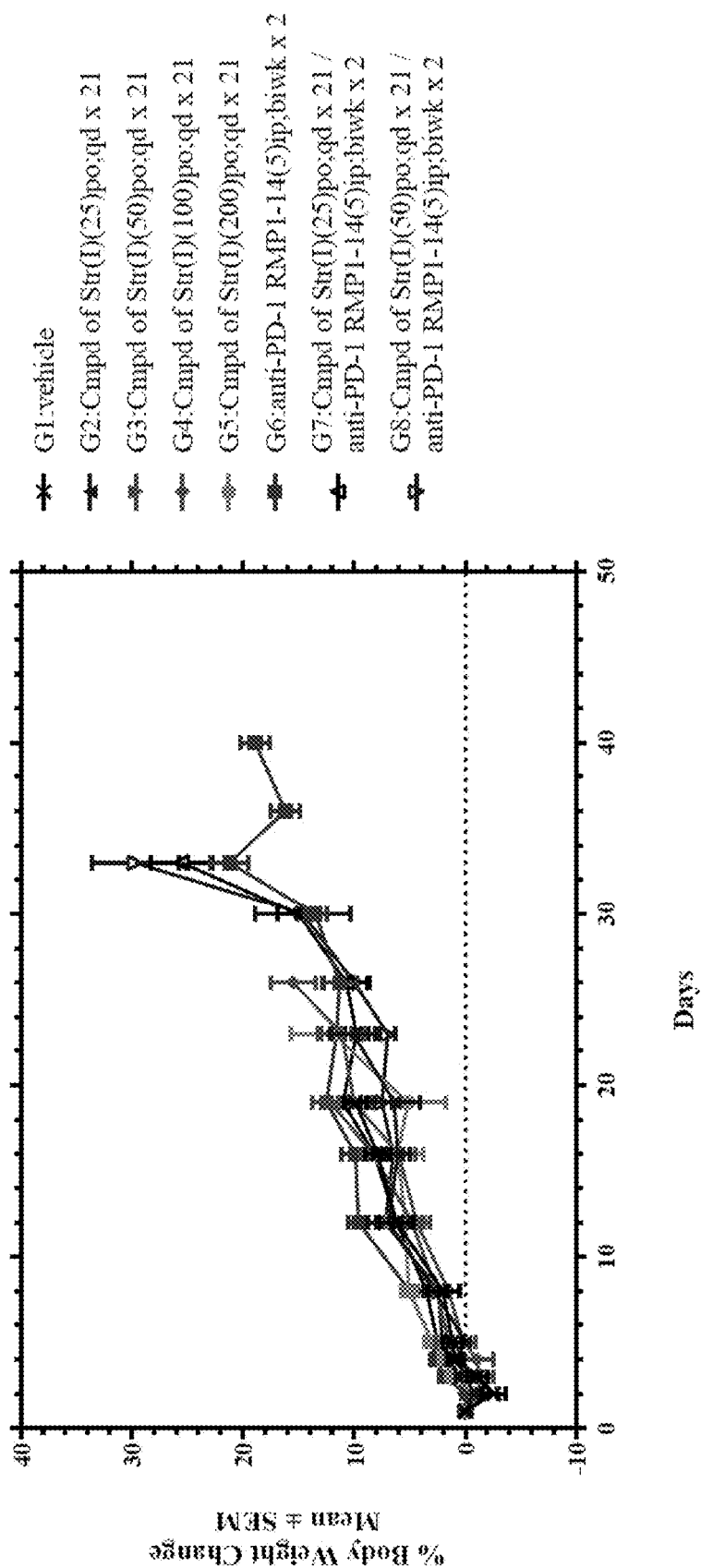
FIGS. 23A and 23B show plots of percent group mean body weight changes from day 1 in mice for the MC38-e423 study described in Example 11.
Figure 23B:
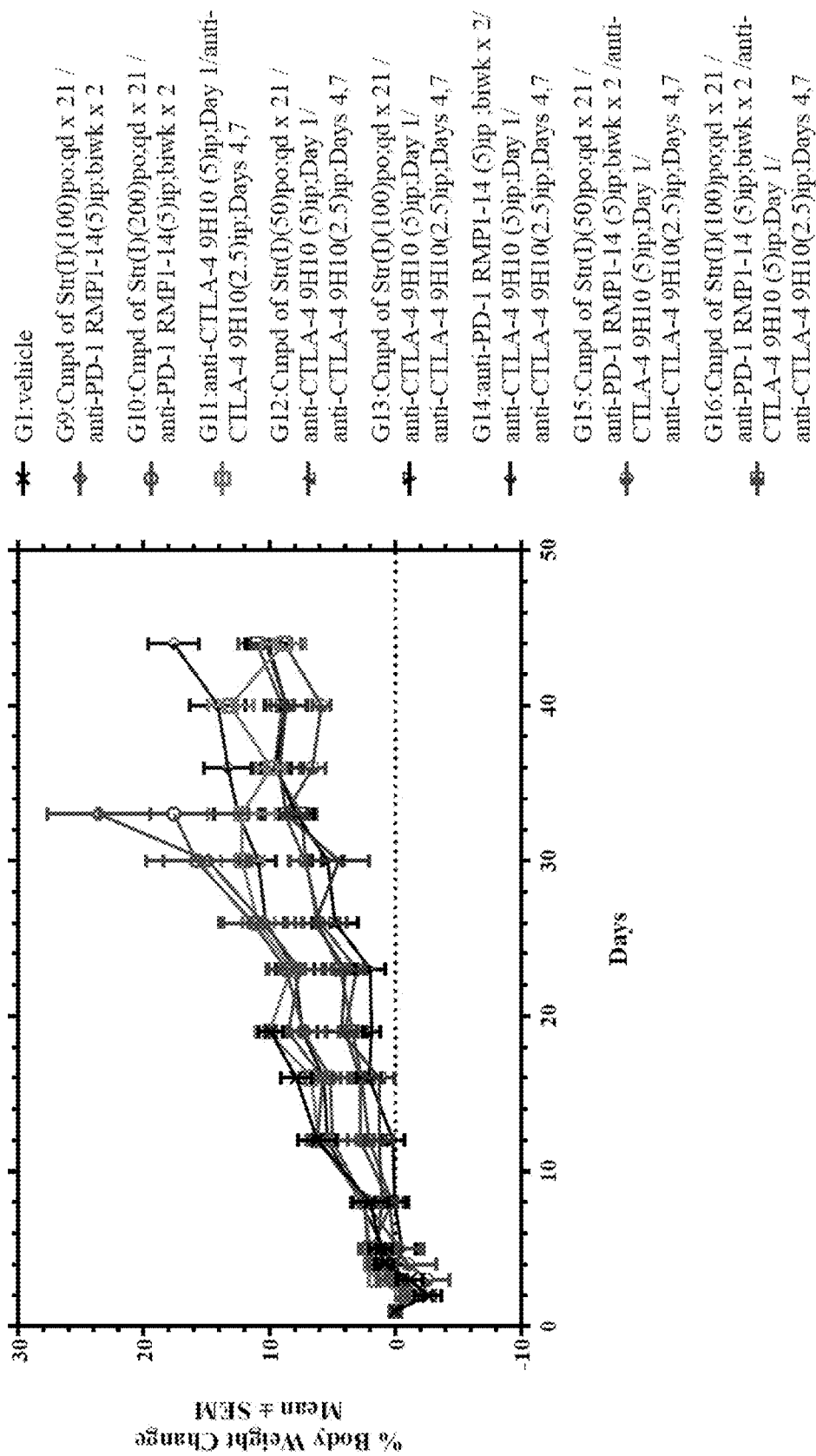

Group body weight changes over the course of the study were plotted as percent mean change from Day 1 (FIGS. 23A and 23B).

Tumor growth and body weight plots excluded the data for animals assessed as NTR deaths, and were truncated when fewer than 50% of the animals in a group remained in the study.

Results

Figure 20A:
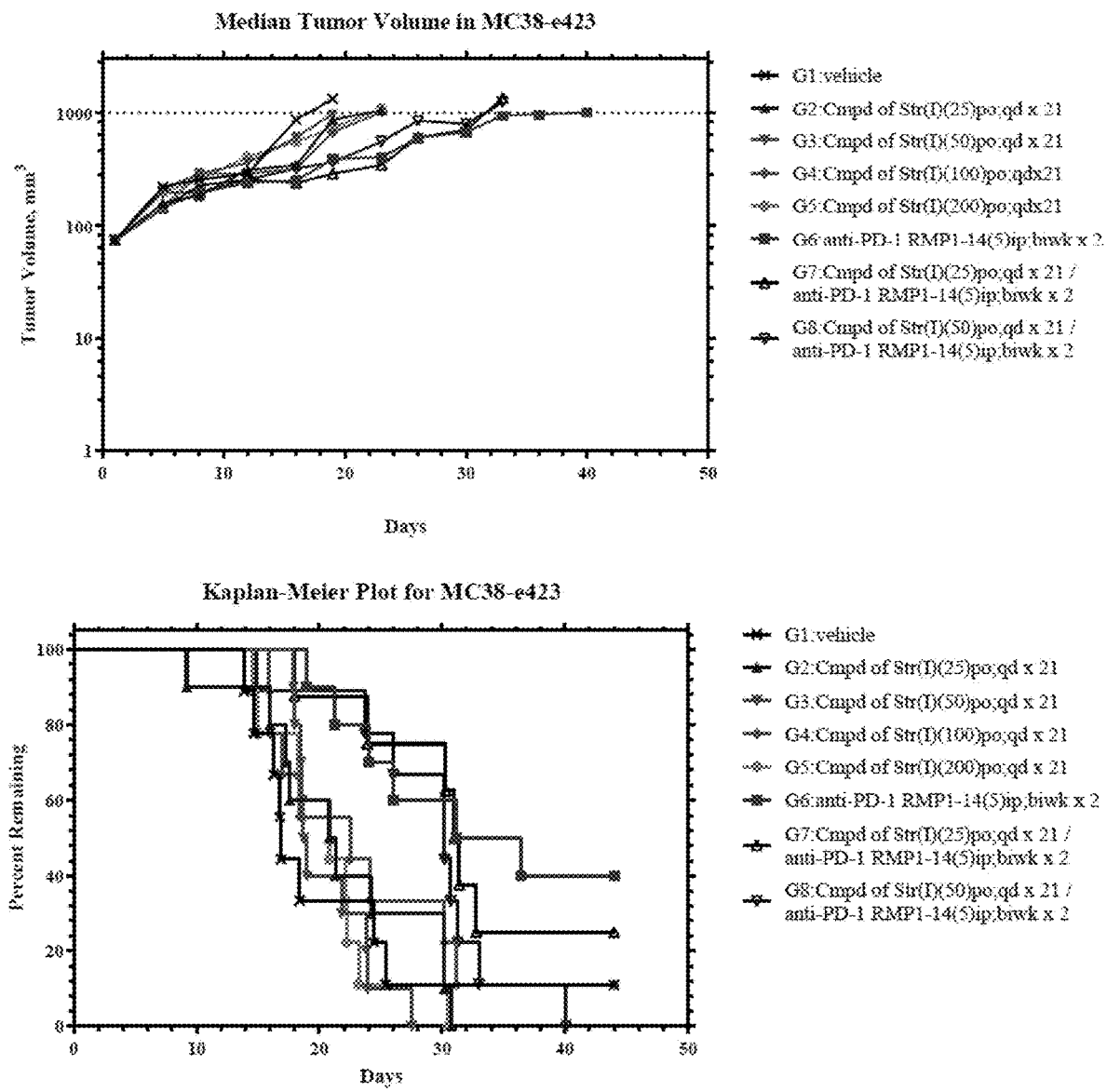
FIGS. 20A and 20B show plots of median tumor growth (upper panel) and Kaplan-Meier (lower panel) plots for mice in the MC38-e423 study described in Example 11.
Figure 20B:
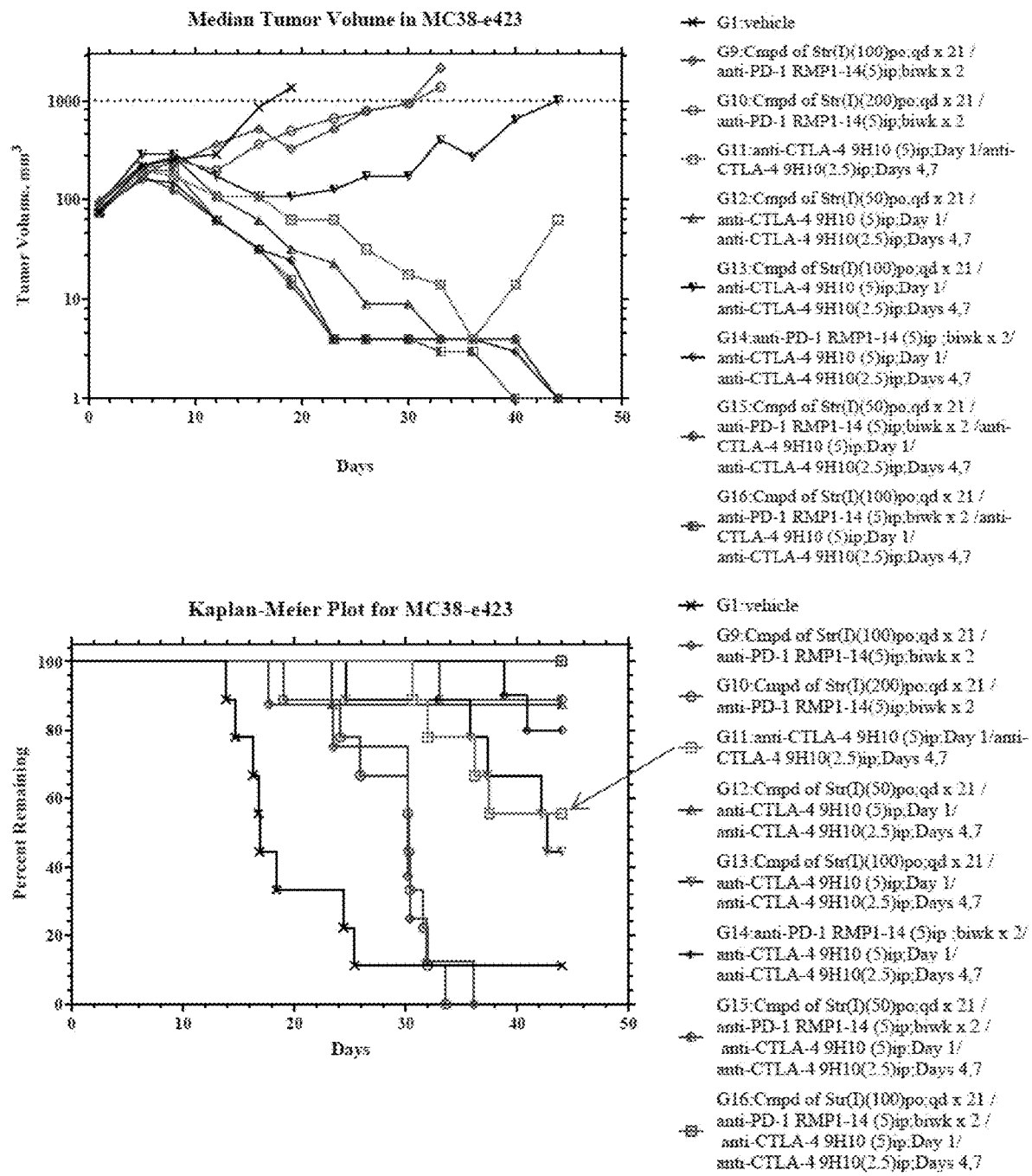
Figure 21A:
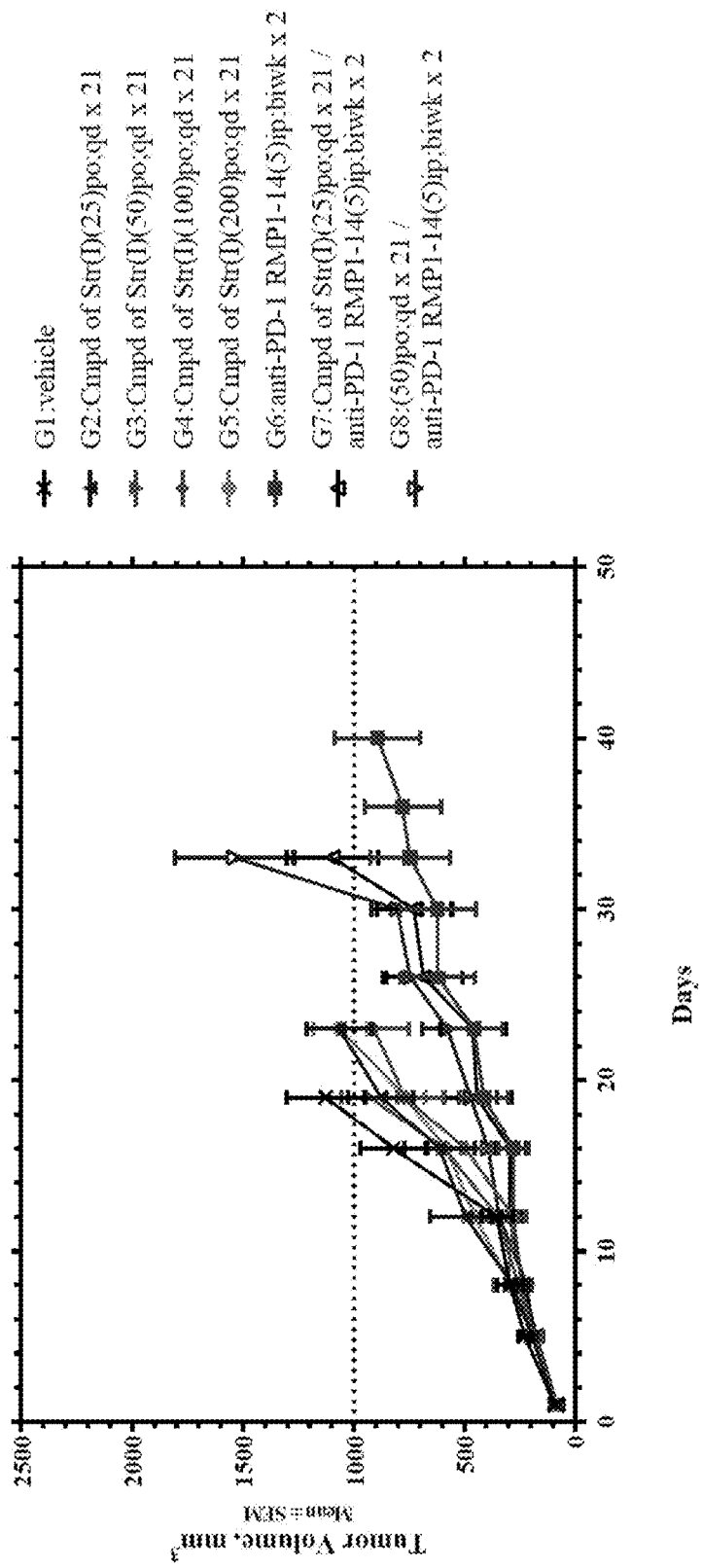
FIGS. 21A and 21B show plots of mean tumor volume in mice for the MC38-e423 study described in Example 11.
Figure 21B:
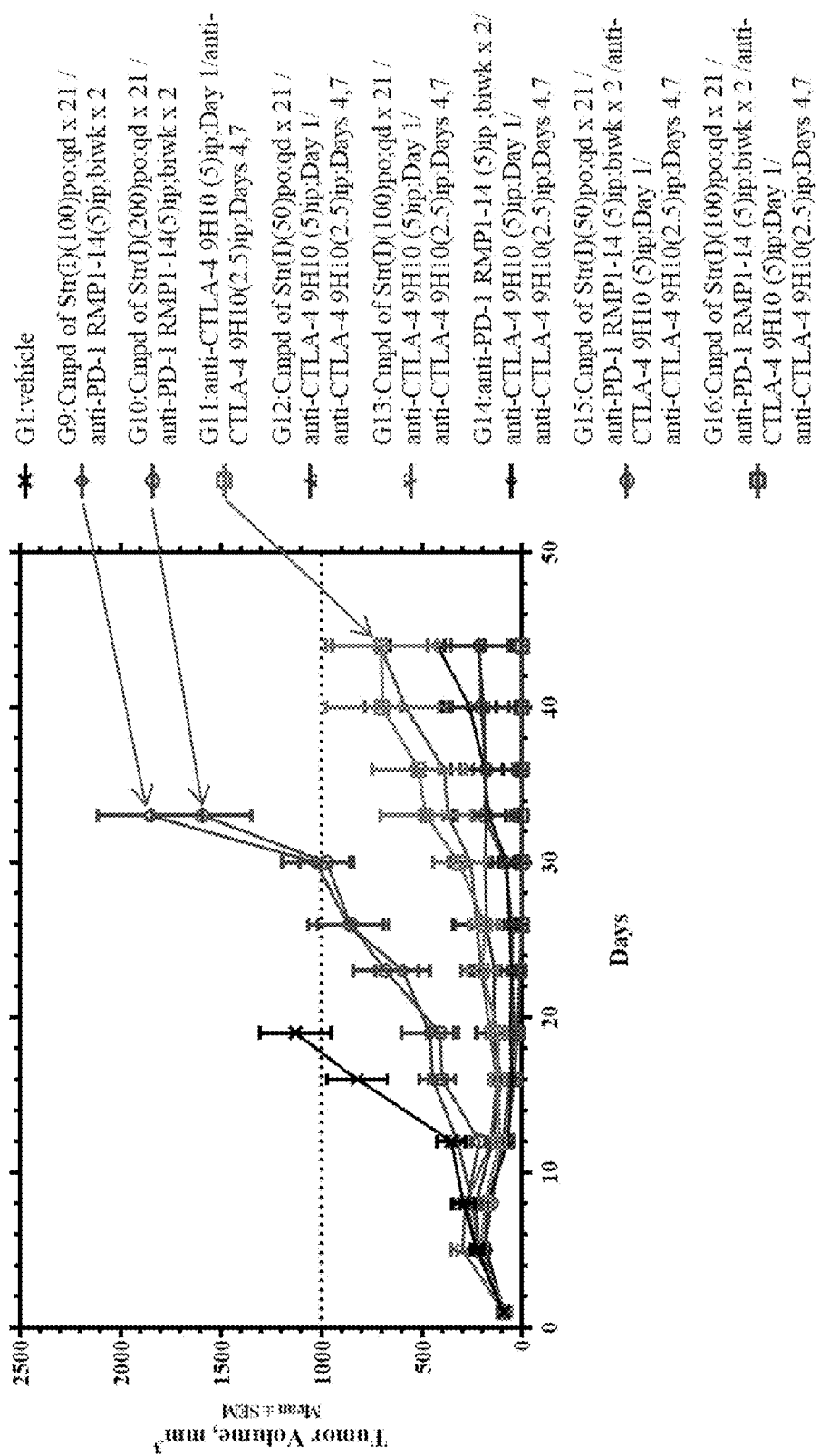
Figure 22A:
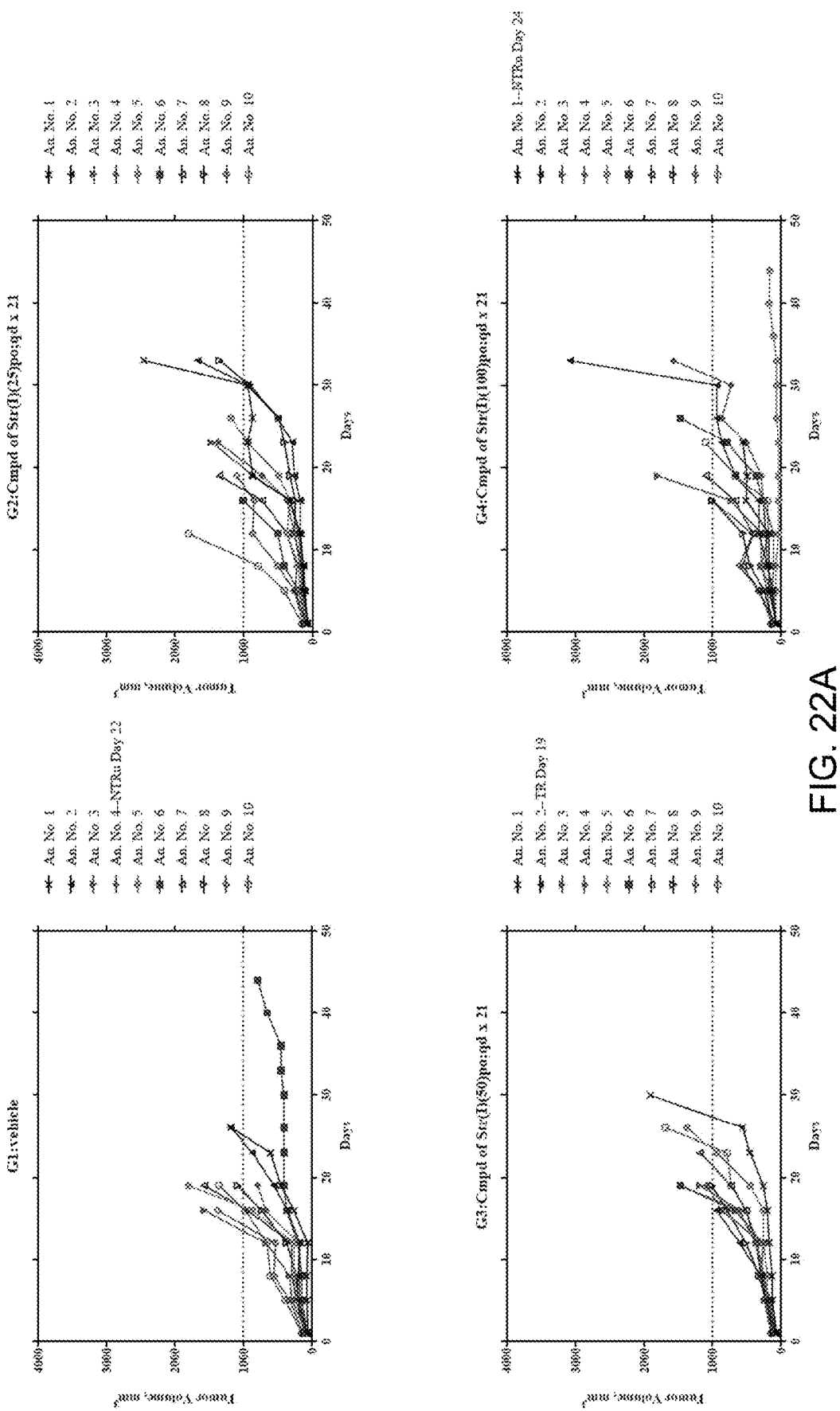
FIGS. 22A-22D show plots of individual tumor growth curves in mice for the MC38-e423 study described in Example 11.

Groups in the MC38-e423 study were treated in accordance with the protocol summarized in Table 4. Table 5 presents the tumor growth delay (TGD) treatment responses for each group and Table 6 summarizes Day 19 tumor growth inhibition (TGI) results. FIGS. 18A and 18B provide scatter plots showing the individual times to endpoint (TTEs) by group. FIGS. 19A and 19B illustrate tumor volume distribution by group on Day 19 using a box and whisker plot. FIGS. 20A and 20B include plots of group median tumor growth (upper panels) and Kaplan-Meier survival (lower panels) for the study. FIGS. 21A and 21B plot group mean tumor growth±SEM, and FIGS. 22A through 22D provide individual tumor growth curves by group. FIGS. 23A and 23B illustrate percent mean body weight changes from Day 1 for each group.

Efficacy

Growth of MC38 Tumors in Vehicle-Treated Control Mice (Group 1)

Group 1 mice received vehicle (Tween 80, ethanol, and PEG400 in DI water (ratio 2:10:30:58)) p.o., qd×21 and provided the standard of comparison for all treatment groups. The control times to endpoint (TTEs) ranged from 13.9 to 44 days (FIG. 18A). The median tumor volume (MTV) on Day 19 reached 1216 mm$^3$ (FIG. 19A, Table 6). The median TTE for Group 1 was 16.9 days, establishing a maximum possible tumor growth delay TGD of 27.1 days (160%) in this 44-day study (FIG. 18A, Table 5). Control tumor growth was progressive (FIG. 20A (upper panel), FIG. 21A, and FIG. 22A.). One animal was found dead due to unknown causes (NTRu) on Day 22, and one animal reached the end of the study with a tumor volume of 787 mm$^3$.

Response to Treatment with the Compound of Structure (I) (Groups 2 Through 5)

Group 2 received the compound of Structure (I) at 25 mg/kg p.o. qd×21. The Group 2 MTV at Day 19 was 864 mm$^3$, corresponding to a nonsignificant (ns) 29% inhibition of tumor growth (TGI) compared to Group 1 (P>0.05, Table 6, FIG. 19A). The median TTE for Group 2 was 21.1 days (FIG. 18A), corresponding to a statistically nonsignificant TGD of 25% compared to control Group 1 (P<0.05, Table 5). Group 2 tumor growth was progressive (FIG. 20A (upper panel), FIG. 21A, and FIG. 22A.). All animals exited the study before Day 44 (Table 5).

Group 3 received the compound of Structure (I) at 50 mg/kg p.o. qd×21. The Group 3 MTV at Day 19 was 1008 mm$^3$, corresponding to a nonsignificant 17% TGI compared to Group 1 (Table 6, FIG. 19A). The median TTE for Group 3 was 18.9 days (FIG. 18A), corresponding to a statistically nonsignificant 12% TGD (P<0.05, Table 5). One treatment related (TR) death occurred on Day 19, and all animals exited the study before Day 44. Group 3 tumor growth was progressive (FIG. 20A (upper panel), FIG. 21A, and FIG. 22A.).

Group 4 received the compound of Structure (I) at 100 mg/kg p.o. qd×21. The Group 4 MTV at Day 19 was 666 mm$^3$, corresponding to a nonsignificant 45% TGI compared to Group 1 (Table 6, FIG. 19A). The median TTE for Group 4 was 22.5 days (FIG. 18A), corresponding to a statistically nonsignificant 33% TGD (P<0.05, Table 5). One animal displayed partial tumor regression (PR) and reached the end of the study with a tumor volume of 162 mm$^3$, and one NTRu death occurred on Day 24. Group 4 tumor growth was progressive (FIG. 20A (upper panel), FIG. 21A, and FIG. 22A.).

Group 5 received the compound of Structure (I) at 200 mg/kg p.o. qd×21. The Group 5 MTV at Day 19 was 726 mm$^3$, corresponding to a nonsignificant 40% TGI compared to Group 1 (Table 6, FIG. 19A). The median TTE for Group 5 was 20.8 days, corresponding to 23% TGD (FIG. 18A); due to one TR death on Day 15 and one NTRu death on Day 21 this group was statistically non-evaluable (ne) (Table 5). All animals exited the study before Day 44, and Group 5 tumor growth was progressive (FIG. 20A (upper panel), FIG. 21A, and FIG. 22B).

Response to Treatment with Anti-PD-1 (Group 6)

Group 6 received anti-PD-1 at 5 mg/kg i.p. biwk×2. The Group 6 MTV at Day 19 was 387 mm$^3$, corresponding to a significant 68% TGI compared to Group 1 (P≤0.01, Table 6, FIG. 19A). The median TTE for Group 6 was 33.8 days (FIG. 18A), corresponding to a significant TGD of 100% compared to Group 1 (P≤0.05, Table 5). Four animals reached the last day of the study with tumor volumes of 4 mm$^3$ (classified as a complete regression (CR)), 320, 500 and 787 mm$^3$ (Table 5, FIG. 18A, FIG. 22B).

Response to Treatment with Anti-PD-1 and the Compound of Structure (I) (Groups 7 Through 10)

Figure 22B:
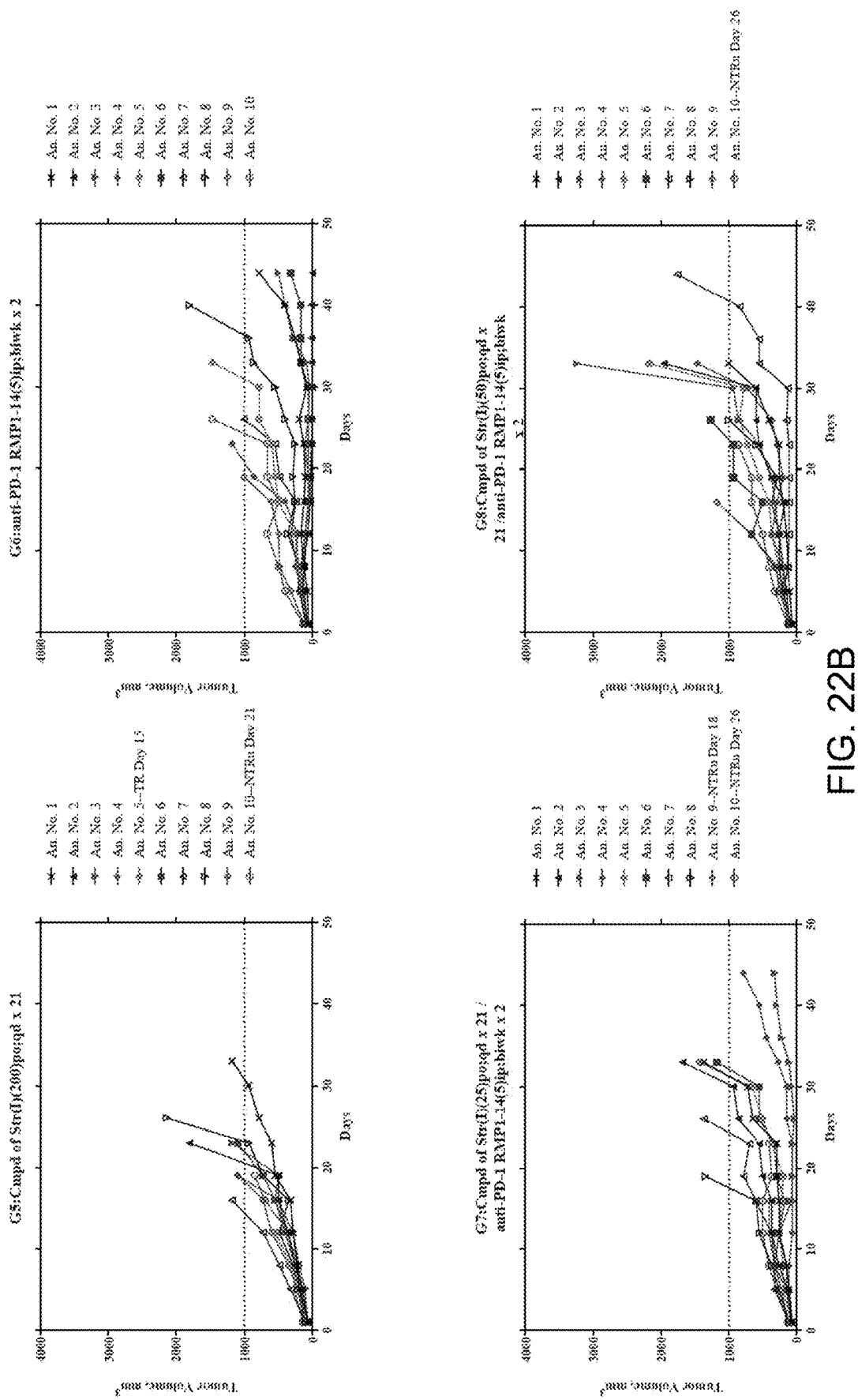
Figure 22C:
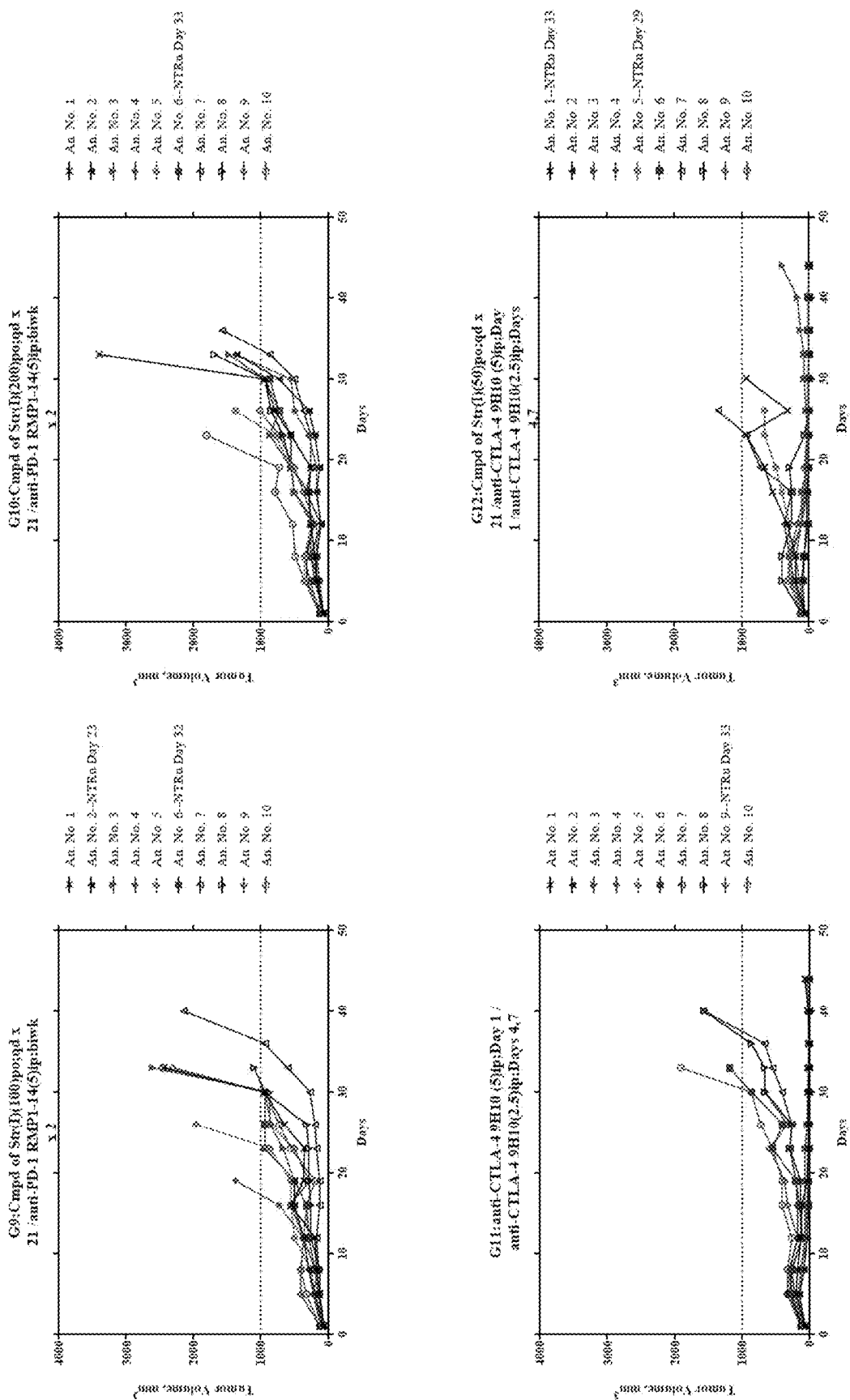
Figure 22D:
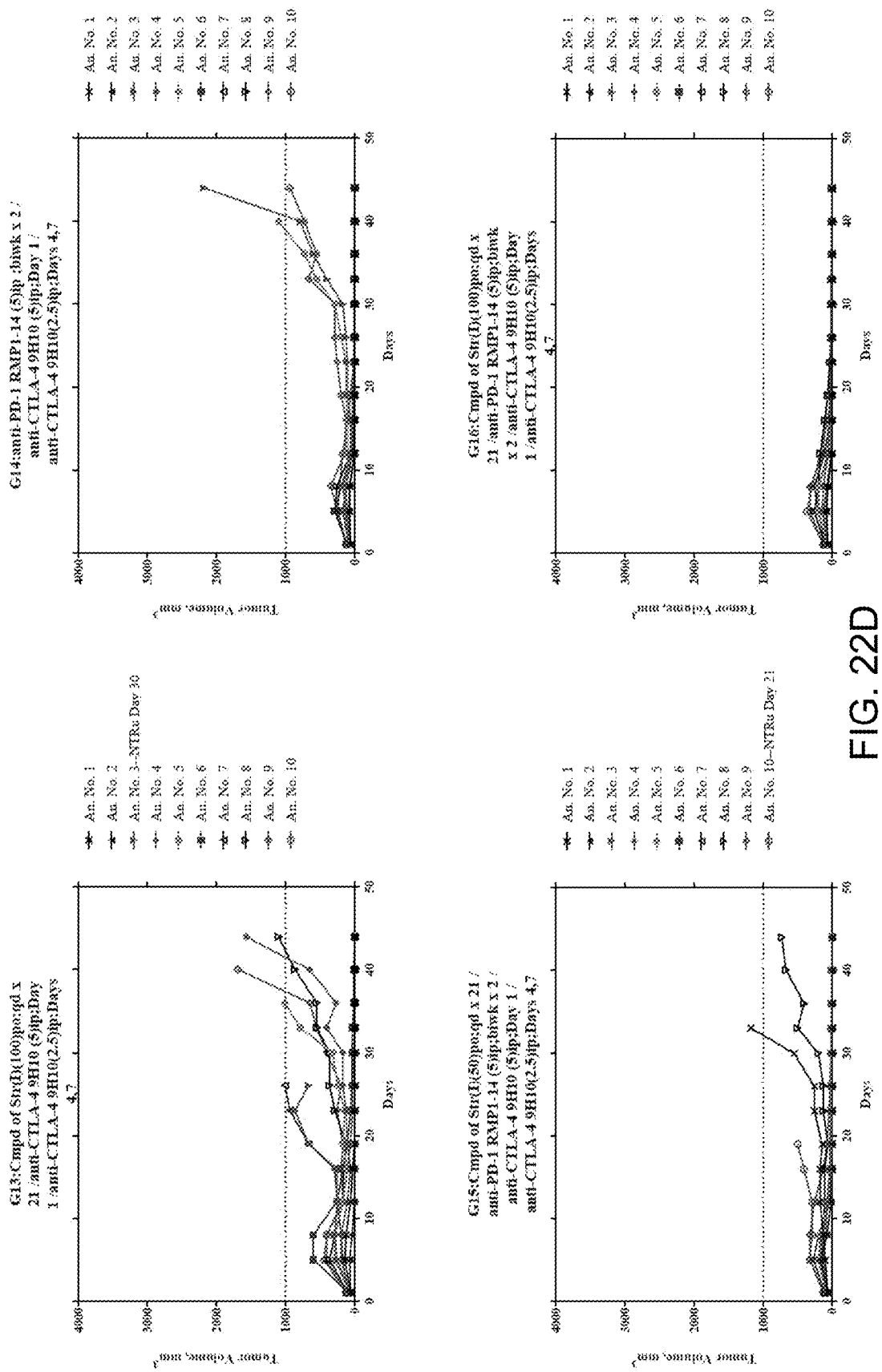

Group 7 received anti-PD-1 and 25 mg/kg of the compound of Structure (I) as described in Table 5. The Group 7 MTV at Day 19 was 288 mm$^3$, corresponding to a significant 76% TGI compared to Group 1 (P<0.05, Table 6, FIG. 19A). The median TTE for Group 7 was 31.2 days (FIG. 18A, FIG. 22B), corresponding to a significant 85% TGD compared to control (P≤0.05 v. Group 1, Table 5). Two NTRu deaths occurred on Days 18 and 26. Two mice reached the end of the study with tumor volumes of 320 and 787 mm$^3$ (FIG. 18A, FIG. 22B).

Group 8 received anti-PD-1 and 50 mg/kg of the compound of Structure (I) as described in Table 5. The Group 8 MTV at Day 19 was 365 mm$^3$, corresponding to a significant 70% TGI compared to Group 1 (P≤0.01) (Table 6, FIG. 19A). The median TTE for Group 8 was 30.2 days (FIG. 18A, FIG. 22B), corresponding to a statistically nonsignificant 79% TGD compared to control (P<0.05, Table 5). One NTRu death occurred on Day 26, and all animals exited the study before Day 44 (FIG. 18A, FIG. 22B, Table 5).

Group 9 received anti-PD-1 and 100 mg/kg of the compound of Structure (I) as described in Table 5. The Group 9 MTV at Day 19 was 433 mm$^3$, corresponding to a significant 64% TGI compared to Group 1 (P<0.01, Table 6, FIG. 19B). The median TTE for Group 9 was 30.2 days (FIG. 18B, FIG. 22C), corresponding to a statistically nonsignificant 79% TGD (Table 5). Two NTRu deaths occurred on Days 23 and 32, and all animals exited the study before Day 44.

Group 10 received anti-PD-1 and 200 mg/kg of the compound of Structure (I) as described in Table 5. The Group 10 MTV at Day 19 was 525 mm$^3$, corresponding to a significant 57% TGI compared to Group 1 (P<0.01, Table 6, FIG. 19B). The median TTE for Group 10 was 30.3 days (FIG. 18B, FIG. 22C), corresponding a statistically nonsignificant 79% TGD (Table 5). One NTRu death occurred on Day 33, and all animals exited the study before Day 44.

Tumor progression in Groups 7 through 10 matched that of anti-PD-1 monotherapy Group 6 (FIGS. 20A and 20B, FIGS. 21A and 21B and FIGS. 22B and 22C), which was delayed compared to controls. Both TGI and TGD values in Groups 7 through 10 did not differ significantly compared to Group 6.

Response to Treatment with Anti-CTLA-4 (Group 11)

Group 11 received anti-CTLA-4 i.p. at 5 mg/kg i.p. on Day 1 and at 2.5 mg/kg on Days 4 and 7. The Group 11 MTV at Day 19 was 95 mm$^3$, corresponding to a significant 92% TGI compared to Group 1 (P≤0.001, Table 6, FIG. 19B). The median TTE for Group 11 was 44.0 days (FIG. 19B), corresponding to the maximum TGD of 160% compared to Group 1 (P≤0.01, Table 5). Five animals demonstrated complete tumor regression (CR); all reached the end of the study with a MTV of 1 mm$^3$ when three were further classified tumor free survivors (TFS) (Table 5, FIG. 18B, FIG. 22C). One NTRu death occurred on Day 33.

Response to Treatment with Anti-CTLA-4 and the Compound of Structure (I) (Groups 12 and 13)

Group 12 received anti-CTLA-4 and 50 mg/kg of the compound of Structure (I) as described in Table 5. The Group 12 MTV on Day 19 was 48 mm$^3$, corresponding to a significant 96% TGI compared to Group 1 (P<0.001, Table 6, FIG. 19B). The median TTE for Group 12 was 44.0 days (FIG. 18B), corresponding to the maximum TGD of 160% compared to Group 1 (P<0.01, Table 5). Seven animals reached the last day of the study with a MTV of 1 mm$^3$; six of these had displayed CR and all but one of the six was further classified as TFS (Table 5, FIG. 18B, FIG. 22C). Two NTRu deaths were recorded on Days 29 and 33.

Group 13 received anti-CTLA-4 and 100 mg/kg of the compound of Structure (I) as described in Table 5. The Group 13 MTV on Day 19 was 117 mm$^3$, corresponding to a significant 90% TGI compared to Group 1 (P<0.001, Table 6, FIG. 19B). The median TTE for Group 13 was 42.7 days (FIG. 18B), corresponding to a significant TGD of 153% compared to Group 1 (P<0.01, Table 5). Four animals reached the last day of the study with a MTV of 1 mm$^3$; all four of these animals had displayed CR and all but one of the four was further classified as TFS (Table 5, FIG. 18B, FIG. 22D). One NTRu death was recorded on Day 30.

Tumor progression in Groups 12 and 13 matched that of anti-CTLA-4 monotherapy Group 11 (FIG. 20B, FIG. 21B and FIGS. 22C and 22D), which was profoundly delayed compared to controls. Both TGI and TGD values in Groups 12 and 13 did not differ significantly compared to Group 11.

Response to Anti-PD-1 and Anti-CTLA-4 Combination Therapy (Group 14)

Group 14 received anti-PD-1 and anti-CTLA-4 as described in Table 5. The Group 14 MTV at Day 19 was 25 mm$^3$, corresponding to a significant 98% TGI compared to Group 1 (P≤0.001, Table 6, FIG. 19B). The median TTE for Group 14 was 44.0 days (FIG. 18B), corresponding to the maximum TGD of 160% compared to Group 1 (P≤0.001, Table 5). Eight animals reached the end of the study with a MTV of 1 mm$^3$; seven of these demonstrated complete tumor regression (CR) and were further classified tumor free survivors (TFS) (Table 5, FIG. 18B, FIG. 22D).

Response to Anti-PD-1, Anti-CTLA-4, and the Compound of Structure (I) (Group 15 and Group 16)

Group 15 received anti-PD-1, anti-CTLA-4 and 50 mg/kg of the compound of Structure (I) as described in Table 5. The Group 15 MTV at Day 19 was 23 mm$^3$, corresponding to a significant 98% TGI compared to Group 1 (P≤0.001, Table 6, FIG. 19B). The median TTE for Group 15 was 44.0 days (FIG. 18B), corresponding to the maximum TGD of 160% compared to Group 1 (P≤0.001, Table 5). Eight animals reached the end of the study with a MTV of 1 mm$^3$; seven of these demonstrated complete tumor regression (CR) and were further classified tumor free survivors (TFS) (Table 5, FIG. 18B, FIG. 22D). One NTRu death was recorded on Day 21.

Group 16 received anti-PD-1, anti-CTLA-4 and 100 mg/kg of the compound of Structure (I) as described in Table 5. The Group 16 MTV at Day 19 was 16 mm$^3$, corresponding to a significant 99% TGI compared to Group 1 (P<0.001, Table 6, FIG. 19B). The median TTE for Group 16 was 44.0 days (FIG. 18B), corresponding to the maximum TGD of 160% compared to Group 1 (P<0.001, Table 5). Ten of ten animals reached the end of the study with a MTV of 1 mm$^3$; all of these demonstrated complete tumor regression (CR) and were further classified tumor free survivors (TFS) (Table 5, FIG. 18B, FIG. 22D).

Tumor progression in Groups 15 and 16 matched that of anti-PD-1/anti-CTLA-4 combination therapy Group 14 (FIG. 20B, FIG. 21B and FIG. 22D), which was profoundly delayed compared to controls. Both TGI and TGD values in Groups 15 and 16 did not differ significantly compared to Group 14.

Adverse Events

Table 5 provides a summary of maximum group mean body weight (BW) losses, treatment related (TR) and non-treatment related (NTR) deaths. FIGS. 23A and 23B plot percent mean BW changes from Day 1 for each group. Clinical signs were recorded when observed. Group mean BW losses were negligible, ranging from 0 in Group 7 (which received anti-PD-1 and 25 mg/kg of the compound of Structure (I)) to 2.6% on Day 2 in control Group 1. Tumor ulcerations, morbidity (suppressed body temperature, breathing and activity, hunching and ruffled fur) and/or palpable masses, which are all associated with tumor progression, were observed in no more than one member of less than half of the study groups. Nevertheless, all but four groups (Group 2, Group 6, Group 14 and Group 16) experienced at least one death during the course of the study, including one NTRu death in control Group 1 on Day 22. In all but one case (Animal 9 Group 7 was euthanized on Day 18 with tumor ulcerations, a large red spleen and pale liver and kidneys), 15 of 16 animals were found dead. Six of fifteen animals found dead displayed mild to severe tumor ulcerations, which may have contributed to death; these included Group 4 Animal 1 (NTRu Day 24), Group 5 Animal 10 (NTRu Day 21), Group 7 Animal 10 (NTRu Day 26), Group 8 Animal 10 (NTRu Day 26), Group 13 Animal 3 (NTRu Day 30) and Group 15 Animal 10 (NTRu Day 21). Toxicity offered an explanation to account for those animals found dead without prior signs of morbidity; even so, control Group 1 Animal 4 (NTRu Day 22) was included in this category. Also found dead with no prior clinical signs were Group 3 Animal 2 (TR Day 19), Group 5 Animal 5 (TR Day 15), Group 9 Animals 2 and 6 (NTRus Days 23 and 32), Group 10 Animal 6 (NTRu Day 33), Group 11 Animal 9 (NTRu Day 33) and Group 12 Animals 5 and 1 (NTRus Days 29 and 33).

Distinguishing between treatment and non-treatment related deaths was complicated by several factors. First, the dosing schedule of the compound of Structure (I) overlapped with the timing of five deaths, and all deaths took place within 14 days of the last the compound of Structure (I) dose. Second, no obvious clinical signs were observed prior to the two deaths designated as TR on Day 15 (in Group 5 which received 200 mg/kg of the compound of Structure (I)) and Day 19 (in Group 3 which received 50 mg/kg of the compound of Structure (I)). Unfortunately, none of the animals found dead were available for necropsy to evaluate pathological evidence for toxicity. Arguments against toxicity are a lack of dose-dependence and a Day 22 death in control Group 1.

Summary

The efficacy of the compound of Structure (I) alone or in combination with the immune checkpoint inhibitors anti-PD-1 and/or anti-CTLA-4 against established syngeneic MC38 murine colon carcinoma tumors in C57BL/6 mice was tested. Under the conditions of this study, the compound of Structure (I) monotherapy at doses of 25, 50, 100 or 200 mg/kg did not significantly slow the progression of MC38 tumors based on measurements of Day 19 median tumor volumes (MTVs) used to determine tumor growth inhibition (TGI) or median times to the Day 44 study endpoint (TTEs) used to determine tumor growth delay (TGD). Statistical analysis indicated that the addition of the compound of Structure (I) at doses of 25, 50, 100 and/or 200 mg/kg did not significantly improve the efficacy of immune checkpoint inhibitor anti-PD-1 monotherapy, anti-CTLA-4 monotherapy or anti-PD-1/anti-CTLA-4 combination therapy. However, 100 mg/kg of the compound of Structure (I)/anti-PD-1/anti-CTLA-4 triple therapy produced 10/10 tumor free survivors (TFS) compared to 7/10 TFS among animals that received anti-PD-1/anti-CTLA-4.

Figure 24A:
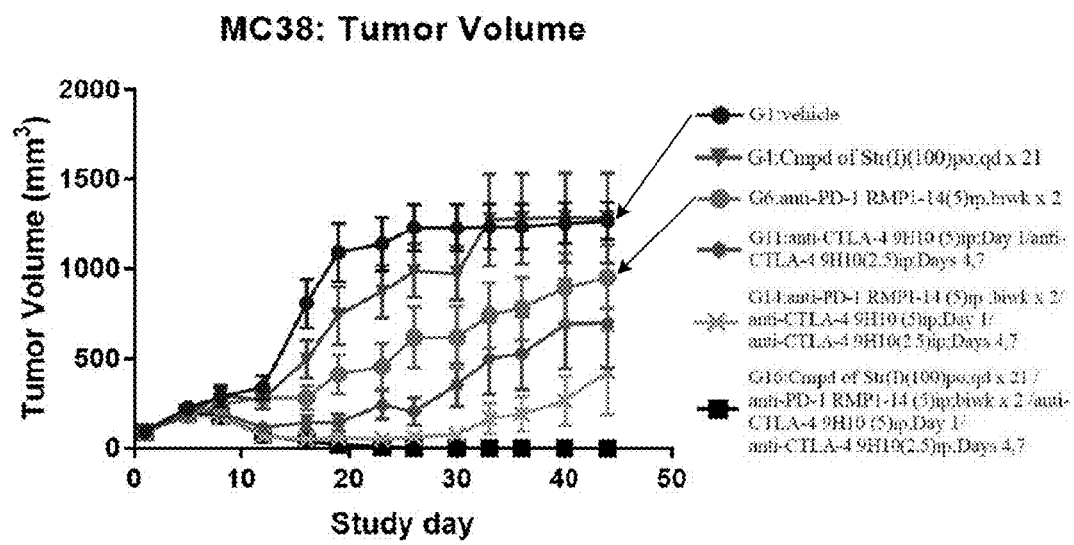
FIGS. 24A-24C show summary plots of median tumor growth for mice in Groups 1, 4, 6, 11, 14, and 16 (FIG. 24A), Kaplan-Meier plots for mice in Groups 1, 7, 12, and 16 (FIG. 24B), and Kaplan-Meier plots for mice in Groups 1, 4, 6, 11, 14, and 16 (FIG. 24C) in the MC38-e423 study described in Example 11.

In summary, the compound of Structure (I) in combination with anti-PD-1 and anti-CTLA-4 resulted in tumor regression in the MC38 syngeneic mouse colorectal cancer model with no adverse toxicity or effects on body weights. Additionally, the compound of Structure (I) administered at a dose of 25 mg/kg in combination with anti-PD-1 resulted in tumor growth inhibition (TGI) of 76%; the compound of Structure (I) administered at a dose of 50 mg/kg in combination with anti-CTLA-4 resulted in TGI of 96%; and the compound of Structure (I) administered at a dose of 100 mg/kg in triple combination with anti-PD-1 and anti-CTLA-4 resulted in TGI of 99% in the MC38 model. FIG. 24A shows a summary plot of median tumor growth for Groups 1, 4, 6, 11, 14 and 16.

Figure 24B:
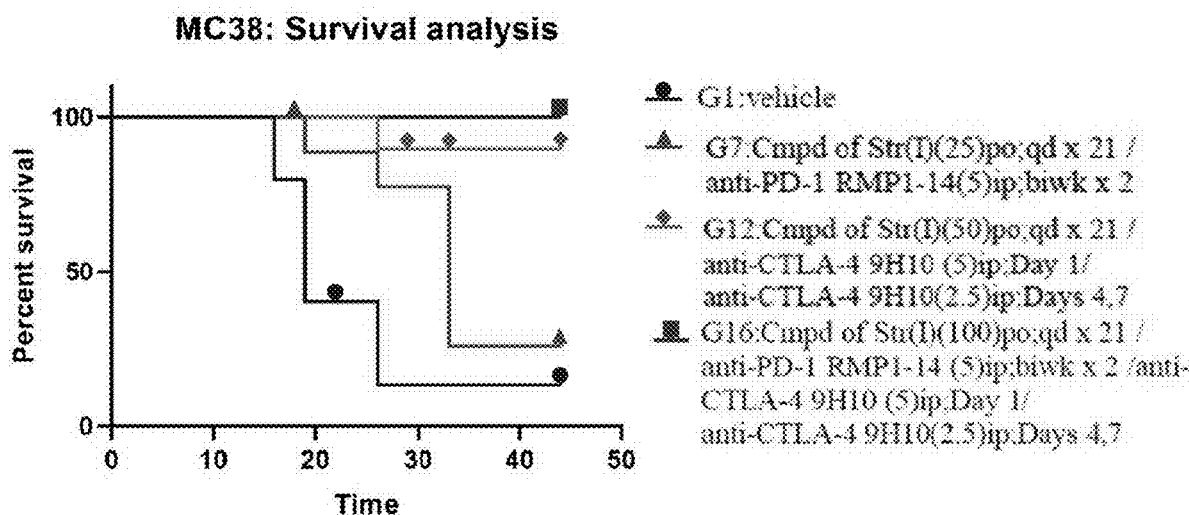
Figure 24C:
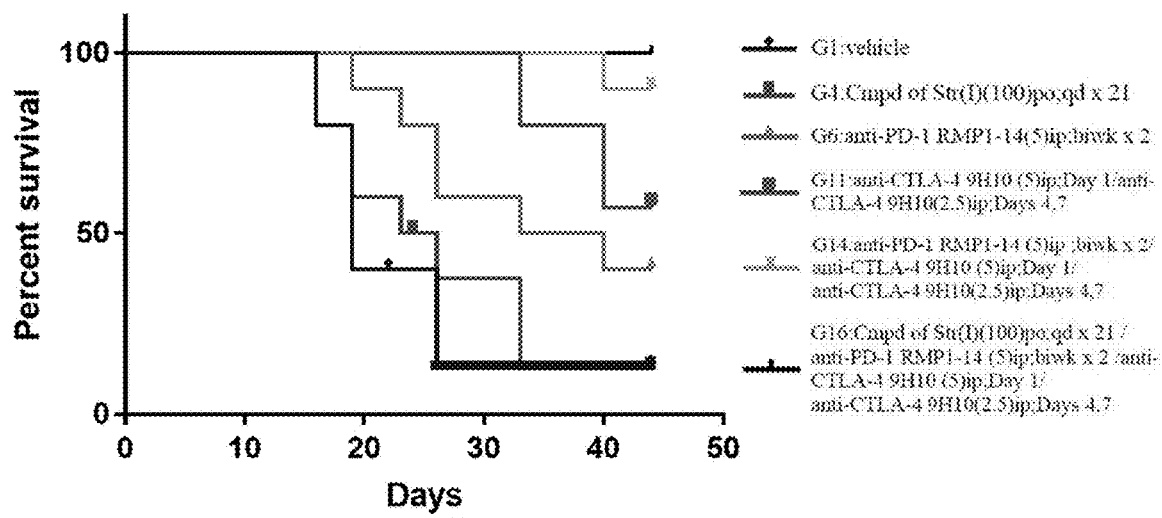

As shown in FIG. 24B, survival analysis using Kaplan Meier plots for Groups 1, 7, 12, and 16 revealed 90% survival for mice treated with 50 mg/kg of the compound of Structure (I) in combination with anti-CTLA-4, and 100% survival for mice treated with 100 mg/kg of the compound of Structure (I) in combination with anti-CTLA-4 or triple combination with anti-PD-1 and anti-CTLA-4, which is a significant improvement over the 10% survival of the vehicle group. FIG. 24C shows summary Kaplan-Meier plots for Groups 1, 4, 6, 11, 14 and 16.

Increased levels of glucose and decreased levels of glucose 6-phosphate, phosphoglycerate, phosphoenolpyruvate and lactate were observed in compound of Structure (I)-treated, compared to vehicle-treated, MC38 tumors. Potential downstream biomarkers, including metabolism, immune gene alterations and immune phenotyping are currently under evaluation using LC-MS/MS, NanoString and flow cytometry.

These preclinical studies strongly suggest the potential therapeutic activity of the compound of Structure (I) in cancer models through metabolism and tumor microenvironment modulation.

Example 12

In Vivo Synergy Between a PKM2 Activator and Immunotherapy Agents in a Syngeneic CT26 Colon Carcinoma Mouse Model The efficacy of the compound of Structure (I) alone or in combination with anti-PD-1 antibodies in a syngeneic CT26 colon carcinoma mouse model was investigated.

Study Summary

Female Balb/c mice bearing CT26 tumors were sorted into 4 groups (n=10) with initial group mean tumor volumes of approximately 77 mm$^3$. Mice received oral (p.o.) doses of control vehicle, or the compound of Structure (I) and/or intraperitoneal (i.p.) doses of anti-PD-1 antibodies. The anti-PD-1 antibody is directed against the programmed cell death protein 1 (PD-1) surface receptor expressed on T cells, B cells, and macrophages.

Treatment groups were as follows: Group 1 (control) received vehicle; Group 2 received 5 mg/kg of the anti-PD-1 antibody; Group 3 received 50 mg/kg of the compound of Structure (I); and Group 4 received 5 mg/kg of the anti-PD-1 antibody and 50 mg/kg of the compound of Structure (I). All animals received a dose volume of 5 mL/kg per test item. Tumor volumes were measured three times per week using standard methods. The study endpoint occurred when the mean tumor volume ($\bar{x}$TV) of the control group and test groups reached 1500 mm$^3$ or Day 21, whichever came first.

All groups were analyzed for tumor growth inhibition (TGI) through Day 16 Groups 1,2, and 3 reached mean tumor volumes 2000 mm$^3$ on this day and thus their study end point was also reached. Group 4 continued until the last day of the study (Day 21) and final measurements were taken on Day 23.

At the study endpoint, blood and tumors were collected from all available animals in all groups as described below. TGI observed at the study endpoint for monotherapy groups, receiving either the compound of Structure (I) or anti-PD-1 alone, was less than 10% in the CT26 colorectal syngeneic model. However, the combination therapy group, which received both the compound of Structure (I) and anti-PD-1, demonstrated in vivo synergy with 68% TGI.

Test group mean body weight losses were negligible, with Group 4 showing the greatest weight loss, at ~2% on Day 4. By Day 16 all groups had demonstrated mean body weight increases.

Methods and Materials

Mice

Female Balb/c mice (JAX, Bar Harbor and/or Ellsworth, Me.) were at least 6-8 weeks old with a body weight (BW) of at least 18 grams (g). The mean body weight of each test group on Day 0 was ~21 g. The animals were fed ad libitum water (reverse osmosis, 2 ppm C12), and Teklad 2919 irradiated test rodent diet consisting of 19% crude protein, 9% crude fat, and 4% fiber. The mice were housed in individual HEPA ventilated cages using 100% virgin kraft nesting enrichment sheets (Innorichment™) for bedding on a 14-10 hour light-dark cycle at 20-23° C. (68-74° F.) and 30-70% humidity.

Animals exhibiting >10% weight loss when compared to Day 0 were given DietGel® ad libitum. Any animal exhibiting >20% net weight loss for a period lasting 7 days, or if mice display >30% net weight loss when compared to Day 0 will be considered moribund and euthanized.

In Vivo Implantation and Tumor Growth

On the day of implant, cultured CT26 cells were harvested at a concentration of 3×10$^6$ cells/mL. Tumors were initiated by subcutaneously implanting 3×10$^5$ CT26 cells (0.1 mL suspension) into the left flank of each test animal.

Tumors were monitored beginning four to five days after injection, as their volumes approached the target range of 50-150 mm$^3$. Once the target was reached, animals were sorted into four groups (n=10), each group having mean tumor volumes of 77 mm$^3$. Tumors were measured according to standard procedures known in the art.

Triple antibiotic ointment was applied three times per week on all tumors after tumor volume measurements. Mice with tumor ulceration greater than 50% of the tumor total surface area or an impact on overall health and well-being were euthanized.

Therapeutic Agents

The compound of Structure (I) was stored at −20° C. Anti-PD-1 was stored at 2-8° C. and protected from the light. The vehicle was 2% Tween80:10% Ethanol:30% PEG400: 58% deionized water (DI H2O).

Dosing solutions of the compound of Structure (I) were prepared weekly by suspending the compound in ethanol with vortexing, then adding Tween80 and PEG400 with gentle vortexing followed by deionized water (DI H$_2$O) to yield opaque suspensions with a final concentration of 10 mg/mL. Dosing solution was stored at 2-8° C.

On the day of dosing, the antibody stock solution was diluted with PBS to a final concentration of 1 mg/mL, which delivered 5 mg/kg, when administered in a volume of 5 mL/kg. Dosing solution was stored at 2-8° C.

Treatment

On Day 0 of the study, female Balb/c mice with established subcutaneous CT26 tumors were sorted into four groups (n=10), and dosing was initiated according to the following plan. All therapies were dosed at 5 mL/kg, scaled to the body weight of each animal (0.100 mL per 20 gram mouse).

Group 1 received the vehicle (Tween 80, ethanol, and PEG400 in DI water (ratio 2:10:30:58)) orally (p.o.) once a day until the study end point was reached, and served as the control and benchmark group for tumor engraftment and progression.

Group 2 received the anti-PD-1 antibody at 5 mg/kg, intraperitoneally (i.p.), twice a week for two weeks (biw×2).

Group 3 received the compound of Structure (I) at 50 mg/kg, p.o., once a day until the study end point was reached.

Group 4 received the anti-PD-1 antibody at 5 mg/kg, i.p., twice a week for two weeks (biw×2) in combination with the compound of Structure (I) at 50 mg/kg, p.o., once a day until the study end point was reached.

Sampling

Endpoints were at the end of the study (Day 21) or when mean group tumor volumes reached 1500 mm³. Endpoint blood, serum, and tumor samples were collected from animals in all groups at endpoint.

Maximum possible blood volume, or at least 300 uL blood was collected by cardiac puncture. The collected blood was transferred to a K2-EDTA tube and gently mixed by inversion (by hand) 8-10 times. For flow cytometry, the sample tubes were placed on wet ice until processed. For plasma collection, after inversion, sample tubes were stored on wet ice until being centrifuged at 3500 RPM for 10 minutes at 2-4° C. The resultant plasma was separated, transferred to polypropylene tubes, frozen immediately, and stored at −80° C.

Tumors were collected from all animals from each group at study completion. Tumors from all mice were collected and separated into two portions. One half was snap frozen: flash frozen, placed on dry ice, and stored at −80° C. The second half was placed in 10% neutral buffered formalin for 18-24 hours, transferred to 70% ethanol, and stored at room temperature. Formalin fixed samples were paraffin embedded. Tumors that were <250 mm³ were processed as single snap frozen samples.

Results

Tumor Growth Inhibition (TGI) Analysis

Individual tumor volumes were measured three times per week. A final tumor volume was taken on the day the study reached endpoint or if the animal was found moribund. Tumor growth inhibition (TGI) was determined several times using group mean tumor volume ($\bar{x}$TV). Daily TVs were determined by subtracting initial mean tumor volume (Day 0) from the current measurement. Percent tumor growth inhibition (% TGI) was defined as the difference between the $\bar{x}$TV of the designated control group (Group 1) and the $\bar{x}$TV of the treatment group (Groups 2-4), expressed as a percentage of the $\bar{x}$TV of the control group:

$$\% \text{ TGI}=[1-(\bar{x}\text{TV}_{drug\ treated}/\bar{x}\text{TV}_{control})]\times 100$$

Figure 25:
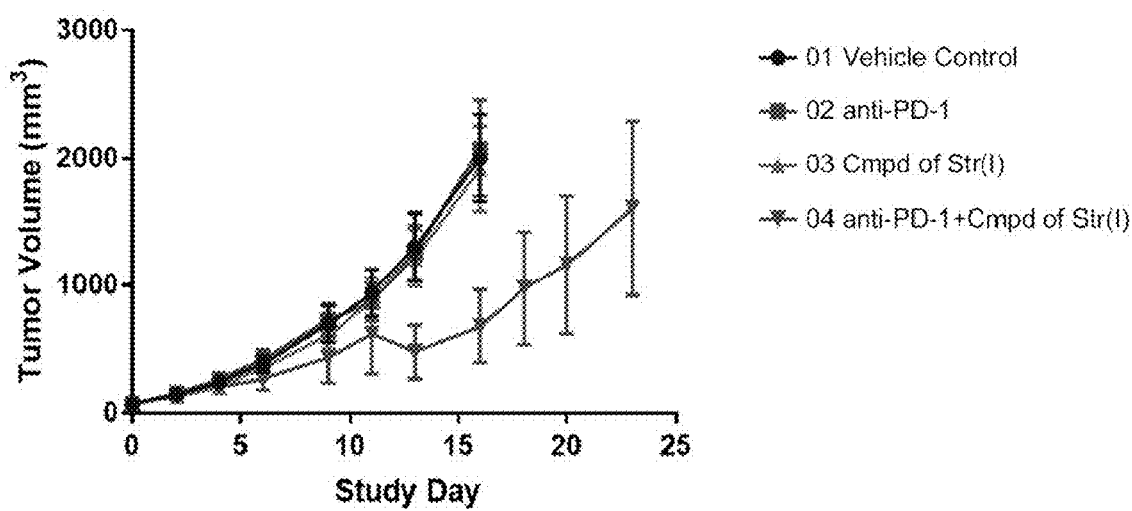
FIG. 25 shows a plot of mean tumor volume in mice for the CT26 study described in Example 12.

Plotted daily group mean tumor volumes ($\bar{x}$TVs) for each of the test groups are shown in FIG. 25. Combination therapy test group, Group 4 demonstrated reduced tumor growth.

Control Group 1 displayed a mean tumor volume ($\bar{x}$TV) of 2002 mm³ on Day 16. By comparison, Group 4 shows significant Day 16 tumor growth inhibition having an $\bar{x}$TV of 680 mm³ corresponding to 68.7% TGI.

Toxicity

Beginning on Day 0, animals were observed daily and weighed three times weekly using a digital scale. A final weight was taken on the day the study reached endpoint or if the animal was found moribund. Data including individual and mean gram weights (mean±SEM) and mean percent weight change versus Day 0 (% vD0) were recorded for each group. Single agent or combination groups reporting a mean % vD0>20% and/or >10% mortality are considered above the maximum tolerated dose (MTD) for that treatment on the evaluated regimen.

Figure 26A:
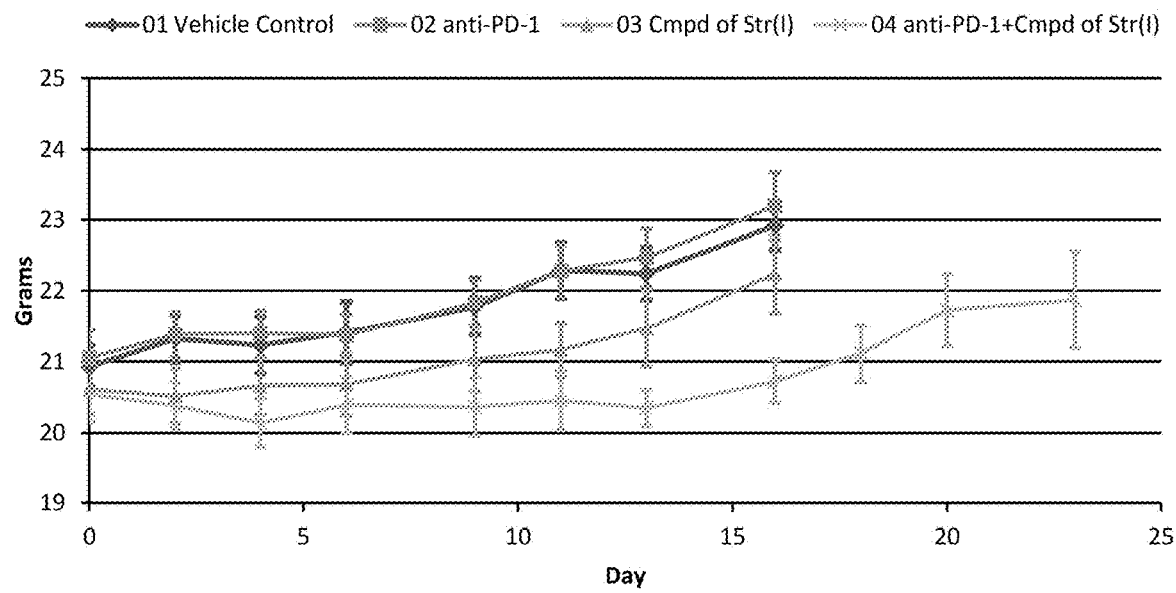
FIGS. 26A and 26B show plots of daily group mean body weights and percent group mean body weight changes from Day 0, respectively, in mice for the CT26 study described in Example 12.
Figure 26B:
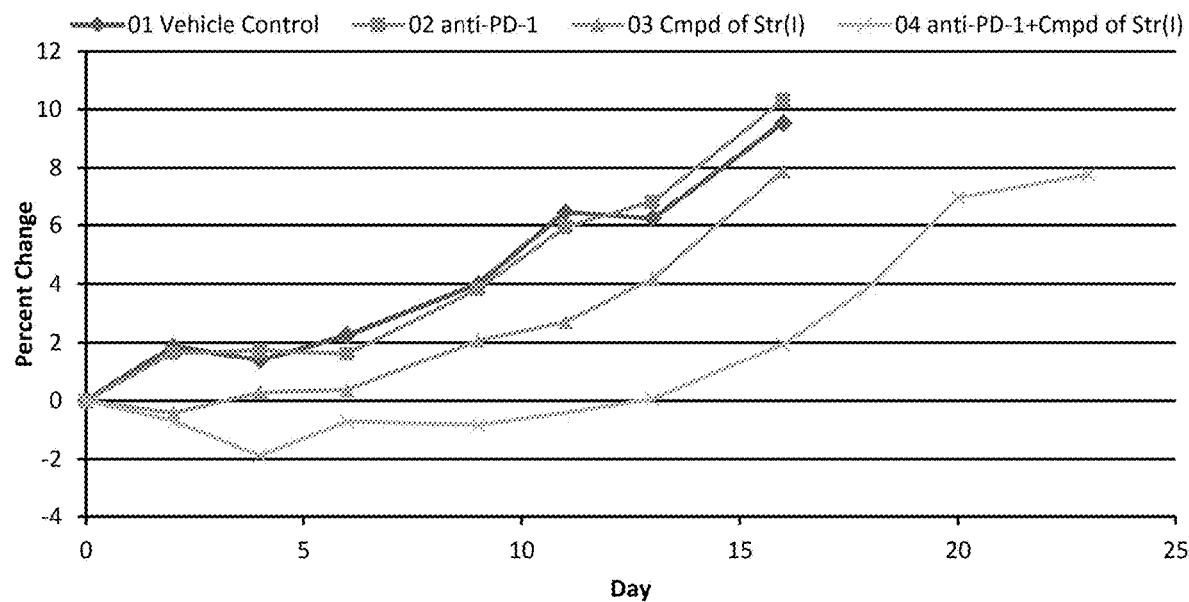

FIGS. 26A and 26B show plots of daily group mean body weights and percent group mean body weight changes from Day 0, respectively. None of the groups demonstrated significant weight loss, suggesting favorable initial tolerability. All groups showed an increase in body weight by Day 16. The highest average weight loss observed (~2%) was for Group 4 on Day 4, which is well within the allowed range.

Example 13

Evaluation of Tumor Immune Microenvironment in Mouse Model Tumors Treated with the Compound Structure 1 for 10 Days Murine syngeneic models sensitive to immune checkpoint inhibition (MC-38 and CT26, colorectal) and resistant to immune checkpoint inhibition (RENCA, renal cell carcinoma and 4T1, breast adenocarcinoma) were prepared in accordance with the above-described procedures and treated for 10 days with vehicle or a combination of the compound of Formula 1+PD-1 inhibitor (identify PD-1 inhibitor) according to the following schedule:

TABLE 7

Study Design

| Group | -n- | Agent | Dose Level | Dose Volume | ROA/ Schedule | Total Doses |
|---|---|---|---|---|---|---|
| 1 | 10 | Vehicle Control | — | 5 mL/kg | PO/QDx11 | 11 |
| 2 | 10 | Anti-m-PD1 | 5 mg/kg | 5 mL/kg | IP/BIWx2 | 4 |
| 3 | 10 | TP-1454 | 50 mg/kg | 5 mL/kg | PO/QDx11 | 11 |
| 4 | 10 | Anti-m-PD1 | 5 mg/kg | 5 mL/kg | IP/BIWx2 | 4 |

Each animal was administered the indicated test article at the indicated frequency. Tumor volumes and animal weights were recorded three times weekly. The study endpoint was Day 10, 2 hours post administration of the last dose.

At study termination, tumors and spleens were placed in MACS buffer and processed for flow cytometry.

The following procedures were used to process the tissues harvested from the study and to perform flow cytometry on the samples to provide analysis of the immune environment in test animals.

1 Materials and Methods: Tissue Dissociation, Mouse Tumors 1.1 Overview 10.11 To dissociate murine tumors into single cell suspension for subsequent analysis by flow cytometry or other cell assay. The kit is optimized to maintain cell viability, provide high cell yields, and to preserve cell surface epitopes. The procedure involves cutting the tumor into pieces, incubation with an enzyme cocktail, mechanical dissociation with the gentleMACS tissue dissociator using C-tubes, filtration, and cell counting. Cells include murine tumor tissue in a range of 0.04 to 1 g in a volume of approximately 2.5 mL enzyme mix. For cell culture experiments subsequent to tissue dissociation, all steps should be performed under sterile conditions.

10.3 Equipment 10.3.1 GentleMACS Tissue Dissociator (Miltenyi catalog #130-093-235, equipment ID FL-012) or GentleMACS Octo Dissociator (catalog #130-096-427, equipment ID FL-011), or equivalent.

10.3.2 Centrifuge, Eppendorf 5180R (equipment IDs FL-003, FL-004), or equivalent.

10.3.3 Biosafety cabinet, equipment ID FL-007, or equivalent.

10.3.4 Refrigerator set at 2-8° C., equipment IDs FL005, FL022, or equivalent.

10.3.5 Freezer set at −20° C. nominal, equipment ID FL-006, or equivalent.

10.3.6 Freezer set at −80° C. nominal, equipment ID FL-021, or equivalent.

10.3.7 Adjustable volume pipettes.

10.3.8 Vortex mixer, equipment IDs FL-014, FL-015, FL-016, FL-017, FL018, or equivalent.

10.3.9 Strainers, 70 uM, Miltenyi cat #130-098-462, or equivalent 10.3.10 GentleMACS C tubes, Miltenyi cat #130-093-237.

10.3.11 SOFTWARE 10.3.12 GentleMACS software associate with machine.

10.4 Reagents 10.4.1 A list of reagents is below.

TABLE 8

Reagents

| Vendor | Catalog # | Description | Storage |
|---|---|---|---|
| Gibco | 61870036 | RPMI w/glutamax | 2-8° C. |
| Gibco | 11995040 | DMEM | 2-8° C. |
| BD | 555899 | RBC Pharm Lyse | 2-8° C. |
| Miltenyi | 130-096-730 | Enzyme D (lyophilized powder) | −80° C. |
| Miltenyi | 130-096-730 | Enzyme R (lyophilized powder) | −80° C. |
| Miltenyi | 130-096-730 | Enzyme A (lyophilized powder) | −80° C. |
| Miltenyi | 130-100-008 | MACS tissue storage solution | 2-8° C. |
| Gibco | 14190-136 | 1XPBS | Ambient |
| Thermo Scientific | 23-751-628 | DI Water | Ambient |

10.5 Preparation of Reagents.

10.5.1 Enzyme D. 1. Prepare Enzyme D by reconstitution of the lyophilized powder in each vial with 3 mL of RPMI 1640 or DMEM. Prepare aliquots of appropriate volume to avoid repeated freeze-thaw-cycles. Store aliquots at −20° C. This solution is stable for 6 months after reconstitution. For cell culture experiments subsequent to tissue dissociation, Enzyme D should be sterile filtered prior to aliquoting.

10.5.2 Enzyme R. 2. Prepare Enzyme R by reconstitution of the lyophilized powder in the vial with 2.7 mL RPMI 1640 or DMEM. Prepare aliquots of appropriate volume to avoid repeated freeze-thaw-cycles. Store aliquots at −20° C. This solution is stable for 6 months after reconstitution. Make sure to thoroughly mix the suspension immediately before withdrawing the required reaction volume.

10.5.3 Enzyme A. Prepare Enzyme A by reconstitution of the lyophilized powder in the vial with 1 mL of Buffer A supplied with the kit. Do not vortex. Prepare aliquots of appropriate volume to avoid repeated freeze-thaw cycles. Store aliquots at −20° C. This solution is stable for 6 months after reconstitution.

10.6 Sample Type 10.6.1 Murine Tumors 10.7 Method for Soft and Medium Tumors 10.7.1 Notes:

10.7.1.1 Appropriate worksheets and forms will be prepared to document sample processing.

10.7.1.2 The procedure will be performed at room temperature protected from light whenever possible, unless otherwise noted.

10.7.2 Receive Tumors. Cut tumors into small pieces of 2-4 mm.

10.7.3 Prepare enzyme mix by adding 2.35 mL of RPMI 1640 or DMEM, 100 µL of Enzyme D, 50 µL of Enzyme R, and 12.5 µL of Enzyme A into a gentleMACS C Tube.

10.7.4 Transfer the tissue into the gentleMACS C Tube containing the enzyme mix.

10.7.5 Tightly close C Tube and attach it upside down onto the sleeve of the gentleMACS Dissociator. Note: It has to be ensured that the sample material is located in the area of the rotor/stator.
10.7.6 Run the gentleMACS Program m_impTumor_02.
10.7.7 If using the heating function of the gentleMACS Octo Dissociator with Heaters run program 37C_m_TDK_1 and continue with step 10.7.12.
10.7.8 After termination of the program, detach C Tube from the gentleMACS Dissociator.
10.7.9 Incubate sample for 40 minutes at 37° C. with continuous rotation using the MACSmix Tube Rotator or equivalent.
10.7.10 Attach C Tube upside down onto the sleeve of the gentleMACS Dissociator. Note: It has to be ensured that the sample material is located in the area of the rotor/stator.
10.7.11 Run the gentleMACS Program m_impTumor_03.
10.7.12 (Optional) After termination of the program, detach C Tube from the gentleMACS Dissociator and perform a short spin up to 300×g to collect the sample at the bottom of the tube.
10.7.13 Resuspend sample and apply the cell suspension to a MACS SmartStrainer (70 μm) placed on a 15 mL tube.
10.7.14 Wash MACS SmartStrainer (70 μm) with 10 mL of RPMI 1640 or DMEM.
10.7.15 Centrifuge cell suspension at 300×g for 7 minutes. Aspirate supernatant completely.
10.7.16 Resuspend cells with an appropriate buffer to the required volume for further applications.
10.7.17 (Optional) To remove erythrocytes or dead cells, use Red Blood Cell Lysis Solution (10×) (#130-094-183), or perform a density gradient centrifugation step.
10.8 Method for Tough Tumors
10.8.1 Notes:
10.8.2 Appropriate worksheets and forms will be prepared to document sample processing.
10.8.3 The procedure will be performed at room temperature protected from light whenever possible, unless otherwise noted.
10.8.4 Receive Tumors. Cut tumors into small pieces of 2-4 mm.
10.8.5 Prepare enzyme mix by adding 2.35 mL of RPMI 1640 or DMEM, 100 μL of Enzyme D, 50 μL of Enzyme R, and 12.5 μL of Enzyme A into a gentleMACS C Tube.
10.8.6 Transfer the tissue into the gentleMACS C Tube containing the enzyme mix.
10.8.7 Tightly close C Tube and attach it upside down onto the sleeve of the gentleMACS Dissociator. Note: It has to be ensured that the sample material is located in the area of the rotor/stator.
10.8.8 Run the gentleMACS Program m_impTumor_02.
10.8.9 If using the heating function of the gentleMACS Octo Dissociator with Heaters run program 37C_m_TDK_2 and continue with step 10.
10.8.10 After termination of the program, detach C Tube from the gentleMACS Dissociator.
10.8.11 Incubate sample for 40 minutes at 37° C. with continuous rotation using the MACSmix Tube Rotator.
10.8.12 Attach C Tube upside down onto the sleeve of the gentleMACS Dissociator. Note: It has to be ensured that the sample material is located in the area of the rotor/stator.
10.8.13 Run the gentleMACS Program m_impTumor_03 twice.
10.8.14 (Optional) Some larger pieces of tissue may remain. To further increase the cell yield, allow the remaining tissue to settle and remove 1.5 mL of the supernatant to a fresh tube. Insert the C Tube with the remaining tissue pieces onto the sleeve of the gentleMACS Dissociator and run program m_imptumor_01. Combine the resulting cell suspension with the previously removed supernatant.
10.8.15 (Optional) After termination of the program, detach C Tube from the gentleMACS Dissociator and perform a short spin up to 300×g to collect the sample at the bottom of the tube.
10.8.16 Resuspend sample and apply the cell suspension to a MACS SmartStrainer (70 μm) placed on a 15 mL tube. Note: Dissociated tissue can be removed from the closed C Tube by pipetting through the septum-sealed opening in the center of the cap of the C Tube. Use ART 1000 REACH 1000 μL pipette tips.
10.8.17 Wash MACS SmartStrainer (70 μm) with 10 mL of RPMI 1640 or DMEM.

11 Materials and Methods: Staining for Flow Cytometry
11.1 Equipment
11.1.1 MACSQuant Analyzer 10, Vendor: Miltenyi Biotec Serial number 2838
11.1.2 Centrifuge, Eppendorf 5180R (equipment IDs FL-003, FL-004), or equivalent.
11.1.3 Biosafety cabinet, equipment ID FL-007, or equivalent.
11.1.4 Refrigerator set at 2-8□C, equipment IDs FL005, FL022, or equivalent.
11.1.5 Freezer set at −20° C. nominal, equipment ID FL-006, or equivalent.
11.1.6 Freezer set at −80° C. nominal, equipment ID FL-021, or equivalent.
11.1.7 Adjustable volume pipettes.
11.1.8 Vortex mixer, equipment IDs FL-014, FL-015, FL-016, FL-017, FL018, or equivalent.
11.2 Reagents
11.2.1 Reagents are listed in the table below

TABLE 9

Reagents

| Vendor | Catalog # | Description | Storage |
|---|---|---|---|
| Streck | 23-046-500D | CD-Chex Plus Immunophenotyping control | 2-8° C. |
| BD | 564220 | Human Fc Block | 2-8° C. |
| BD | 555899 | Pharm Lyse | 2-8° C. |
| Miltenyi | 130-092-747 | Running Buffer (FACS buffer) | 2-8° C. |
| Miltenyi | N/A | FACS buffer + 5% FBS | 2-8° C. |
| Thermo Fisher | C36950 | CountBright counting beads | 2-8° C. |
| Gibco | 14190-136 | 1X PBS | Ambient |
| Thermo Scientific | 23-751-628 | DI Water | Ambient |

11.3 Antibody Panels

TABLE 10

Antibody Panel 1

| Antibody Description | Antibody Description | Conjugate | Channel | Clone |
|---|---|---|---|---|
| mCD25 | IL-2Ra, activated T, B, some thymocytes, myeloid precursors, oligodendrocytes, and TILs | BV421 | V1 | PC61 |
| mCD8a | Cytotoxic T | BV510 | V2 | 53-6.7 |
| mPDL-1 | CD274, myeloid, cancer cells | BV605 | V3 | 10F.9G2 |
| mCD45 | pan-leukocyte | BV711 | V4 | 30-F11 |
| mCD3 | T lymphocytes | FITC | B1 | 17A2 |
| mFOXP3* | T reg | PE | B2 | MF-14 |

TABLE 10-continued

Antibody Panel 1

| Antibody Description | Antibody Description | Conjugate | Channel | Clone |
|---|---|---|---|---|
| mCD4 | Helper T | PerCp Cy 5.5 | B3 | RM4-5 |
| mCD44 | widely expressed, thymocyte subsets, T memory | PE-Cy7 | B4 | IM7 |
| mGranzymeB* | Cytotoxic T, NK, basophils, mast cells | AF647 | R1 | GB11 |
| Viability | live/dead | FVS700 | R2 | N/A |
| mPD-1 | Activated T, Treg, activated B, pro-B, myeloid | APC Cy7 | R3 | 29F.1A12 |

TABLE 11

Antibody Panel 2

| Antibody Description | Antibody Description | Conjugate | Channel | Clone |
|---|---|---|---|---|
| CD206 | mannose receptor, M2 macrophages, DCs. | BV421 | V1 | C068C2 |
| mCD45 | pan leukocyte | BV510 | V2 | 30F11 |
| mLy6C | myeloid, M-MDSCs | Fitc | B1 | HK1.4 |
| mLy6G | myeloid, G-MDSCs | PE | B2 | 1A8 |
| FVS620 | live/dead | L-D | B3 | NA |
| F4/80 | Macrophage | PE Cy7 | B4 | BM8 |
| mMHCII | M1 macrophages, APCs. | APC | R1 | M5/114.15.2 |
| CD11b | myeloid | APC-Fire750 | R3 | M1/70 |

11.4 Staining Whole Blood in 96 Well Plates 11.4.1 Aliquot 60 uL whole blood per sample to each well (include CD-Chex Plus as positive control in the first well and pool small aliquots of blood for unstained negative control).

11.4.2 Incubate samples with 2 ul (0.6 ul BD Fc Block+0.14 ul Stain buffer containing FBS) (2.5 µg/million cells) for 10 minutes.

11.4.3 Make flow antibody staining cocktail according to flow panel.

11.4.4 Add recommended antibody cocktail to each whole blood sample.

11.4.5 Incubate samples at room temperature (RT) in the dark for 30 minutes.

11.4.6 Add 1.25 mL/sample of 1× Lysing Buffer.

11.4.7 Incubate samples at RT on tube rocker for 20 minutes (cover with aluminum foil).

11.4.8 Centrifuge samples at 1400 rpm 5° C. for 5 minutes and discard supernatant.

11.4.9 Wash off excess antibody and lysing buffer by adding 1.25 mL/sample FACS Buffer centrifuge at 1400 rpm at 5° C. for 5 min, discard supernatant. Repeat this step for a total of 2 washes.

11.4.10 After the last wash, discard cell supernatant, and re-suspend each cell pellet in a final total volume of 150 uL FACS Buffer.

11.4.11 Add 1 µL/sample of viability stain (7-AAD).

11.4.12 Incubate at RT in dark for 5 min.

11.4.13 Add 50 uL CountBright absolute counting beads if applicable.

11.4.14 Allow the beads to come to room temperature, and gently vortex the tube for 30 seconds to completely resuspend.

11.4.15 Immediately after vortexing the beads add 50 uL of beads to each sample by reverse pipetting and vortex.

11.4.16 Acquire on flow cytometer.

11.5 Flow Cytometry Analysis Panel 1

11.5.1 Gating was set for panel 1 according to FIG. 1.

11.5.2 Plot 1: Bead gate: FSC-A vs CD8 was created and all events were gated on CD8 positive to define bead events.

11.5.3 Plot 2. Scatter plot: A FSC-H vs SSC-A plot was created and all events were gated on a large gate to exclude debris and define scatter events.

11.5.4 Plot 3: Singlets: A FSC-H vs FSC-A plot was created and scatter events were plotted to draw a gate around single cells.

11.5.5 Plot 4: Live cell gate: A SSC vs live/dead plot was created and singlet events were gated on FVS700 negative cells to define live cells.

11.5.6 Plot 5: CD45+ gate: A SSC-A vs CD45 plot was created and live cells were gated on CD45 positive cells to describe CD45+ cells (white blood cells WBC).

11.5.7 Plot 6: CD45+PD-L1+ gate: A PD-L1 vs CD45 plot was created and live cells were gated on CD45+PD-L1+ events to define PD-L1 expressing WBCs.

11.5.8 Plot 7: Lymphocyte gate: A FSC-A vs SSC-A plot was created and WBCs were gated on FSC-A low, SSC-A low events to define lymphocytes.

11.5.9 Plot 8: Total T cells. A SSC-A vs CD3 plot was created and total T lymphocytes were gated on CD3 positive events to describe total T lymphocytes.

11.5.10 Plot 9: CD4 T helper (Th) and CD8 T cytotoxic (Tc) lymphocytes: A CD4 vs CD8 plot was created and total T lymphoyctes were gated on CD4+CD8− to describe T helper cells and CD4−CD8+ to describe T cytotoxic cells 11.5.11 Plot 10: CD8+ Tregs: A CD25 vs FoxP3 plot was created and CD8+ T cells were gated on CD25+FoxP3+ events to describe CD8+ Tregs.

11.5.12 Plot 11: CD4+ Tregs: A CD25 vs FoxP3 plot was created and CD4+ T cells were gated on CD25+FoxP3+ events to describe CD4+ Tregs.

11.5.13 Plot 12: CD4+PD-1+ Tregs: A SSC-A vs PD-1 plot was created and CD4+ Treg cells were gated on PD-1+ events to describe CD4+PD-1+ Tregs.

11.5.14 Plot 13: CD3+CD44+ cells: A CD44 vs CD3 plot was created and lymphocytes were gated on CD3+CD44+ events to describe CD3+CD44+ cells.

11.5.15 Plot 14: CD3+PD-1+ cells: A PD-1 vs CD3 plot was created and lymphocytes were gated on CD3+PD-1+ events to describe CD3+PD-1+ cells.

11.5.16 Plot 15: CD3+PD-L1+ cells: A PD-L1 vs CD3 plot was created and lymphocytes were gated on CD3+PD-L1+ events to describe CD3+PD-L1+ cells.

11.5.17 Plot 16: CD3+GRANZYME B+ cells: A GRANZYME B vs CD3 plot was created and lymphocytes were gated on CD3+GRANZYME B+ events to describe CD3+GRANZYME B+ cells.

11.5.18 Plot 17: CD4+PD-1+ cells: A PD-1 vs CD4 plot was created and lymphocytes were gated on CD4+PD-1+ events to describe CD4+PD-1+ cells.

11.5.19 Plot 18: CD4+CD25+ cells: A CD25 vs CD4 plot was created and lymphocytes were gated on CD4+CD25+ events to describe CD4+CD25+ cells.

11.5.20 Plot 19: CD4+CD44+ cells: A CD44 vs CD4 plot was created and lymphocytes were gated on CD4+CD44+ events to describe CD4+CD44+ cells.

11.5.21 Plot 20: CD8+CD44+ cells: A CD44 vs CD8 plot was created and lymphocytes were gated on CD8+CD44+ events to describe CD8+CD44+ cells.

11.5.22 Plot 21: CD8+PD-1+ cells: A PD-1 vs CD8 plot was created and lymphocytes were gated on CD8+PD-1+ events to describe CD8+PD-1+ cells.
11.5.23 Plot 22: CD8+CD25+ cells: A CD25 vs CD8 plot was created and lymphocytes were gated on CD8+CD25+ events to describe CD8+CD25+ cells.
11.6 Flow Cytometry Analysis Panel 2
11.6.1 Gating was set for panel 2 according to FIG. 2.
11.6.2 Plot 1: Beads: A FSC-A vs CD45 plot was created and beads were defined by a CD45+ gate.
11.6.3 Plot 2: Scatter plot: A FSC-A vs SSC-A plot was created and all events were gated on FSClowSSClow to exclude debris.
11.6.4 Plot 3: Singlets: A FSC-H vs FSC-A plot was created and scatter events were gated on a singlet gate to identify single cells.
11.6.5 Plot 4: Live cell gate: A SSC vs live/dead plot was created and singlet events were gated on FVS620 negative cells to define live cells.
11.6.6 Plot 5: CD45+(WBC) gate: A SSC-A vs CD45 plot was created and live cells were gated on CD45 positive cells to describe WBCs.
11.6.7 Plot 6: CD11b+ gate: A SSC-A vs CD11b plot was created and WBCs were gated on CD45+ to describe CD11b+ cells.
11.6.8 Plot 7: MDSC gate: A Ly6-C vs Ly-6G plot was created. A gate on Ly-6C+Ly-G− was used to define M-MDSC cells, and a gate on Ly-6C-Ly-6G+ was used to define G-MDSC cells.
11.6.9 Plot 8: Macrophage gate: A F4/80 vs CD11b plot was created and WBCs were gated on CD11b+F4/80+ cells to describe macrophages.
11.6.10 Plot 9: M1 and M2 macrophage gate: A MHCII vs CD206 plot was created and macrophage cells were gated on MHCII+CD206− to define M1 macrophages, and MHCII-CD206+ to define M2 macrophages.
12 Results and Summary Flow cytometry results from spleen and tumor samples are listed in Tables 23-107 and summary statistical results in Tables 9-22. Panel 1 evaluated T cell subsets including total T, CD4 T helper, CD8 T cytotoxic, regulatory T, and further analyzed these subsets for expression of the following checkpoint, proliferation, and activation markers: Granzyme B, CD44, PD-1, PD-L1, and CD25. Panel 2 evaluated macrophage subsets (M1 and M2) and MDSC subsets (M-MDSC and G-MDSC). All animals in all groups reached termination and were evaluated.

Statistical analysis was reported in tables 9-22. In tumor samples from panel 1, the 4T1 model led to the highest numbers of statistically significant results (44), followed by RENCA (17), and CT26 (14). The MC38 model resulted in only 7 significant results. Similar results were determined in spleen samples from panel 1, with the 4T1 model having the highest numbers of significant results (22), followed by RENCA (18), and with CT26 having only 4 significant results. Spleen was not analyzed in MC38 animals. The 4T1 model also had the most significant P values ($P \leq 0.0001$) at 14, with only 2 results in each of RENCA and CT26.

In panel 2, tumor samples had few significant findings, with 0 for 4T1, 4 for CT26, 1 for RENCA, and none for MC38. Spleen samples had more significant results, with 11 for 4T1 and 12 for RENCa, and 2 for CT26.

In 4T1 tumors, a decrease in CD4 Tregs was observed (FIG. 5). This occurred as a percentage, and also absolute counts (FIG. 8). Spleen cells from 4T1 mice also had similar decreases following drug treatment (FIGS. 11, 14). This decrease was not observed in RENCA tumors, as there were too few cells to analyze. RENCA spleen samples had a bit more Tregs, but still quite low, and did not observe a decrease in Tregs in dosed animals.

An increase in CD4 T cell percentage and concentration was observed in CT26 spleen samples for dosed groups (2-4). However, most of the significant flow cytometry results for CT26 animals occurred in the tumor samples and when treated with both TP-1454 and anti-PD-1 (group 4). This included increased percentage of CD45+PD-L1+ cells, increased percentage and concentration of CD3+PD-L1+ cells, and increases in CD3+Granzymeb+ cells and CD4+ CD25+ activated T cells (FIGS. 20,21, 23, 24).

PD-L1 concentration was also increased in RENCA spleen samples from animals dosed with TP-1454 and anti-PD-1 (FIG. 7), and percentages increased in 4T1 tumor samples from animals in all dosed groups (FIG. 4).
12 Statistical Analysis Statistical analysis: Flow cytometry cell subsets including percentages and absolute counts defined in the gating reportable tables for panels 1 and 2 were analyzed for statistical significance by using a one-way ANOVA with Dunnet's test. Statistically significant P values were recorded in the P value column with asterisks according to the table below.

TABLE 12

| P value nomenclature | |
|---|---|
| Symbol | P value |
| none | $P > 0.05$ |
| * | $P \leq 0.05$ |
| ** | $P \leq 0.01$ |
| *** | $P \leq 0.001$ |
| **** | $P \leq 0.0001$ |

The results of this analysis is presented graphically in the table below:

TABLE 13

| | 4T1-Tumor (Breast, immune checkpoint resistant) (Mean, %) | | 4T1-Spleen (Mean, %) | | |
|---|---|---|---|---|---|
| | Treg PD-1 | CD3+ GranzB | Treg PD-1 | CD3+ GranzB | Comments |
| vehicle | 35.9 | 0.8 | 9.6 | N.D. | Reduction in immune suppressive cells in tumor environment and systemic (spleen) |
| Cmpd 1 + PD1 Inhib | 0 | 0.3 | 0.7 | N.D. | |

TABLE 13-continued

| CT26-Tumor (Colon, immune checkpoint sensitive) (Mean, %) | | | | | |
|---|---|---|---|---|---|
| CD3+ | | | CT-26 Spleen | | |
| PDL-1+ | CD4+ CD25+ | CD4T | CD8T | | |
| vehicle | 3.5 | 16 | 59 | 34 | Increase in infiltrating lymphocytes in tumor, slight increase in systemic lymphocytes (spleen) |
| Cmpd 1 + PD1 Inhib | 19 | 37 | 61 | 31 | |

| RENCA-Tumor Renal Cell Carcinoma (immune checkpoint resistant) (Cells/uL) | | | RENCA-Spleen (% Mean) | | |
|---|---|---|---|---|---|
| CD45+ PDL-1 | PDL-1 | CD45+ PDL-1 | CD45+ | | |
| vehicle | 123 | 31 | 4.9 | 90 | Increase in infiltrating lymphocytes in tumor, increase in overall immune resistant markers, decrease in systemic lymphocytes (spleen) |
| Cmpd 1 + PD1 Inhib | 258 | 59 | 3.1 | 70 | |

| MC38-Tumor Colorectal Cancer (immune checkpoint sensitive) (%, Mean) | | |
|---|---|---|
| CD4T FOXP3+ CD25+ | Treg PD-1+ | |
| vehicle | 49 | 45 | Decrease in immune suppressive cells in tumor microenvironment |
| Cmpd 1 + PD1 Inhib | 27 | 24 | |

These data are indicative of increase lymphocyte infiltration and depletion of T-regulatory cells with the combination of a compound of Formula 1 and an immune checkpoint inhibitor in a wide variety of tumor environments, including tumor environments that are not responsive to IO therapy, for example, checkpoint inhibitors. To the extent that such tumors do not respond to checkpoint inhibitor therapy, these data indicate also that treatment with a PD-1 inhibitor in the presence of a compound of Formula I alters the tumor microenvironment by depletion of T-regulatory cells and leaves the tumor susceptible to treatment with a second checkpoint inhibitor such as a CTLA4 inhibitor or additional immune modulating agents. A similar trend in these indicators is observed in immune competent cancer models by treatment with the compound of Formula I alone, that is, treatment of these models with the compound of Formula I alone lead to a decrease in T-regulatory cells and/or an increase in lymphocyte infiltration, indicating that the compound of Formula I has unique therapeutic activity and alters the microenvironment in tumors and may render such tumors susceptible to treatment with an immunotherapy agent.

Accordingly, these data indicate that many tumor environments may be treated with the compound of Formula I, alone or in combination one or more immunotherapy agent(s), for example, one or more checkpoint inhibitors. Alteration of the tumor microenvironment in this matter includes rendering some types of tumors which do not respond to IO compounds, vulnerable to treatment with them. For example, treatment of such tumors with a compound of Formula I, in addition to a PD-1 inhibitor, and a CTLA-4 inhibitor, for example, treatment with the combination of a compound of Formula I and either or both of Nivolumab and Ipilimumab, can lead to tumor regression or death. Examples of indications which would in particular benefit from such therapy include renal cell carcinoma, melanoma, colorectal cancer, particularly where patients are MSI-H or dMMR, and advanced renal cell carcinoma which has previously failed on anti-angiogenic therapy or in patients with low tumor cell infiltration and/or high levels of immune suppressive regulatory cells.

The following table shows examples of specific tumor types which may be beneficially treated with a combination of the compound of Formula I and one or more checkpoint inhibitors:

TABLE 14

| Combination | Indication |
|---|---|
| Compound of Formula 1 once or twice daily 120 mg-720 mg Nivolumab (3 mg/kg) contemporaneous with Ipilimumab (1 mg/kg) every 3 weeks for 4 doses followed by dosing Nivolumab: 240 mg every 2 weeks or 480 mg every 4 weeks | First Line IMDC classification Intermediate- or Poor-risk stage IV Renal Cell Carcinoma |
| Compound of Formula 1 once or twice daily 120 mg-720 mg Nivolumab (3 mg/kg) contemporaneous with Ipilimumab (1 mg/kg) every 3 weeks for 4 doses followed by dosing Nivolumab: 240 mg every 2 weeks or 480 mg every 4 weeks | First Line Stage III or IV unresectable advanced melanoma |
| Compound of Formula 1 once or twice daily 120 mg-720 mg Nivolumab (3 mg/kg) contemporaneous with Ipilimumab (1 mg/kg) every 3 weeks for 4 doses followed by dosing Nivolumab: 240 mg every 2 weeks or 480 mg every 4 weeks | Patients over 12 years of age with microsatellite instability-High (MSI-H) or mismatch repair deficient (dMMR) metastatic colorectal cancer that has progressed following treatment with a fluoropyrimidine, oxaliplatin, and irinotecan |
| Compound of Formula 1 once or twice daily 120 mg-720 mg contemporaneously with intravenous infusion over 60 minutes of Nivolumab (3 mg/kg), with repeat of Nivolumab infusion every three weeks | Patients with advanced renal cell carcinoma who have failed prior anti-angiogenic therapy |

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

The teachings of all patents, published applications and references cited herein, including but not limited to U.S. Provisional Application Ser. No. 62/822,751 filed Mar. 22, 2019, U.S. Provisional Application Ser. No. 62/875,940 filed Jul. 18, 2019, and U.S. Provisional Application Ser. No. 62/926,417 filed Oct. 25, 2019, are incorporated by reference in their entirety.

TABLE 1

Protocol Design

| Group | n | Treatment Regimen 1 | | | | Treatment Regimen 2 | | | |
|---|---|---|---|---|---|---|---|---|---|
| | | Agent | mg/kg | Route | Schedule | Agent | mg/kg | Route | Schedule |
| 1 | 8 | vehicle | — | po | qd x 21 | — | — | — | — |
| 2 | 8 | Cmpd of Structure (I) | 50 | po | qd x 21 | — | — | — | — |
| 3 | 8 | Cmpd of Structure (I) | 100 | po | qd x 21 | — | — | — | — |
| 4 | 8 | anti-PD-1 RMP1-14 | 5 | ip | biwk x 2 | — | — | — | — |
| 5 | 8 | Cmpd of Structure (I) | 50 | po | qd x 21 | anti-PD-1 RMP1-14 | 5 | ip | biwk x 2 |
| 6 | 8 | Cmpd of Strructure (I) | 100 | po | qd x 21 | anti-PD-1 RMP1-14 | 5 | ip | biwk x 2 |

Table 1 displays the study design as of Day 1 of the study.

vehicle = Tween80, Ethanol, and PEG400, in water (in the following ratio: 2:10:30:58)

TABLE 2

Response Summary

| Group | n | Treatment Regimen Agent | mg/kg | Route | Schedule | Median TTE | T-C | % TGD | Statistical Significance vs G1 | vs G5 | vs G6 | MTV (n) Day 46 | Regressions PR | CR | TFS | Mean BW Nadir | Deaths IR | NTR |
|---|---|---|---|---|---|---|---|---|---|---|---|---|---|---|---|---|---|---|
| 1 | 8 | vehicle | — | po | qd x 21 | 19.1 | — | — | — | *** | *** | — | 0 | 0 | 0 | — | 0 | 0 |
| 2 | 6 | Cmpd of Structure (I) | 50 | po | qd x 21 | 22.7 | 3.6 | 19 | ns | * | — | 0 (1) | 0 | 1 | 1 | — | 0 | 2 |
| 3 | 7 | Cmpd of Structure (I) | 100 | po | qd x 21 | 32.5 | 13.4 | 70 | *** | — | ns | 446 (1) | 0 | 0 | 0 | — | 0 | 1 |
| 4 | 7 | anti-PD-1 RMP1-14 | 5 | ip | biwk x 2 | 42.2 | 23.1 | 121 | ** | ns | ns | 424 (2) | 0 | 1 | 1 | −0.6% Day 3 | 0 | 1 |
| 5 | 5 | Cmpd of Str (I) | 50 | po | qd x 21 | 46.0 | 26.9 | 141 | *** | — | — | 63 (4) | 1 | 2 | 2 | −0.8% Day 5 | 0 | 2 |
|   |   | anti-PD-1 RMP1-14 | 5 | ip | biwk x 2 |   |   |   |   |   |   |   |   |   |   |   |   |   |
| 6 | 7 | Cmpd of Str (I) | 100 | po | qd x 21 | 46.0 | 26.9 | 141 | *** | — | — | 398 (4) | 0 | 1 | 1 | −0.4% Day 3 | 0 | 1 |
|   |   | anti-PD-1 RMP1-14 | 5 | ip | biwk x 2 |   |   |   |   |   |   |   |   |   |   |   |   |   |

Table 2 displays the scheduled treatment regimen at completion of the study.
vehicle = Tween80, Ethanol, and PEG400, in water (in the following ratio: 2:10:30:58)
Reduced n per group due to tumors in range at start. Sep. 16, 2018 ER
Study was converted to TGD on Day 21. Oct. 8, 2018 EGO
Extended study one Day (Day 46) for full biwk schedule, and clarified sampling. Oct. 29, 2018 ER
Study Endpoint = 1000 mm$^3$; Study Duration = 46 Days
n = number of animals in a group not dead from accidental or unknown causes, or euthanized for sampling
TTE = time to endpoint, T-C = difference between median TTE (Days) of treated versus control group, % TGD = [(T-C/C] x 100
The maximum T-C in this study is 26.9 Days (141%), compared to Group 1
Statistical Significance (Logrank test): ne = not evaluable, ns = not significant, * = $P < 0.05$,  = $P < 0.01$, * = $P < 0.001$, compared to group indicated
MTV (n) = median tumor volume (mm$^3$) for the number of animals on the Day of TGD analysis (excludes animals with tumor volume at endpoint)
PR = partial regressions; CR = total number complete regressions; TFS = tumor free survivors, i.e., CRs at end of study
Mean BW Nadir = lowest group mean body weight, as % change from Day 1; — indicates no decrease in mean body weight was observed
TR = treatment-related death; NTR = non-treatment-related death

TABLE 3

Tumor Growth Inhibition

| Group | n | Treatment Regimen Agent | mg/kg | Route | Schedule | MTV (n) Day 21 | % TGI | Statistical Significance vs G1 | vs G5 | vs G6 | Regressions PR | CR | Mean BW Nadir | Deaths TR | NTR |
|---|---|---|---|---|---|---|---|---|---|---|---|---|---|---|---|
| 1 | 8 | vehicle | — | po | qd x 21 | 1576 (8) | — | — | *** | ** | 0 | 0 | — | 0 | 0 |
| 2 | 6 | Cmpd of Str (I) | 50 | po | qd x 21 | 925 (6) | 41 | ns | * | — | 0 | 1 | — | 0 | 2 |
| 3 | 7 | Cmpd of Str (I) | 100 | po | qd x 21 | 550 (7) | 65 | ** | — | ns | 0 | 0 | — | 0 | 1 |
| 4 | 7 | anti-PD-1 RMP1-14 | 5 | ip | biwk x 2 | 485 (8) | 69 | ** | ns | ns | 0 | 0 | −0.6% Day 3 | 0 | 0 |
| 5 | 5 | Cmpd of Str (I) | 50 | po | qd x 21 | 108 (7) | 93 | *** | — | — | 1 | 1 | −0.8% Day 5 | 0 | 1 |
|   |   | anti-PD-1 RMP1-14 | 5 | ip | biwk x 2 |   |   |   |   |   |   |   |   |   |   |
| 6 | 7 | Cmpd of Str (I) | 100 | po | qd x 21 | 144 (7) | 91 | ** | — | — | 1 | 0 | −0.4% Day 3 | 0 | 1 |
|   |   | anti-PD-1 RMP1-14 | 5 | ip | biwk x 2 |   |   |   |   |   |   |   |   |   |   |

Table 3 displays the scheduled treatment regimen at completion of the study.
vehicle = Tween80, Ethanol, and PEG400, in water (in the following ratio: 2:10:30:58)
Reduced n per group due to tumors in range at start. Sep. 16, 2018 ER
Study was converted to TGD on Day 21. Oct. 8, 2018 EGO
Extended study one Day (Day 46) for full biwk schedule, and clarified sampling. Oct. 29, 2018 ER
Study Endpoint = 1000 mm$^3$; Study Duration = 21 Days
n = number of animals in a group not dead from accidental or unknown causes, or euthanized for sampling
% TGI = [1-($^{MTV}$drug treated/$^{MTV}$control)] x 100 = percent tumor growth inhibition, compared to Group 1
Statistical Significance (Mann-Whitney U test); ne = not evaluable, ns = not significant, * = $P < 0.05$. = $P < 0.01$, * = $P < 0.001$, compared to group indicated MTV (n) = median tumor volume (mm$^3$) for the number of animals on the day of TGI analysis (includes animals with tumor volume at endpoint)
PR = partial regression; CR = complete regression
Mean BW Nadir = lowest group mean body weight, as % change from Day 1; — indicates no decrease in mean body weight was observed
TR = treatment-related death, NTR = non-treatment-related death

TABLE 4

Protocol Design for the MC38-e423 Study

| | | Treatment Regimen 1 | | | | Treatment Regimen 2 | | | |
|---|---|---|---|---|---|---|---|---|---|
| Group | n | Agent | mg/kg | Route | Schedule | Agent | mg/kg | Route | Schedule |
| 1 | 10 | vehicle | — | po | qd x 21 | — | — | — | — |
| 2 | 10 | Cmpd of Str (I) | 25 | po | qd x 21 | — | — | — | — |
| 3 | 10 | Cmpd of Str (I) | 50 | po | qd x 21 | — | — | — | — |
| 4 | 10 | Cmpd of Str (I) | 100 | po | qd x 21 | — | — | — | — |
| 5 | 10 | Cmpd of Str (I) | 200 | po | qd x 21 | — | — | — | — |
| 6 | 10 | anti-PD-1 RMP1-14 | 5 | ip | biwk x 2 | — | — | — | — |
| 7 | 10 | Cmpd of Str (I) | 25 | po | qd x 21 | anti-PD-1 RMP1-14 | 5 | ip | biwk x2 |
| 8 | 10 | Cmpd of Str (I) | 50 | po | qd x 21 | anti-PD-1 RMP1-14 | 5 | ip | biwk x 2 |
| 9 | 10 | Cmpd of Str (I) | 100 | po | qd x 21 | anti-PD-1 RMP1-14 | 5 | ip | biwk x 2 |
| 10 | 10 | Cmpd of Str (I) | 200 | po | qd x 21 | anti-PD-1 RMP1-14 | 5 | ip | biwk x 2 |
| 11 | 10 | anti-CTLA-4 9H10 | 5 | ip | Day 1 | anti-CTLA-4 9H10 | 2.5 | ip | Days 4, 7 |
| 12 | 10 | Cmpd of Str (I) | 50 | po | qd x 21 | anti-CTLA-4 9H10 | 5 | ip | Day 1 |
| 13 | 10 | Cmpd of Str (I) | 100 | po | qd x 21 | anti-CTLA-4 9H10 | 5 | ip | Day 1 |
| 14 | 10 | anti-PD-1 RMP1-14 | 5 | ip | biwk x 2 | anti-CTLA-4 9H10 | 5 | ip | Day 1 |
| 15 | 10 | Cmpd of Str (I) | 50 | po | qd x 21 | anti-PD-1 RMP1-14 | 5 | ip | biwk x 2 |
| 16 | 10 | Cmpd of Str (I) | 100 | po | qd x 21 | anti-PD-1 RMP1-14 | 5 | ip | biwk x 2 |

| | | Treatment Regimen 3 | | | | Treatment Regimen 4 | | | |
|---|---|---|---|---|---|---|---|---|---|
| Group | n | Agent | mg/kg | Route | Schedule | Agent | mg/kg | Route | Schedule |
| 1 | 10 | — | — | — | — | — | — | — | — |
| 2 | 10 | — | — | — | — | — | — | — | — |
| 3 | 10 | — | — | — | — | — | — | — | — |
| 4 | 10 | — | — | — | — | — | — | — | — |
| 5 | 10 | — | — | — | — | — | — | — | — |
| 6 | 10 | — | — | — | — | — | — | — | — |
| 7 | 10 | — | — | — | — | — | — | — | — |
| 8 | 10 | — | — | — | — | — | — | — | — |
| 9 | 10 | — | — | — | — | — | — | — | — |
| 10 | 10 | — | — | — | — | — | — | — | — |
| 11 | 10 | — | — | — | — | — | — | — | — |
| 12 | 10 | anti-CTLA-4 9H10 | 2.5 | ip | Days 4, 7 | — | — | — | — |
| 13 | 10 | anti-CTLA-4 9H10 | 2.5 | ip | Days 4, 7 | — | — | — | — |
| 14 | 10 | anti-CTLA-4 9H10 | 2.5 | ip | Days 4, 7 | — | — | — | — |
| 15 | 10 | anti-CTLA-4 9H10 | 5 | ip | Day 1 | anti-CTLA-4 9H10 | 2.5 | ip | Days 4, 7 |
| 16 | 10 | anti-CTLA-4 9H10 | 5 | ip | Day 1 | anti-CTLA-4 9H10 | 2.5 | ip | Days 4, 7 |

Table 4 displays the study design as of Day 1 of the study.
Vehicle = 2% Tween80:10% Ethanol:30% PEG400:58% DIH20

TABLE 5

Response Summary in the MC38-e423 Study

| Group | n | Treatment Regimen | | | | | Median TTE | T-C | % TGD | Statistical Significance | | | | MTV (n) Day 44 | Regressions | | | Mean BW Nadir | Deaths | |
|---|---|---|---|---|---|---|---|---|---|---|---|---|---|---|---|---|---|---|---|---|
| | | Agent | mg/kg | Route | Schedule | | | | | vs G1 | vs G6 | vs G11 | vs G14 | | PR | CR | TFS | | TR | NTHn |
| 1 | 9 | vehicle | — | po | qd x 21 | 16.9 | — | — | — | — | — | — | 787 (1) | 0 | 0 | 0 | -2.6% Day 2 | 0 | 1 |
| 2 | 10 | Cmpd of Str (I) | 25 | po | qd x 21 | 21.1 | 4.2 | 25 | ns | * | ** | *** | — | 0 | 0 | 0 | -0.7% Day 2 | 0 | 0 |
| 3 | 10 | Cmpd of Str (I) | 50 | po | qd x 21 | 18.9 | 2.0 | 12 | ns | — | — | — | — | 0 | 0 | 0 | -1.7% Day 2 | 1 | 0 |
| 4 | 9 | Cmpd of Str (I) | 100 | po | qd x 21 | 22.5 | 5.6 | 33 | ns | — | — | — | 162 (1) | 1 | 0 | 0 | -1.8% Day 2 | 0 | 1 |
| 5 | 9 | Cmpd of Str (I) | 200 | po | qd x 21 | 20.8 | 3.9 | 23 | ns | — | — | — | — | 0 | 0 | 0 | -0.9% Day 2 | 1 | 1 |
| 6 | 10 | anti-PD-1 RMP1-14 | 5 | ip | biwk x 2 | 33.8 | 16.9 | 100 | * | — | — | — | 410 (4) | 0 | 1 | 0 | -0.1% Day 2 | 0 | 0 |
| 7 | 8 | Cmpd of Str (I) anti-PD-1 RMP1-14 | 25 5 | po ip | qd x 21 biwk x 2 | 31.2 | 14.3 | 85 | * | ns | — | — | 554 (2) | 0 | 0 | 0 | — | 0 | 2 |
| 8 | 9 | Cmpd of Str (I) anti-PD-1 RMP1-14 | 50 5 | po ip | qd x 21 biwk x 2 | 30.2 | 13.3 | 79 | ns | ns | — | — | — | 0 | 0 | 0 | -0.6% Day 2 | 0 | 1 |
| 9 | 8 | Cmpd of Str (I) anti-PD-1 RMP1-14 | 100 5 | po ip | qd x 21 biwk x 2 | 30.2 | 13.3 | 79 | ns | ns | — | — | — | 0 | 0 | 0 | -1.2% Day 2 | 0 | 2 |
| 10 | 9 | Cmpd of Str (I) anti-PD-1 RMP1-14 | 200 5 | po ip | qd x 21 biwk x 2 | 30.3 | 13.4 | 79 | ns | ns | — | — | — | 0 | 0 | 0 | -1.3% Day 2 | 0 | 1 |
| 11 | 9 | anti-CTLA-4 9H10 anti-CTLA-4 9H10 | 5 2.5 | ip ip | Day 1 Days 4, 7 | 44.0 | 27.1 | 160 | ** | — | — | — | 1 (5) | 0 | 5 | 3 | -0.9% Day | 0 | 1 |

TABLE 5-continued

Response Summary in the MC38-e423 Study

| Group | n | Treatment Regimen | | | | | Median | | | Statistical Significance | | | | MTV (n) | Regressions | | | Mean BW | Deaths | |
|---|---|---|---|---|---|---|---|---|---|---|---|---|---|---|---|---|---|---|---|---|
| | | Agent | mg/kg | Route | Schedule | | TTE | T-C | % TGD | vs G1 | vs G6 | vs G11 | vs G14 | Day 44 | PR | CR | TFS | Nadir | TR | NTHn |
| 12 | 8 | Cmpd of Str (I) | 50 | po | qd x 21 | | 44.0 | 27.1 | 160 | ** | — | ns | — | 1 (7) | 0 | 6 | 5 | −1.4% Day 2 | 0 | 2 |
| | | anti-CTLA-4 9H10 | 5 | ip | Day 1 | | | | | | | | | | | | | | | |
| | | anti-CTLA-4 9H10 | 2.5 | ip | Days 4, 7 | | | | | | | | | | | | | | | |
| 13 | 9 | Cmpd of Str (I) | 100 | po | qd x 21 | | 42.7 | 25.8 | 153 | ** | — | ns | — | 1 (4) | 0 | 4 | 3 | −1.5% Day 2 | 0 | 1 |
| | | anti-CTLA-4 9H10 | 5 | ip | Day 1 | | | | | | | | | | | | | | | |
| | | anti-CTLA-4 9H10 | 2.5 | ip | Days 4, 7 | | | | | | | | | | | | | | | |
| 14 | 10 | anti-PD-1 RMP1-14 | 5 | ip | biwk x 2 | | 44.0 | 27.1 | 160 | *** | — | ns | — | 1 (8) | 0 | 7 | 7 | −1.9% Day 2 | 0 | 0 |
| | | anti-CTLA-4 9H10 | 5 | ip | Day 1 | | | | | | | | | | | | | | | |
| | | anti-CTLA-4 9H10 | 2.5 | ip | Days 4, 7 | | | | | | | | | | | | | | | |
| 15 | 9 | Cmpd of Str (I) | 50 | po | qd x 21 | | 44.0 | 27.1 | 160 | *** | — | — | ns | 1 (8) | 0 | 7 | 7 | −2.5% Day 3 | 0 | 1 |
| | | anti-PD-1 RMP1-14 | 5 | ip | biwk x 2 | | | | | | | | | | | | | | | |
| | | anti-CTLA-4 9H10 | 5 | ip | Day 1 | | | | | | | | | | | | | | | |
| | | anti-CTLA-4 9H10 | 2.5 | ip | Days 4, 7 | | | | | | | | | | | | | | | |
| 16 | 10 | Cmpd of Str (I) | 100 | po | qd x 21 | | 44.0 | 27.1 | 160 | *** | — | — | ns | 1 (10) | 0 | 10 | 10 | −0.5% Day 2 | 0 | 0 |
| | | anti-PD-1 RMP1-14 | 5 | ip | biwk x 2 | | | | | | | | | | | | | | | |
| | | anti-CTLA-4 9H10 | 5 | ip | Day 1 | | | | | | | | | | | | | | | |
| | | anti-CTLA-4 9H10 | 2.5 | ip | Days 4, 7 | | | | | | | | | | | | | | | |

Table 5 displays the scheduled treatment regimen at completion of the study.
Vehicle = 2% Tween80:10% Ethanol:38% PEG400:58% DIH2O
Added details for sampling small/nonexistent tumors. Apr. 22, 2019 ER
Study Endpoint = 1000 mm³; Study Duration = 44 Days
n = number of animals in a group not dead from accidental or unknown causes, or euthanized for sampling
TTE = time to endpoint, T-C = difference between median TTE (Days) of treated versus control group, % TGD = [(T-C)/C × 100
The maximum T-C in this study is 27.1 Days (160%) compared to Group 1
Statistical Significance (Logrank test); ne = not evaluable, ns = not significant, * = P < 0.05,  = P < 0.01, * = P < 0.001, compared to Group 1
MTV (n) = median tumor volume (mm³) for the number of animals on the day of TGD analysis (excludes animals with tumor volume at endpoint)
PR = partial regression; CR = total number complete regressions; TFS = tumor free survivors, i.e., tumor volumes ≤13.5 mm³ for the final three measurements of the study
Mean BW Nadir = lowest group mean body weight, as % change from Day 1; — indicates no decrease in mean body weight was observed
TR = treatment-related death, NTRn = non-treatment-related deathdue to unknown cause

TABLE 6

Tumor Growth Inhibition in the MC38-e423 Study

| Group | n | Agent | mg/kg | Route | Schedule | MTV (n) Day 19 | % TGI | vs G1 | vs G6 | vs G11 | vs G14 | PR | CR | Mean BW Nadir | TR | NTRu |
|---|---|---|---|---|---|---|---|---|---|---|---|---|---|---|---|---|
| 1 | 10 | vehicle | — | po | qd x 21 | 1216 (10) | — | — | * | ** | *** | 0 | 0 | -2.6% Day 2 | 0 | 0 |
| 2 | 10 | Cmpd of Str (I) | 25 | po | qd x 21 | 864 (10) | 29 | ns | — | — | — | 0 | 0 | -0.7% Day 2 | 0 | 0 |
| 3 | 10 | Cmpd of Str (I) | 50 | po | qd x 21 | 1008 (9) | 17 | ns | — | — | — | 0 | 0 | -1.7% Day 2 | 1 | 0 |
| 4 | 10 | Cmpd of Str (I) | 100 | po | qd x 21 | 666 (10) | 45 | ns | — | — | — | 1 | 0 | -1.8% Day 2 | 0 | 0 |
| 5 | 10 | Cmpd of Str (I) | 200 | po | qd x 21 | 726 (9) | 40 | ns | — | — | — | 0 | 0 | -0.9% Day 2 | 1 | 0 |
| 6 | 10 | anti-PD-1 RMP1-14 | 5 | ip | biwk x 2 | 387 (10) | 68 | ** | — | — | — | 0 | 1 | -0.1% Day 2 | 0 | 0 |
| 7 | 9 | Cmpd of Str (I) anti-PD-1 RMP1-14 | 25 5 | po ip | qd x 21 biwk x 2 | 288 (9) | 76 | ** | ns | — | — | 0 | 0 | — | 0 | 1 |
| 8 | 9 | Cmpd of Str (I) anti-PD-1 RMP1-14 | 50 5 | po ip | qd x 21 biwk x 2 | 365 (10) | 70 | ** | ns | — | — | 0 | 0 | -0.6% Day 2 | 0 | 1 |
| 9 | 10 | Cmpd of Str (I) anti-PD-1 RMP1-14 | 100 5 | po ip | qd x 21 biwk x 2 | 433 (10) | 64 | ** | ns | — | — | 0 | 0 | -1.2% Day 2 | 0 | 0 |
| 10 | 10 | Cmpd of Str (I) anti-PD-1 RMP1-14 | 200 5 | po ip | qd x 21 biwk x 2 | 525 (10) | 57 | ** | ns | — | — | 0 | 0 | -1.3% Day 2 | 0 | 0 |
| 11 | 10 | anti-CTLA-4 9H10 anti-CTLA-4 9H10 | 5 2.5 | ip ip | Day 1 Days 4, 7 | 95 (10) | 92 | *** | — | — | — | 0 | 5 | -0.9% Day | 0 | 0 |
| 12 | 10 | Cmpd of Str (I) anti-CTLA-4 9H10 anti-CTLA-4 9H10 | 50 5 2.5 | po ip ip | qd x 21 Day 1 Days 4,7 | 48 (10) | 96 | *** | — | ns | — | 0 | 6 | -1.4% Day 2 | 0 | 0 |
| 13 | 10 | Cmpd of Str (I) anti-CTLA-4 9H10 anti-CTLA-4 9H10 | 100 5 2.5 | po ip ip | qd x 21 Day 1 Days 4,7 | 117 (10) | 90 | *** | — | ns | — | 0 | 4 | -1.5% Day 2 | 0 | 0 |
| 14 | 10 | anti-PD-1 RMP1-14 anti-CTLA-4 9H10 anti-CTLA-4 9H10 | 5 5 2.5 | ip ip ip | biwk x 2 Day 1 Days 4, 7 | 25 (10) | 98 | *** | — | ns | — | 0 | 7 | -1.9% Day 2 | 0 | 0 |

TABLE 6-continued

Tumor Growth Inibition in the MC38-e423 Study

| Group | n | Treatment Regimen Agent | mg/kg | Route | Schedule | MTV (n) Day 19 | % TGI | Statistical Significance vs G1 | vs G6 | vs G11 | vs G14 | Regressions PR | CR | Mean BW Nadir | Deaths TR | NTRu |
|---|---|---|---|---|---|---|---|---|---|---|---|---|---|---|---|---|
| 15 | 10 | Cmpd of Str (I) | 50 | po | qd x 21 | 23 (10) | 98 | *** | — | — | ns | 0 | 7 | −2.5% Day 3 | 0 | 0 |
|  |  | anti-PD-1 RMP1-14 | 5 | ip | biwk x 2 |  |  |  |  |  |  |  |  |  |  |  |
|  |  | anti-CTLA-4 9H10 | 5 | ip | Day 1 |  |  |  |  |  |  |  |  |  |  |  |
|  |  | anti-CTLA-4 9H10 | 2.5 | ip | Days 4, 7 |  |  |  |  |  |  |  |  |  |  |  |
| 16 | 10 | Cmpd of Str (I) | 100 | po | qd x 21 | 16 (10) | 99 | *** | — | — | ns | 0 | 10 | −0.5% Day 2 | 0 | 0 |
|  |  | anti-PD-1 RMP1-14 | 5 | ip | biwk x 2 |  |  |  |  |  |  |  |  |  |  |  |
|  |  | anti-CTLA-4 9H10 | 5 | ip | Day 1 |  |  |  |  |  |  |  |  |  |  |  |
|  |  | anti-CTLA-4 9H10 | 2.5 | ip | Days 4, 7 |  |  |  |  |  |  |  |  |  |  |  |

Table 6 displays the scheduled treatment regimen at completion of the study?
Vehicle = 2% Tween80:10% Ethanol:30% PEG400:58% DIH20?
Added details for sampling small/nonexistent tumors. Apr. 22, 2019 ER?
Study Endpoint = 1000 mm³; Study Duration = 19 Days?
n = number of animals in a group not dead from accidental or unknown causes, or euthanized for sampling
% TGI = [1-(MTVdrug treated/MTVcontrol)] × 100 = percent tumor growth inhibition, compared to Group 1
Statistical Significance (Mann-Whitney U test); ne = not evaluable, ns = not significant, * = P < 0.05. = P < 0.01, * = P < 0.001, compared to Group 1
MTV (n) = median tumor volume (mm³) for the number of animals on the day of TGI analysis (includes animals with tumor volume at endpoint
PR = partial regression, CR = complete regression
Mean BW Nadir = lowest group mean body weight, as % change from Day 1; — indicates no decrease in mean body weight was observed
TR = treatment-related death, NTRn = non-treatment-related deathdue to unknown cause

The invention claimed is:

1. A method of treating a cancer, comprising administering to a subject in need thereof an effective amount of a compound of Structure (I):

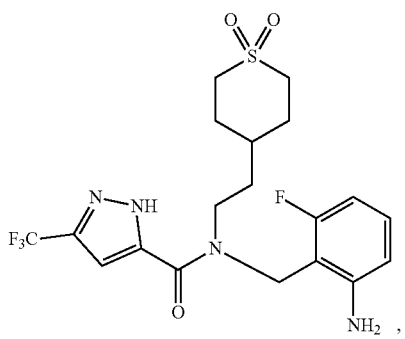

or a pharmaceutically acceptable salt thereof, in combination with a PD-1 inhibitor, wherein the PD-1 inhibitor is nivolumab, and the cancer is resistant to checkpoint inhibitor therapy in the absence of the compound of Structure (I).

2. The method of claim 1, wherein the compound of Structure I, or a pharmaceutically acceptable salt thereof, is administered in a unit dosage of about 1 mg to about 500 mg of a compound of Structure I, or a pharmaceutically acceptable salt thereof.

3. The method of claim 1, wherein the cancer (i) is a solid tumor cancer, (ii) has progressed on an immuno-oncology agent, (iii) is melanoma, renal cell carcinoma, colorectal cancer, hepatocellular carcinoma, or non-small cell lung cancer, (iv) is lung cancer, or (v) is non-small cell lung cancer.

4. The method of claim 1, wherein the cancer is (i) first line IMDC classification Intermediate- or Poor-risk Stage IV renal cell carcinoma, (ii) first line Stage III or IV unresectable advanced melanoma, (iii) metastatic colorectal cancer displaying MSI-H or dMMR that has progressed following treatment with fluoropyrimidine, oxaliplatin, and irinotecan, or (iv) advanced renal cell carcinoma which has failed on antiangiogenic therapy.

5. The method of claim 1, wherein the compound of Structure I, or a pharmaceutically acceptable salt thereof, is administered in a single daily dose, or in divided doses two, three, or four times daily.

6. The method of claim 1, wherein the compound of Structure I, or a pharmaceutically acceptable salt thereof, is administered once daily or twice daily.

7. The method of claim 1, wherein from 120 mg to 720 mg of the compound of Structure I, or a pharmaceutically acceptable salt thereof, is administered daily.

8. The method of claim 1, wherein 3 mg/kg of nivolumab is administered by intravenous infusion every three weeks.

9. The method of claim 1, wherein from 120 mg to 720 mg of the compound of Structure I, or a pharmaceutically acceptable salt thereof, is administered daily, and 3 mg/kg of nivolumab is administered by intravenous infusion every three weeks.

10. A method of treating a cancer, comprising administering to a subject in need thereof an effective amount of a compound of Structure (I):

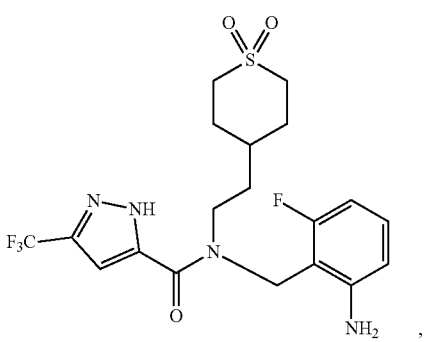

(I)

or a pharmaceutically acceptable salt thereof, in combination with a PD-1 inhibitor and a CTLA-4 inhibitor, wherein the PD-1 inhibitor is nivolumab and the CTLA-4 inhibitor is ipilimumab, and the cancer is resistant to checkpoint inhibitor therapy in the absence of the compound of Structure (I).

11. The method of claim 10, wherein the cancer (i) is a solid tumor cancer, (ii) has progressed on an immuno-oncology agent, (iii) is melanoma, renal cell carcinoma, colorectal cancer, hepatocellular carcinoma, or non-small cell lung cancer, (iv) is lung cancer, or (v) is non-small cell lung cancer.

12. The method of claim 10, wherein the cancer is (i) first line IMDC classification Intermediate- or Poor-risk Stage IV renal cell carcinoma; (ii) first line Stage III or IV unresectable advanced melanoma; (iii) metastatic colorectal cancer displaying MSI-H or dMMR that has progressed following treatment with fluoropyrimidine, oxaliplatin, and irinotecan; or (iv) advanced renal cell carcinoma which has failed on antiangiogenic therapy.

13. The method of claim 10, wherein the compound of Structure I, or a pharmaceutically acceptable salt thereof, is administered in a single daily dose, or in divided doses two, three, or four times daily.

14. The method of claim 10, wherein the compound of Structure I, or a pharmaceutically acceptable salt thereof, is administered once daily or twice daily.

15. The method of claim 10, wherein from 120 mg to 720 mg of the compound of Structure I, or a pharmaceutically acceptable salt thereof, is administered daily.

16. The method of claim 10, wherein 3 mg/kg of nivolumab is administered by intravenous infusion every three weeks for four doses, followed by 240 mg of nivolumab, administered by intravenous infusion every 2 weeks, or 480 mg of nivolumab, administered by intravenous infusion every 4 weeks.

17. The method of claim 10, wherein 1 mg/kg ipilimumab is administered by intravenous infusion every three weeks for four doses.

18. The method of claim 10, wherein from 120 mg to 720 mg of the compound of Structure I, or a pharmaceutically acceptable salt thereof, is administered daily; 3 mg/kg of nivolumab is administered by intravenous infusion every three weeks for four doses, followed by 240 mg of nivolumab, administered by intravenous infusion every 2 weeks, or 480 mg of nivolumab, administered by intravenous infusion every 4 weeks; and 1 mg/kg ipilimumab is administered by intravenous infusion every three weeks for four doses.

19. The method of claim 18, wherein the administration of ipilimumab is discontinued after four weeks.

* * * * *